(12) United States Patent
Spivey et al.

(10) Patent No.: US 8,992,422 B2
(45) Date of Patent: Mar. 31, 2015

(54) ROBOTICALLY-CONTROLLED ENDOSCOPIC ACCESSORY CHANNEL

(75) Inventors: James T. Spivey, Cincinnati, OH (US); Mark S. Ortiz, Milford, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 102 days.

(21) Appl. No.: 13/118,194

(22) Filed: May 27, 2011

(65) Prior Publication Data

US 2011/0295242 A1 Dec. 1, 2011

Related U.S. Application Data

(63) Continuation-in-part of application No. 11/277,324, filed on Mar. 23, 2006, now abandoned.

(51) Int. Cl.
*A61B 1/00* (2006.01)
*A61B 1/04* (2006.01)
(Continued)

(52) U.S. Cl.
CPC ....... *A61B 17/07207* (2013.01); *A61B 19/2203* (2013.01); *A61B 17/072* (2013.01); *A61B 17/115* (2013.01); *A61B 17/32053* (2013.01); *A61B 19/026* (2013.01); *A61B 19/0287* (2013.01); *A61B 19/5225* (2013.01); *A61B 2017/00199* (2013.01); *A61B 2017/0023* (2013.01); *A61B 2017/003* (2013.01); *A61B 2017/00327* (2013.01); *A61B 2017/0042* (2013.01); *A61B 2017/00473* (2013.01); *A61B 2017/00477* (2013.01); *A61B 2017/00685* (2013.01); *A61B 2017/00734* (2013.01);
(Continued)

(58) Field of Classification Search
CPC ........................... A61B 19/22; A61B 19/2203
USPC .......... 600/102, 104, 139, 141, 142, 146, 153
See application file for complete search history.

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2010214687 A1 | 9/2010 |
|---|---|---|
| CA | 2458946 A1 | 3/2003 |

(Continued)

OTHER PUBLICATIONS

European Search Report, Application No. 07251221.3, Issued Apr. 23, 2009 (10 pages).

(Continued)

*Primary Examiner* — Matthew J Kasztejna
*Assistant Examiner* — Kevin G. Barry, III

(57) ABSTRACT

Devices and systems are provided for controlling movement of a working end of a surgical device by means of a robotic system. In one embodiment, systems and devices are provided for moving an end effector on a distal end of a surgical fastening device. Movement can include rotational movement of the end effector about an axis of the shaft, articulation of the end effector relative to the shaft, and actuation of an end effector, e.g., closing, firing, and/or cutting.

11 Claims, 109 Drawing Sheets

(51) Int. Cl.
*A61B 17/072* (2006.01)
*A61B 19/00* (2006.01)
*A61B 17/115* (2006.01)
*A61B 17/3205* (2006.01)
*A61B 19/02* (2006.01)
*A61B 17/00* (2006.01)
*A61B 17/068* (2006.01)
*A61B 17/29* (2006.01)
*A61B 17/32* (2006.01)

(52) U.S. Cl.
CPC .............. *A61B 2017/0688* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/2905* (2013.01); *A61B 2017/2919* (2013.01); *A61B 2017/2923* (2013.01); *A61B 2017/2927* (2013.01); *A61B 2017/2947* (2013.01); *A61B 2017/320052* (2013.01); *A61B 2019/2242* (2013.01); *A61B 2019/5229* (2013.01)
USPC .................. 600/153; 600/102; 600/104

(56) References Cited

U.S. PATENT DOCUMENTS

| | | |
|---|---|---|
| 951,393 A | 3/1910 | Hahn |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,441,096 A | 5/1948 | Happe |
| 2,526,902 A | 10/1950 | Rublee |
| 2,674,149 A | 4/1954 | Benson |
| 2,804,848 A | 9/1957 | O'Farrell et al. |
| 2,808,482 A | 10/1957 | Zanichkowsky et al. |
| 2,853,074 A | 9/1958 | Olson |
| 3,032,769 A | 5/1962 | Palmer |
| 3,075,062 A | 1/1963 | Iaccarino |
| 3,078,465 A | 2/1963 | Bobrov |
| 3,166,072 A | 1/1965 | Sullivan, Jr. |
| 3,266,494 A | 8/1966 | Brownrigg et al. |
| 3,269,630 A | 8/1966 | Fleischer |
| 3,357,296 A | 12/1967 | Lefever |
| 3,490,675 A | 1/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,207,898 A | 6/1980 | Becht |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Siegel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,486,928 A | 12/1984 | Tucker et al. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |

(56) References Cited

U.S. PATENT DOCUMENTS

| | | |
|---|---|---|
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,155,941 A | 10/1992 | Takahashi et al. |
| 5,156,315 A | 10/1992 | Green et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,368,015 A | 11/1994 | Wilk |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |

(56) References Cited

U.S. PATENT DOCUMENTS

| | | |
|---|---|---|
| 5,403,312 A | 4/1995 | Yates et al. |
| 5,405,072 A | 4/1995 | Zlock et al. |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,439,479 A | 8/1995 | Schichman et al. |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,470,006 A | 11/1995 | Rodak |
| 5,470,007 A | 11/1995 | Plyley et al. |
| 5,470,009 A | 11/1995 | Rodak |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A * | 1/1996 | Fontayne .................. 227/178.1 |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,611,709 A | 3/1997 | McAnulty |

(56) References Cited

U.S. PATENT DOCUMENTS

| | | |
|---|---|---|
| 5,613,966 A | 3/1997 | Makower et al. |
| 5,618,294 A | 4/1997 | Aust et al. |
| 5,618,303 A | 4/1997 | Marlow et al. |
| 5,618,307 A | 4/1997 | Donlon et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |

(56) References Cited

U.S. PATENT DOCUMENTS

| | | |
|---|---|---|
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,971,916 A | 10/1999 | Koren |
| 5,988,479 A | 11/1999 | Palmer |
| 5,997,528 A | 12/1999 | Bisch et al. |
| 6,003,517 A | 12/1999 | Sheffield et al. |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,390 A | 4/2000 | Green et al. |
| 6,056,735 A | 5/2000 | Okada et al. |
| 6,056,746 A | 5/2000 | Goble et al. |
| 6,063,097 A | 5/2000 | Oi et al. |
| 6,063,098 A | 5/2000 | Houser et al. |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,120,433 A * | 9/2000 | Mizuno et al. ............... 600/102 |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,338,737 B1 | 1/2002 | Toledano |

(56) References Cited

U.S. PATENT DOCUMENTS

| | | |
|---|---|---|
| 6,346,077 B1 | 2/2002 | Taylor et al. |
| 6,352,503 B1 | 3/2002 | Matsui et al. |
| 6,352,532 B1 | 3/2002 | Kramer et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,454,781 B1 | 9/2002 | Witt et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,588,643 B2 | 7/2003 | Bolduc et al. |
| 6,589,164 B1 | 7/2003 | Flaherty |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| 6,641,528 B2 | 11/2003 | Torii |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,409 B2 | 8/2004 | Truckai et al. |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |

(56) References Cited

U.S. PATENT DOCUMENTS

| | | |
|---|---|---|
| 6,849,071 B2 | 2/2005 | Whitman et al. |
| RE38,708 E | 3/2005 | Bolanos et al. |
| 6,866,178 B2 | 3/2005 | Adams et al. |
| 6,866,671 B2 | 3/2005 | Tierney et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,189,207 B2 | 3/2007 | Viola |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |

(56) References Cited

U.S. PATENT DOCUMENTS

| | | |
|---|---|---|
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,308,998 B2 | 12/2007 | Mastri et al. |
| 7,322,975 B2 | 1/2008 | Goble et al. |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,343,920 B2 | 3/2008 | Toby et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,563,862 B2 | 7/2009 | Sieg et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,591,783 B2 | 9/2009 | Boulais et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,003 B2 | 11/2009 | Stefanchik et al. |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,648,519 B2 | 1/2010 | Lee et al. |
| 7,651,498 B2 | 1/2010 | Shifrin et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,307 B2 | 3/2010 | Danitz et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,204 B2 | 4/2010 | Viola |
| 7,699,835 B2 | 4/2010 | Lee et al. |
| 7,699,859 B2 | 4/2010 | Bombard et al. |
| 7,708,180 B2 | 5/2010 | Murray et al. |
| 7,708,758 B2 | 5/2010 | Lee et al. |
| 7,714,239 B2 | 5/2010 | Smith |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |

(56) References Cited

U.S. PATENT DOCUMENTS

| | | | |
|---|---|---|---|
| 7,721,936 B2 | 5/2010 | Shelton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,775 B2 | 8/2010 | Shelton, IV et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,789,875 B2 | 9/2010 | Brock et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,871,418 B2 | 1/2011 | Thompson et al. |
| 7,887,530 B2 | 2/2011 | Zemlok et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,191 B2 | 3/2011 | Baker et al. |
| 7,909,221 B2 | 3/2011 | Viola et al. |
| 7,913,891 B2 | 3/2011 | Doll et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,934,631 B2 | 5/2011 | Balbierz et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,050 B2 | 6/2011 | Smith et al. |
| 7,959,051 B2 | 6/2011 | Smith et al. |
| 7,963,963 B2 | 6/2011 | Francischelli et al. |
| 7,966,799 B2 | 6/2011 | Morgan et al. |
| 7,967,180 B2 | 6/2011 | Scirica |
| 7,972,298 B2 | 7/2011 | Wallace et al. |
| 7,980,443 B2 | 7/2011 | Scheib et al. |
| 7,997,469 B2 | 8/2011 | Olson et al. |
| 8,002,795 B2 | 8/2011 | Beetel |
| 8,011,551 B2 | 9/2011 | Marczyk et al. |
| 8,011,555 B2 | 9/2011 | Tarinelli et al. |
| 8,020,743 B2 | 9/2011 | Shelton, IV |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,091,756 B2 | 1/2012 | Viola |
| 8,097,017 B2 | 1/2012 | Viola |
| 8,108,072 B2 | 1/2012 | Zhao et al. |
| 8,113,410 B2 | 2/2012 | Hall et al. |
| 8,123,103 B2 | 2/2012 | Milliman |
| 8,136,712 B2 | 3/2012 | Zingman |
| 8,141,762 B2 | 3/2012 | Bedi et al. |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,167,185 B2 | 5/2012 | Shelton, IV et al. |
| 8,167,895 B2 | 5/2012 | D'Agostino et al. |
| 8,172,124 B2 | 5/2012 | Shelton, IV et al. |
| 8,186,555 B2 | 5/2012 | Shelton, IV et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,211,125 B2 | 7/2012 | Spivey |
| 8,215,531 B2 | 7/2012 | Shelton, IV et al. |
| 8,220,468 B2 | 7/2012 | Cooper et al. |
| 8,225,799 B2 | 7/2012 | Bettuchi |
| 8,241,271 B2 | 8/2012 | Millman et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,372,094 B2 | 2/2013 | Bettuchi et al. |
| 2001/0025183 A1 | 9/2001 | Shahidi |
| 2001/0031975 A1* | 10/2001 | Whitman et al. ............ 606/167 |
| 2002/0022836 A1 | 2/2002 | Goble et al. |
| 2002/0029036 A1 | 3/2002 | Goble et al. |
| 2002/0095175 A1* | 7/2002 | Brock et al. ................. 606/205 |
| 2002/0117534 A1 | 8/2002 | Green et al. |
| 2002/0134811 A1 | 9/2002 | Napier et al. |
| 2002/0165541 A1 | 11/2002 | Whitman |
| 2003/0036748 A1* | 2/2003 | Cooper et al. .................... 606/1 |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |

(56) References Cited

U.S. PATENT DOCUMENTS

| | | |
|---|---|---|
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0070369 A1 | 4/2004 | Sakahibara |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban Iii et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0183246 A1 | 8/2006 | Wiesner et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0245971 A1 | 11/2006 | Burns et al. |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |

(56) References Cited

U.S. PATENT DOCUMENTS

| | | |
|---|---|---|
| 2007/0083193 A1 | 4/2007 | Werneth et al. |
| 2007/0084897 A1 | 4/2007 | Shelton, IV et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0114261 A1 | 5/2007 | Ortiz et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0295780 A1 | 12/2007 | Shelton et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0078736 A1 | 3/2009 | Van Lue |
| 2009/0088774 A1 | 4/2009 | Swarup et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0012704 A1 | 1/2010 | Tarinelli Racenet et al. |
| 2010/0023024 A1 | 1/2010 | Zeiner et al. |
| 2010/0049084 A1 | 2/2010 | Nock et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0186219 A1 | 7/2010 | Smith |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |

(56) References Cited

U.S. PATENT DOCUMENTS

| | | |
|---|---|---|
| 2010/0200637 A1 | 8/2010 | Beetel |
| 2010/0213241 A1 | 8/2010 | Bedi |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0312261 A1 | 12/2010 | Suzuki et al. |
| 2010/0331856 A1 | 12/2010 | Carlson et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118754 A1 | 5/2011 | Dachs, II et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163146 A1 | 7/2011 | Ortiz et al. |
| 2011/0163147 A1 | 7/2011 | Laurent et al. |
| 2011/0174861 A1 | 7/2011 | Shelton, IV et al. |
| 2011/0174863 A1 | 7/2011 | Shelton, IV et al. |
| 2011/0178536 A1 | 7/2011 | Kostrzewski |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0022523 A1 | 1/2012 | Smith et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0150192 A1 | 6/2012 | Dachs, II et al. |
| 2012/0160721 A1 | 6/2012 | Shelton, IV et al. |
| 2012/0175399 A1 | 7/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0209289 A1 | 8/2012 | Duque et al. |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |

(56) References Cited

U.S. PATENT DOCUMENTS

| | | |
|---|---|---|
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0283748 A1 | 11/2012 | Ortiz et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |
| 2013/0048697 A1 | 2/2013 | Shelton, IV et al. |
| 2013/0123822 A1 | 5/2013 | Wellman et al. |
| 2013/0197556 A1 | 8/2013 | Shelton, IV et al. |
| 2013/0200132 A1 | 8/2013 | Moore et al. |

FOREIGN PATENT DOCUMENTS

| | | |
|---|---|---|
| CA | 2512960 A1 | 1/2006 |
| CA | 2514274 A1 | 1/2006 |
| CN | 2488482 Y | 5/2002 |
| CN | 1634601 A | 7/2005 |
| CN | 1726874 A | 2/2006 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |

(56) References Cited

FOREIGN PATENT DOCUMENTS

| | | | |
|---|---|---|---|
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1459695 | A1 | 9/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1520521 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621145 | A2 | 2/2006 |
| EP | 1621151 | A2 | 2/2006 |
| EP | 1034746 | B1 | 3/2006 |
| EP | 1632191 | A2 | 3/2006 |
| EP | 1065981 | B1 | 5/2006 |
| EP | 1082944 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1897502 | A1 | 3/2008 |
| EP | 1611856 | B1 | 4/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1693008 | B1 | 12/2008 |
| EP | 1759640 | B1 | 12/2008 |
| EP | 2000102 | A2 | 12/2008 |
| EP | 2008595 | A2 | 12/2008 |
| EP | 1736104 | B1 | 3/2009 |
| EP | 1749486 | B1 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550409 | B1 | 6/2009 |
| EP | 1550413 | B1 | 6/2009 |
| EP | 1745748 | B1 | 8/2009 |
| EP | 2090237 | A1 | 8/2009 |
| EP | 2090244 | A2 | 8/2009 |
| EP | 2090245 | A2 | 8/2009 |
| EP | 2090256 | A2 | 8/2009 |
| EP | 2095777 | A2 | 9/2009 |
| EP | 2110082 | A1 | 10/2009 |
| EP | 1813208 | B1 | 11/2009 |
| EP | 2116195 | A1 | 11/2009 |
| EP | 1607050 | B1 | 12/2009 |
| EP | 1815804 | B1 | 12/2009 |
| EP | 1566150 | B1 | 4/2010 |
| EP | 1813206 | B1 | 4/2010 |
| EP | 1769754 | B1 | 6/2010 |
| EP | 1535565 | B1 | 10/2010 |
| EP | 1702570 | B1 | 10/2010 |

(56) References Cited

FOREIGN PATENT DOCUMENTS

| | | |
|---|---|---|
| EP | 1785098 B1 | 10/2010 |
| EP | 2005896 B1 | 10/2010 |
| EP | 2030578 B1 | 11/2010 |
| EP | 1627605 B1 | 12/2010 |
| EP | 1813205 B1 | 6/2011 |
| EP | 2090243 B1 | 6/2011 |
| EP | 1836986 B1 | 11/2011 |
| EP | 1785102 B1 | 1/2012 |
| FR | 999646 A | 2/1952 |
| FR | 1112936 A | 3/1956 |
| FR | 2598905 A1 | 11/1987 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | 50-33988 U | 4/1975 |
| JP | 585000053 A | 1/1983 |
| JP | 61-98249 A | 5/1986 |
| JP | S61502036 A | 9/1986 |
| JP | 63-203149 | 8/1988 |
| JP | 3-12126 A | 1/1991 |
| JP | 5-212039 A | 8/1993 |
| JP | 6007357 A | 1/1994 |
| JP | 7051273 A | 2/1995 |
| JP | 7-124166 A | 5/1995 |
| JP | 7-255735 A | 10/1995 |
| JP | 8-33642 A | 2/1996 |
| JP | 8033641 A | 2/1996 |
| JP | 8-164141 A | 6/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002-51974 A | 2/2002 |
| JP | 2002143078 A | 5/2002 |
| JP | 2002369820 A | 12/2002 |
| JP | 2003-500153 A | 1/2003 |
| JP | 2003-135473 A | 5/2003 |
| JP | 2003-521301 A | 7/2003 |
| JP | 2004-329624 A | 11/2004 |
| JP | 2004-337617 A | 12/2004 |
| JP | 2004-344663 | 12/2004 |
| JP | 2005-028149 A | 2/2005 |
| JP | 2005505322 T | 2/2005 |
| JP | 2005-103280 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2005-296412 A | 10/2005 |
| JP | 2005-328882 A | 12/2005 |
| JP | 2006-034975 A | 2/2006 |
| JP | 2006-034978 A | 2/2006 |
| JP | 2006-281405 A | 10/2006 |
| RU | 2008830 C1 | 3/1994 |
| RU | 2141279 C1 | 11/1999 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |

(56) References Cited

FOREIGN PATENT DOCUMENTS

| | | |
|---|---|---|
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A2 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/146987 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/101228 A2 | 8/2008 |
| WO | WO 2008/109125 A1 | 9/2008 |
| WO | WO 2008/124748 A1 | 10/2008 |
| WO | WO 2010/050771 A2 | 5/2010 |
| WO | WO 2010/063795 A1 | 6/2010 |

(56) References Cited

FOREIGN PATENT DOCUMENTS

| WO | WO 2010/098871 A2 | 9/2010 |
| WO | WO 2012/021671 A1 | 2/2012 |
| WO | WO 2012/044844 A2 | 4/2012 |

OTHER PUBLICATIONS

European Search Report, Application No. 07250393.1, dated Aug. 9, 2007 (8 pages).
U.S. Appl. No. 13/118,241, filed May 27, 2011.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
U.S. Appl. No. 12/031,368, filed Feb. 14, 2008.
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/488,903, filed Jun. 5, 2012.
U.S. Appl. No. 13/310,107, filed Dec. 2, 2011.
U.S. Appl. No. 13/369,561, filed Feb. 9, 2012.
U.S. Appl. No. 13/369,569, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601, filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/372,195, filed Feb. 13, 2012.
U.S. Appl. No. 13/486,175, filed Jun. 1, 2012.
U.S. Appl. No. 13/480,263, filed May 24, 2012.
Partial European Search Report, Application No. 07251221.3, dated Dec. 29, 2008 (6 pages).
European Examination Report, Application No. 07251221.3, dated Dec. 10, 2009 (5 pages).
European Search Report, Application No. 07251225.4, dated Sep. 20, 2007 (10 pages).
European Search Report, Application No. 07251237.9, dated Sep. 20, 2007 (11 pages).
International Search Report for Application No. PCT/US2012/026985, dated Jun. 5, 2012 (6 pages).
International Preliminary Report on Patentability for Application No. PCT/US2012/026985, dated Sep. 3, 2013 (7 pages).
Written Opinion for Application No. PCT/US2012/039290, dated Oct. 12, 2012 (17 pages).
International Preliminary Report on Patentability for Application No. PCT/US2012/039290, dated Dec. 2, 2013 (17 pages).

* cited by examiner

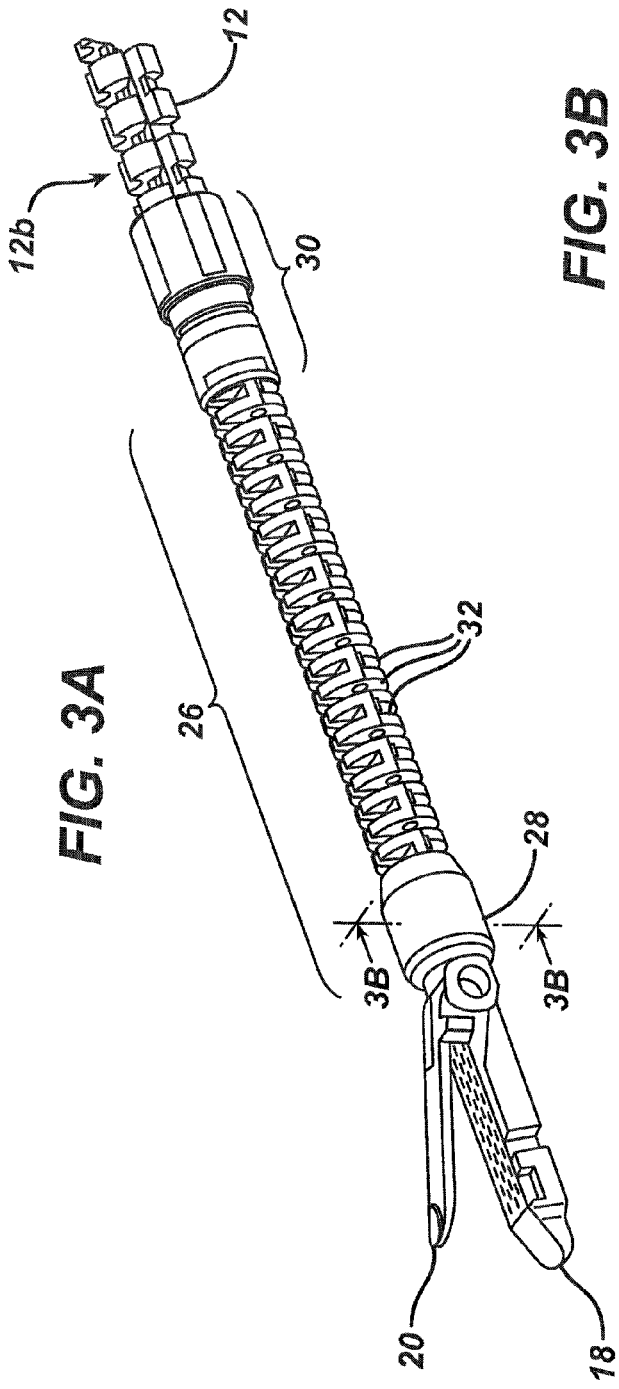
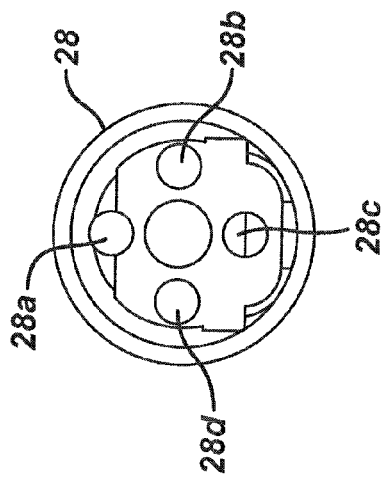

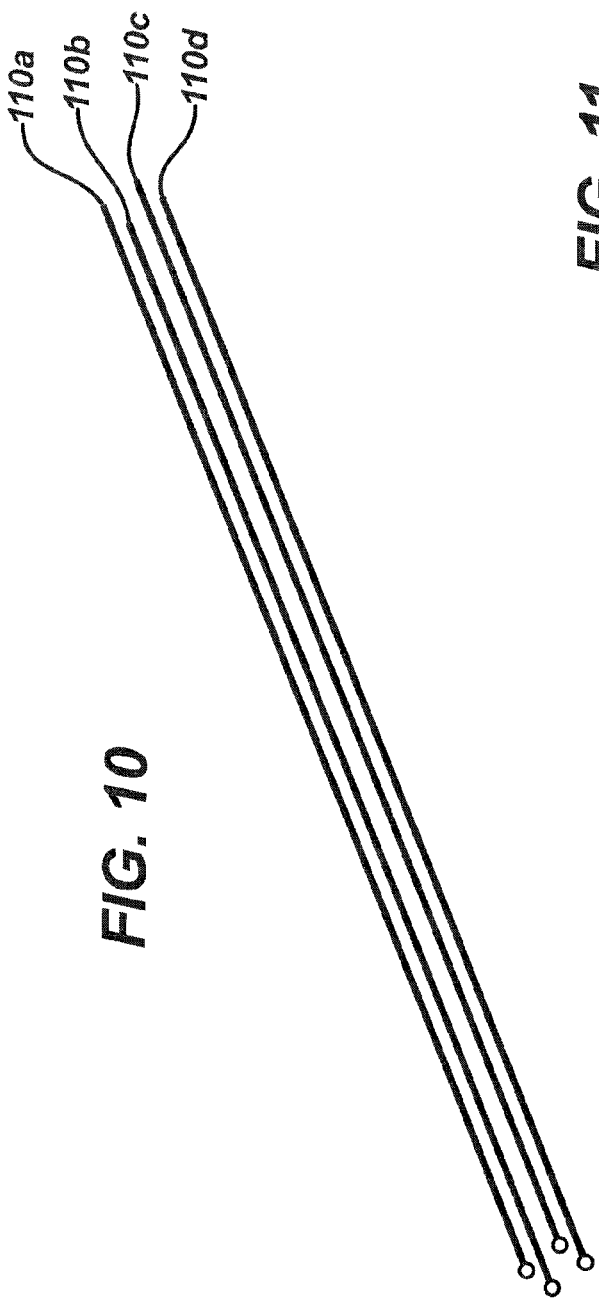
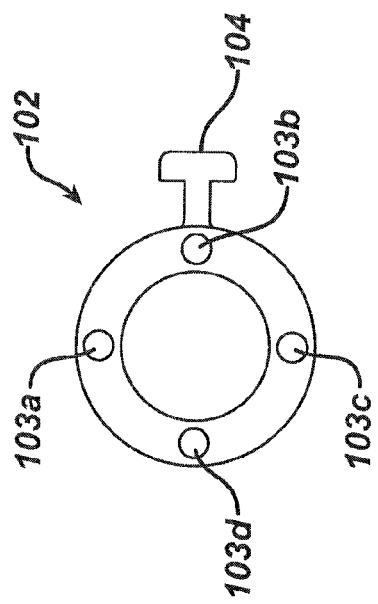

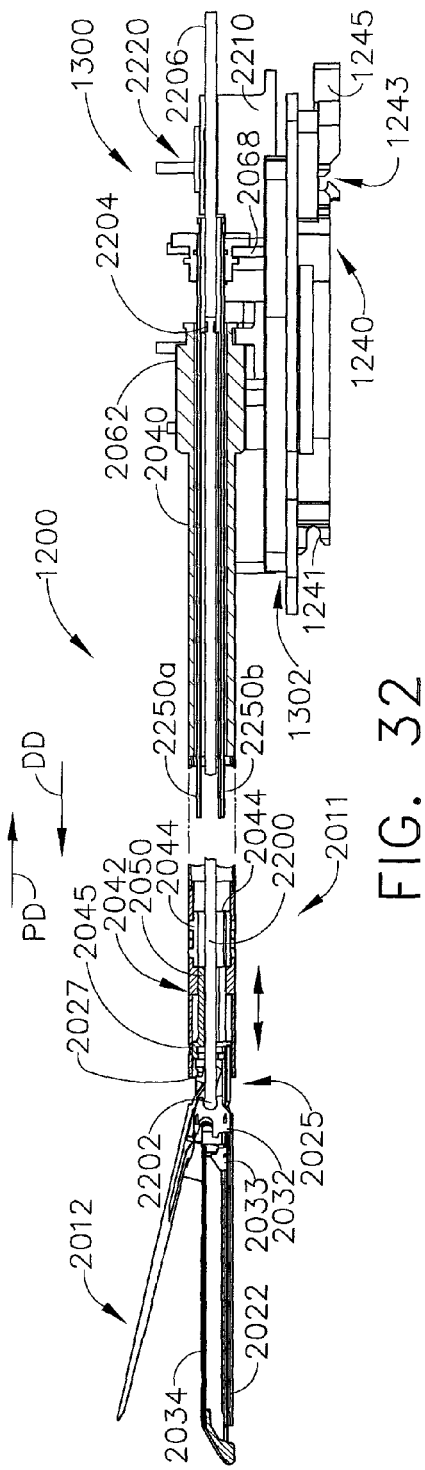
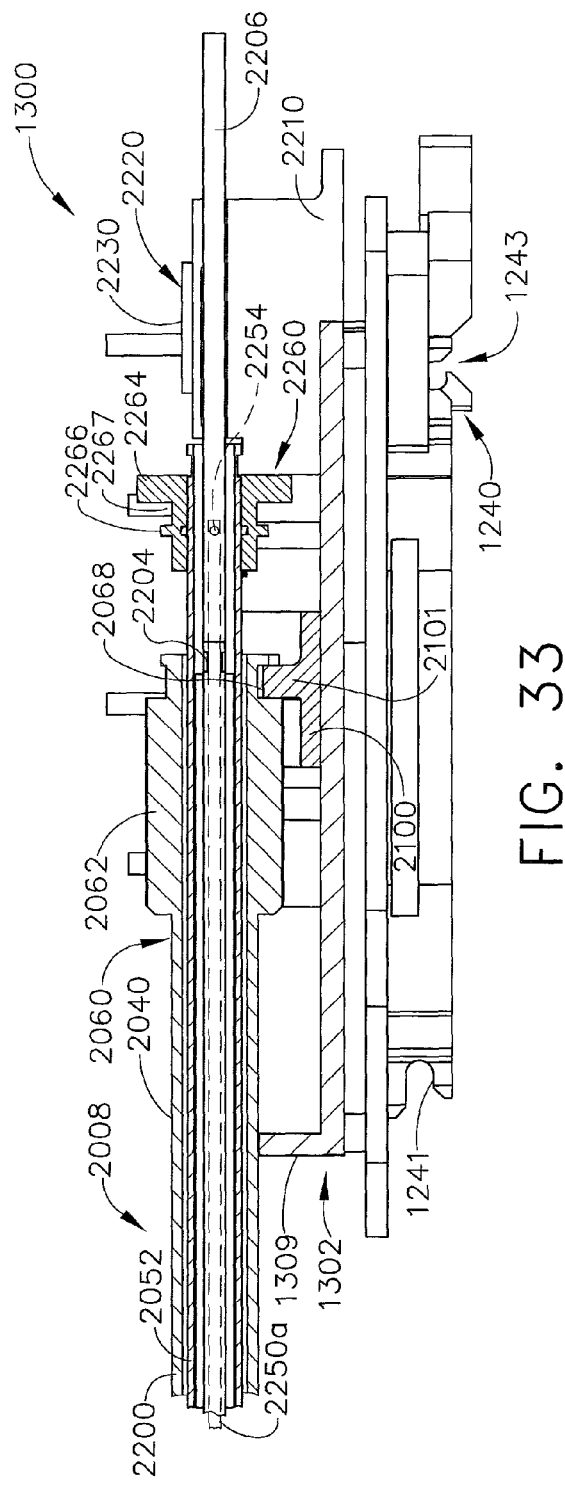

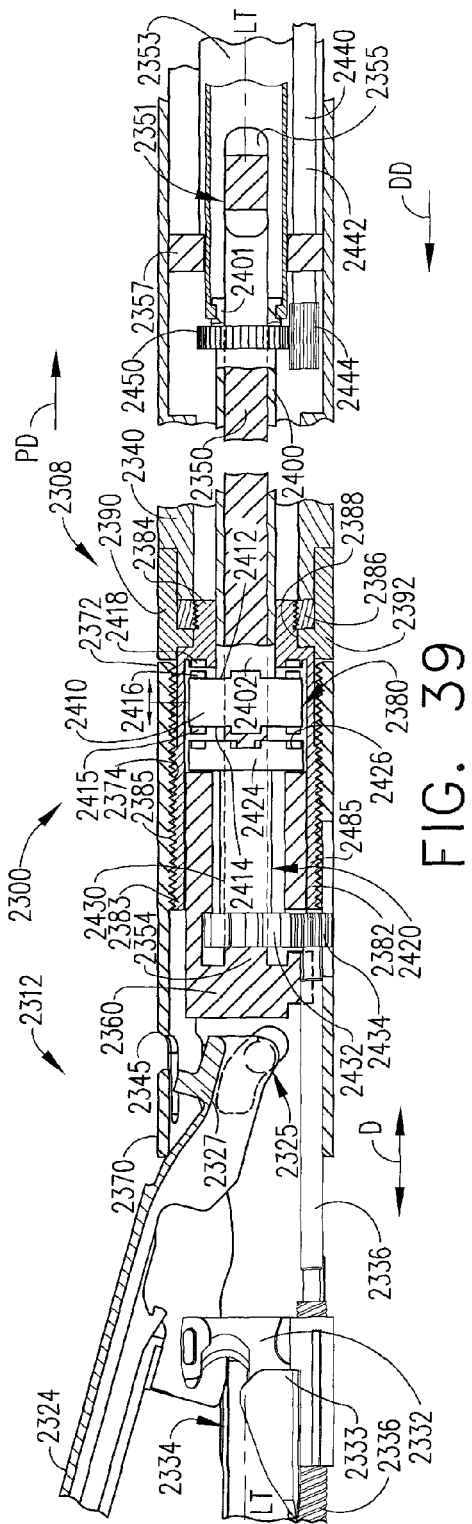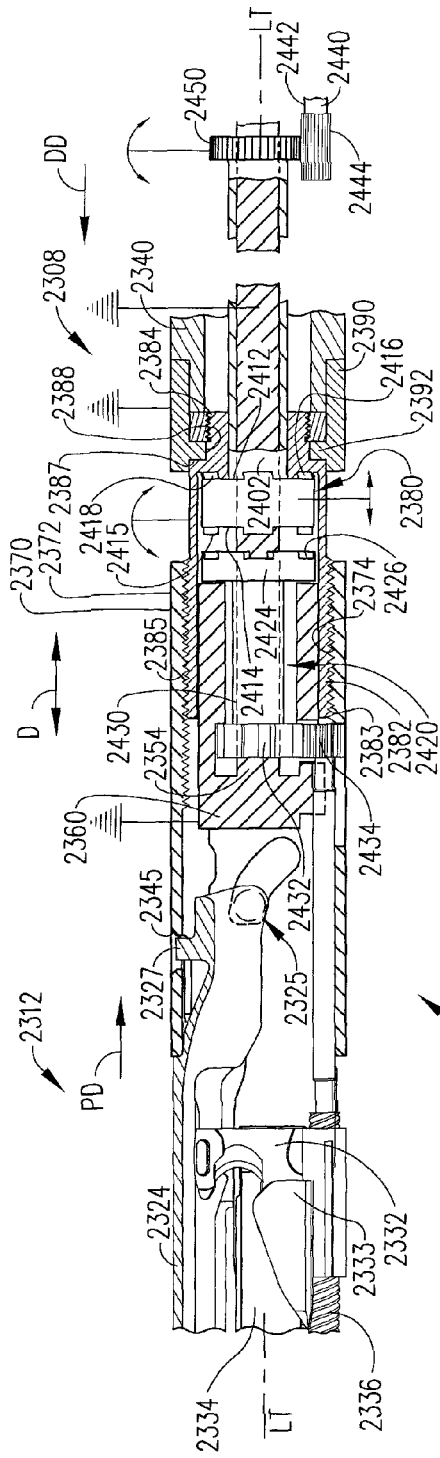

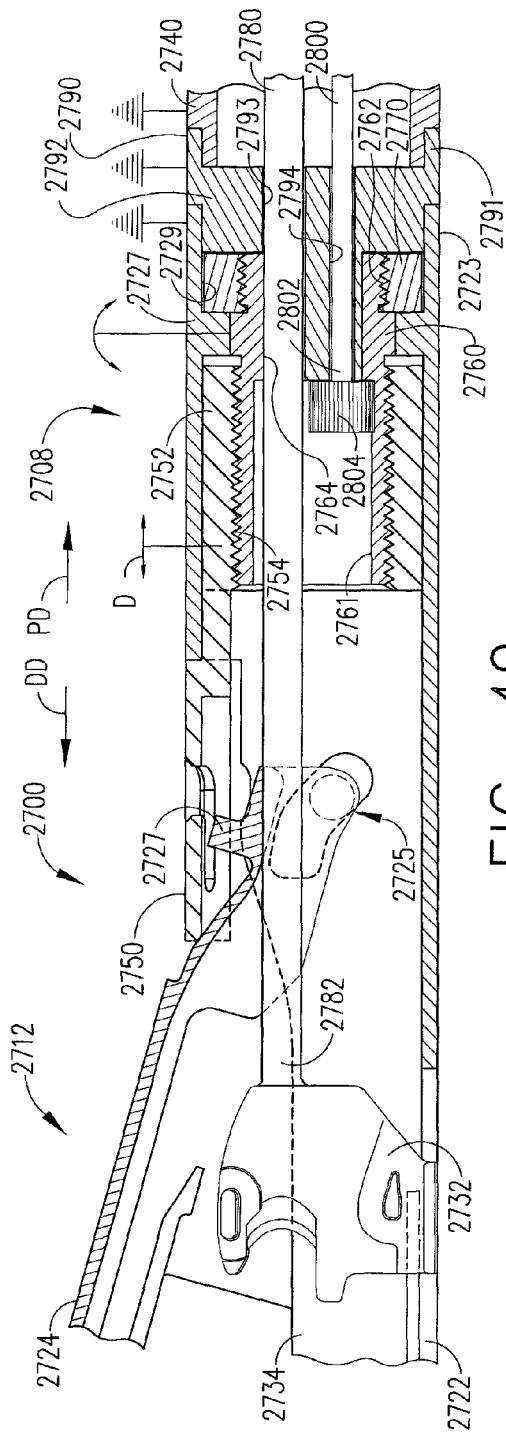
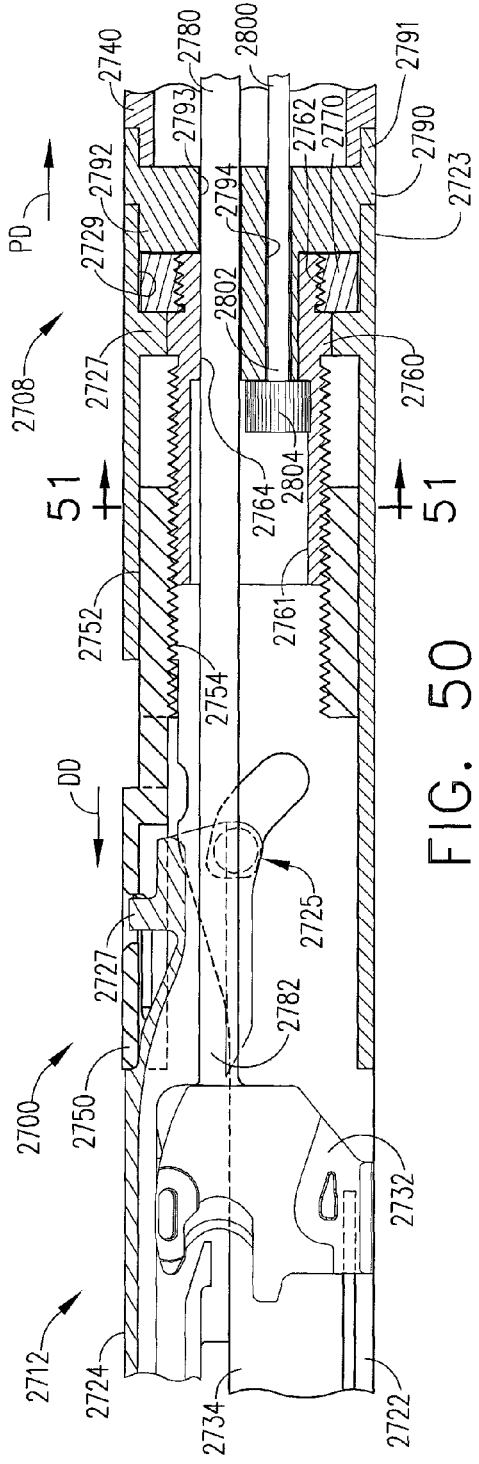

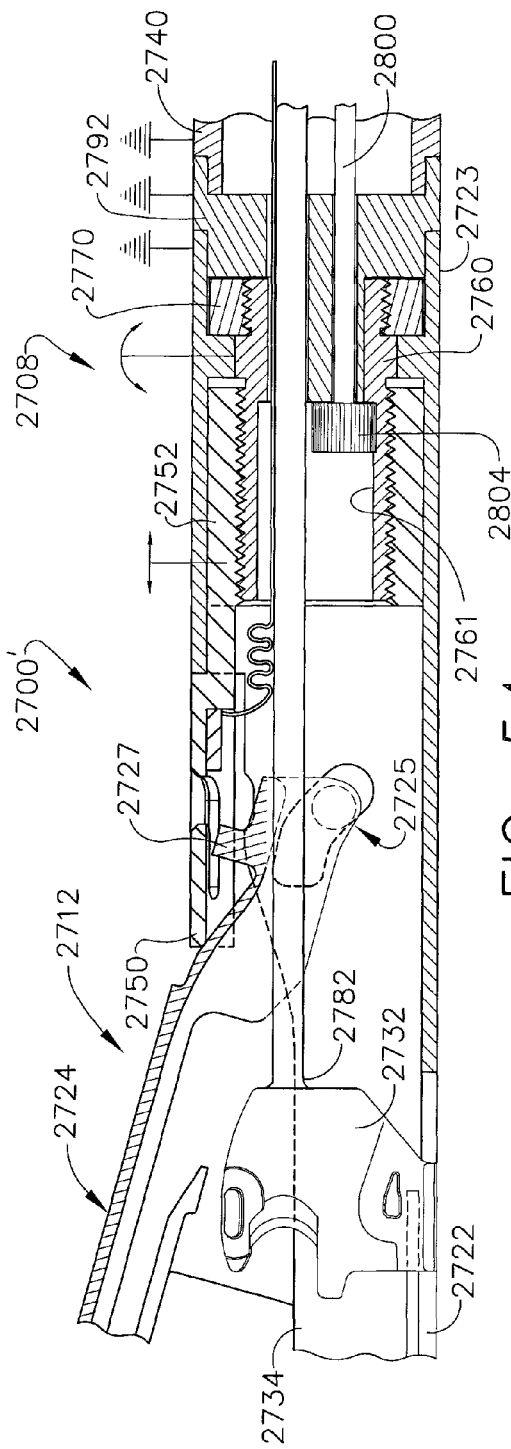
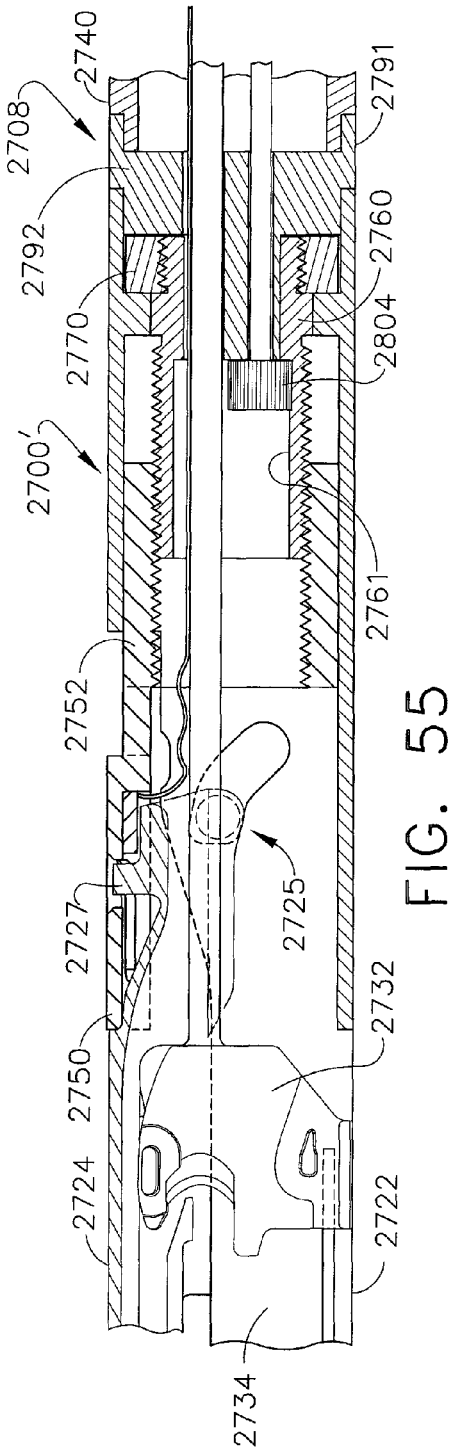
FIG. 54
FIG. 55

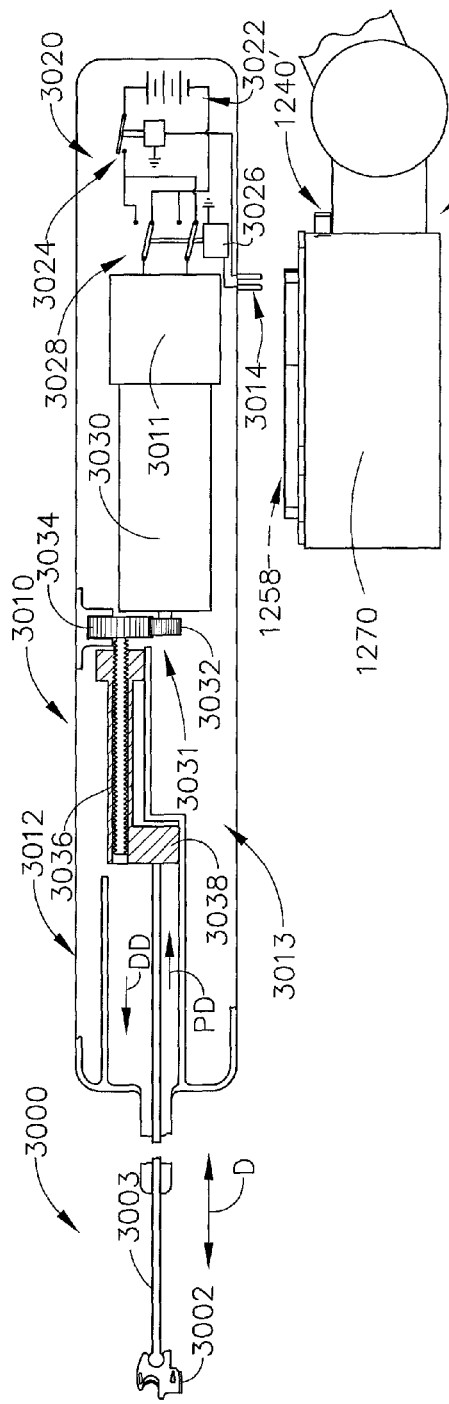
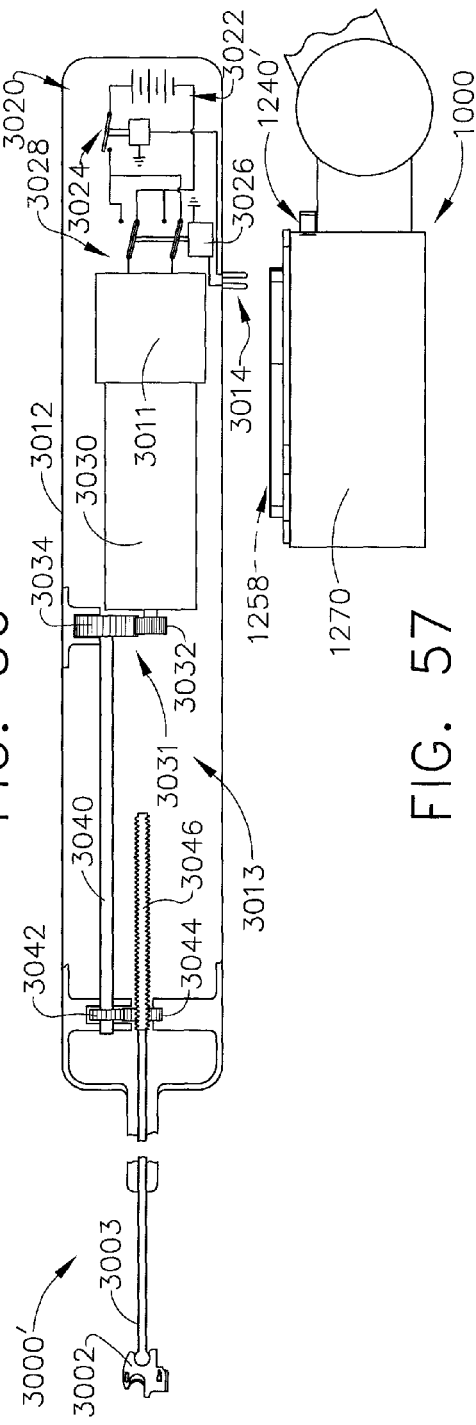
FIG. 56
FIG. 57

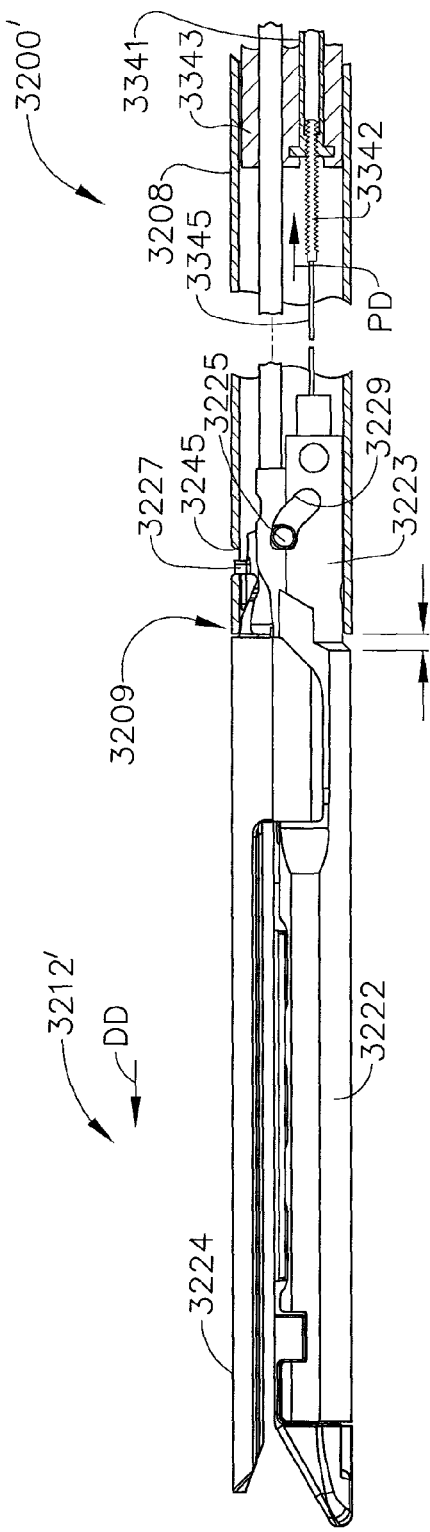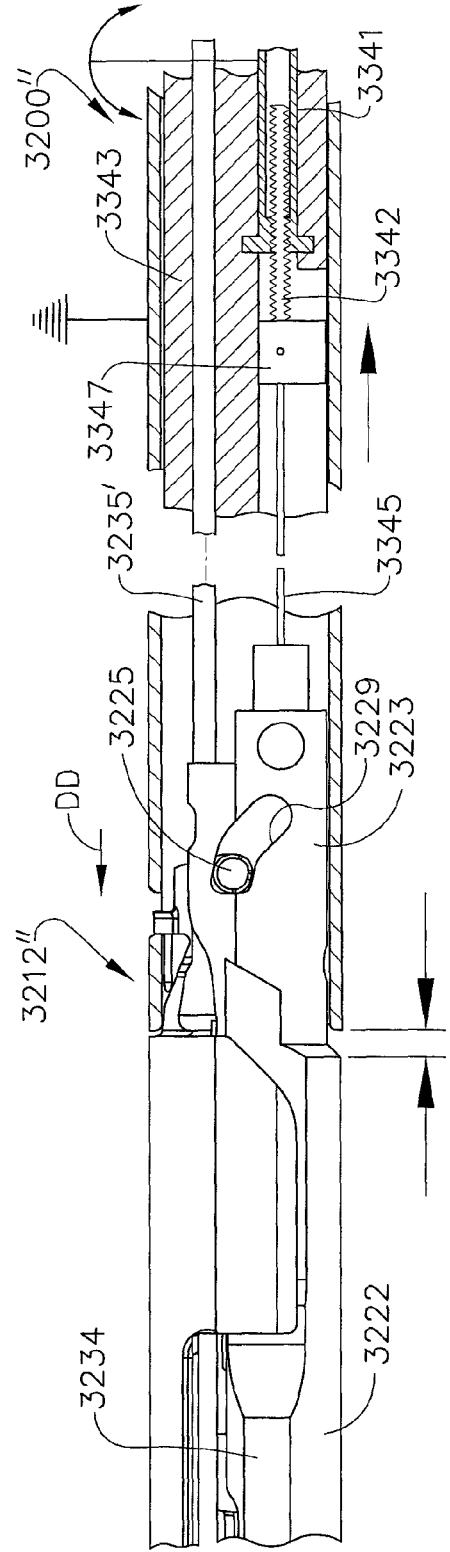

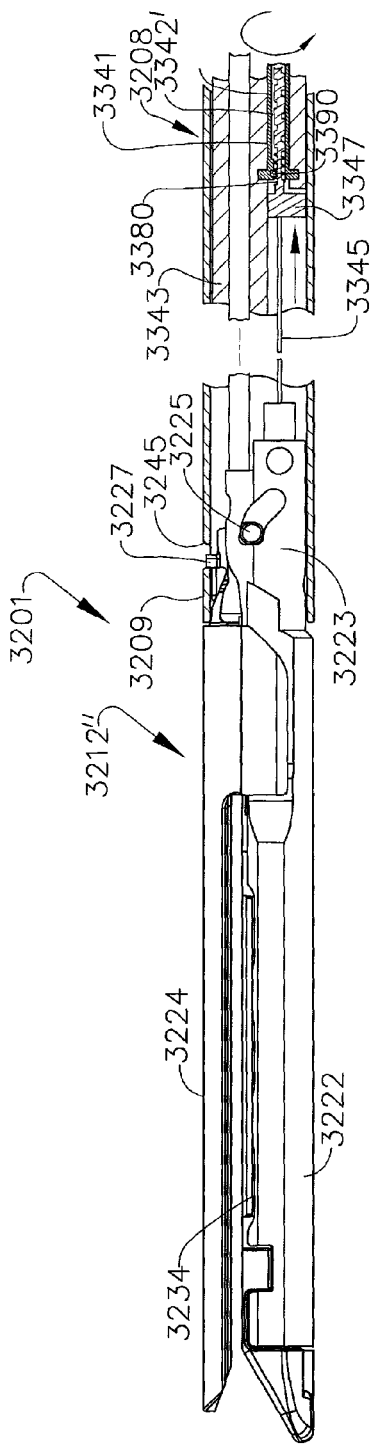
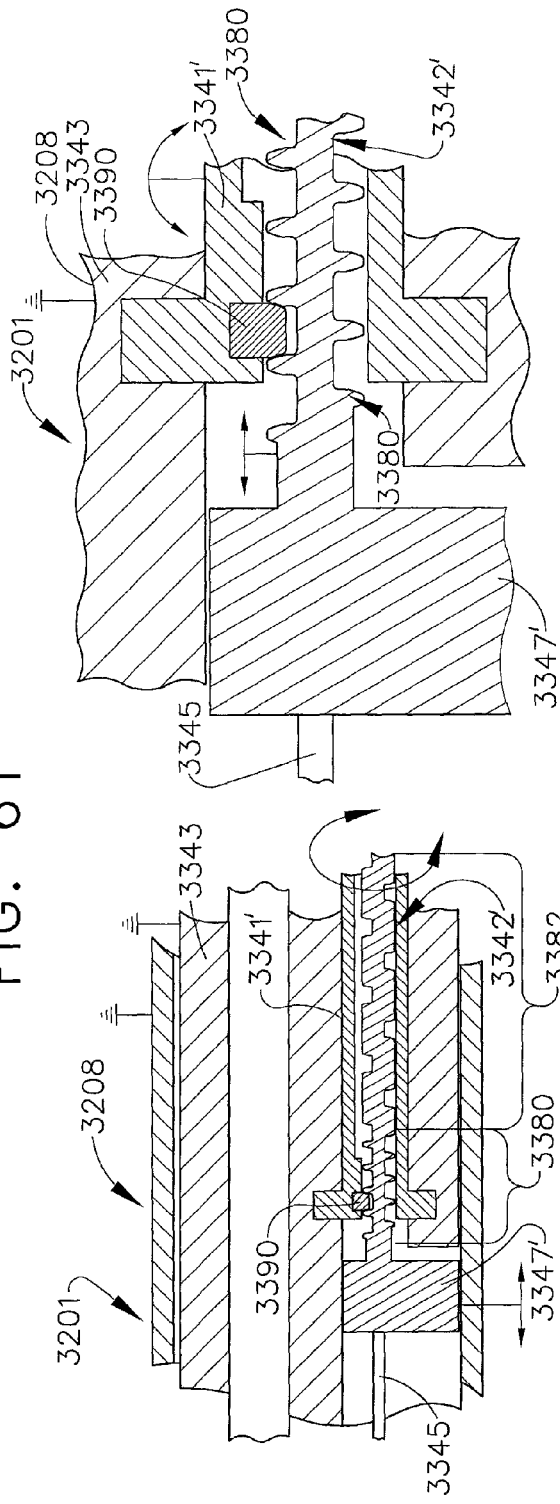
FIG. 61
FIG. 62
FIG. 63

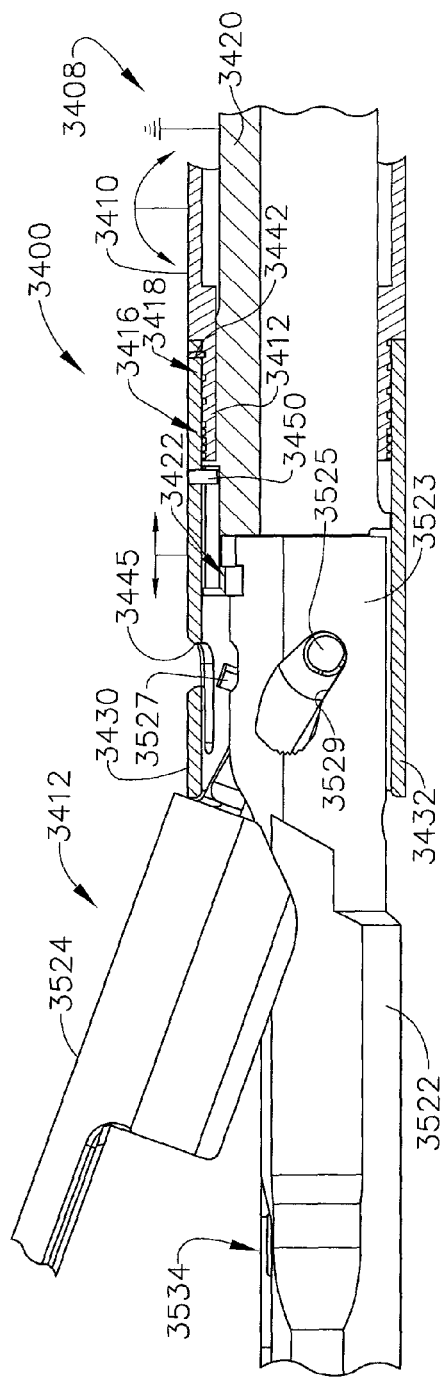
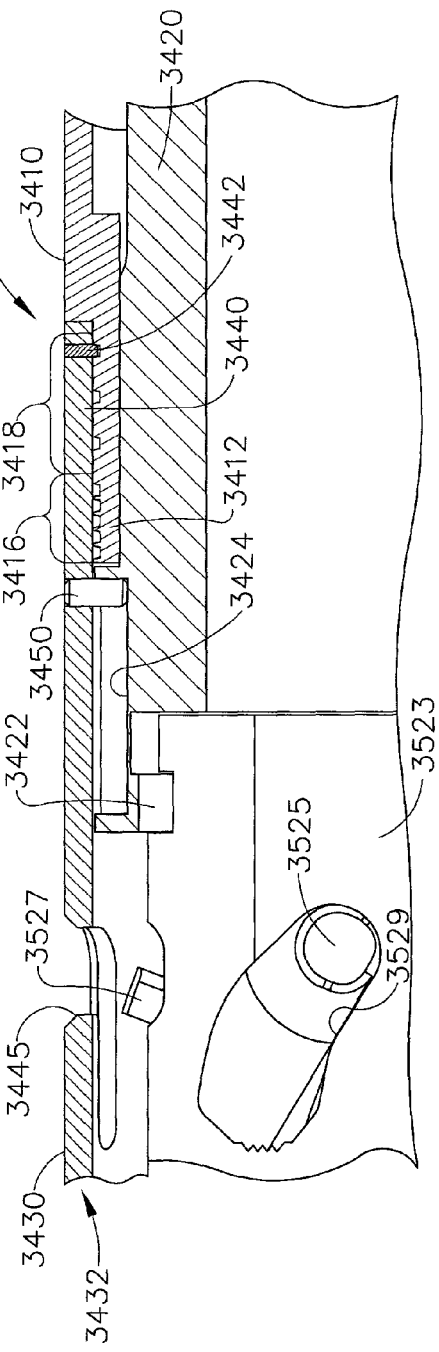

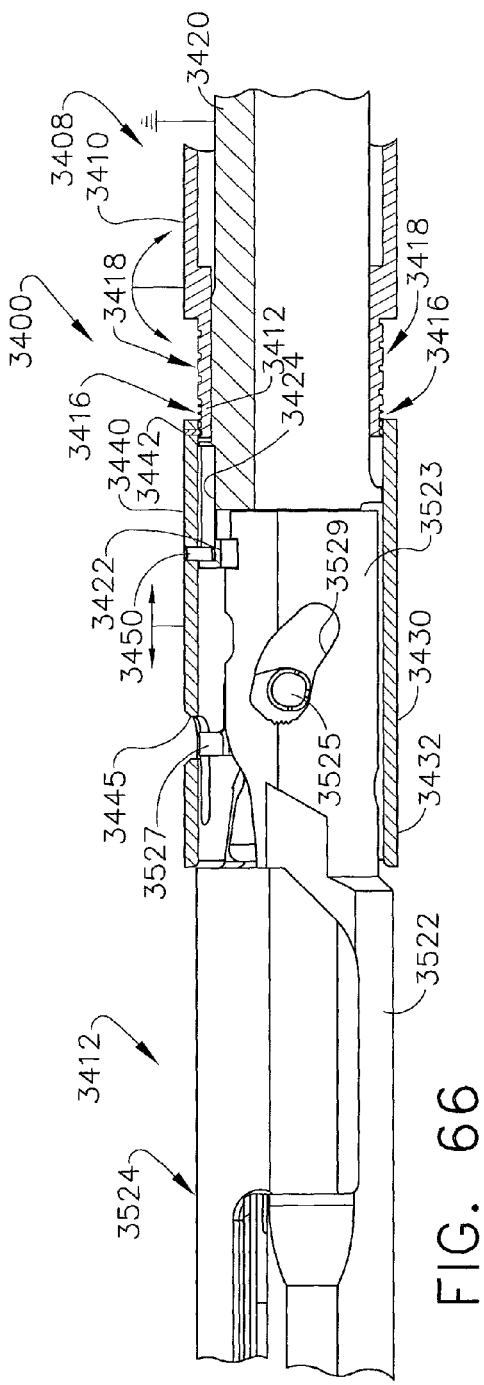
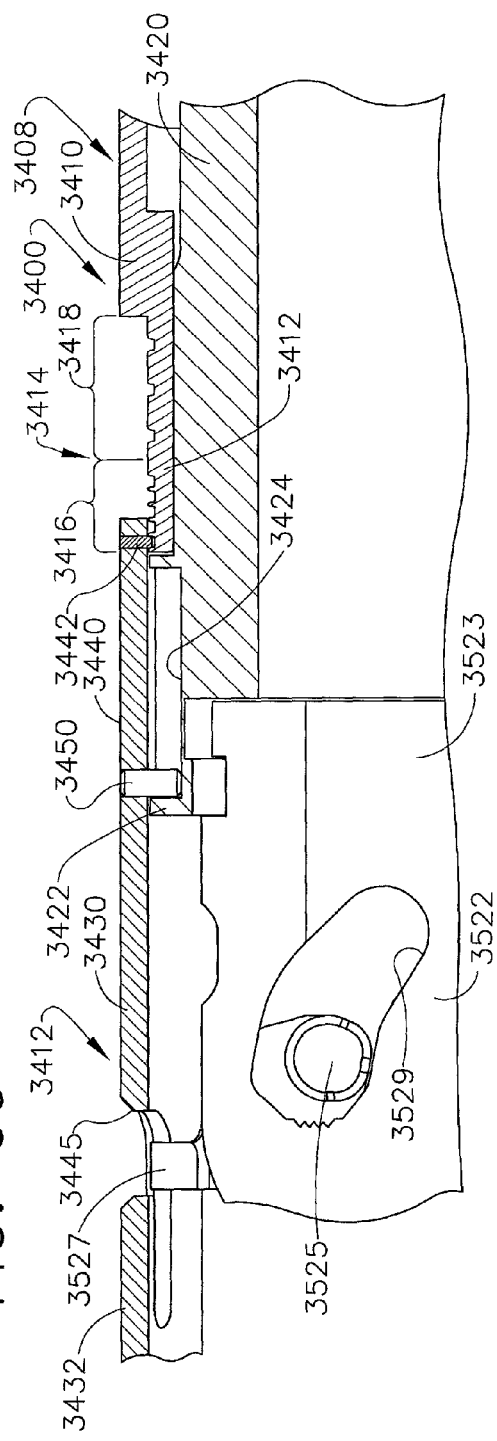
FIG. 66
FIG. 67

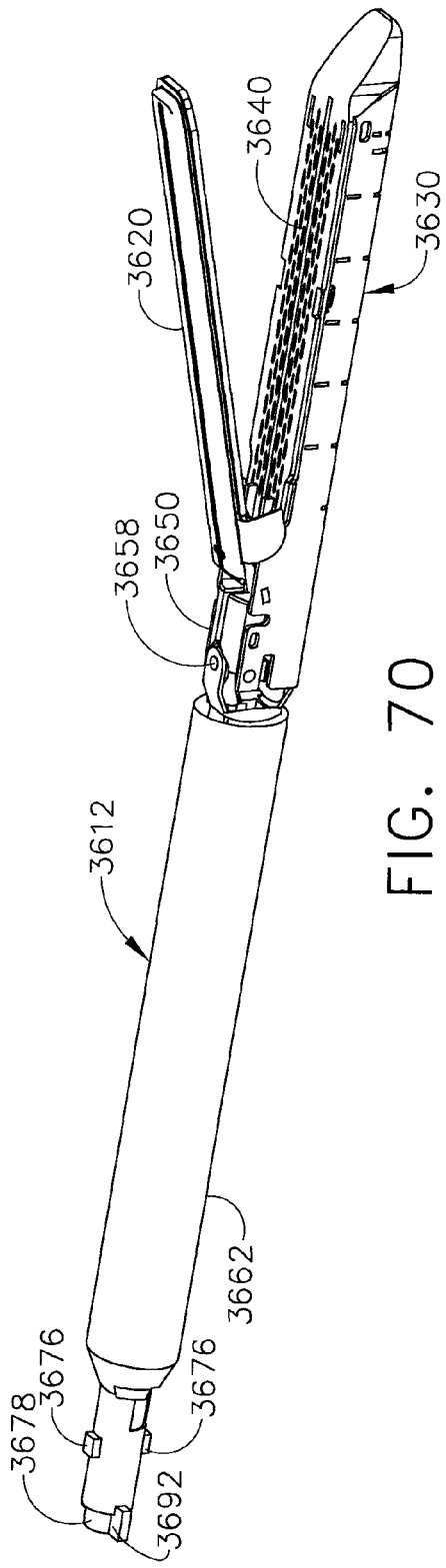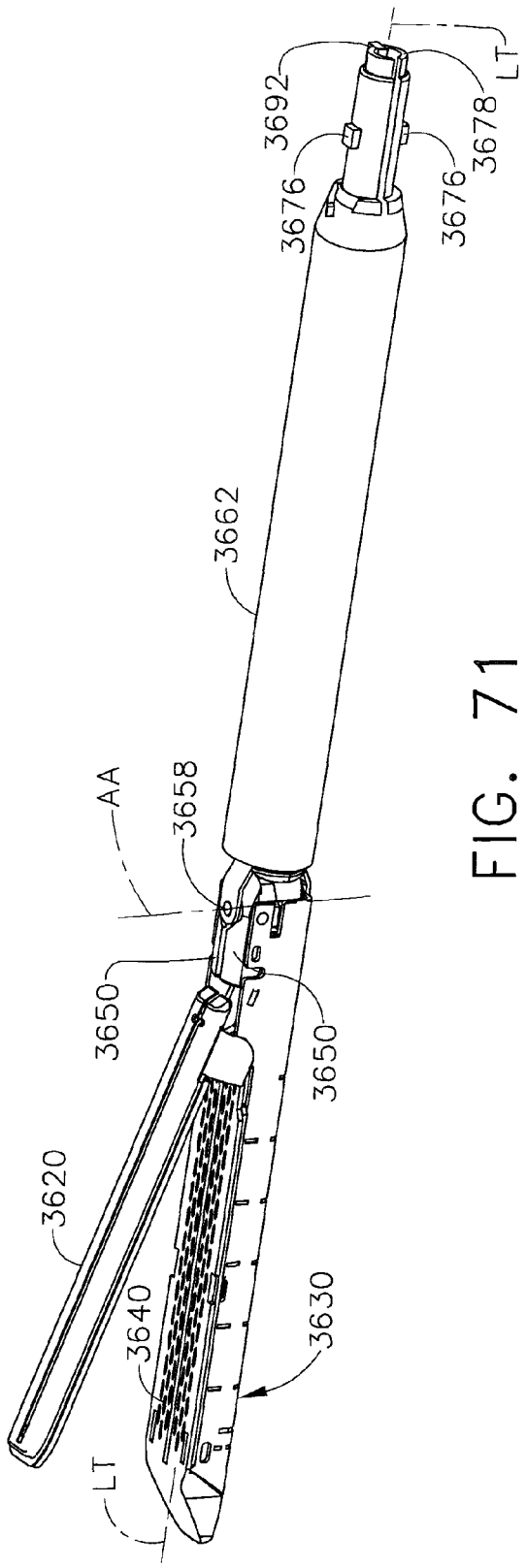

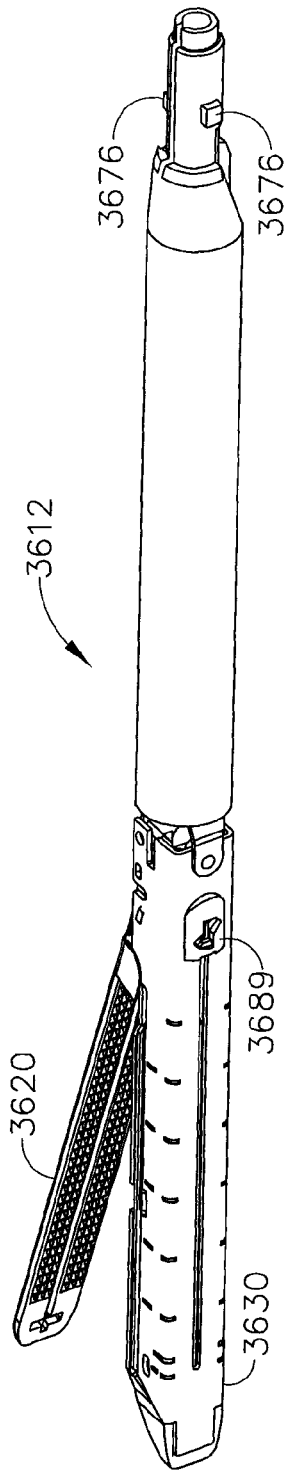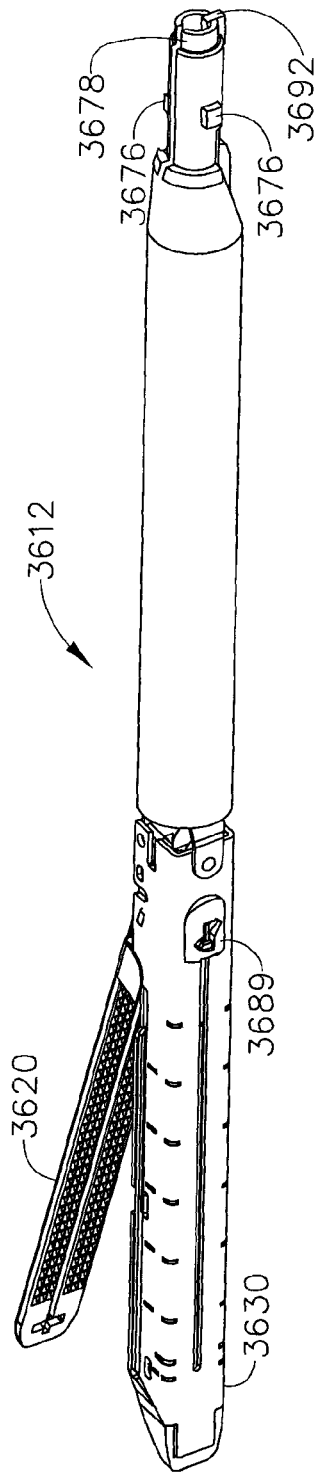

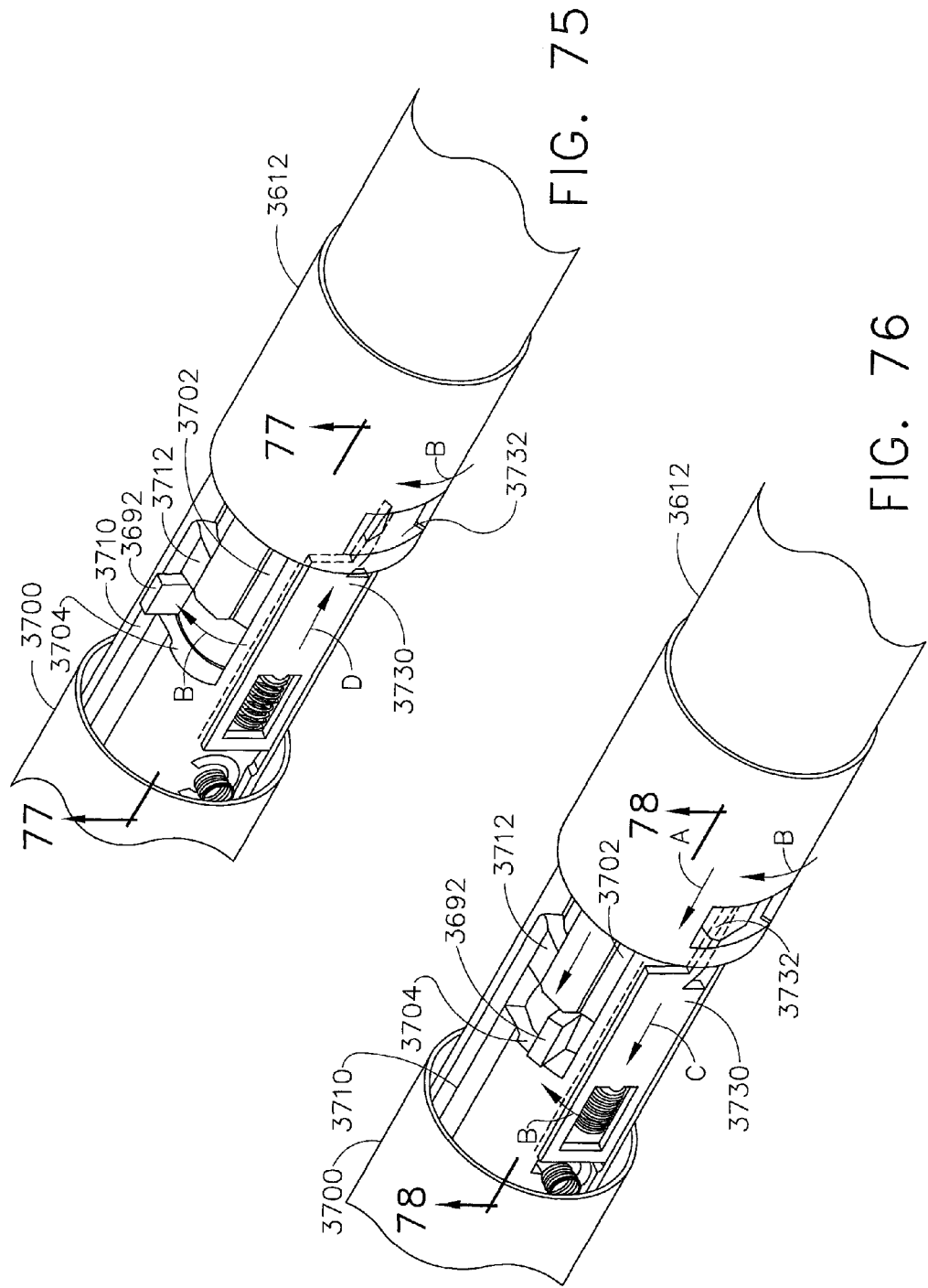

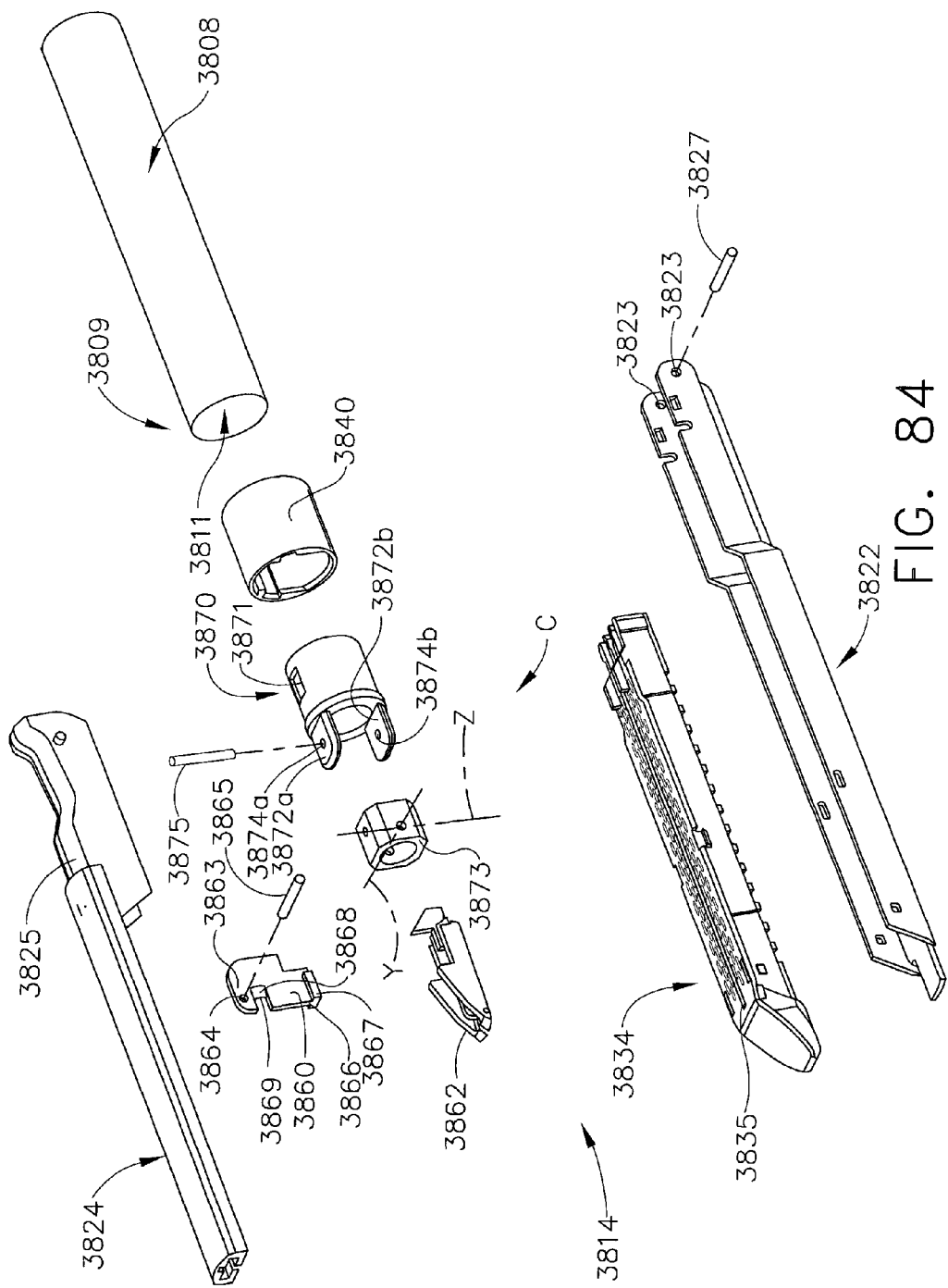

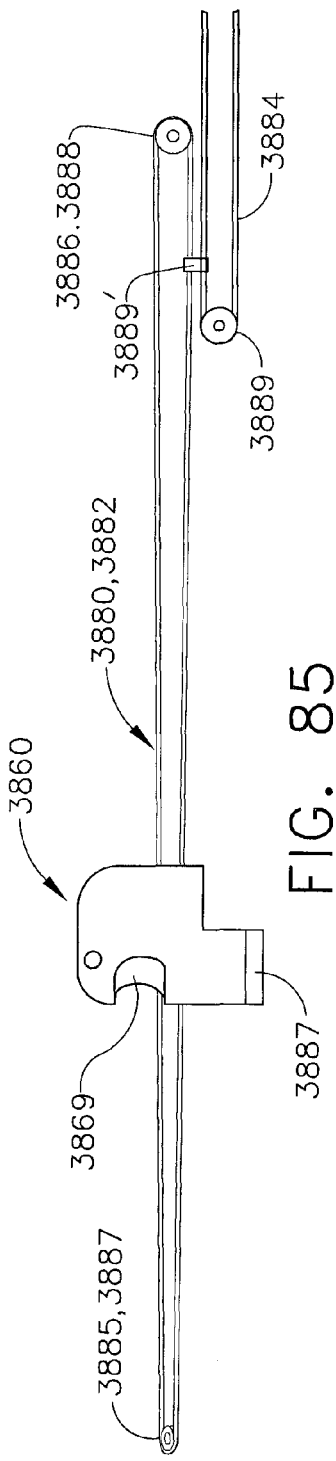
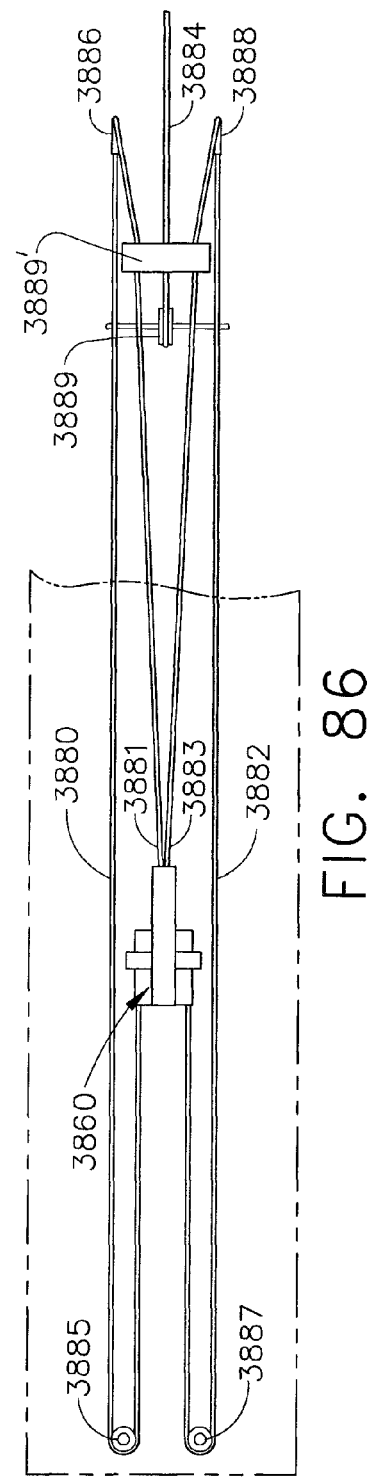

ROBOTICALLY-CONTROLLED ENDOSCOPIC ACCESSORY CHANNEL

CROSS-REFERENCE TO RELATED APPLICATIONS

This non-provisional patent application is a continuation-in-part patent application of and claims the benefit of U.S. patent application Ser. No. 11/277,324, filed Mar. 23, 2006, U.S. Patent Publication No. US 2007/0225562-A1, the disclosure of which is herein incorporated by reference in its entirety.

FIELD OF THE INVENTION

The present invention relates broadly to methods and devices for controlling movement of a working end of a surgical device.

BACKGROUND OF THE INVENTION

Endoscopic surgical instruments are often preferred over traditional open surgical devices since the use of a natural orifice tends to reduce the post-operative recovery time and complications. Consequently, significant development has gone into a range of endoscopic surgical instruments that are suitable for precise placement of a working end of a tool at a desired surgical site through a natural orifice. These tools can be used to engage and/or treat tissue in a number of ways to achieve a diagnostic or therapeutic effect.

Endoscopic surgery requires that the shaft of the device be flexible while still allowing the working end to be articulated to angularly orient the working end relative to the tissue, and in some cases to be actuated to fire or otherwise effect movement of the working end. Integration of the controls for articulating and actuating a working end of an endoscopic device tend to be complicated by the use of a flexible shaft and by the size constraints of an endoscopic instrument. Generally, the control motions are all transferred through the shaft as longitudinal translations, which can interfere with the flexibility of the shaft. There is also a desire to lower the force necessary to articulate and/or actuate the working end to a level that all or a great majority of surgeons can handle. One known solution to lower the force-to-fire is to use electrical motors. However, surgeons typically prefer to experience feedback from the working end to assure proper operation of the end effector. The user-feedback effects are not suitably realizable in present motor-driven devices.

Accordingly, there remains a need for improved methods and devices for controlling movement of a working end of an endoscopic surgical device.

SUMMARY OF THE INVENTION

In one embodiment, a surgical device is provided having an elongate shaft with a proximal end having a handle movably coupled thereto, and a distal end having a flexible neck extending therefrom. The handle and the flexible neck can be operatively associated such that movement of the handle is effective to cause the flexible neck to articulate in multiple planes. In certain exemplary embodiments, movement of the handle can be mimicked by the flexible neck. The device can also include an actuator extending between the handle and the flexible neck and configured to transfer movement from the handle to the flexible neck.

The handle of the device can have a variety of configurations, but in one embodiment the handle can be adapted to articulate relative to the proximal end of the elongate shaft. For example, the handle can be coupled to the proximal end of the elongate shaft by a joint, such as a ball and socket joint, a hinge joint, or a flexing joint. The actuator of the device can also have a variety of configurations, and in one embodiment the actuator can be at least one cable extending along a length of the elongate shaft. For example, the device can include a plurality of cables extending along a length of the shaft and equally spaced apart from one another around a circumference of the actuator. The cables are configured to slide relative to an axis of the elongate shaft and to apply tension to the elongate shaft to cause at least a portion of the elongate shaft to flex and bend. The handle and/or the cables can also optionally include a locking mechanism associated therewith and configured to maintain the handle and/or cables in a fixed position. In an exemplary embodiment, the elongate shaft is configured to passively flex and bend when it is inserted through a tortuous lumen.

The elongate shaft can also have a variety of configurations, but in one embodiment the device can be in the form of a surgical stapler and the elongate shaft can include an end effector coupled to a distal end of the flexible neck and adapted to engage tissue and deliver at least one fastener into the engaged tissue. The handle and the end effector can be coupled such that movement of the handle is mimicked by the end effector. For example, the handle can be coupled to the proximal end of the elongate shaft by a joint, such as a ball and socket joint, a hinge joint, and a flexing joint, and the flexible neck can be formed on or coupled to the end effector to allow the end effector to proportionally mimic movement of the handle. The device can also include an actuator extending between the handle and the end effector and configured to transfer movement from the handle to the flexible neck. The actuator can be, for example, a plurality of cables extending along a length of the elongate shaft. The cables can be equally spaced apart from one another around a circumference of the elongate shaft.

In another embodiment, the device can be in the form of an accessory channel and the elongate shaft can be in the form of a tube having an inner lumen adapted to receive a tool therethrough. The flexible neck extending from the distal end of the elongate tube can be configured to flex to orient a tool extending through the elongate tube. The flexible neck can have a variety of configurations, but in one embodiment it includes a plurality of slits formed therein to facilitate flexion thereof. The slits can be configured to cause the flexible neck to flex into a desired orientation. For example, the flexible neck can include a distal region of slits and a proximal region of slits, and the slits can be configured such that tension applied to the flexible neck will cause the flexible neck to bend at the proximal and distal regions. A handle can be coupled to the proximal end of the elongate tube, and it can operatively associate with the flexible neck such that movement of the handle is mimicked by the flexible neck. The handle can also have a variety of configurations, and in one embodiment the handle can include a stationary member and a movable member adapted to articulate relative to the stationary member. The movable member can be coupled to the stationary member by a joint, such as a ball and socket joint, a hinge joint, and a flexing joint. In use, the accessory channel can be configured to releasably attach to an endoscope. For example, a mating element can be formed on and extend along a length of an external surface thereof for mating to a complementary mating element formed on a sleeve adapted to receive an endoscope. The device can also include an actuator extending between the handle and the flexible neck. The actuator can be configured to transfer movement from the handle to the flexible neck. In certain exemplary embodiments, the actuator is in the form of at least one cable extending along a length of the elongate tube. Where the actuator includes multiple cables, the cables are preferably equally spaced apart from one another around a circumference of the elongate tube. The cables can extend along the elongate tube using various techniques. For example, the elongate tube can include at least one lumen formed in a sidewall thereof and extending along the length thereof, and the cable(s) can be slidably disposed within the lumen(s). The device can also include a locking mechanism positioned to engage at least one of the handle and the cable(s) to lock the handle and the cable(s) in a fixed position.

The present invention also provides an endoscopic system having an elongate sleeve configured to be disposed around an endoscope, and an accessory channel removably matable to the elongate sleeve. The accessory channel can have an inner lumen extending therethrough between proximal and distal ends thereof for receiving a tool, a flexible portion formed on a distal portion thereof and being made flexible by a plurality of slits formed therein, and at least one handle coupled to the proximal end thereof and operatively associated with the flexible portion such that the handle(s) is configured to cause the flexible portion to articulate in at least one plane. The handle(s) can be operatively associated with the flexible portion by at least one cable, and the handle(s) can be configured to axially move the cable(s) relative to the accessory channel to cause the cable(s) to apply tension to the flexible portion of the accessory channel such that the flexible portion articulates in at least one plane. In one embodiment, the device can include a single handle configured to cause the flexible portion to articulate in multiple planes. The single handle can include a stationary member coupled to the proximal end of the accessory channel, and a movable member configured to articulate relative to the stationary member. The single handle and the flexible portion can be operatively associated such that movement of the single handle is mimicked by the flexible portion. In another embodiment, the handle can include a first member configured to cause the flexible portion to articulate in a first plane, and a second member configured to cause the flexible portion to articulate in a second plane. In particular, the handle can include a stationary member coupled to the proximal end of the accessory channel, and the first and second members can be rotatably coupled to the stationary member. The device can further include a first spool coupled to the first member and having at least one cable extending therefrom and coupled to the flexible portion, and a second spool coupled to the second member and having at least one cable extending therefrom and coupled to the flexible portion. The first and second members can be effective to rotate the first and second spools and thereby move the cables axially to cause the flexible portion to articulate.

The surgical devices disclosed herein can also include a variety of other features. For example, the device can include an optical image gathering unit disposed on a distal end of the elongate shaft. The optical image gathering unit can be adapted to acquire images during endoscopic procedures. An image display screen can be disposed on a proximal portion of the device and adapted to communicate with the optical image gathering unit to display the acquired images. In other embodiments, the end effector of the device can include a cartridge removably disposed therein and containing a plurality of staples for stapling tissue and a blade for cutting stapled tissue.

In other aspects, a surgical method is provided and includes inserting an elongate shaft into a body lumen to position a flexible neck coupled to a distal end of the elongate shaft adjacent to tissue to be treated, and moving a handle pivotally coupled to a proximal end of the elongate shaft to cause the flexible neck to mimic the motion of the handle. The flexible neck can mirror movement of the handle, or movement of the flexible neck can directly correspond to movement of the handle. In certain exemplary embodiments, the movement is proportional.

In one exemplary embodiment, an end effector coupled to a distal end of the elongate shaft is positioned adjacent to tissue to be fastened, and a handle pivotally coupled to a proximal end of the elongate shaft is moved to cause the end effector to proportionally mimic the motion of the handle. The end effector can mirror movement of the handle, or movement of the end effector can directly correspond to movement of the handle. In an exemplary embodiment, the handle is pivotally articulated about the proximal end of the elongate shaft to cause the end effector to mimic the motion of the handle. The method can further include engaging tissue between opposed jaws of the end effector, and driving at least one fastener from the end effector into the tissue. Tissue can be engaging by moving a translating member formed on the handle from a first position to a second position to close the opposed jaws, and the fasteners can be fired by rotating a rotatable member formed on the handle to actuate a driver mechanism disposed within the end effector to cause the driver mechanism to drive a plurality of fasteners into the tissue. In another embodiment, prior to moving the translating member from the first position to the second position, the rotatable member can be rotated to rotate the end effector relative to the flexible neck without actuating the driver mechanism.

In yet another aspect, the elongate shaft can be in the form of an accessory channel that is slidably mated to an endoscope disposed within a body cavity to position a distal end of the accessory channel in proximity to a distal end of the endoscope. A tool is inserted through a lumen in the accessory channel such that the tool extends distally beyond the distal end of the accessory channel, and a handle coupled to a proximal end of the accessory channel can be moved to cause a flexible neck on the distal end of the accessory channel to articulate, thereby causing a working end of the tool to be oriented in a desired position. The handle can be moved by pivotally articulating the handle relative to the accessory channel, or alternatively is can be moved by rotating at least one rotatable member on the handle.

In accordance with other general aspects of the various embodiments of the present invention, there is provided a surgical device that includes an end effector that is configured to perform at least one surgical procedure in response to at least one control motion applied thereto from a control unit of a robotic system. An elongate shaft is coupled to the end effector and is configured to facilitate the transmission of at least one control motion to the end effector from the robotic system. The elongate shaft defines a shaft axis and is configured to facilitate articulation of the end effector in two planes that are substantially perpendicular to the shaft axis upon manipulation of the control unit relative to the elongate shaft such that movement of the control unit is mimicked by the end effector.

In accordance with still other general aspects of various embodiments of the present invention, there is provided an accessory channel for releasable attachment to an endoscope. In various embodiments, the accessory channel comprises an elongate tube that has an inner lumen extending therethrough between proximal and distal ends thereof for receiving a tool. The accessory channel further comprises a flexible neck that extends from the distal end of the elongate tube and is configured to flex to orient a tool extending through the elongate tube. The flexible neck is configured to be operably coupled to at least a portion of a robotic system such that movement of the at least a portion of the robotic system is mimicked by the flexible neck.

In accordance with still other general aspects of various embodiments of the present invention, there is provided an endoscopic system for use with a robotic system. In various forms, the endoscopic system comprises an elongate sleeve that is configured to be disposed around an endoscope. An accessory channel is removably matable to the elongate sleeve. The accessory channel has an inner lumen extending therethrough between proximal and distal ends thereof for receiving a tool. A flexible portion is formed on a distal portion thereof and is made flexible by a plurality of slits formed therein. The proximal end of the accessory channel is configured for operable attachment to at least a portion of the robotic system such that actuation of the at least a portion of the robotic system causes the flexible portion to articulate in at least one plane.

BRIEF DESCRIPTION OF THE DRAWINGS

The invention will be more fully understood from the following detailed description taken in conjunction with the accompanying drawings, in which:

FIG. 3A is a perspective view of a distal portion of the device shown in FIGS. 1A and 1B, showing an end effector and the flexible neck of FIG. 2 coupled thereto;

FIG. 3B is a cross-sectional view taken across line 3B-3B of the end effector shown in FIG. 3A;

FIG. 10 is a perspective view of a plurality of cable actuators for use with the device of FIG. 7;

FIG. 11 is a cross-sectional view of a shaft of the accessory channel of FIG. 7;

FIG. 32 is a partial cross-sectional side view of the surgical tool embodiment of FIG. 26;

FIG. 33 is an enlarged cross-sectional view of a portion of the surgical tool depicted in FIG. 32;

FIG. 39 is a cross-sectional side view of a portion of the surgical end effector and elongated shaft assembly of the surgical tool embodiment of FIG. 38 with the anvil in the open position and the closure clutch assembly in a neutral position;

FIG. 40 is another cross-sectional side view of the surgical end effector and elongated shaft assembly shown in FIG. 39 with the clutch assembly engaged in a closure position;

FIG. 49 is a cross-sectional side view of a portion of the surgical end effector and elongated shaft assembly of the surgical tool embodiment of FIG. 48 with the anvil in the open position;

FIG. 50 is another cross-sectional side view of a portion of the surgical end effector and elongated shaft assembly of the surgical tool embodiment of FIG. 49 with the anvil in the closed position;

FIG. 54 is a cross-sectional side view of a portion of a surgical end effector and elongated shaft assembly of another surgical tool embodiment of the present invention employing a pressure sensor arrangement with the anvil in the open position;

FIG. 55 is another cross-sectional side view of a portion of the surgical end effector and elongated shaft assembly of the surgical tool embodiment of FIG. 54 with the anvil in the closed position;

FIG. 56 is a side view of a portion of another surgical tool embodiment of the present invention in relation to a tool holder portion of a robotic system with some of the components thereof shown in cross-section;

FIG. 57 is a side view of a portion of another surgical tool embodiment of the present invention in relation to a tool holder portion of a robotic system with some of the components thereof shown in cross-section;

FIG. 59 is a side view of a portion of another surgical end effector embodiment of a portion of a surgical tool embodiment of the present invention with some components thereof shown in cross-section;

FIG. 60 is a side view of a portion of another surgical end effector embodiment of a portion of a surgical tool embodiment of the present invention with some components thereof shown in cross-section;

FIG. 61 is a side view of a portion of another surgical end effector embodiment of a portion of a surgical tool embodiment of the present invention with some components thereof shown in cross-section;

FIG. 62 is an enlarged cross-sectional view of a portion of the end effector of FIG. 61;

FIG. 63 is another cross-sectional view of a portion of the end effector of FIGS. 61 and 62;

FIG. 64 is a cross-sectional side view of a portion of a surgical end effector and elongated shaft assembly of another surgical tool embodiment of the present invention with the anvil in the open position;

FIG. 65 is an enlarged cross-sectional side view of a portion of the surgical end effector and elongated shaft assembly of the surgical tool embodiment of FIG. 64;

FIG. 66 is another cross-sectional side view of a portion of the surgical end effector and elongated shaft assembly of FIGS. 64 and 65 with the anvil thereof in the closed position;

FIG. 67 is an enlarged cross-sectional side view of a portion of the surgical end effector and elongated shaft assembly of the surgical tool embodiment of FIGS. 64-66;

FIG. 70 is a front perspective view of a disposable loading unit arrangement that may be employed with various surgical tool embodiments of the present invention;

FIG. 71 is a rear perspective view of the disposable loading unit of FIG. 70;

FIG. 72 is a bottom perspective view of the disposable loading unit of FIGS. 70 and 71;

FIG. 73 is a bottom perspective view of another disposable loading unit embodiment that may be employed with various surgical tool embodiments of the present invention;

FIG. 75 is a perspective view of a portion of a disposable loading unit and an elongated shaft assembly embodiment of a surgical tool embodiment of the present invention with the disposable loading unit in a first position;

FIG. 76 is another perspective view of a portion of the disposable loading unit and elongated shaft assembly of FIG. 75 with the disposable loading unit in a second position;

FIG. 84 is an exploded assembly view of a surgical end effector embodiment that may be used in connection with various surgical tool embodiments of the present invention;

FIG. 85 is a side view of a portion of a cable-driven system for driving a cutting instrument employed in various surgical end effector embodiments of the present invention;

FIG. 86 is a top view of the cable-driven system and cutting instrument of FIG. 85;

FIG. 111 is a partial cross-sectional perspective view of a portion of a surgical end effector embodiment of a surgical tool embodiment of the present invention;

FIG. 112 is another partial cross-sectional perspective view of the surgical end effector embodiment of FIG. 111 with a sled assembly axially advancing therethrough;

FIG. 113 is a perspective view of another sled assembly embodiment of another surgical tool embodiment of the present invention;

FIG. 114 is a partial top view of a portion of the surgical end effector embodiment depicted in FIGS. 111 and 112 with the sled assembly axially advancing therethrough;

FIG. 115 is another partial top view of the surgical end effector embodiment of FIG. 114 with the top surface of the surgical staple cartridge omitted for clarity;

FIG. 116 is a partial cross-sectional side view of a rotary driver embodiment and staple pusher embodiment of the surgical end effector depicted in FIGS. 111 and 112;

FIG. 117 is a perspective view of an automated reloading system embodiment of the present invention with a surgical end effector in extractive engagement with the extraction system thereof;

FIG. 118 is another perspective view of the automated reloading system embodiment depicted in FIG. 117;

FIG. 119 is a cross-sectional elevational view of the automated reloading system embodiment depicted in FIGS. 117 and 118;

FIG. 120 is another cross-sectional elevational view of the automated reloading system embodiment depicted in FIGS. 117-119 with the extraction system thereof removing a spent surgical staple cartridge from the surgical end effector;

FIG. 121 is another cross-sectional elevational view of the automated reloading system embodiment depicted in FIGS. 117-120 illustrating the loading of a new surgical staple cartridge into a surgical end effector;

FIG. 122 is a perspective view of another automated reloading system embodiment of the present invention with some components shown in cross-section;

Figure 122:
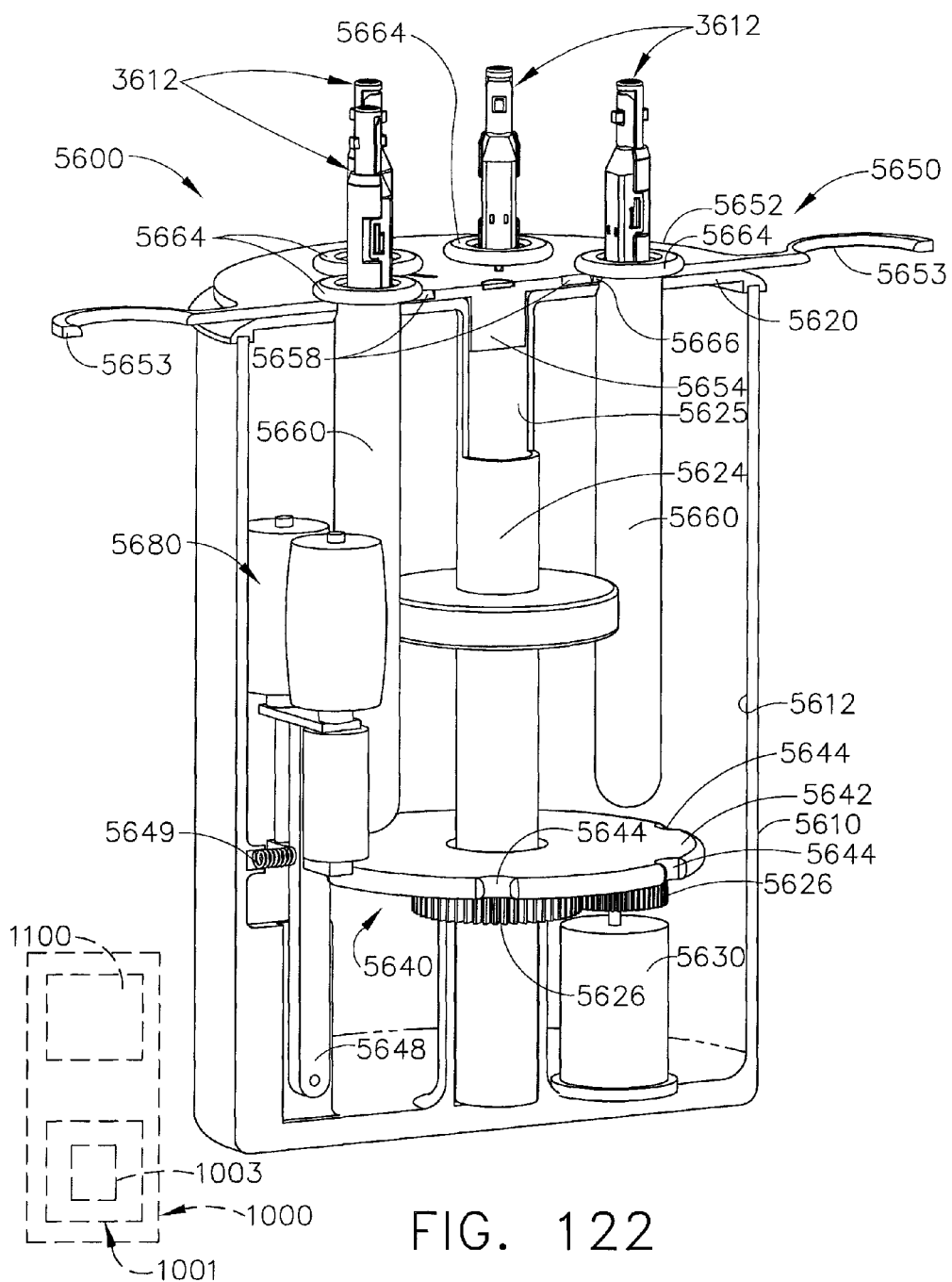
Figure 123:
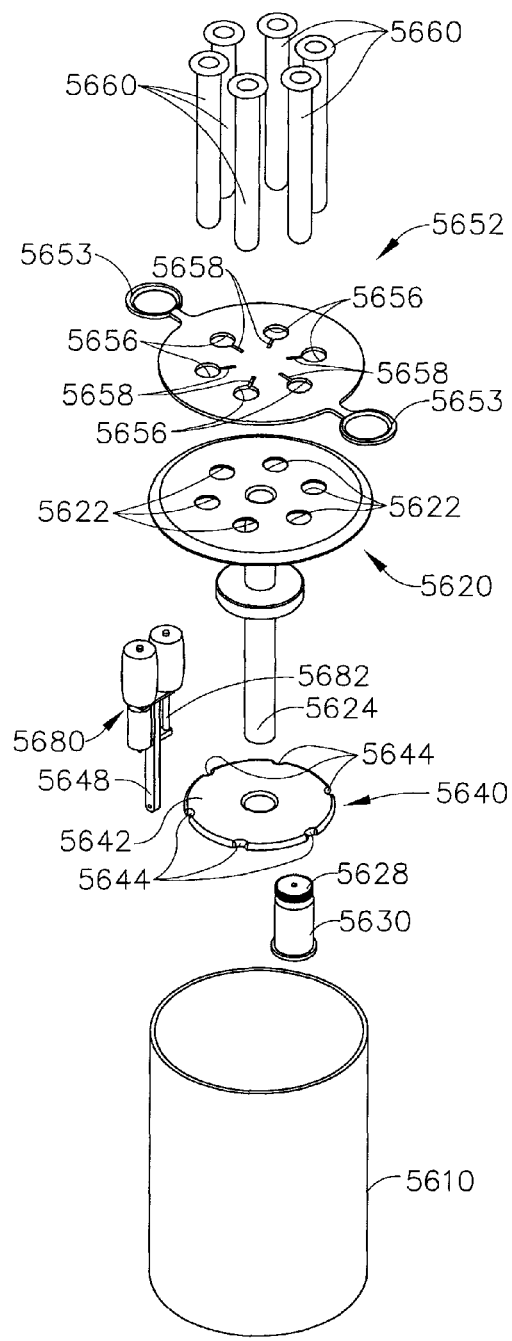
Figure 124:
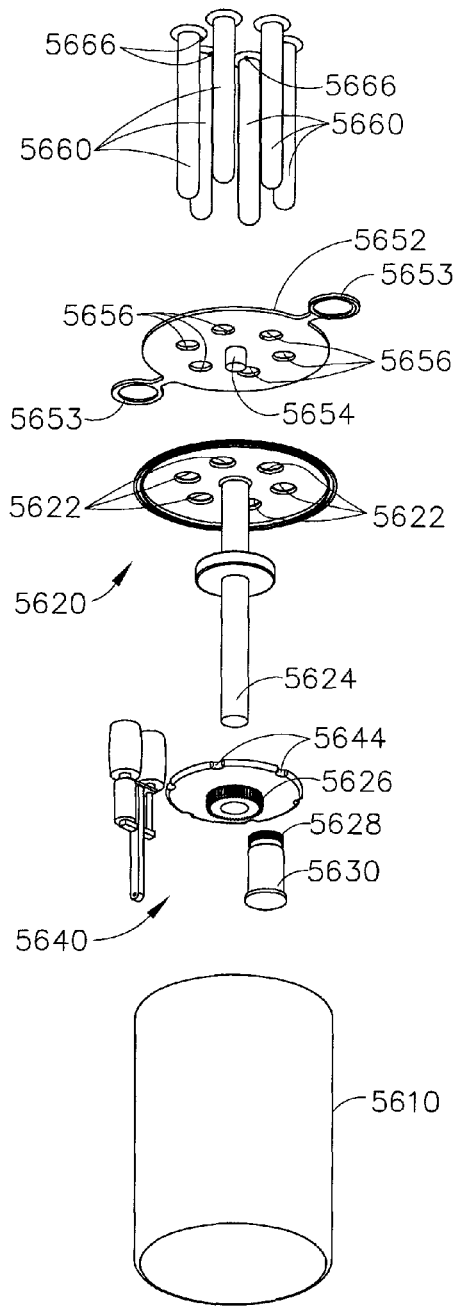
Figure 125:
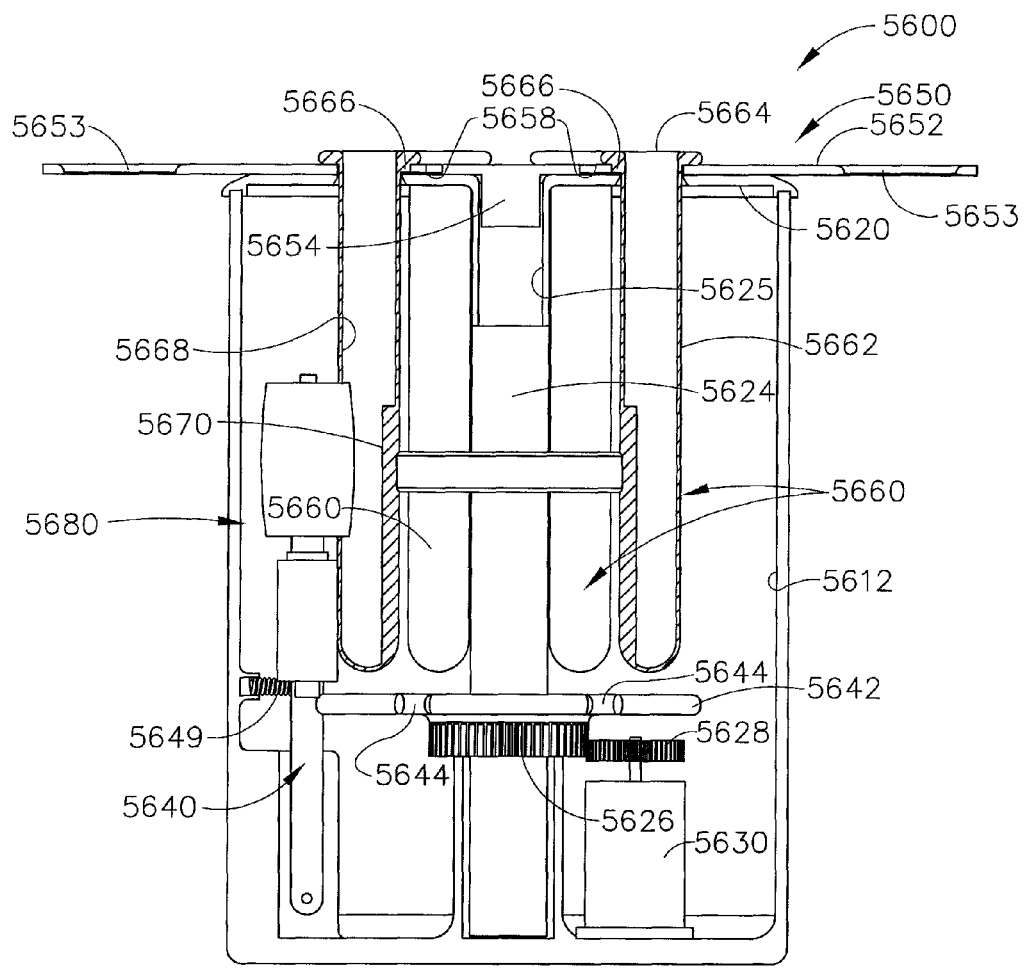
Figure 126:
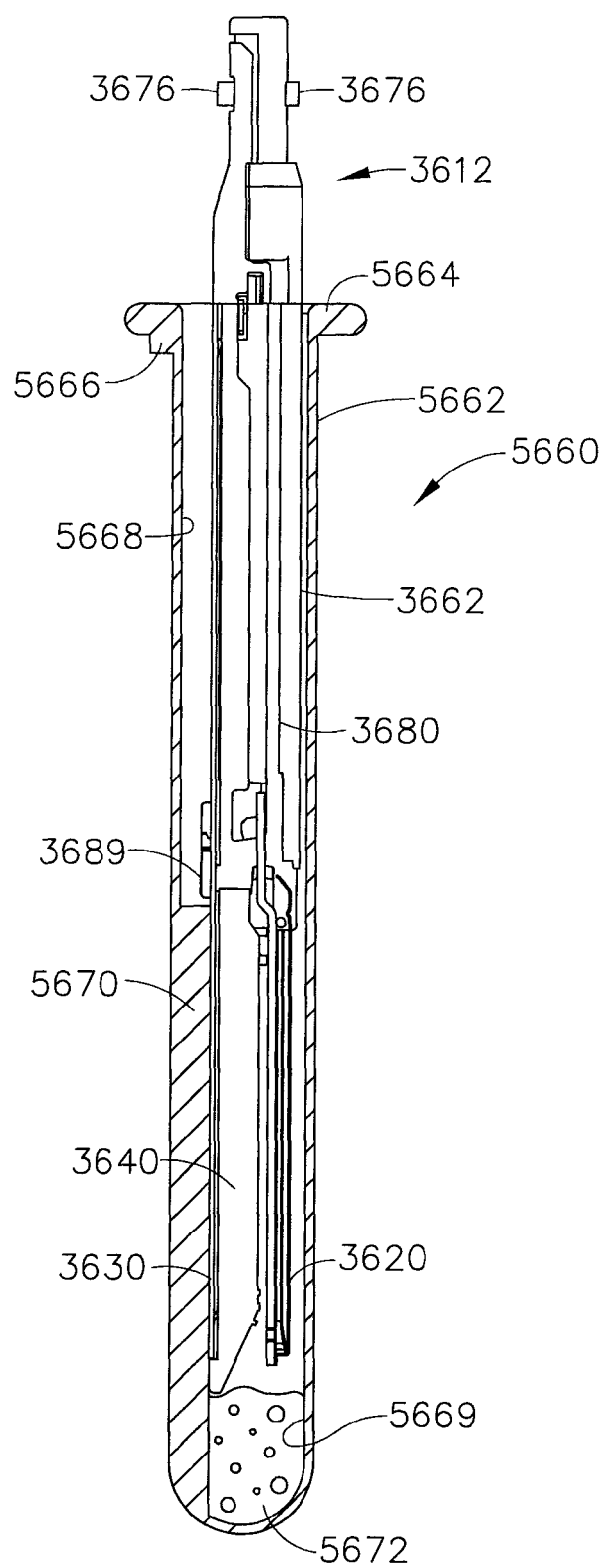
Figure 127:
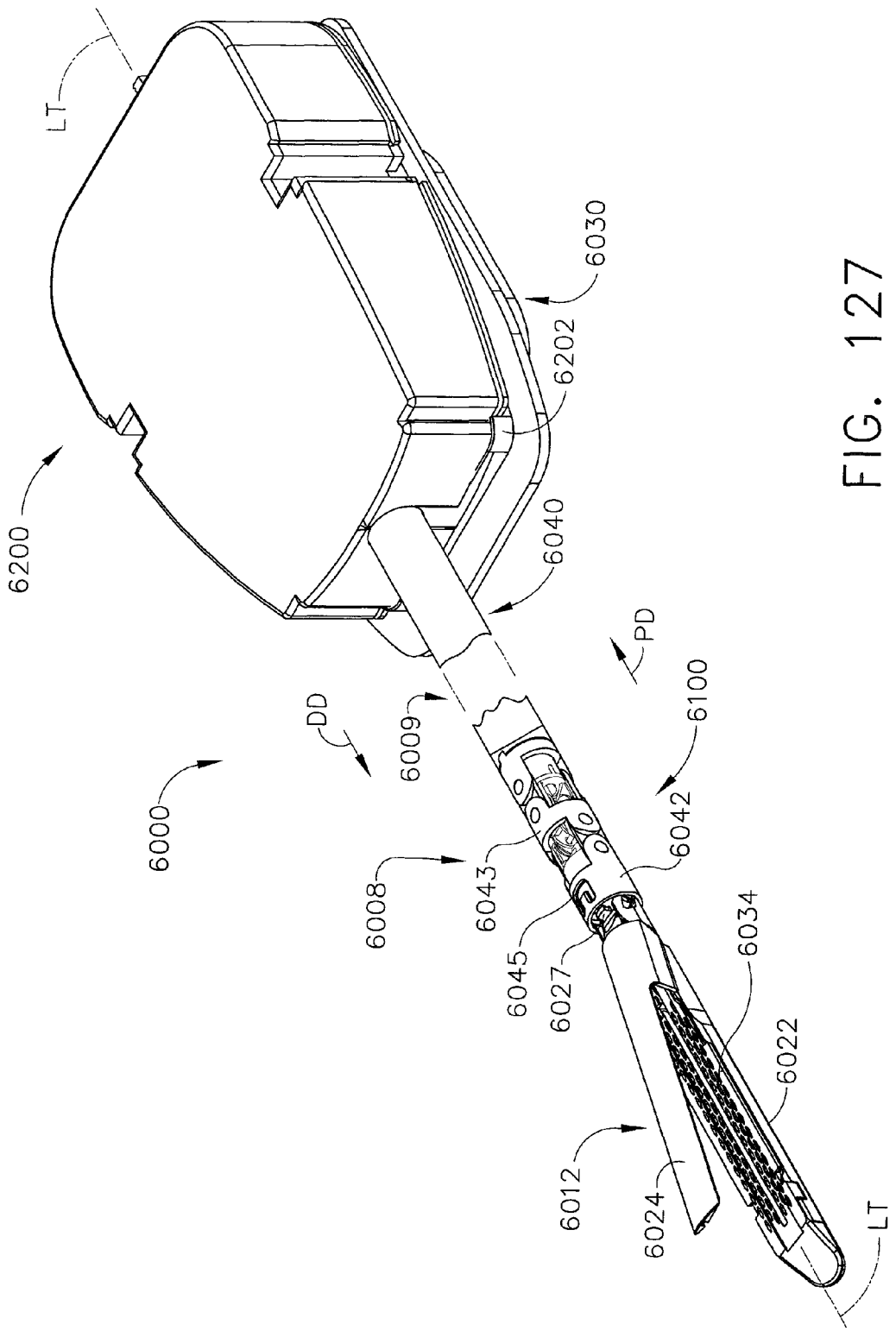
Figure 128:
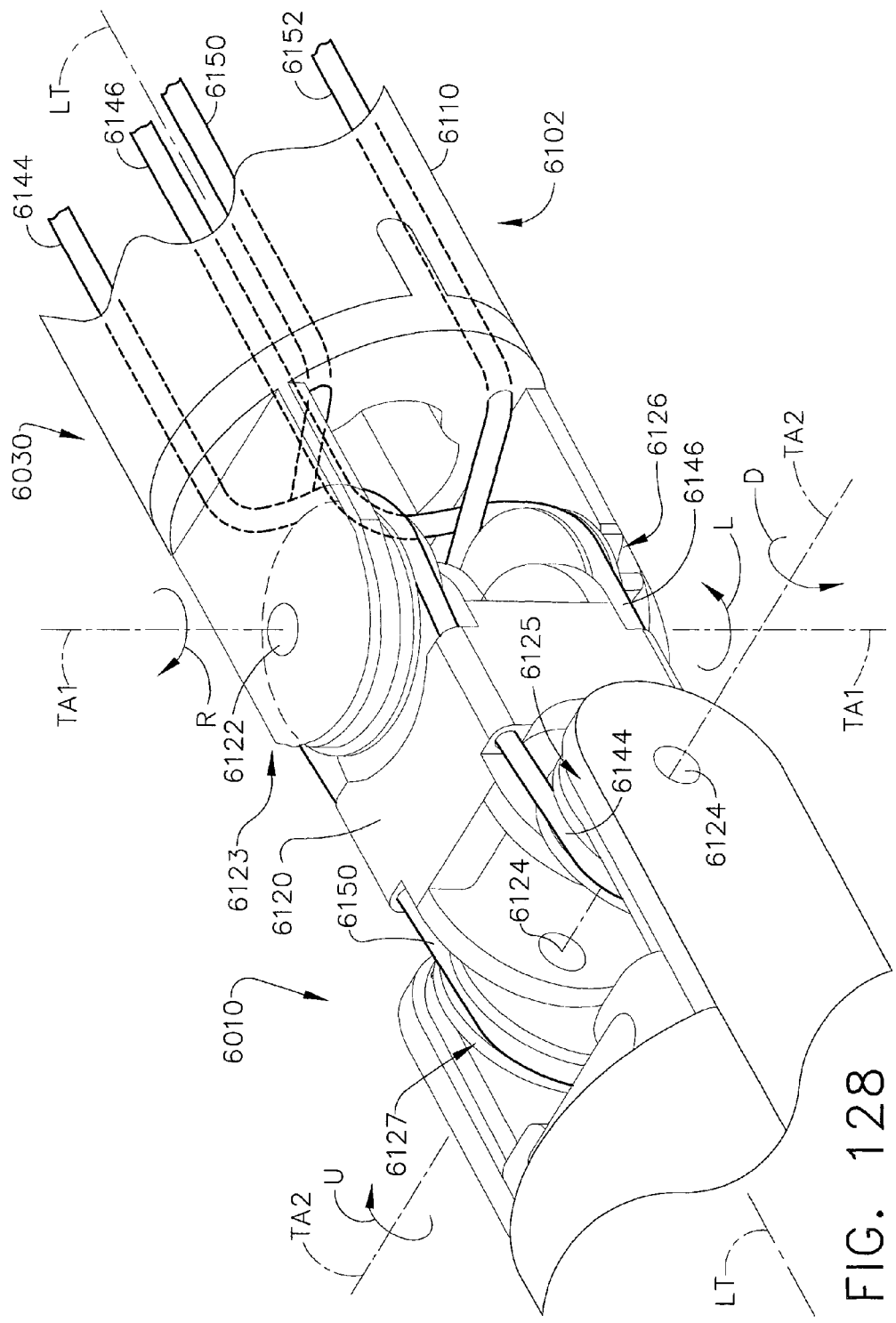
Figure 129:
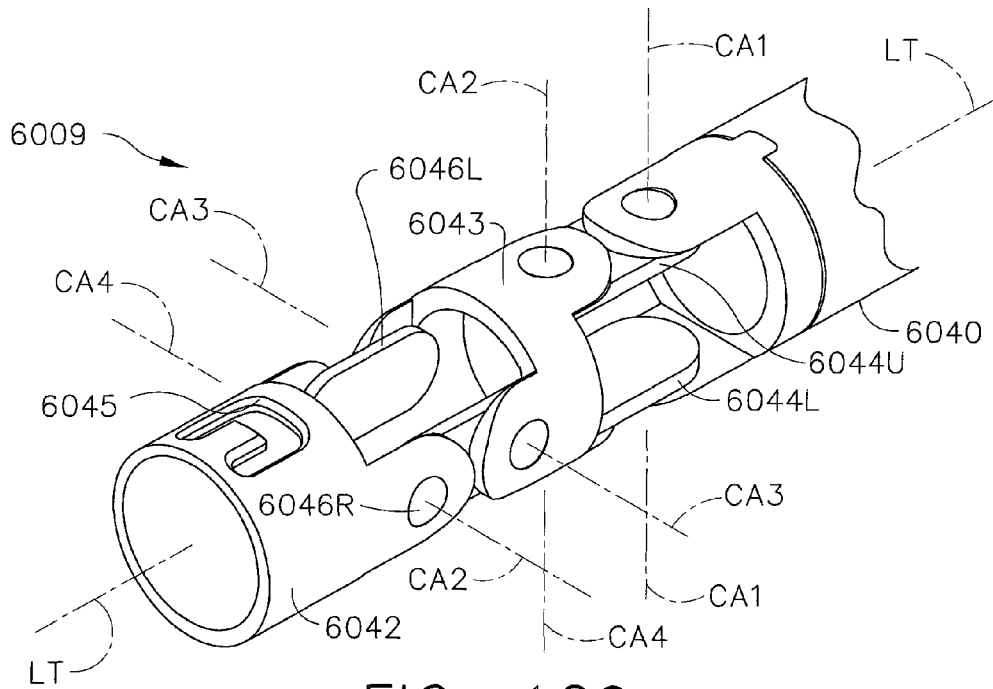
Figure 130:
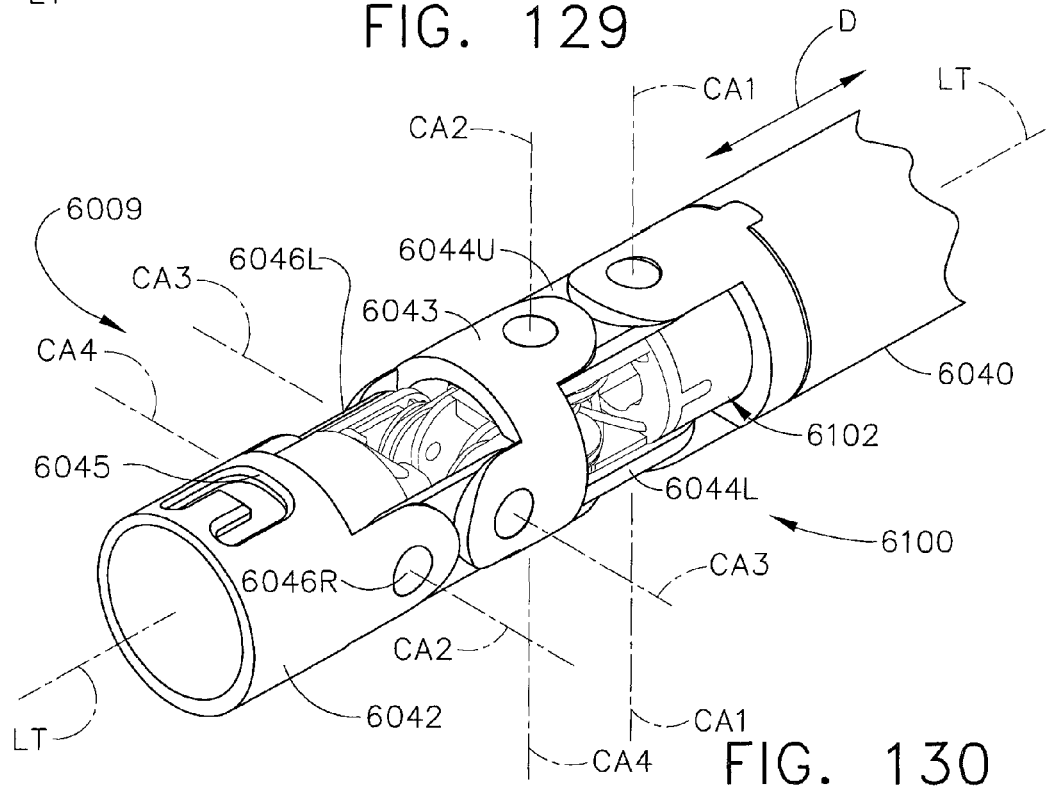
Figure 131:
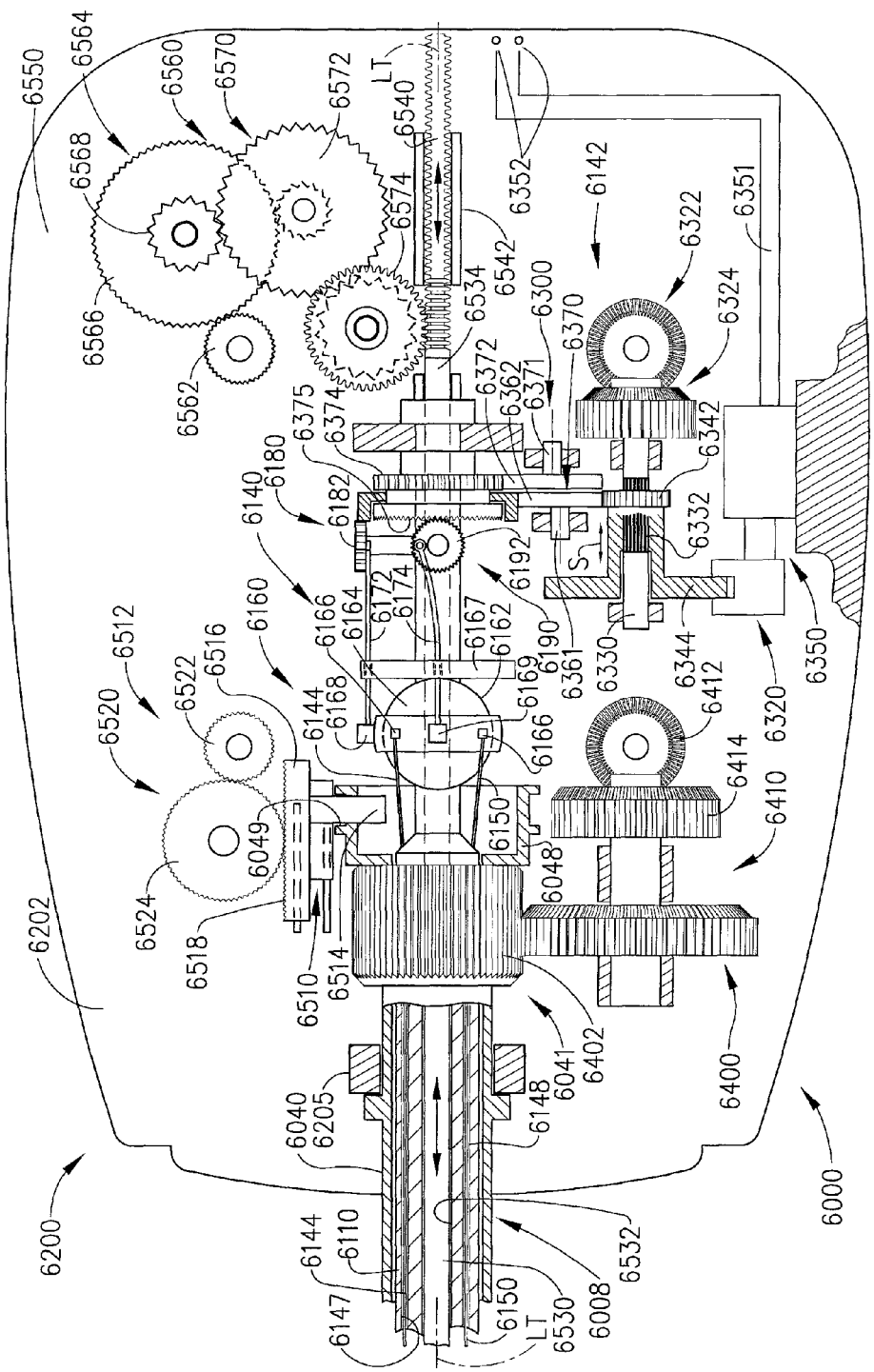
Figure 132:
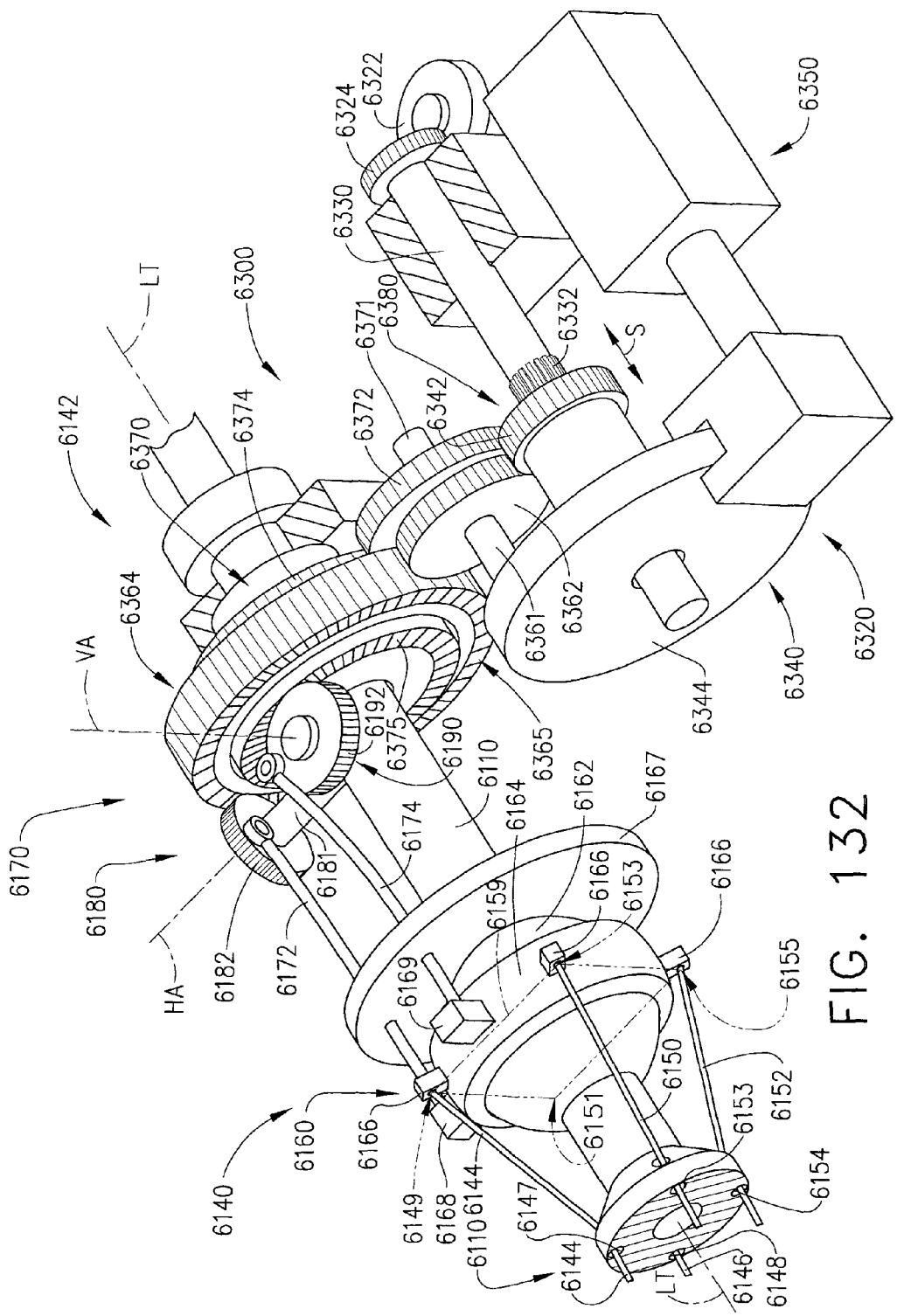
Figure 133:
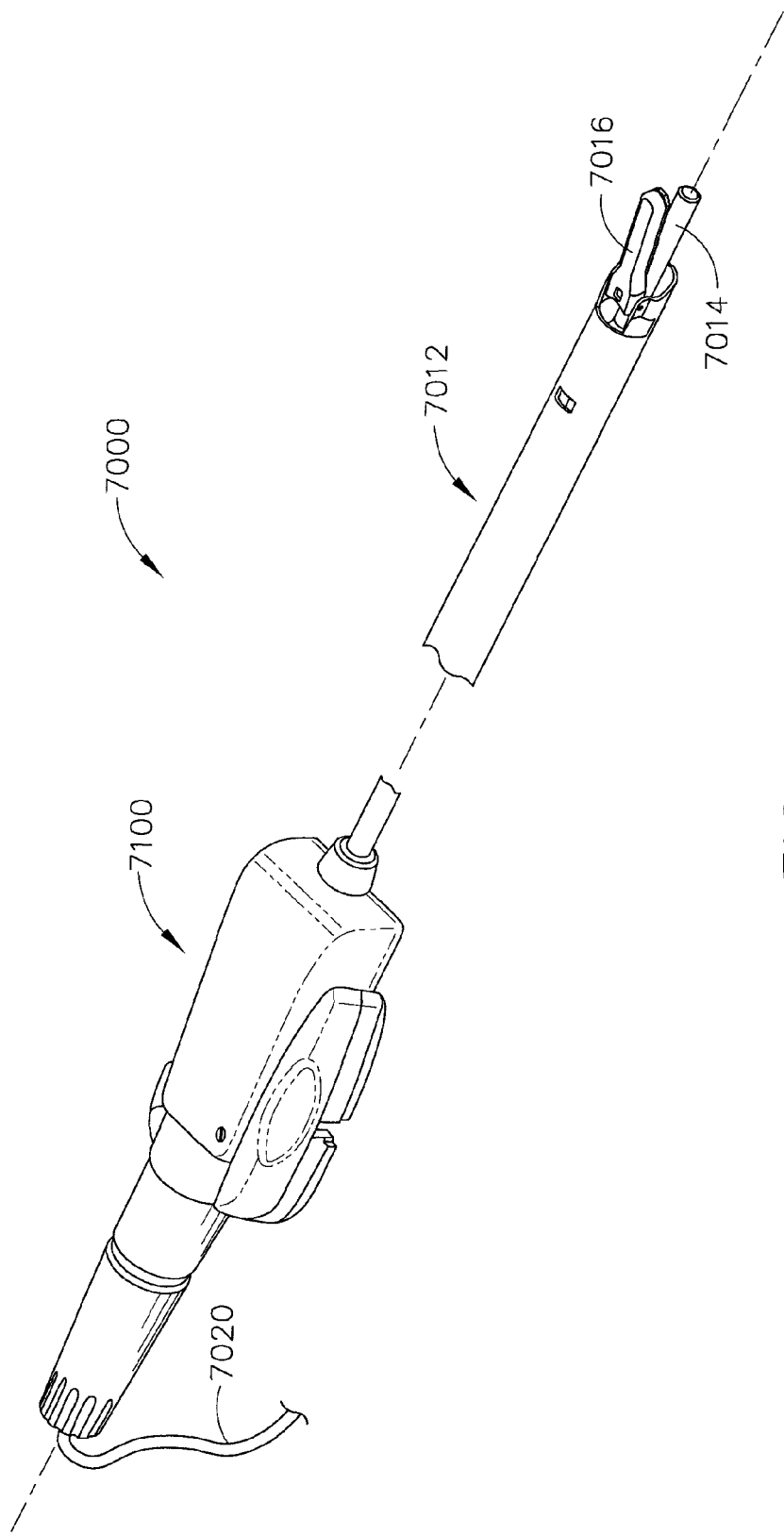
Figure 134:
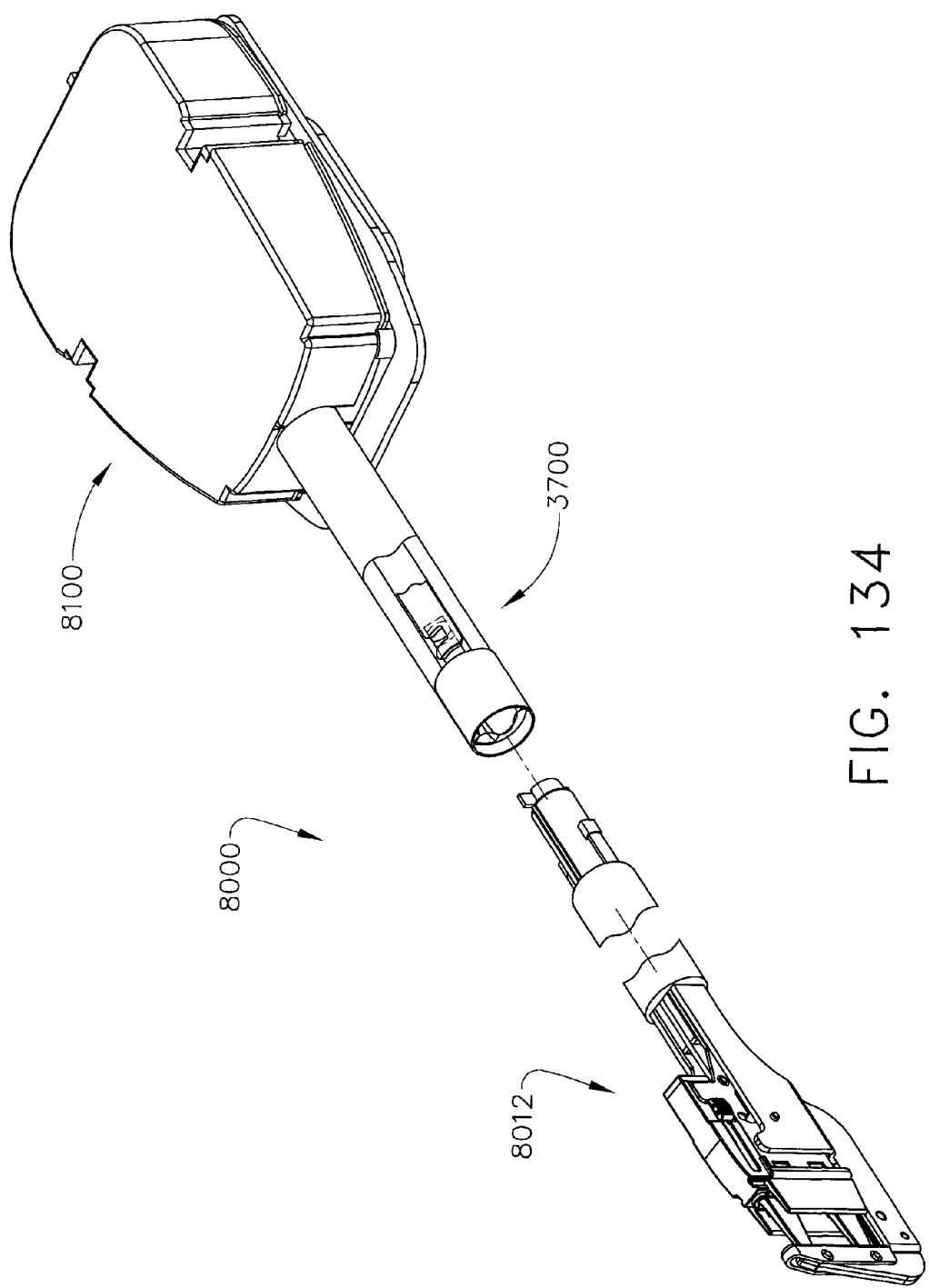

FIG. 123 is an exploded perspective view of a portion of the automated reloading system embodiment of FIG. 122;

FIG. 124 is another exploded perspective view of the portion of the automated reloading system embodiment depicted in FIG. 123;

FIG. 125 is a cross-sectional elevational view of the automated reloading system embodiment of FIGS. 122-124;

FIG. 126 is a cross-sectional view of an orientation tube embodiment supporting a disposable loading unit therein;

FIG. 127 is a perspective view of another surgical tool embodiment of the present invention;

FIG. 128 is a partial perspective view of an articulation joint embodiment of a surgical tool embodiment of the present invention;

FIG. 129 is a perspective view of a closure tube embodiment of a surgical tool embodiment of the present invention;

FIG. 130 is a perspective view of the closure tube embodiment of FIG. 129 assembled on the articulation joint embodiment of FIG. 128;

FIG. 131 is a top view of a portion of a tool mounting portion embodiment of a surgical tool embodiment of the present invention;

FIG. 132 is a perspective view of an articulation drive assembly embodiment employed in the tool mounting portion embodiment of FIG. 131;

FIG. 133 is a perspective view of another surgical tool embodiment of the present invention; and FIG. 134 is a perspective view of another surgical tool embodiment of the present invention.

DETAILED DESCRIPTION

Applicant of the present application also owns the following patent applications that have been filed on even date herewith and which are each herein incorporated by reference in their respective entireties:

U.S. patent application Ser. No. 13/118,259, now U.S. Patent Application Publication No. 2011/0295270, entitled "Surgical Instrument With Wireless Communication Between a Control Unit of a Robotic System and Remote Sensor";

U.S. patent application Ser. No. 13/118,210, now U.S. Patent Application Publication No. 2011/0290855, entitled "Robotically-Controlled Disposable Motor Driven Loading Unit";

U.S. patent application Ser. No. 13/118,253, now U.S. Patent Application Publication No. 2011/0295269, entitled "Robotically-Controlled Motorized Surgical Instrument";

U.S. patent application Ser. No. 13/118,278, now U.S. Patent Application Publication No. 2011/0290851, entitled "Robotically-Controlled Surgical Stapling Devices That Produce Formed Staples Having Different Lengths";

U.S. patent application Ser. No. 13/118,190, now U.S. Patent Application Publication No. 2011/0288573, entitled "Robotically-Controlled Motorized Cutting and Fastening Instrument";

U.S. patent application Ser. No. 13/118,223, now U.S. Patent Application Publication No. 2011/0290854, entitled "Robotically-Controlled Shaft Based Rotary Drive Systems For Surgical Instruments";

U.S. patent application Ser. No. 13/118,263, now U.S. Patent Application Publication No. 2011/0295295, entitled "Robotically-Controlled Surgical Instrument Having Recording Capabilities";

U.S. patent application Ser. No. 13/118,272, now U.S. Patent Application Publication No. 2011/0290856, entitled "Robotically-Controlled Surgical Instrument With Force Feedback Capabilities";

U.S. patent application Ser. No. 13/118,246, now U.S. Patent Application Publication No. 2011/0290853, entitled "Robotically-Driven Surgical Instrument With E-Beam Driver"; and U.S. patent application Ser. No. 13/118,241, now U.S. Patent Application Publication No. 2012/0298719, entitled "Surgical Stapling Instruments With Rotatable Staple Deployment Arrangements".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Uses of the phrases "in various embodiments," "in some embodiments," "in one embodiment", or "in an embodiment", or the like, throughout the specification are not necessarily all referring to the same embodiment. Furthermore, the particular features, structures, or characteristics of one or more embodiments may be combined in any suitable manner in one or more other embodiments. Such modifications and variations are intended to be included within the scope of the present invention.

The present invention provides method and devices for controlling a working end of an endoscopic surgical device. In general, the endoscopic surgical devices include an elongate shaft having a distal working end with a flexible neck, and a proximal end with a handle for controlling movement of the flexible neck on the distal working end. In certain exemplary embodiments, this can be achieved using, for example, one or more cables that extend between the handle and the flexible neck such that movement of the handle applies a force to one or more of the cables to cause the flexible portion to flex and thereby move the working end of the device. Various other features are also provided to facilitate use of the device. A person skilled in the art will appreciate that the particular device being controlled, and the particular configuration of the working end, can vary and that the various control techniques described herein can be used on virtually any surgical device in which it is desirable to control movement of the working end.

Figure 1A:
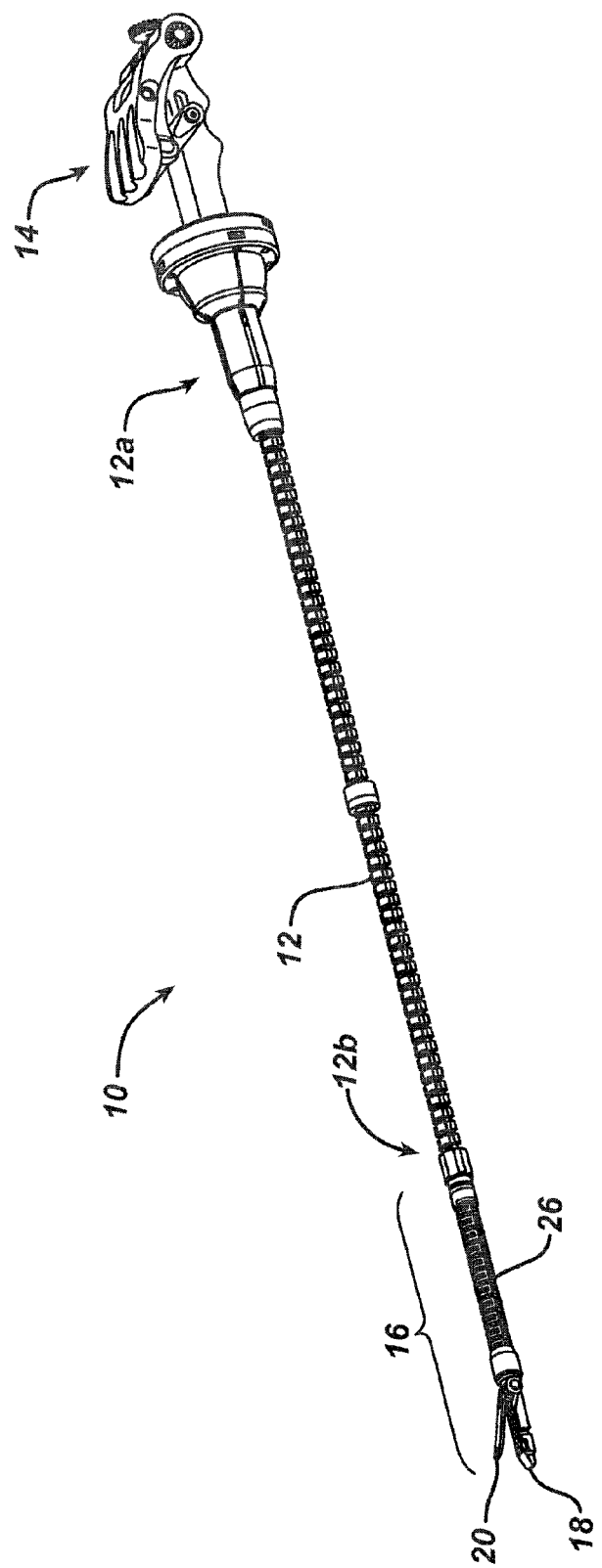
FIG. 1A is a perspective view of one embodiment of a surgical stapling and cutting device, showing a working end of the device in an initial position.
Figure 1B:
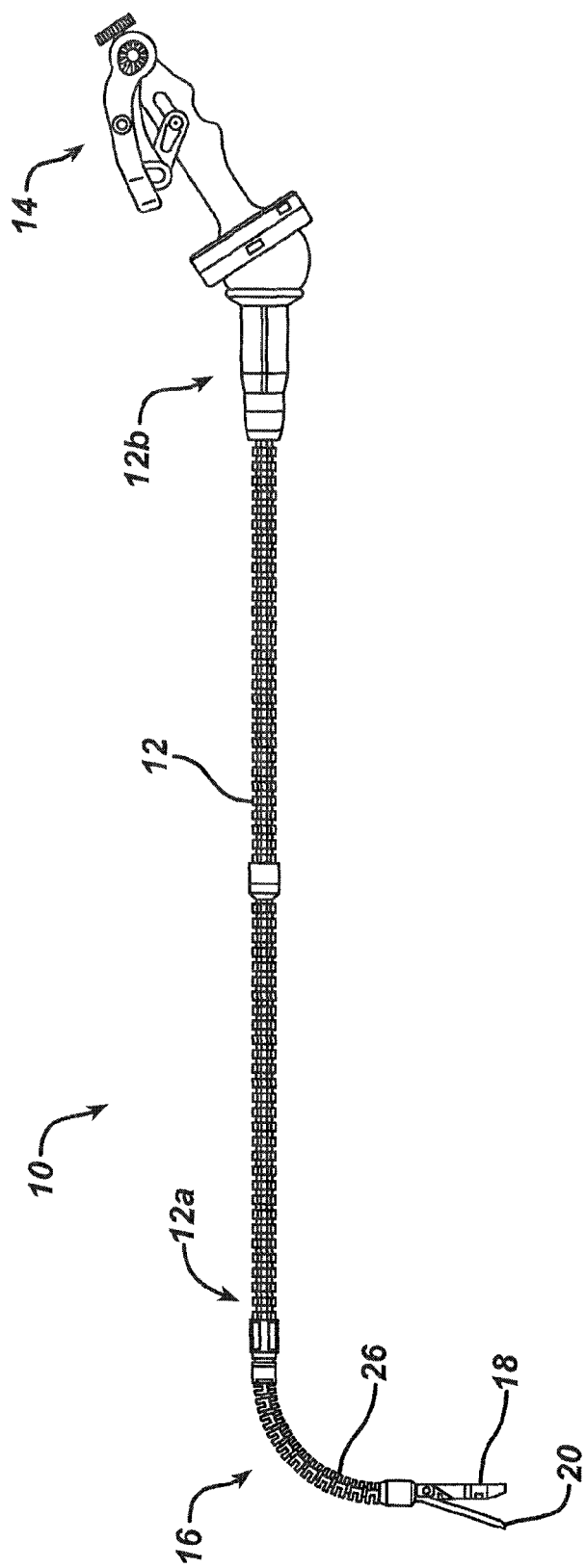
FIG. 1B is a perspective view of the surgical stapling and cutting device of FIG. 1A, showing the working end of the device in an articulated position.

FIGS. 1A and 1B illustrate one exemplary embodiment of a technique for controlling articulation of the end effector, and in particular for causing the end effector to mimic and simultaneously move with the handle. In this embodiment, the device is in the form of a linear stapling and cutting device 10 for applying multiple linear rows of staples to tissue and for cutting the stapled tissue. As shown, the device 10 generally includes an elongate shaft 12 having a proximal end 12a with a handle 14 coupled thereto, and a distal, working end 12a having an end effector 16 coupled thereto or formed thereon, as will be discussed in more detail below. In use, the end effector 16 is configured to mimic movement of the handle 14. Mimicking motion between the handle 14 and the end effector 16 can generally be achieved using an actuator (not shown) that extends between the handle 14 and the end effector 16, and that is effective to transfer forces from the handle 14 to the end effector 16. In an exemplary embodiment, the actuator is in the form of several cables that are spaced around a circumference of the elongate shaft 12, and that extend along the length of the elongate shaft 12. Movement of the handle 14 about the proximal end 12a of the shaft 12 will apply a force to one or more of the cables to cause the cables to apply a force to the end effector 16, thereby causing the end effector 16 to mimic the motion of the handle 14. Mimicking motion can include corresponding motion, whereby the end effector 16 moves in the same direction and orientation as the handle 14, or mirrored motion, whereby the end effector 16 moves in an opposite direction and orientation as the handle 14. The mimicking motion can also be proportional to the movement of the handle.

Figure 2:
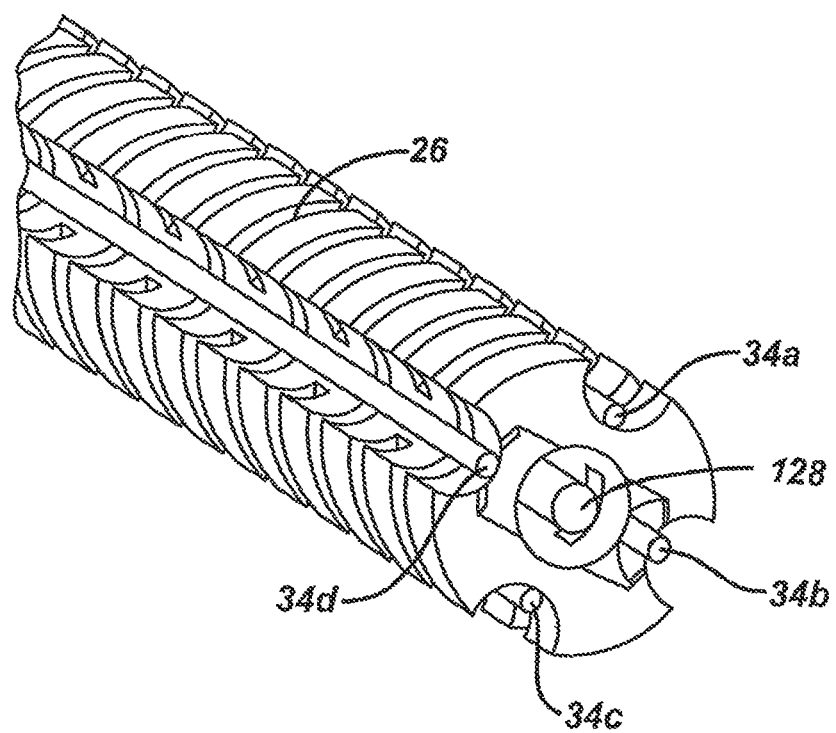
FIG. 2 is a perspective view of a portion of a flexible neck of the device shown in FIGS. 1A and 1B.

The elongate shaft 12 of the device 10 can have a variety of configurations. For example, it can be solid or hollow, and it can be formed from a single component or multiple segments. As shown in FIG. 2, the elongate shaft 12 is hollow and is formed from multiple connecting segments to allow the elongate shaft 12 to flex. The flexibility of the shaft 12, as well as a relatively small diameter, allows the shaft 12 to be used in endoscopic procedures, whereby the device is introduced translumenally through a natural orifice. The shaft can also vary in length depending on the intended application.

FIG. 2 further illustrates one exemplary embodiment of an actuator 22 in the form of several cables 34a, 34b, 34c, 34d that are spaced around a circumference of the elongate shaft 12, and that extend along the length of the elongate shaft 12. The number and location of the cables can vary. For example, three cables can be spaced approximately 120° apart from one another around the circumference of the shaft 12. In the embodiment shown in FIG. 2, four cables 34a, 34b, 34c, 34d are spaced approximately 90° apart from one another around the circumference of the shaft 12. Each cable 34a-d can extend through a pathway, such as a lumen, formed on, in, or around the elongate shaft 12. FIG. 2 illustrates each cable 34a-d extending through a cut-out formed on an external surface of each segment of the shaft 12. Thus, each segment includes four cut-outs spaced equidistant around the circumference of the shaft 12 to maintain the cables 34a-d equidistant from one another. The cut-outs preferably have a size that is effective to retain the cables 34a-d therein while allowing the cables 34a-d to freely slide relative to the shaft 12.

The distal end of the cables 34a-d can be mated to the end effector 16 to control movement of the end effector 16. While the end effector 16 can have a variety of configurations, and various end effectors known in the art can be used, FIG. 3A illustrates one exemplary embodiment of an end effector 16 which generally includes opposed first and second jaws 18, 20 that are adapted to receive tissue therebetween. The first jaw 18 is adapted to contain a staple cartridge having multiple staples disposed therein and configured to be driven into tissue, and the second jaw 20 forms an anvil for deforming the staples. The particular configuration and the basic operation of the end effector 16 can vary, and various end effectors 16 known in the art can be used. By way of non-limiting example, U.S. Pat. No. 6,978,921 entitled "Surgical Stapling Instrument Incorporating an E-Beam Firing Mechanism," which is incorporated herein in its entirety, discloses one embodiment of an end effector that can be used with the present invention.

In order to allow movement of the end effector 16 relative to the elongate shaft 12, the end effector 16 can be movably coupled to the distal end 12b of the elongate shaft 12. For example, the end effector 16 can be pivotally coupled to the distal end 12b of the elongate shaft 12 by a pivoting or rotating joint. Alternatively, the end effector 16 can include a flexible neck 26 formed thereon, as shown, for allowing movement of the end effector 16 relative to the elongate shaft 12. The flexible neck 26 can be formed integrally with the distal end 12b of the shaft 12 and/or the proximal end of the jaws 18, 20, or it can be a separate member that extends between the shaft 12 and the jaws 18, 20. As shown in FIG. 3A, the flexible neck 26 includes a first coupler 28 for mating the flexible neck 26 to the proximal end of the opposed jaws 18, 20, and a second coupler 30 for mating the flexible neck 26 to the distal end of the elongate shaft 12. The couplers 28, 30 can be removably of fixedly mated to the flexible neck 26 and/or to the jaws 18, 20 and the shaft 12. The couplers 28, 30 also function to house certain components of the end effector 16. For example, the first coupler 28 can function to anchor the cables therein, as will be discussed below, and it can also function to house a gear and driver assembly for actuating (e.g., closing and firing) the jaws 18, 20.

In order to facilitate flexion of the flexible neck 26, the neck 26 can include one or more slits 32 formed therein. The quantity, location, and size of the slits 32 can vary to obtain a desired flexibility. In the embodiment shown in FIG. 3A, the flexible neck 26 includes multiple rows of slits 32, each row extending radially around the flexible neck 26 and each row being spaced axially along the length of the flexible neck 26. Each row of slits contains two slits extending around the circumference of the neck 26, and each row of slits 32 is axially offset from one another. As a result, the flexible neck 26 includes alternating slits 32. A person skilled in the particular pattern of the slits 32 can vary, and that FIG. 3A merely illustrates one pattern for forming slits 32 to allow flexion of the flexible neck 26. Other exemplary slit configurations will be discussed in more detail below.

As indicated above, the cables 34a-d can be coupled to the end effector 16 to allow the end effector 16 to move in coordination with the handle 14. The connecting location of the cables 34a-d with the end effector 16 can vary depending on the desired movement. In the illustrated embodiment, the distal end of the cables 34a-d is connected to the distal end of the flexible neck 26, and in particular they extend into and connect to the first coupler 28. FIG. 3B illustrates a cross-sectional view of the first coupler 28 showing four bores 28a, 28b, 28c, 28d for receiving the four cables 34a, 34b, 34c, 34d, respectively. Virtually any technique known in the art can be used to connect the cables 34a-d to the coupler 28 including, for example, mechanical mating techniques such as adhesives, an interference fit, a ball-and-socket connection, threads, etc. In use, the connection of the cables 34a-d at the distal end of the flexible neck 26 will allow the cables 34a-d to apply a tension to the flexible neck 26 when an axial force is applied to the cables 34a-d by the handle 14. This tension will cause the neck 26 to flex in a direction dictated by the amount of tension applied to each cable 34a-d, as will be discussed in more detail below.

Figure 4A:
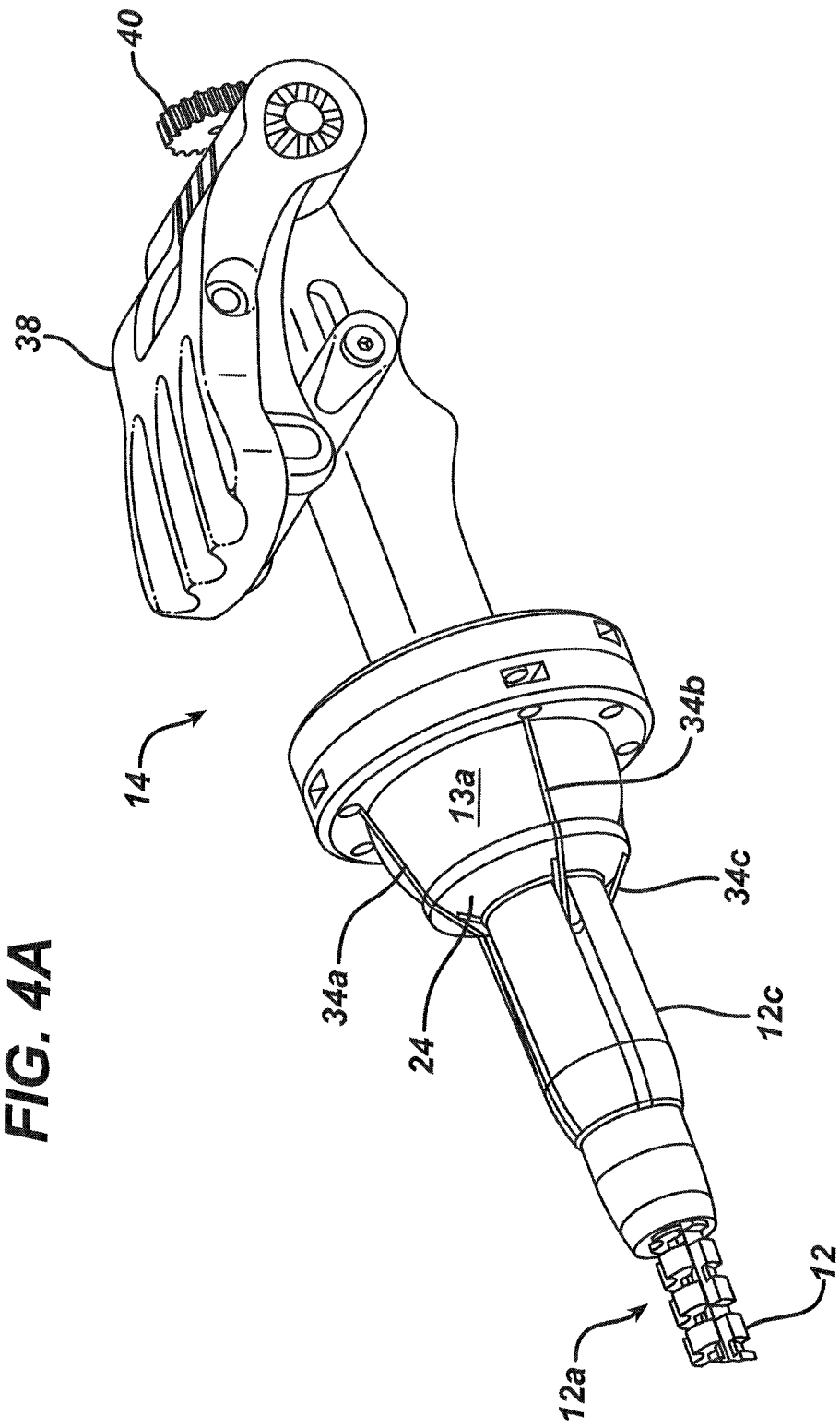
FIG. 4A is a perspective view of a proximal portion of the device shown in FIGS. 1A and 1B, showing a handle movably coupled to a proximal end of a shaft of the device.
Figure 4B:
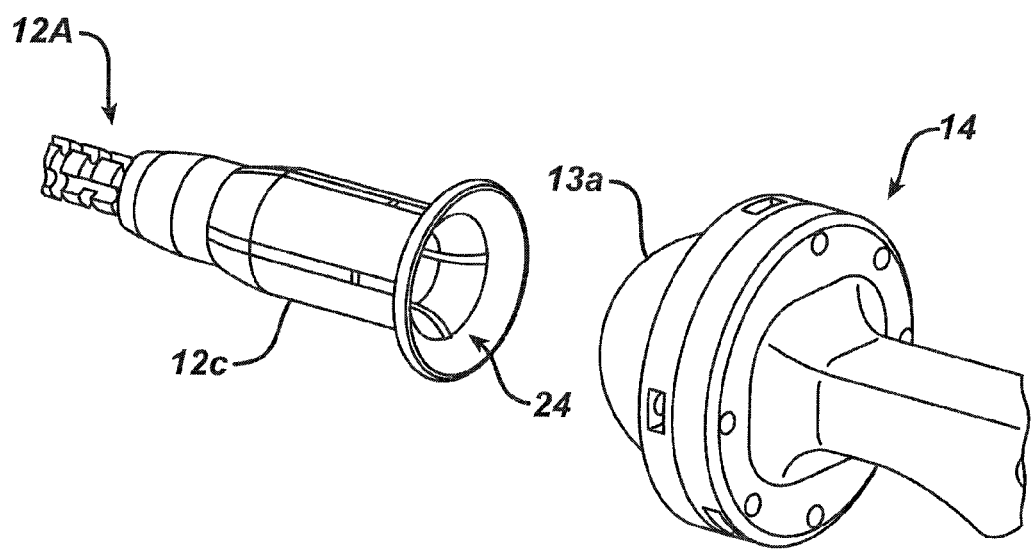
FIG. 4B is an exploded view of the proximal portion of the device shown in FIG. 4A.

The handle 14 of the device 10 can be used to control movement of the end effector 16, and in particular to articulate the end effector 16 and thus angularly orient it relative to a longitudinal axis A of the elongate shaft 12. While the handle 14 can have a variety of configurations, in one exemplary embodiment the handle 14 is movably coupled to the proximal end 12a of the elongate shaft 12 such that movement of the handle 14 can be mimicked by the end effector 16. While various techniques can be used to movably couple the handle 14 to the shaft 12, in the embodiment shown in FIGS. 4A-4C, a ball-and-socket connection is formed between the handle 14 and the proximal end 12a of the elongate shaft 12. As best shown in FIG. 4B, the proximal end 12a of the elongate shaft 12 includes a socket 24 formed therein, and the handle 14 includes a hemi-spherical ball 13a formed on a distal end thereof and configured to be rotatably seated within the socket 24. The socket 24 can be integrally formed with the proximal end 12a of the elongate shaft, or it can be formed by coupling a hollow housing 12c, as shown, to the proximal end 12a of the elongate shaft 12. The hemi-spherical ball 13a can also be formed integrally with the handle 14, or it can be a separate member that is coupled to the handle 14. In order to movably mate the handle 14 to the shaft 12, the hemi-spherical ball 13a on the handle 14 can be retained within the socket 24 using the cables 34a-d, which attach to the handle 14 as will be discussed below. However, other mating techniques can be used to movably mate the handle 14 to the shaft 12. For example, the ball 13a can be spherical and it can be captured within a spherical socket formed in the proximal end 12a of the elongate shaft 12, or a mating element, such as a pin, can extend through the ball 13a to retain the ball 13a within the socket 24. While FIG. 4B illustrates a ball 13a formed on the handle 14 and a socket 24 formed in the shaft 12, the ball-and-socket connection can be reversed such that the ball is on the shaft 12 and the socket is in the handle 14. Moreover, a person skilled in the art will appreciate that a variety of other techniques can be used to movably couple the handle 14 to the proximal end 12a of the elongate shaft 12.

In use, the handle 14 can articulate or pivotally move relative to the shaft 12 to cause the end effector 16 to mimic the movement of the handle 14. This can be achieved by coupling the proximal end of the cables 34a-d to the handle 14. The connecting location of the cables 34a-d with the handle 14 can vary depending on the desired movement. In the illustrated embodiment, the cables (only three cables 34a, 34b and 34c are shown in FIG. 4A) extend from the elongate shaft 12, through the hollow housing 12c, and out of slots or openings formed in a proximal end of the hollow housing 12c. The cables 34a-d then extend around the ball 13a on the handle 14 and connect to a distal-facing surface on the handle 14 that surrounds the ball 13a. Virtually any technique known in the art can be used to connect the cables 34a-d to the handle 14 including, for example, mechanical mating techniques such as adhesives, an interference fit, threads, etc. As shown in FIG. 4A, the handle 14 includes openings formed therein, and the proximal ends (not shown) of the cables 34a-d can have a ball or other element formed thereon and configured to be captured within the openings. As further shown in FIG. 4A, the cables (only three cables 34a, 34b and 34c are shown) can remain spaced circumferentially around the handle 14. This will allow movement of the handle 14 to be mirrored by the end effector 16, as will be discussed in more detail below. Alternatively, the cables 34a-d can be crossed before they connect to the handle 14 to cause the end effector 16 to move in the same direction as the handle 14. For example, opposed cables 34a and 34c can cross one another and can connect to opposed sides of the handle 14, and opposed cables 34b and 34d can likewise cross one another and can connect to opposed sides of the handle 14. The cables 34a-d can be crossed at any location, such as within the hollow housing 12c on the proximal end 12a of the shaft 12.

As further shown in FIGS. 4A and 4B, the handle 14 can also include other features to facilitate use of the device. For example, the handle 14 can include a translating member 38 that is effective to close the jaws 18, 20 on the end effector 16, and a rotating member 40 that is effective to selectively rotate and actuate the end effector 16. The translating and rotating members 38, 40 are described in more detail in an application entitled "Surgical Fastener And Cutter With Single Cable Actuator" by Mark Ortiz et al. and filed on even date herewith, now U.S. Pat. No. 7,575,144 and which is hereby incorporated by reference in its entirety. In other embodiments, the handle 14 can include triggers, knobs, etc. for rotating and/or actuating the end effector 16. In addition, the device 10 can also include an actuation mechanism for controlling movement and actuation of the end effector 16. Movement can include rotation of the end effector 16 about the longitudinal axis A of the elongate shaft 12, and actuation of the end effector, whereby the jaws 18, 20 are closed to engage tissue and the staples are fired from the end effector into the engaged tissue. Actuation can also include cutting the stapled tissue. In an exemplary embodiment, a single actuation mechanism is operatively associated with the handle and the end effector such that it can effect rotation and actuation of the end effector. While the actuation mechanism can have a variety of configurations, in the illustrated embodiment the actuation mechanism is in the form of a drive shaft 128, which is shown in FIG. 2 extending through a portion of the elongate shaft 12. The drive shaft 128 can be in the form of an elongate cable, multiple wound or braided cables, or a rod or shaft, and it is preferably flexible to allow flexion as the flexible shaft 12 of the device 10 is inserted translumenally through a tortuous pathway. The drive shaft 128 includes proximal and distal ends that are coupled to various portions of the handle 14 and the end effector 16, respectively, as will be discussed in more detail below. In use, the drive shaft 128 is configured to rotate and translate (slide) relative to the elongate shaft 12 to effective rotation and actuation of the end effector 16.

Referring back to FIG. 1B, in use the handle 14 can be pivoted or angularly oriented relative to the proximal end 12a of the elongate shaft 12 to effect mimicking movement of the end effector 16. In particular, pivoting the handle 14 about the elongate shaft 12 in a first direction will apply a force to one or more of cables 34a-d to pull the cable(s) axially. As a result, the actuated cables will apply tension to the flexible neck 26 to cause the neck 26 to flex. In order to prevent the elongate shaft 12 from flexing in response to tension applied to the cables 34a-d by the handle 14, the flexible neck 26 can have a greater flexibility than the elongate shaft 12. This can be achieved, for example, using the alternating slits 32 as previously described, or in other embodiments the material can differ, or the elongate shaft can include a stabilizing element, such as a rod extending therethrough to render the shaft more rigid than the flexible neck.

The direction of movement of the handle 14 will be mimicked by the end effector 16, either in the same direction (i.e., corresponding movement) or in an opposite direction (i.e., mirrored movement), thus allowing a user to precisely control the position of the end effector 16. In an exemplary embodiment, the particular amount of movement of the end effector 16 can be proportional to the amount of movement of the handle 14. That is, the amount of movement of the end effector 16 can be directly equivalent to the amount of movement of the handle 14, or it can be proportionally increased or decreased relative to the amount of movement of the handle 14. In certain embodiments, it may be desirable to have the amount of movement of the end effector 16 be increased relative to the amount of movement of the handle 14. As a result, only small movements of the handle 14 will be necessary to allow large movements of the end effector 16. While various techniques can be achieved to proportionally multiple or increase the movement of the end effector 16, one exemplary embodiment of a force multiplying mechanism is an eccentric cam that is coupled to the cables and that increases the mechanical advantage, either force or displacement, of the cables 34a-d as tension is applied to the cables 34a-d by the handle 14.

A person skilled in the art will appreciate that, while the movement between the handle and the working end of the device can be proportional in theory, in practice some lose of force will likely occur as the force is transferred through the elongate shaft. Accordingly, proportional movement as used herein is intended to include applications in which the handle and working end are configured to move in proportionate amounts, but in which some lose of force may occur during actual operation of the device.

Figure 5:
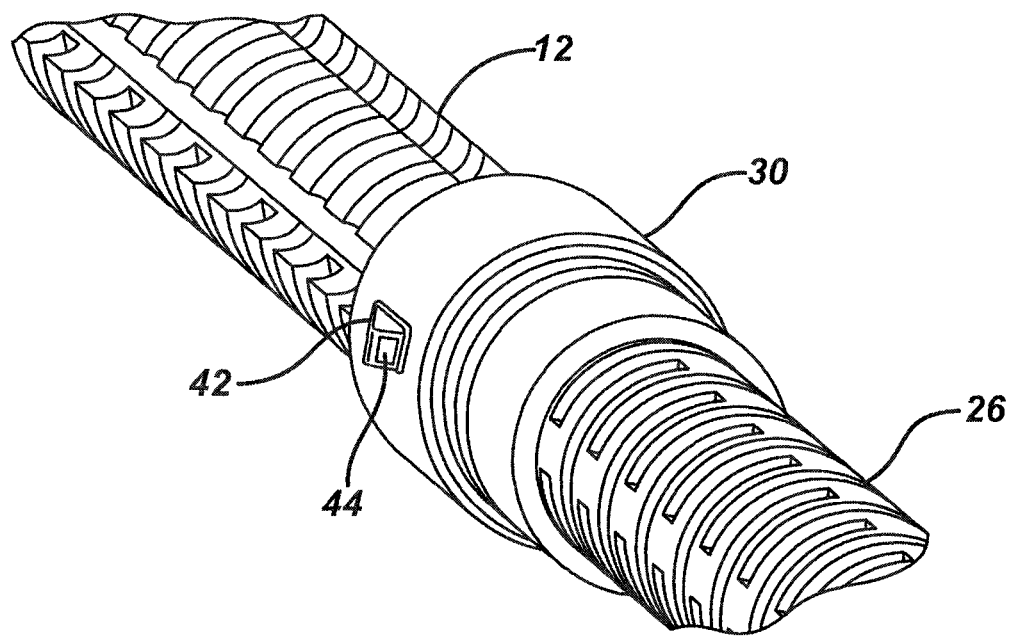
FIG. 5 is a perspective view of coupling element disposed between the flexible neck and elongate shaft of the device shown in FIGS. 1A and 1B, showing an optical image gathering apparatus.
Figure 6:
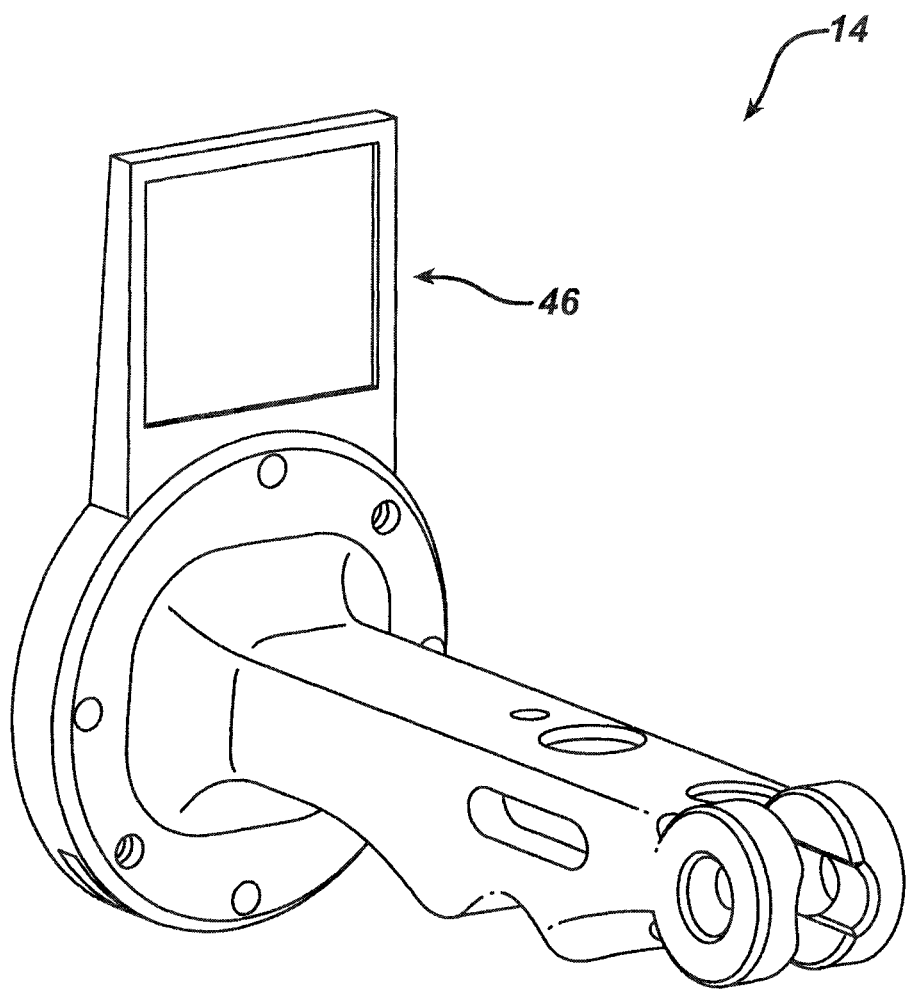
FIG. 6 is a perspective view of the handle of the device shown in FIGS. 1A and 1B, showing an image display screen.

The various devices disclosed herein can also include a variety of other features to facilitate use thereof. For example, the device 10 of FIG. 1A can include an optical image gathering unit disposed on a distal end of the elongate shaft 12 and configured to acquire images during endoscopic procedures. While the location of the unit can vary, in one embodiment the optical image gathering unit can be disposed on the second coupler 30. In particular, FIG. 5 illustrates a ramp-shaped housing 42 that protrudes from an outer surface of the coupler 30, and that contains the optical image gathering unit therein. A viewing window 44 is formed on a distal-facing surface of the housing 42 to allow the unit to acquire images of the end effector 16 and surrounding surgical site. The images from the optical image gathering unit can be transferred to an external image display screen, or alternatively the device 10 can include image display screen disposed on or coupled to a proximal portion of the device. FIG. 6 illustrates one embodiment of an image display screen 46 protruding outward from the handle 14.

Figure 7:
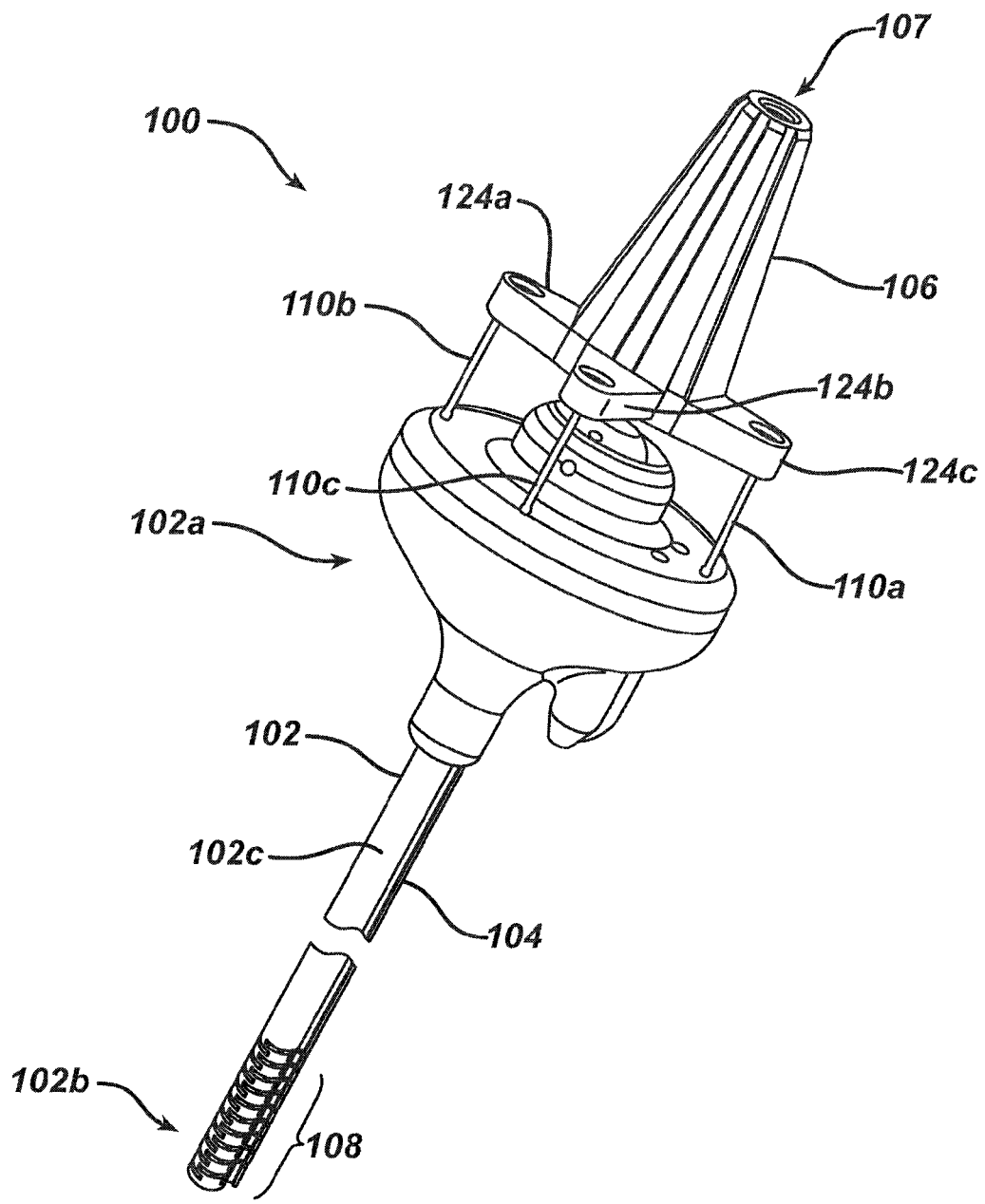
FIG. 7 is a perspective view of an accessory channel for use with an endoscope.

As previously indicated, the various techniques disclosed herein for controlling movement of a working end of an endoscopic surgical device can be used in conjunction with a variety of medical devices. FIG. 7 illustrates another embodiment of a medical device having an actuator for controlling movement of the working end thereof. In this embodiment, the medical device is in the form of an accessory channel 100 for use with an endoscope. An accessory channel 100 is an external device that can mate to and slide along an endoscope to allow other tools, such as grasper, cutters, etc., to be introduced therethrough and positioned in proximity to the viewing end of the endoscope. While the accessory channel 100 can have virtually any configuration, shape, and size, in the embodiment illustrated in FIG. 7 the accessory channel 100 includes an elongate tube or shaft 102 having an inner lumen extending between proximal and distal ends 102a, 102b thereof for receiving a tool therethrough. The accessory channel 100 can also include a mating element formed thereon for mating the accessory channel 100 directly to an endoscope or to a sleeve or other device disposed around an endoscope. While virtually any mating technique can be used, in the illustrated embodiment the mating element on the accessory channel 100 is in the form of a rail 104 that extends along a length of the elongate shaft 102. The rail 104 is configured to be received in a complementary track formed on an endoscope or a device disposed around an endoscope, such as a sleeve. A person skilled in the art will appreciate that a variety of other techniques can be used to mate the accessory channel either directly or indirectly to an endoscope.

In order to control movement of a working end of the accessory channel 100, the device 100 can include features similar to those previously described. In particular, the device 100 can a flexible neck 108 formed on or coupled to the distal end 102b of the elongate shaft 102, a handle 106 formed on or coupled to the proximal end 102a of the elongate shaft 102, and an actuator extending between the handle 106 and the flexible neck 108. In this embodiment, the actuator is configured to transfer forces from the handle 106 to the flexible neck 108 such that movement of the handle 106 is mimicked by the flexible neck 108, thus allowing a tool extending through the accessory channel 100 to be positioned at a desired angular orientation.

Figure 8A:
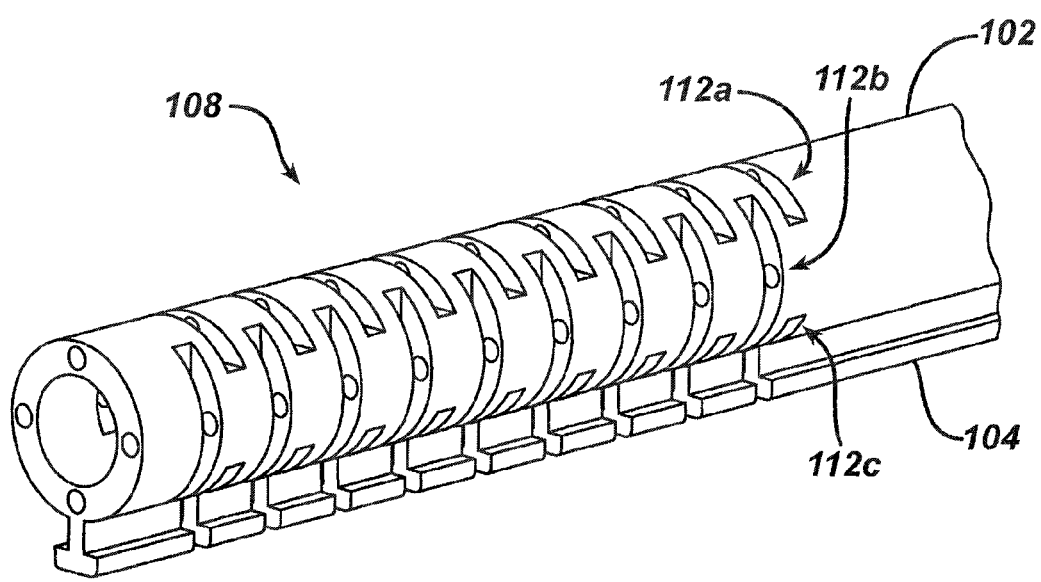
FIG. 8A is a perspective view of a flexible neck of the device shown in FIG. 7.
Figure 8B:
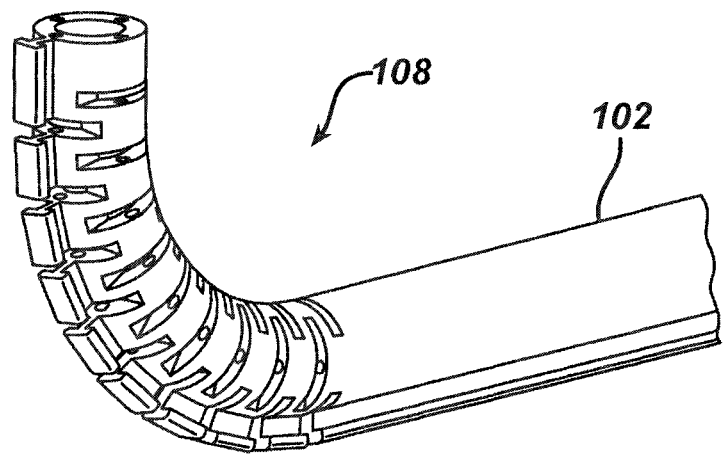
FIG. 8B is a perspective view of the flexible neck shown in FIG. 8A, showing the neck articulated in a first direction.
Figure 8C:
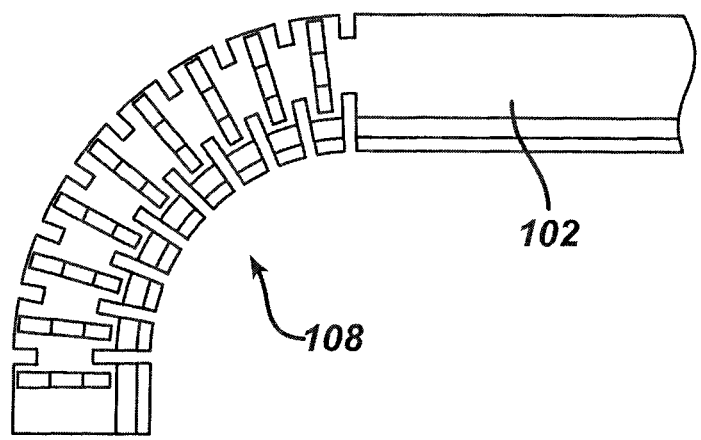
FIG. 8C is a perspective view of the flexible neck shown in FIG. 8A, showing the neck articulated in a second direction.

The flexible neck 108 can have a variety of configurations, and it can be a separate member that is coupled to the elongate shaft 102, or it can be formed integrally with the elongate shaft 102, as shown in FIG. 7. The neck 108 can be made flexible using various techniques. For example, the neck 108 can be formed from one or more segments that move relative to one another, and/or it can be formed from a flexible material. In the exemplary embodiment shown in FIG. 8A, the neck 108 includes several slits 112 formed therein and configured to provide maximum flexibility of the neck 108. While the size, quantity, and orientation of the slits 112 can vary to obtain the desired results, in the illustrated embodiment the flexible neck 108 includes four columns of slits (only three columns of slits, indicated by arrows 112a, 112b, 112c, are shown). Each column extends axially along a length of the flexible neck 108, and each column includes four row of slits spaced radially around circumference of the neck 108. Each column of slits 112 is also axially offset from one another to allow the slits 112 to overlap. In use, when tension is applied to the actuator, the slits 112 will allow the neck 108 to bend or assume a curved configuration such that the neck 108 articulates relative to the remainder of the elongate shaft 102, as shown in FIGS. 8B and 8C.

Figure 9A:
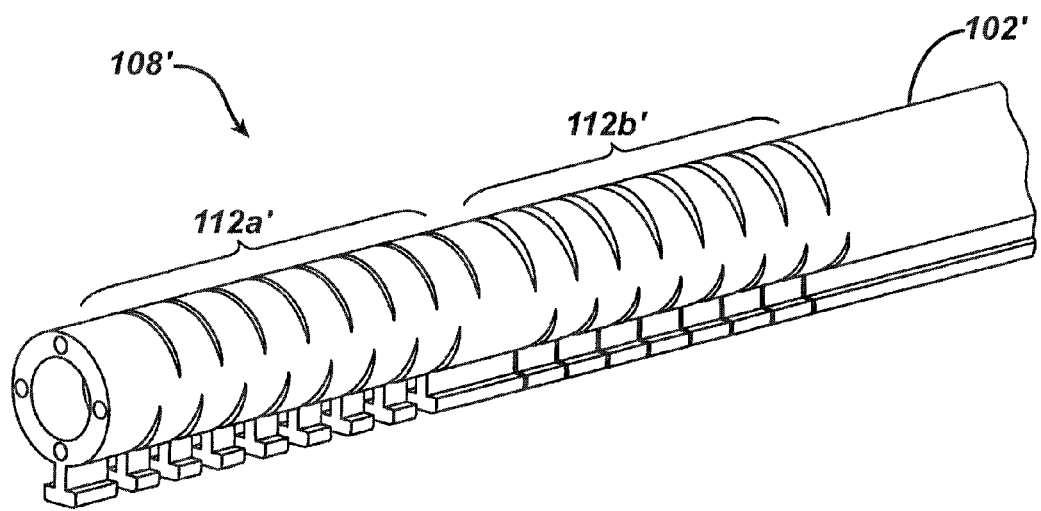
FIG. 9A is a perspective view of another embodiment of a flexible neck for use with an accessory channel.
Figure 9B:
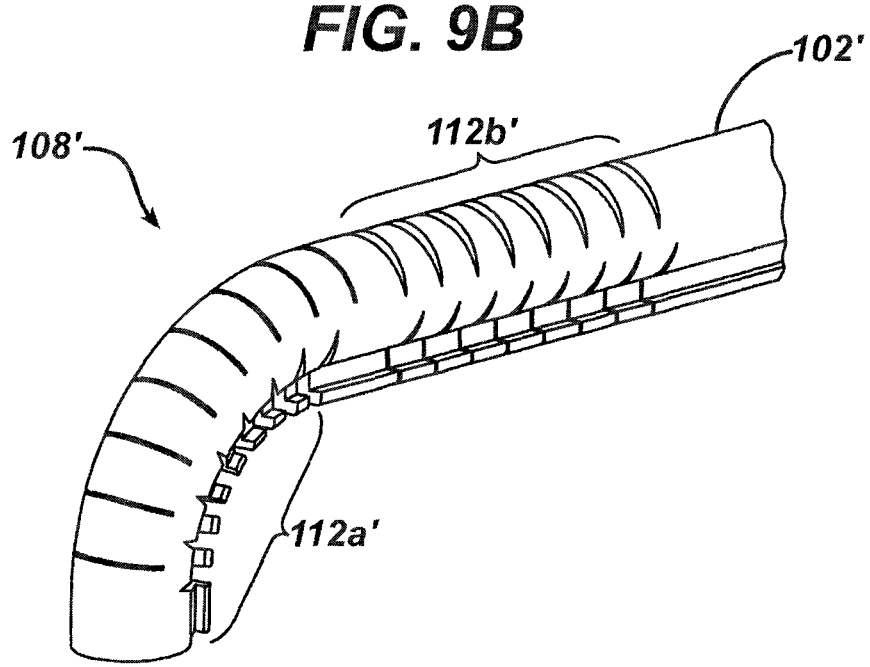
FIG. 9B is a perspective view of the flexible neck shown in FIG. 9A, showing the neck articulated in a first direction.
Figure 9C:
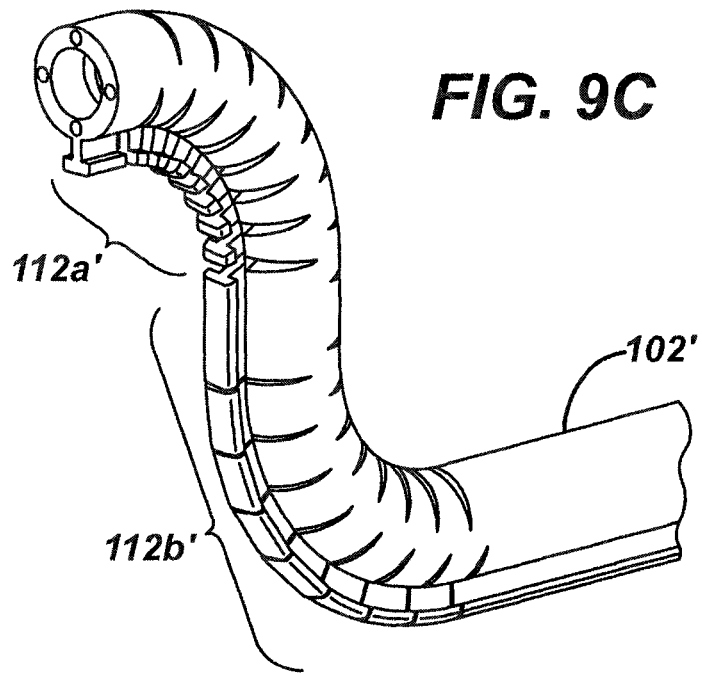
FIG. 9C is a perspective view of the flexible neck shown in FIG. 9A, showing the neck articulated in a second direction.

In other embodiments, the slits can be positioned to allow flexion of the neck at multiple locations or bend points, or to otherwise allow the neck to flex into a predetermined position. By way of non-limiting example, FIG. 9A illustrates another embodiment of a flexible neck 108' having two regions of slits 112' formed therein. In particular, the flexible neck 108' includes a distal region of slits 112a' and a proximal region of slits 112b'. Each region 112a', 112b' can include any number of slits positioned at any location to provide a desired degree of flexibility in one or more desired directions. As shown in FIG. 9A, the proximal end distal regions of slits 112a', 112b' each include two rows of slits formed on opposed sides of and extending along the length of the flexible neck 108'. In use, when tension is applied to the flexible neck 108', as will be discussed in more detail below, the neck 108' will flex at both the proximal and distal regions 112a', 112b' and thereby articulate relative to the remainder of the elongate shaft 102'. As shown in FIG. 9B, flexion can occur first in the distal region 112a' of the neck 108'. Further tension applied to the neck 108' can then cause the proximal region 112b' to flex, as shown in FIG. 9C. In other embodiments, the slits positioning and/or size of the slits can be configured to cause flexion to occur in the proximal region 112b' before it occurs in the distal region 112a', or alternatively the slits can be configured to cause simultaneous flexion of the proximal and distal regions 112b', 112a'. A person skilled in the art will appreciate that the quantity, position, size, and shape of the slits can be adjusted to obtain the desired results. The particular configuration of the cut used to form each slit can also vary. For example, the width and length of the slit can remain constant from an outer surface of the elongate shaft to an inner surface of the elongate shaft, or alternatively the width and length can increase or decrease such that the slit tapers or otherwise varies. By way of non-limiting example, a tapering configuration can be formed by forming a slit having triangular configuration, where the length and width of the slit decrease from the outer surface to the inner surface of the elongate shaft.

As indicated above, the actuator is configured to apply tension to the flexible neck 108 to cause the neck 108 to articulate. The actuator can have a variety of configurations, but in one exemplary embodiment the actuator is similar to the aforementioned actuator and includes one or more cables that extend between the handle 106 and the distal end of the flexible neck 108 such that the handle 106 and the flexible neck 108 are operatively associated. Each cable can be configured to apply tension to the flexible neck 108 to cause the neck 108 to articulate in a plane of motion. Thus, where the device 100 includes only one cable, the flexible neck 108 can articulate in a single plane of motion. Each additional cable can allow the neck 108 to articulate in a different plane of motion. Where multiple cables are provided, the neck 108 can articulate in multiple planes of motion. Moreover, the cables can be simultaneously tensioned, potentially allow for 360° articulation of the flexible neck 108.

While the number of cables can vary, and the device 100 can include only one cable, in the embodiment shown in FIG. 7 the device 100 includes four cables (only three cables 110a, 110b, 110c are shown). A portion of the cables 110a, 110b, 110c, 110d is shown in more detail in FIG. 10. As noted above, the cables 110a-d extend along a length of the elongate shaft 102 between the handle 106 and the flexible neck 108.

The particular location of the cables 110a-d can vary, but in an exemplary embodiment the cables 110a-d are spaced radially around a circumference of the elongate shaft 102 and they extend between the distal-most end of the flexible neck 108 and the handle 106. The cables 110a-d can extend internally through or externally along the elongate shaft 102, or they can extend through lumens or pathways formed in the sidewall of the elongate shaft 102. FIG. 11 illustrates a cross-sectional view of the elongate shaft 102, showing four lumens 103a, 103b, 103c, 103d formed therein. The lumens 103a-d preferably have a size that allows the cables 116a-d to slide therein, and they are spaced circumferentially about the elongate shaft 102. The lumens 103a-d extend between the proximal and distal ends 102a, 102b of the elongate shaft 102 to allow the cables 110a-d to extend between the handle 106 and the distal-most end of the flexible neck 108.

Figure 12:
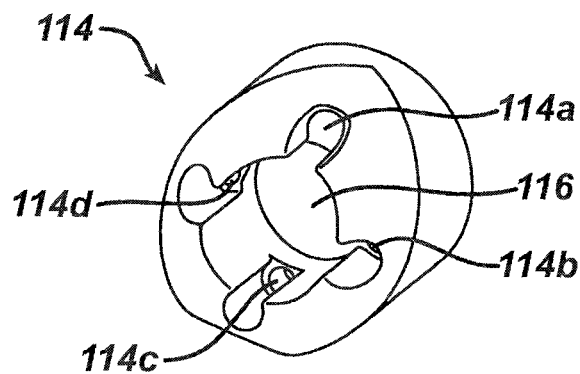
FIG. 12 is a perspective view of one embodiment of an end cap for use with the accessory channel of FIG. 7.

The distal end of the cables 110a-d can mate to the distal most end of the flexible neck 108 using a variety of techniques, but in one embodiment, shown in FIG. 12, the flexible neck 108 includes an end cap 114 coupled to or formed on the distal-most end thereof. While the configuration of the end cap 114 can vary depending on the configuration of the actuator, in the illustrated embodiment the end cap 114 includes four bores 114a, 114b, 114c, 114d formed therein and spaced around a circumference of the end cap 114 such that the bores 114a-d align with the lumens 103a-d in the elongate shaft 102. Each bore 114a-d is configured to receive one of the cables 110a-d. Various mating techniques can be used to retain the cables 110a-d within the bores 114a-d. For example, FIG. 10 illustrates ball formed on the end of each cable 110a-d for retaining the ends of the cables 110a-d in the bores 114a-d in the end cap 114. The end cap 114 can also include a central lumen 116 formed therein for receiving a tool therethrough. The lumen 116 can also function to facilitate positioning of a tool inserted through the accessory channel 100.

The proximal end of the cables 110a-d can be mated to a handle 106 that is coupled to a proximal end of the shaft 102. While the handle 106 can have a variety of configurations, in one exemplary embodiment, previously shown in FIG. 7, the handle 106 can be in the form of a joystick that is movably coupled to the proximal end 102a of the elongate shaft 102, and in particular that is configured to articulate relative to the proximal end 102a of the elongate shaft 102. The articulating movement of the handle 106 can allow the motion of the handle 106 to be mimicked by the flexible neck 108, as will be discussed below.

Figure 13A:
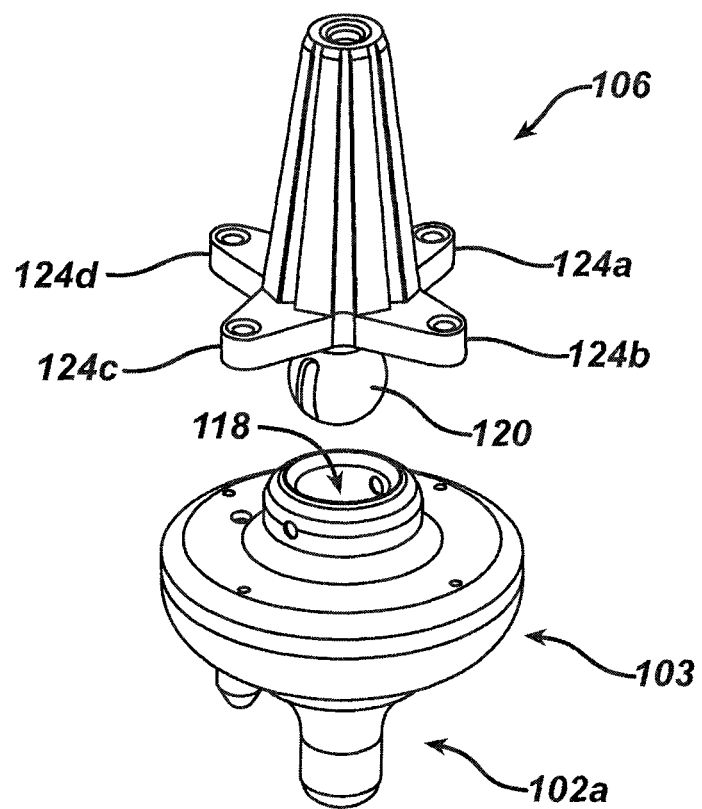
FIG. 13A is an exploded view of the handle and a proximal portion of the elongate shaft of the device shown in FIG. 7.

While articulating movement can be achieved using a variety of types of joints, in the illustrated embodiment a ball-and-socket connection is formed between the handle 106 and the elongate shaft 102. In particular, as shown in more detail in FIGS. 13A and 13B, the proximal end 102a of the elongate shaft 102 includes a housing 103 formed thereon and defining a socket 118 in a proximal end thereof. The handle 106 includes a ball 120 that is movably disposed within the socket 118, and the joystick extends proximally from the ball 120 thus allowing the handle 106 to articulate relative to the elongate shaft 102. A pin or other mechanism can be used to movably retain the ball 120 within the socket 118. A person skilled in the art will appreciate that the handle can have a variety of other shapes, and that various other techniques can be used to movably connect the handle 106 to the elongate shaft 102.

As indicated above, the proximal end of the cables 110a-d is configured to mate to the handle 106. Thus, the handle 106 can include features for mating to the cables 110a-d. While the particular mating features can vary depending on the configuration of the actuator, in an exemplary embodiment the joystick 122 on the handle 106 includes four legs 124a, 124b, 124c, 124d formed thereon. The legs 124a-d are spaced around a circumference of the joystick 122, such that they are substantially aligned with the cables, and each leg 124a-d is configured to mate to a terminal end of one of the cables 110a-d. A ball-and-socket connection, as previously described with respect to the distal ends of the cables 110a-d, can be used to mate the cables 110a-d to the legs, or alternatively any other mating technique known in the art can be used.

Figure 13B:
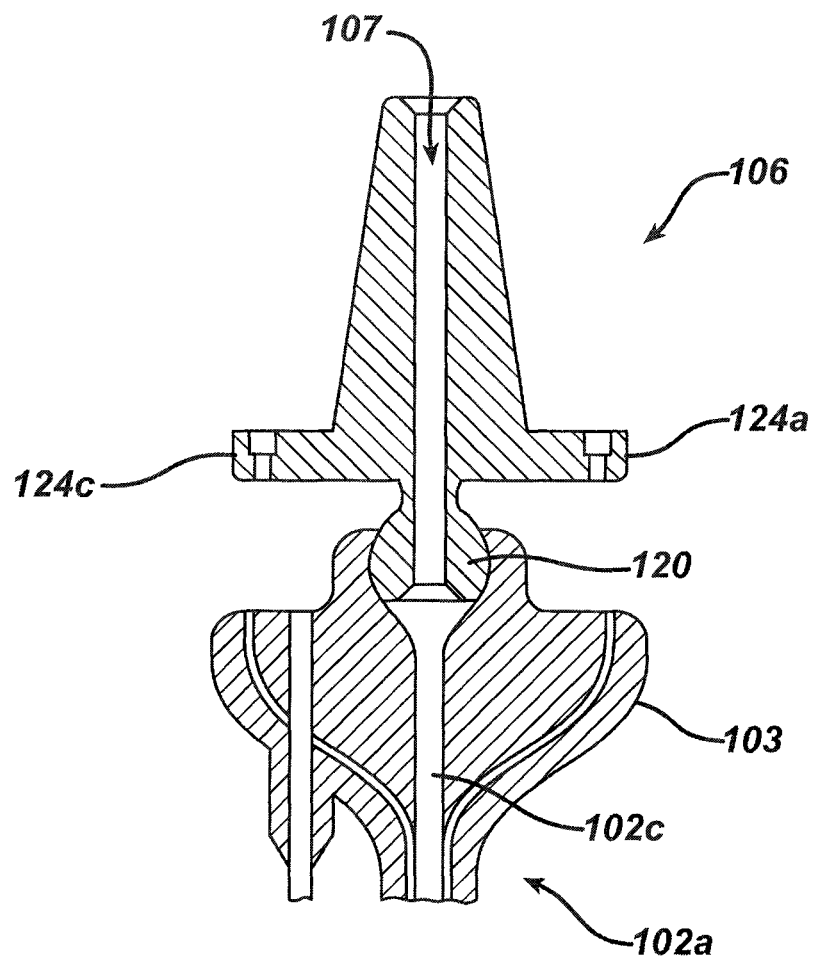
FIG. 13B is a cross-sectional view of the handle and the proximal portion of the elongate shaft of FIG. 13A in an assembled configuration.

Referring back to FIG. 7, in use the handle 106 can be pivoted or angularly oriented relative to the proximal end 102a of the elongate shaft 102 to effect mimicking movement of the flexible neck 108, and to thereby position a tool extending through the flexible neck 108. As shown in FIGS. 7 and 13B, the joystick on the handle 106 can include a lumen 107 formed therethrough and axially aligned with the lumen 102c in the elongate shaft 102 for allowing a tool to be introduced through the device 100. In other embodiments, the handle 106 can be offset from the proximal end 102a of the elongate shaft 102 such that the handle 106 is coupled to the cables, but does not interfere with direct access to the lumen 102c in the elongate shaft 102.

In order to control movement of the flexible neck 108 and thus a tool positioned therethrough, the handle 106 is pivoted or articulated about the proximal end 102a of the elongate shaft 102. For example, movement of the handle 106 in a first direction will cause the legs 124a-d on the handle 106 to apply a force to one or more of cables 110a-d to pull the cable(s) axially. As a result, the actuated cables will apply a tension force to the flexible neck 108 to cause the neck 108 to flex. In order to prevent the elongate shaft 102 from flexing in response to tension applied to the cables 110a-d by the handle 106, the flexible neck 108 can have a greater flexibility than the elongate shaft 102. This can be achieved, for example, using the slits as previously described, or in other embodiments the shaft 102 can include a stabilizing element, such as a rod, extending therethrough to make the shaft 102 more rigid than the flexible neck 108. The direction of movement of the handle 106 will be mimicked by the flexible neck 108, either in the same direction (i.e., corresponding movement) or in an opposite direction (i.e., mirrored movement), thus allowing a user to precisely control the position of the flexible neck 108, and thus to control the position of a tool extending through the flexible neck 108. In an exemplary embodiment, the particular amount of movement of the flexible neck 108 can be proportional to the amount of movement of the handle 106. That is, the amount of movement of the flexible neck 108 can be directly equivalent to the amount of movement of the handle 106, or it can be proportionally increased or decreased relative to the amount of movement of the handle 106. In certain embodiments, it may be desirable to have the amount of movement of the flexible neck 108 be increased relative to the amount of movement of the handle 106. As a result, only small movements of the handle 106 will be necessary to allow large movements of the flexible neck 108. While various techniques can be achieved to proportionally multiple or increase the movement of the flexible neck 108, one exemplary embodiment of a force multiplying mechanism is an eccentric cam that is coupled to the cables and that increases the mechanical advantage, either force or displacement, of the cables 110a-d as tension is applied to the cables 110a-d by the handle 106.

As previously explained, while the movement between the handle and the working end of the device can be proportional in theory, in practice some lose of force will likely occur as the force is transferred through the elongate shaft. Accordingly, proportional movement as used herein is intended to include applications in which the handle and working end are configured to move in proportionate amounts, but in which some loss of force may occur during actual operation of the device.

Figure 14A:
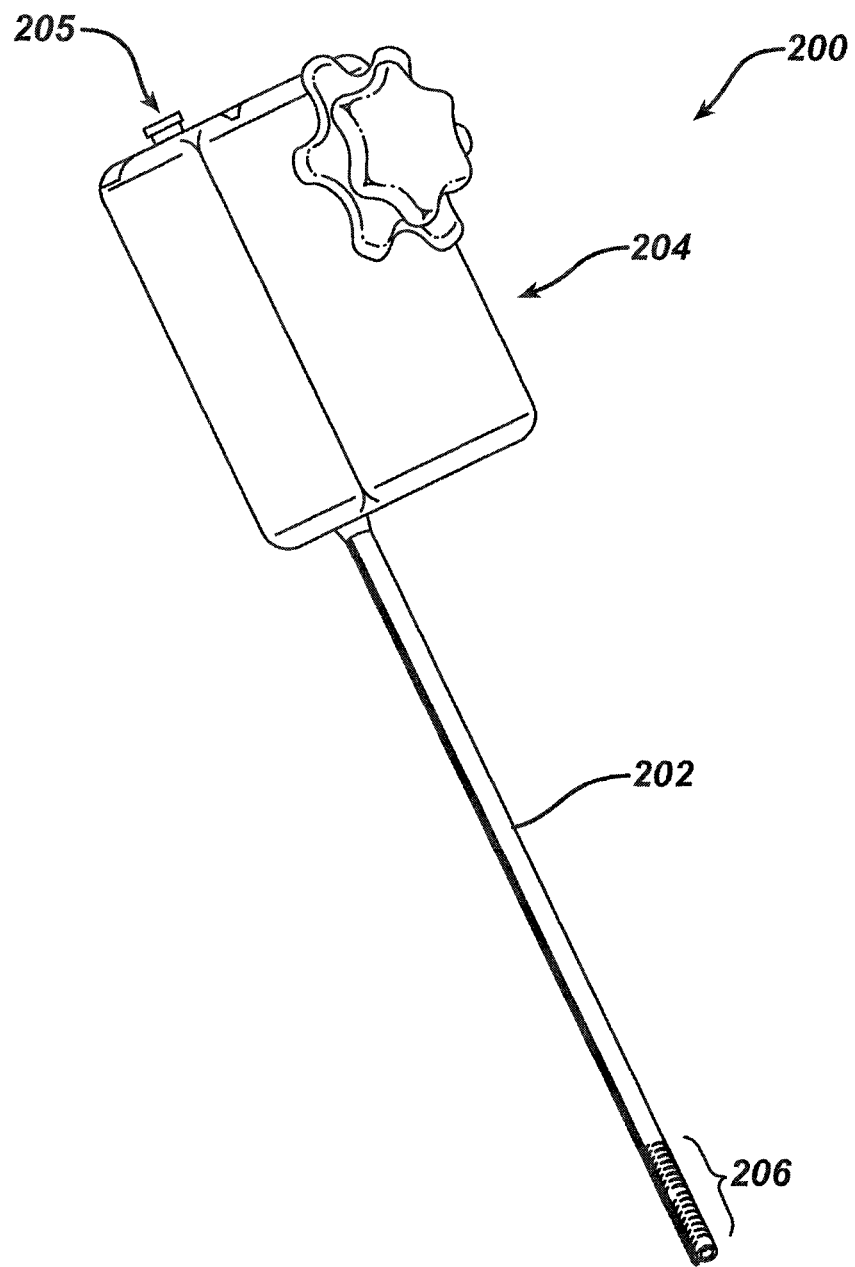
FIG. 14A is a perspective view of another embodiment of an accessory channel.
Figure 14B:
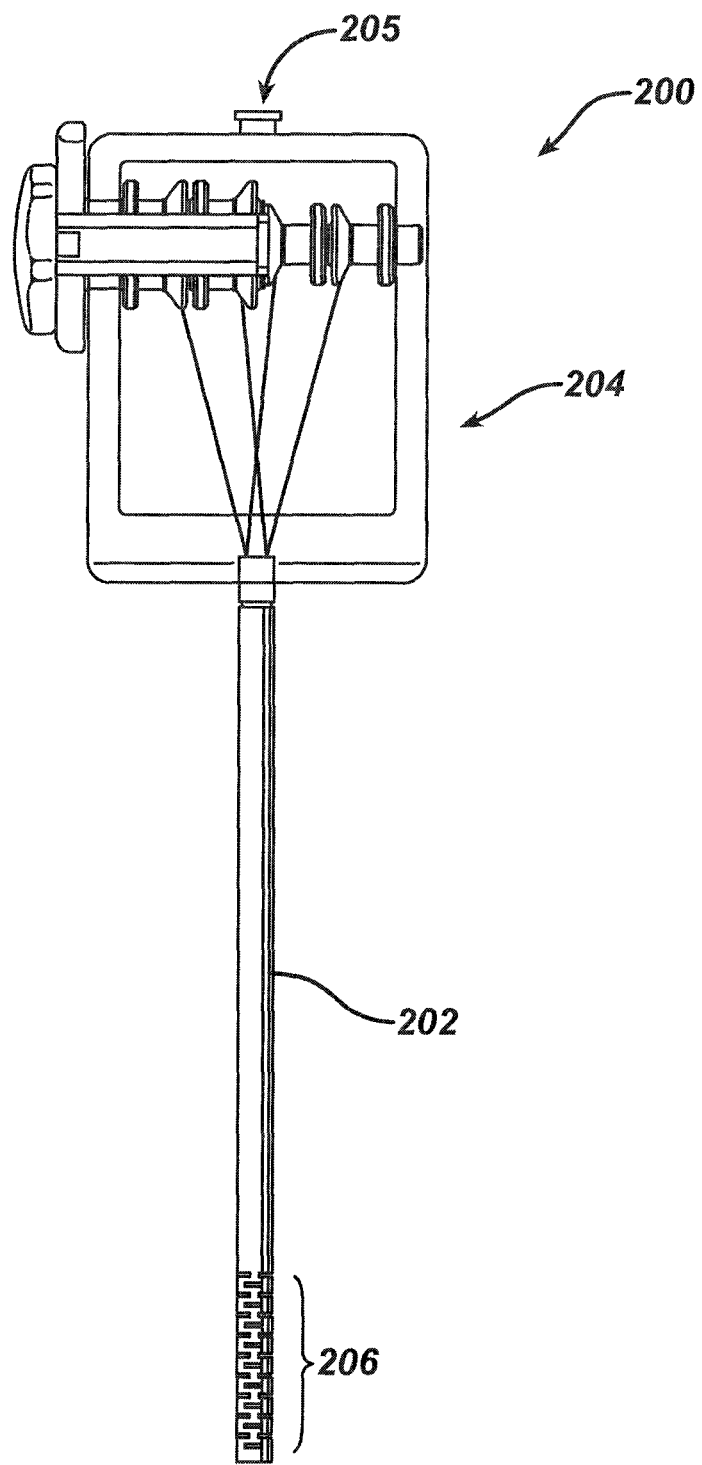
FIG. 14B is a cross-sectional view of the accessory channel shown in FIG. 14A.

While FIGS. 1A and 7 illustrate devices in which the working end mimics movement of the handle, the handle can have a variety of other configurations in which it is effective to articulate the working end of the device without having the working end of the device mimic movement of the handle. FIGS. 14A and 14B illustrate another embodiment of a device 200 having a handle 204 that includes a rotatable member that is effective to articulate a flexible neck 206 in one or more planes of motion relative to an elongate shaft 202 of the device. In general, the elongate shaft 202 of the device 200 is very similar to the elongate shaft 102 previously described, and it generally includes a flexible neck 206 coupled to or formed on a distal end thereof. Four cable actuators (not shown) extend through the elongate shaft between the handle 106 and the flexible neck 206. The shaft 102 and the cable actuators are similar to the shaft 102 and cable actuators 110a-d previously described with respect to device 100, and thus they will not be described in detail.

Figure 15A:
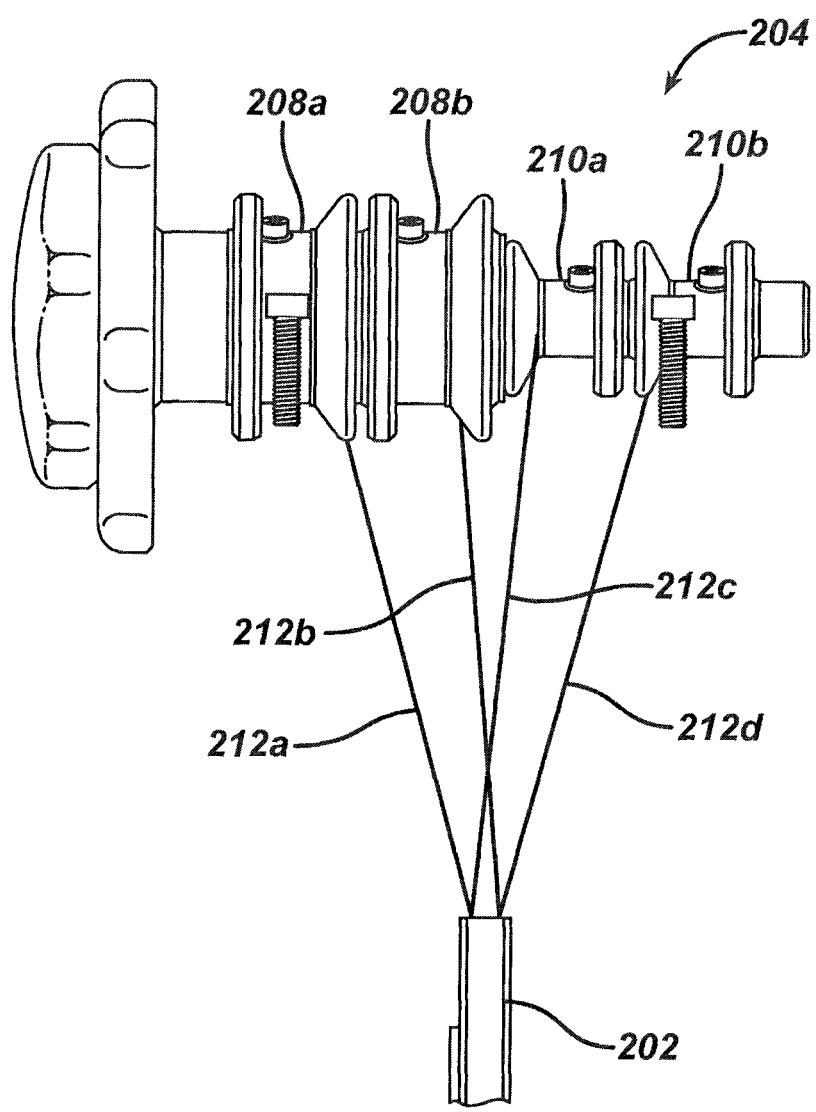
FIG. 15A is a side view of a handle assembly of the device shown in FIGS. 14A and 14B.
Figure 15B:
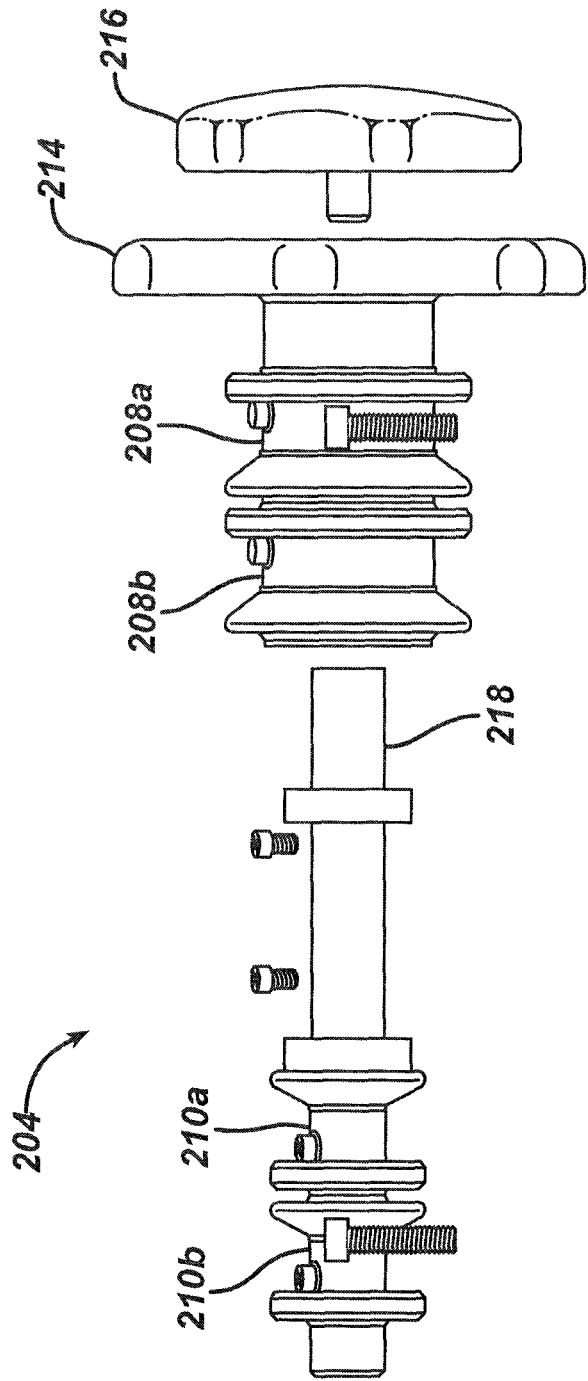
FIG. 15B is an exploded view of the handle assembly of FIG. 15A.

The handle 204 of the device 200 is shown in more detail in FIGS. 15A and 15B. In general, the handle 204 includes one or more spools rotatably disposed therein. Each spool is configured to mate to and control one of the cable actuators. Thus, rotation of each spool will wind up or release the cable, thereby causing the flexible neck 108 to flex and articulate in a particular direction. While the number of spools can vary depending on the number of cable actuators, in the embodiment shown in FIGS. 15A and 15B, the handle 204 includes four spools 208a, 208b, 210a, 210b. The first two spools 208a, 208b are coupled to one another, and the second two spools 210a, 210b are coupled to one another. A first cable 212a is coupled to and wound around the first spool 208a, and a second cable 212b is coupled to and wound around the second spool 208b. The first and second cables 212a, 212b are positioned on and extend along opposite sides of the elongate shaft 202. As a result, tension applied to the first cable 212a will cause the flexible neck 206 to articulate in direction within a first plane of motion, and tension applied to the second cable 212b will cause the flexible neck 206 to articulate in the opposite direction within the same plane of motion. To allow tension to be applied to only one of the cables 212a, 212b, the first and second cables 212a, 212b are wound around the first and second spools 208a, 208b in opposite directions. Thus, rotation of the first and second spools 208a, 208b will wind and apply tension to one of the cables 212a, 212b while unwinding and releasing tension on the other one of the cables 212a, 212b. Third and fourth cables 212c, 212d are likewise wound around the third and fourth spools 210a, 210b such that rotation of the third and fourth and second spools 210a, 210b will wind and apply tension to one of the cables 212c, 212d while unwinding and releasing tension on the other one of the cables 212c, 212d. The third and fourth cables 212c, 212d can extend along the shaft 102 at a position that is radially offset from the first and second cables 212a, 212b such that the third and fourth cables 212c, 212d cause articulation of the flexible neck 206 in a second, different plane of motion. For example, the third and fourth cables 212c, 212d can be offset from the first and second cables 212a, 212b by about 90° such that the cables 212a-d are all spaced substantially equidistant around the circumference of the elongate shaft 202. A person skilled in the art will appreciate that the handle 204 can include any number of spools and cables to effect articulation in a desired number of planes.

In order to control the spools 208a, 208b, 210a, 210b, the device can include one or more grasping members. As shown in FIGS. 15A and 15B, a first rotatable knob 214 is coupled to the first and second spools 208a, 208b, and a second rotatable knob 216 is coupled to the third and fourth spools 210a, 210b. The knobs 214, 216 can be integrally formed with the spools 208a, 208b, 210a, 210b, or they can be coupled to the spools 208a, 208b, 210a, 210b by a shaft that extends through the spools 208a, 208b, 210a, 210b. In the illustrated embodiment, the first knob 214 is formed on or coupled directly to the first spool 208a, and the second knob 216 is coupled to the third and fourth spools 210a, 210b by a shaft 218 that extends from the knob 216 through the first and second spools 208a, 208b, and that couples to the third and fourth spools 210a, 210b. In other words, the first and second spools 208a, 208b are rotatably disposed around the shaft 218.

In certain exemplary embodiments, the spools and the rotatable knobs can also differ in size. In the embodiment shown in FIGS. 15A and 15B, the first and second spools 208a, 208b, as well as the first rotatable knob 214, have a diameter that is greater than a diameter of the third and fourth spools 210a, 210b and the second rotatable knob 216. While not necessary, such a configuration can be advantageous as it spaces the cables 212a-d apart to prevent the cables 212a-d from coming into contact with one another.

In use, a tool can be positioned through the elongate shaft 202, and the knobs 214, 216 can be rotated to articulate the flexible neck 206 on the shaft 202 and thereby position the tool as desired. As shown in FIGS. 14A and 14B, the handle 204 can include a lumen 205 extending therethrough and in alignment with the lumen in the elongate shaft 202 for allowing a tool to be passed through the handle 204 and the shaft 202. In other embodiments, the handle 204 can be offset from the elongate shaft 202 to provide direct access to the lumen in the elongate shaft 202. Once the tool is positioned through the shaft 202, the knobs 214, 214 can be rotated to articulate the flexible neck 206 on the distal end of the elongate shaft 202. In particular, the first knob 214 can be rotated in a first direction, e.g., clockwise, to apply tension to one of the cables, e.g., the first cable 212a, while releasing or unwinding the other cable, e.g., the second cable 212b. As a result, the tension applied to the first cable 212a will pull the distal-most end of the flexible neck 206 in a proximal direction, causing the flexible neck 206 to flex and thereby articulate in a first direction. Rotation of the first knob 214 in an opposite direction, e.g., counterclockwise, will unwind the first cable 212a while winding the second cable 212b. The flexible neck 206 will return to its initial, linear configuration. Further rotation of the first knob 214 will continue to wind the second cable 212b while unwinding the first cable 212a, thereby causing the flexible neck 206 to flex and articulate in an opposite direction along the same plane of motion. The second knob 216 can be likewise rotated to articulate the flexible in a different plane of motion. The knobs 214, 216 can also optionally be rotated simultaneously to articulate the flexible neck 206 in additional planes of motion different than the first and second planes of motion.

Figure 16A:
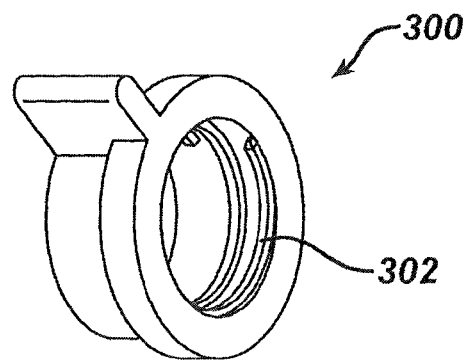
FIG. 16A is a perspective view of one embodiment of a locking mechanism.
Figure 16B:
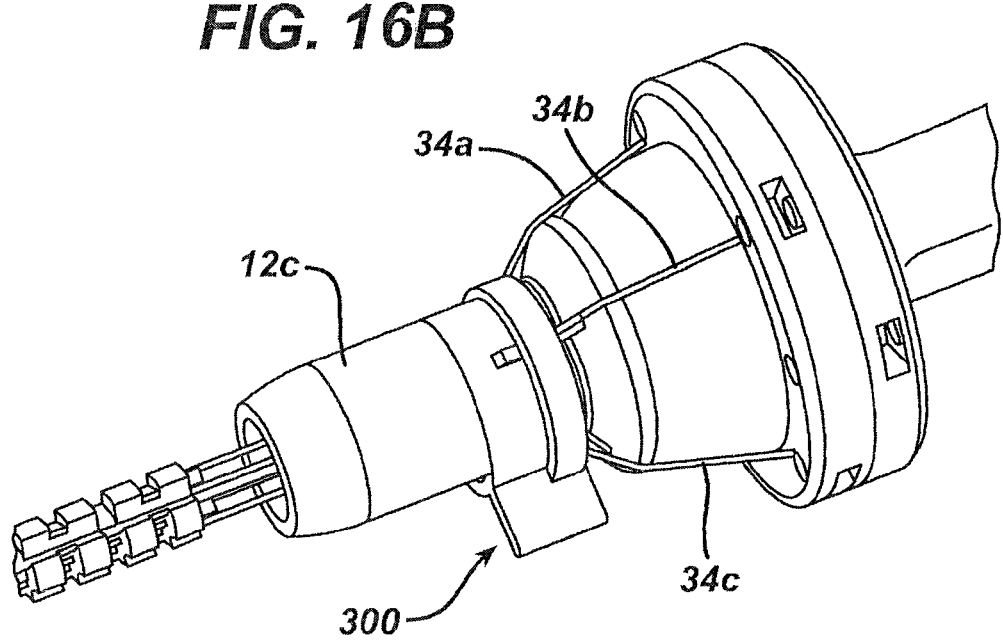
FIG. 16B is a perspective view of the locking mechanism of FIG. 16A coupled to the surgical stapling and cutting device of FIGS. 1A and 1B.

In other embodiments, the various devices disclosed herein can include a locking mechanism for locking the handle(s) and/or actuator in a fixed position to maintain the working end of a device in desired articulated or angular orientation. While the locking mechanism can have a variety of configurations, in one exemplary embodiment the locking mechanism can be in the form of a clamp that is effective to clamp down onto the cables and thereby prevent movement of the cables to lock the working end in a desired orientation. The clamp can have a variety of shapes and sizes, and it can be positioned at various locations on the device. FIGS. 16A and 16B illustrate one exemplary embodiment of a clamp 300 that is disposed around the hollow housing 12c on the surgical fastening and cutting device 10 of FIGS. 1A and 1B. The clamp 300 is generally ring-shaped and can be configured to be slidably or rotatably mated to the hollow housing 12c adjacent to the openings through which the cables (only three cables 34a, 34b, 34c are shown in FIG. 16B) extend. In an initial position, the clamp 300 is spaced apart from the openings to allow free movement of the cables 34a-d therethrough. Once the working end of the device, e.g., the end effector 16, is articulated into a desired position, the clamp 300 can moved axially along the hollow housing 12c until it extends over the openings and engages the cables 34a-d extending therefrom. The clamp 300 will thus prevent movement of the cables 34a-d when the clamp 300 is in the locked position. In order to move the clamp 300 axially and to lock the clamp 300 to the housing 12c, the clamp 300 can include a mating element formed thereon and configured to engage a corresponding mating element formed on the housing 12c. As shown in FIGS. 16A and 16B, the clamp includes threads 302 formed therein that are configured to mate with corresponding threads (not shown) formed on the housing 12c. As a result, rotation of the clamp 300 about the housing 12c will cause the clamp 300 to move between the initial and locked positions. A person skilled in the art will appreciate that various other mating techniques can be used. Moreover, the locking mechanism can have a variety of other configurations. For example, the handle can include a locking element formed thereon and configured to lock the handle in a fixed, articulated position.

In other embodiments, the cables can be used to passively allow articulation of the elongate shaft through a body lumen, and the clamp 300 or other locking mechanism can be used to lock the working end of the device into position when desired. In such a configuration, the handle can merely be used to facilitate grasping of the device.

In other embodiments, the cable actuators disclosed herein used to effect articulation of a working end of a device can be formed from an electroactive polymer material. Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction. Thus, the cable actuators previously disclosed herein can be replaced by EAP actuators, and the handle can be configured to activate an energy source to selectively deliver energy to one or more of the cables. In an exemplary embodiment, movement of the handle can be configured to dictate the amount of the energy source, as well as the cable(s) receiving the energy source. As a result, movement of the handle can still be mimicked by the working end of the device to provide the user with the same, precise control over the position of the working end. The energy source can be an internal source, such as a battery, or it can be an external source. In other embodiments, the EAP cable actuators can supplement the axial force applied to the cables by movement of the handle and thereby proportionally increase the amount of movement of the working end relative to the handle.

In other aspects, the cable actuators can be formed from a shape-memory material, such as Nitinol. Such a configuration allows tension to be applied to the cables to articulate the end effector, yet allows the cables to return to an initial linear configuration without having to manipulate the handle.

In yet another embodiment, the various devices disclosed herein, including portions thereof, can be designed to be disposed of after a single use, or they can be designed to be used multiple times. In either case, the device can be reconditioned for reuse after at least one use. Reconditioning can include any combination of the steps of disassembly of the device, followed by cleaning or replacement of particular pieces, and subsequent reassembly. By way of example, the surgical stapling and fastening device shown in FIGS. 1A and 1B can be reconditioned after the device has been used in a medical procedure. The device can be disassembled, and any number of the particular pieces can be selectively replaced or removed in any combination. For example, for the surgical stapling and cutting device, a cartridge disposed within the end effector and containing a plurality of fasteners can be replaced by adding a new fastener cartridge to the end effector. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

Over the years a variety of minimally invasive robotic (or "telesurgical") systems have been developed to increase surgical dexterity as well as to permit a surgeon to operate on a patient in an intuitive manner. Many of such systems are disclosed in the following U.S. Patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled "Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue.

Figure 17:
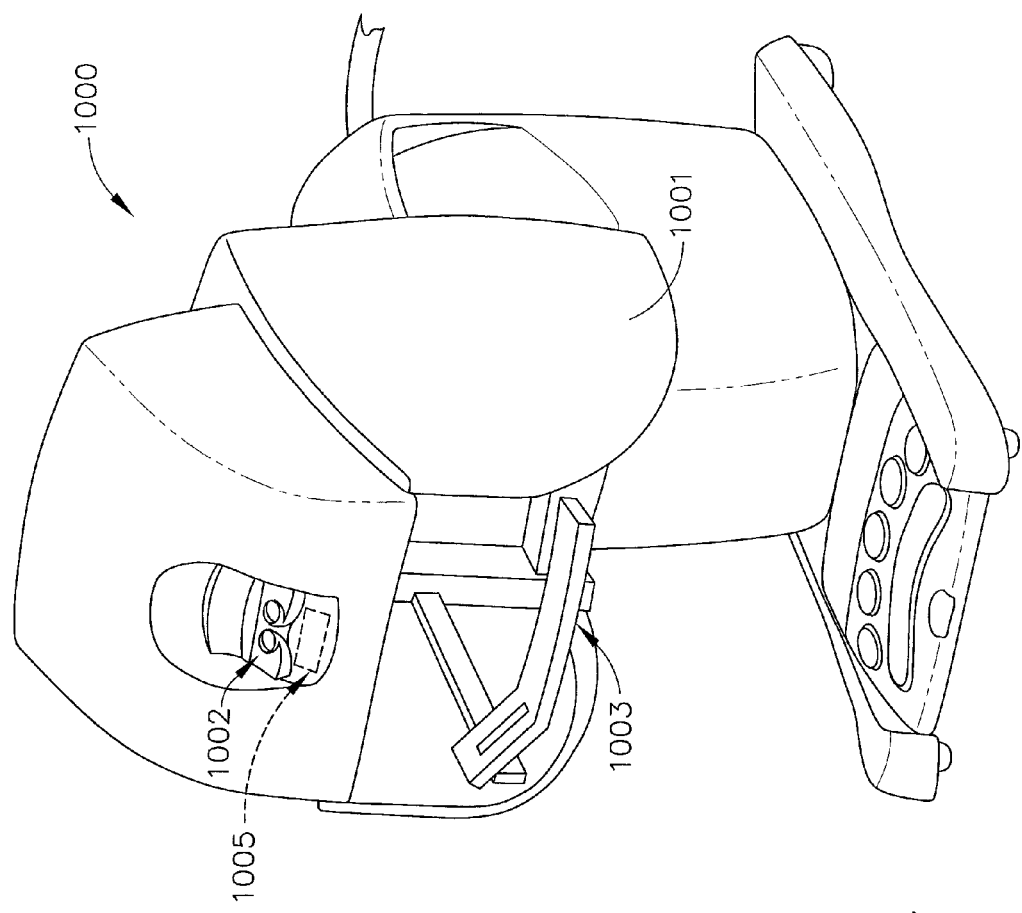
FIG. 17 is a perspective view of one robotic controller embodiment.
Figure 18:
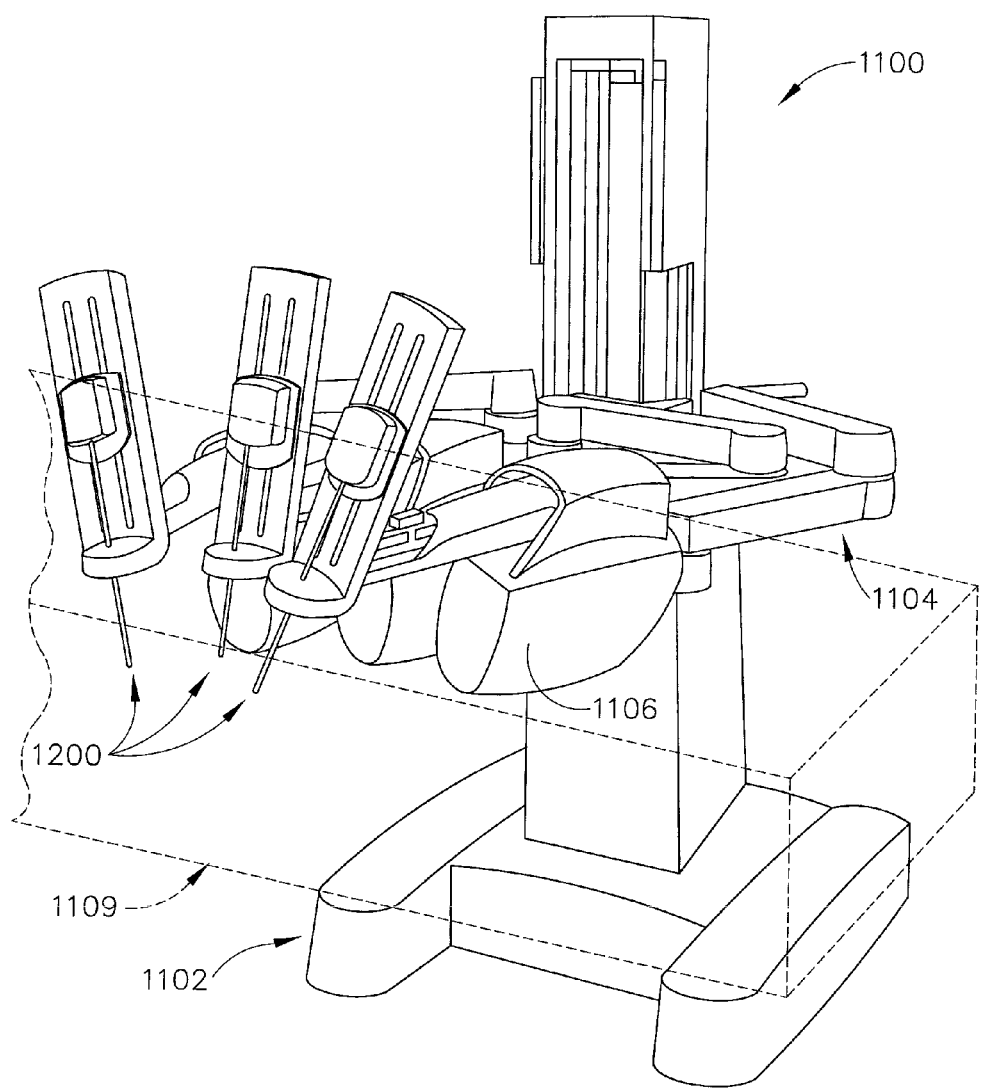
FIG. 18 is a perspective view of one robotic surgical arm cart/manipulator of a robotic system operably supporting a plurality of surgical tool embodiments of the present invention.

FIG. 17 depicts one version of a master controller 1001 that may be used in connection with a robotic arm slave cart 1100 of the type depicted in FIG. 18. Master controller 1001 and robotic arm slave cart 1100, as well as their respective components and control systems are collectively referred to herein as a robotic system 1000. Examples of such systems and devices are disclosed in U.S. Pat. No. 7,524,320 which has been herein incorporated by reference. Thus, various details of such devices will not be described in detail herein beyond that which may be necessary to understand various embodiments and forms of the present invention. As is known, the master controller 1001 generally includes master controllers (generally represented as 1003 in FIG. 17) which are grasped by the surgeon and manipulated in space while the surgeon views the procedure via a stereo display 1002. The master controllers 1001 generally comprise manual input devices which preferably move with multiple degrees of freedom, and which often further have an actuatable handle for actuating tools (for example, for closing grasping saws, applying an electrical potential to an electrode, or the like).

As can be seen in FIG. 18, in one form, the robotic arm cart 1100 is configured to actuate a plurality of surgical tools, generally designated as 1200. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 1100 includes a base 1002 from which, in the illustrated embodiment, three surgical tools 1200 are supported. In various forms, the surgical tools 1200 are each supported by a series of manually articulatable linkages, generally referred to as set-up joints 1104, and a robotic manipulator 1106. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 1100. Cart 1100 will generally have dimensions suitable for transporting the cart 1100 between operating rooms. The cart 1100 may be configured to typically fit through standard operating room doors and onto standard hospital elevators. In various forms, the cart 1100 would preferably have a weight and include a wheel (or other transportation) system that allows the cart 1100 to be positioned adjacent an operating table by a single attendant.

Figure 19:
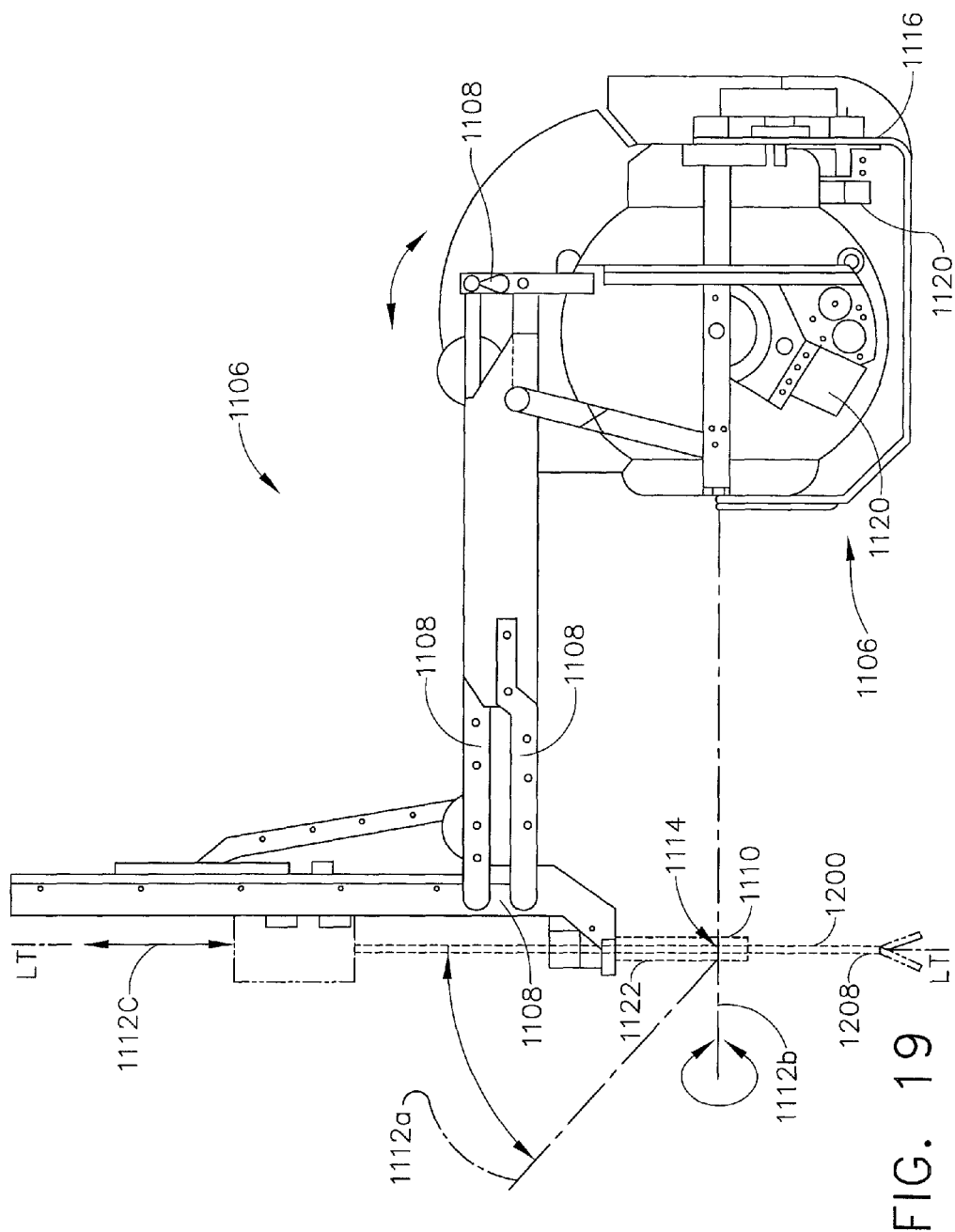
FIG. 19 is a side view of the robotic surgical arm cart/manipulator depicted in FIG. 18.

Referring now to FIG. 19, in at least one form, robotic manipulators 1106 may include a linkage 1108 that constrains movement of the surgical tool 1200. In various embodiments, linkage 1108 includes rigid links coupled together by rotational joints in a parallelogram arrangement so that the surgical tool 1200 rotates around a point in space 1110, as more fully described in issued U.S. Pat. No. 5,817,084, the full disclosure of which is herein incorporated by reference. The parallelogram arrangement constrains rotation to pivoting about an axis 1112a, sometimes called the pitch axis. The links supporting the parallelogram linkage are pivotally mounted to set-up joints 1104 (FIG. 18) so that the surgical tool 1200 further rotates about an axis 1112b, sometimes called the yaw axis. The pitch and yaw axes 1112a, 1112b intersect at the remote center 1114, which is aligned along a shaft 1208 of the surgical tool 1200. The surgical tool 1200 may have further degrees of driven freedom as supported by manipulator 1106, including sliding motion of the surgical tool 1200 along the longitudinal tool axis "LT-LT". As the surgical tool 1200 slides along the tool axis LT-LT relative to manipulator 1106 (arrow 1112c), remote center 1114 remains fixed relative to base 1116 of manipulator 1106. Hence, the entire manipulator is generally moved to re-position remote center 1114. Linkage 1108 of manipulator 1106 is driven by a series of motors 1120. These motors actively move linkage 1108 in response to commands from a processor of a control system. As will be discussed in further detail below, motors 1120 are also employed to manipulate the surgical tool 1200.

Figure 20:
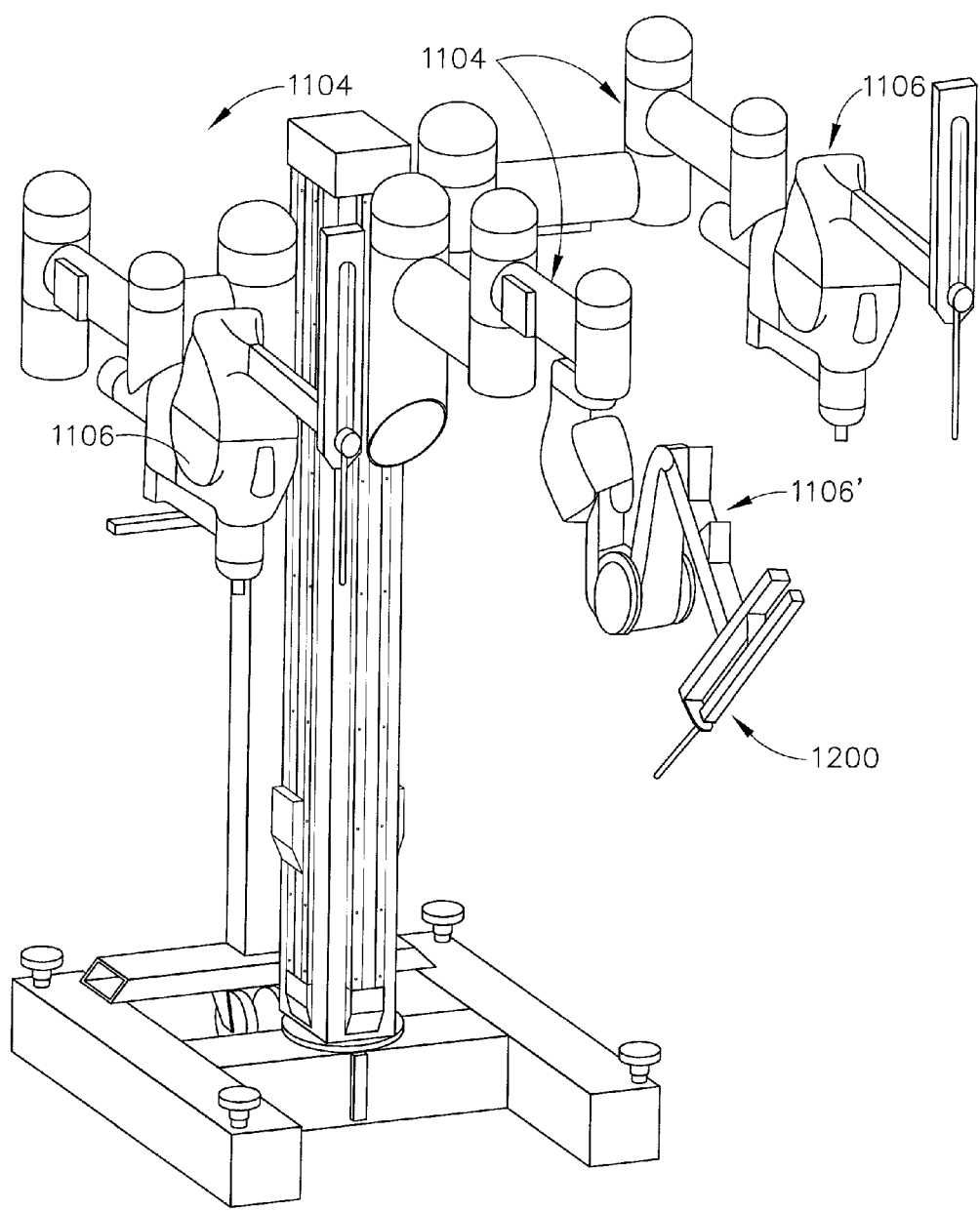
FIG. 20 is a perspective view of an exemplary cart structure with positioning linkages for operably supporting robotic manipulators that may be used with various surgical tool embodiments of the present invention.

An alternative set-up joint structure is illustrated in FIG. 20. In this embodiment, a surgical tool 1200 is supported by an alternative manipulator structure 1106' between two tissue manipulation tools. Those of ordinary skill in the art will appreciate that various embodiments of the present invention may incorporate a wide variety of alternative robotic structures, including those described in U.S. Pat. No. 5,878,193, entitled "Automated Endoscope System For Optimal Positioning", the full disclosure of which is incorporated herein by reference. Additionally, while the data communication between a robotic component and the processor of the robotic surgical system is primarily described herein with reference to communication between the surgical tool 1200 and the master controller 1001, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 21:
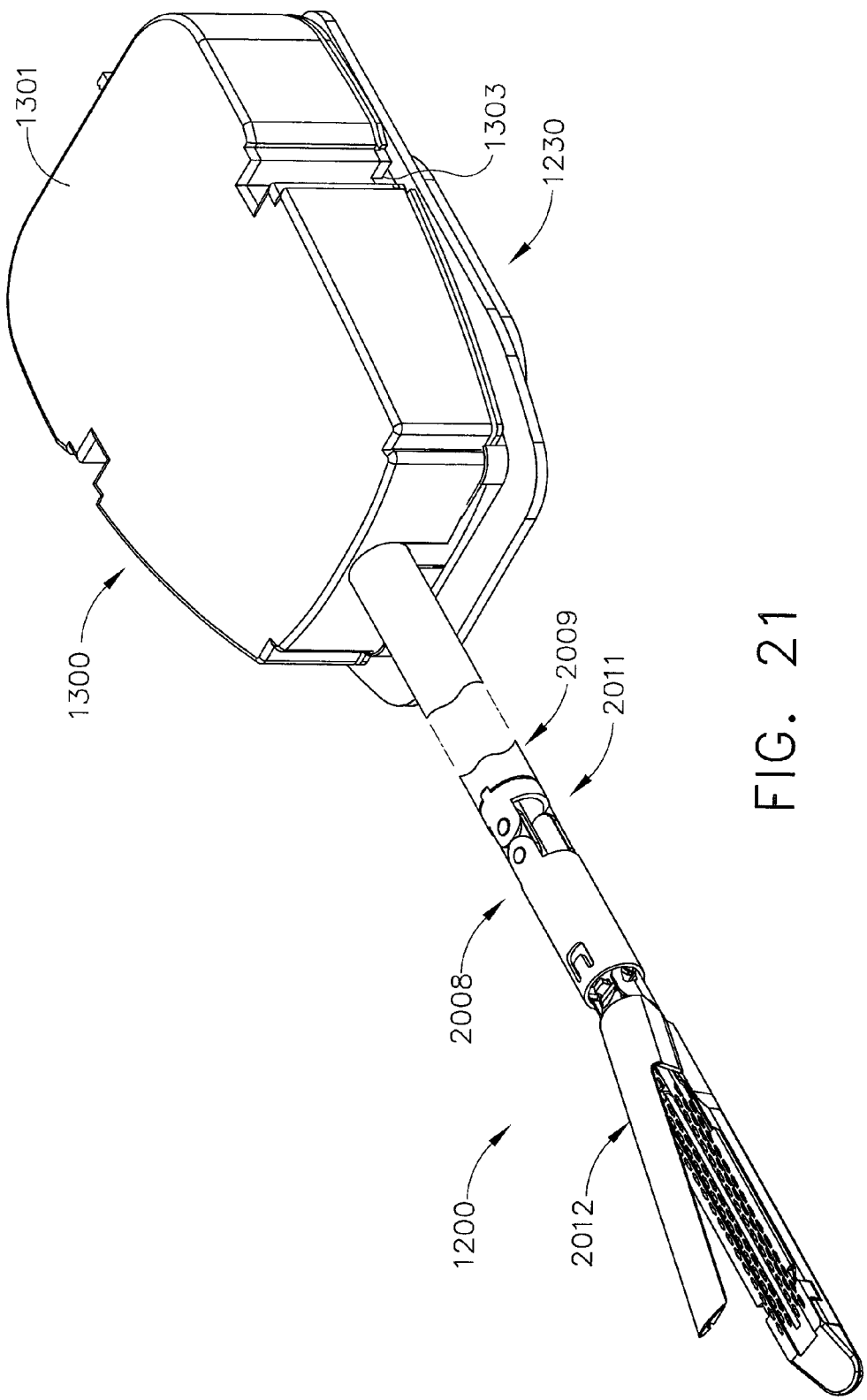
FIG. 21 is a perspective view of a surgical tool embodiment of the present invention.
Figure 26:
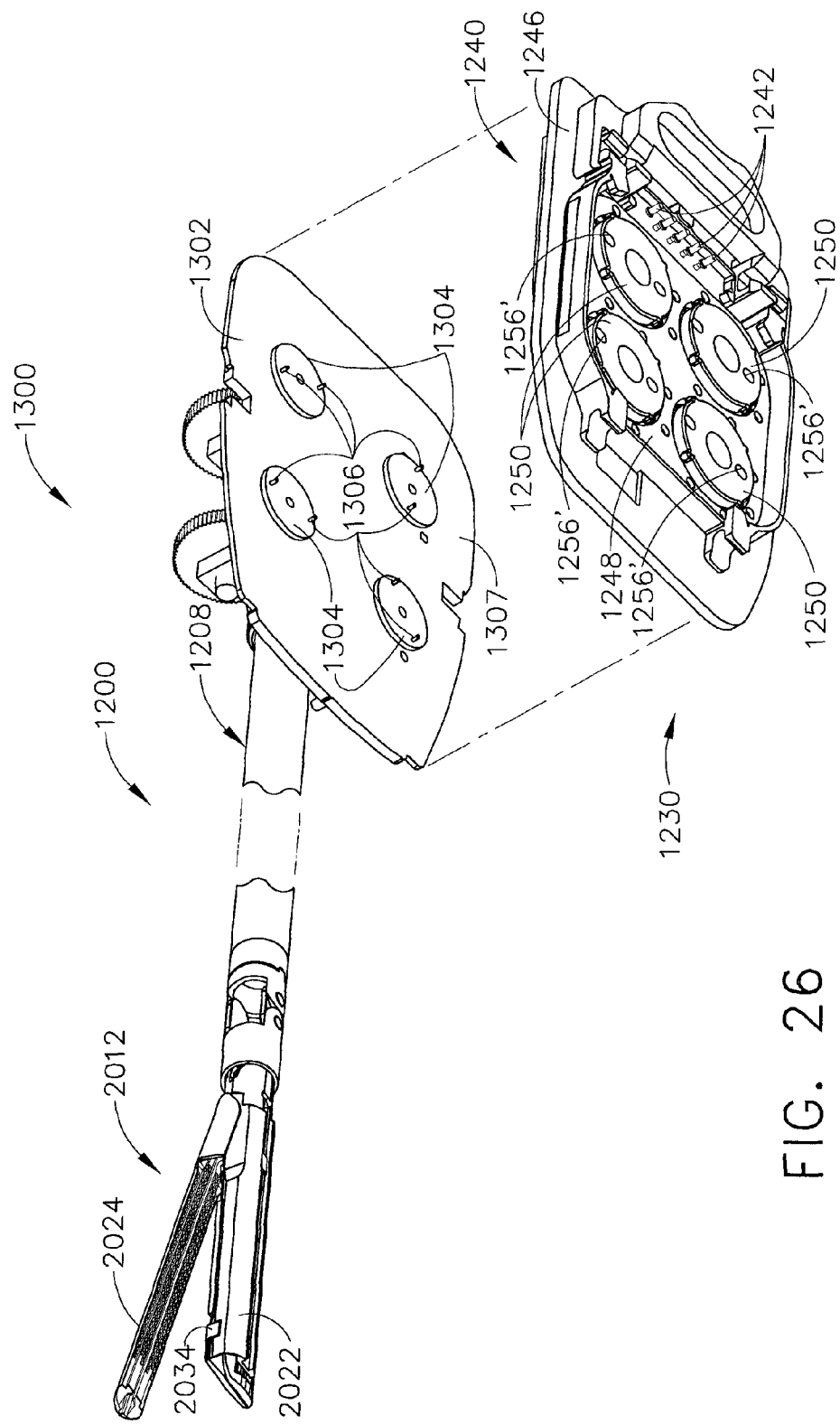
FIG. 26 is a partial bottom perspective view of the surgical tool embodiment of FIG. 21.
Figure 27:
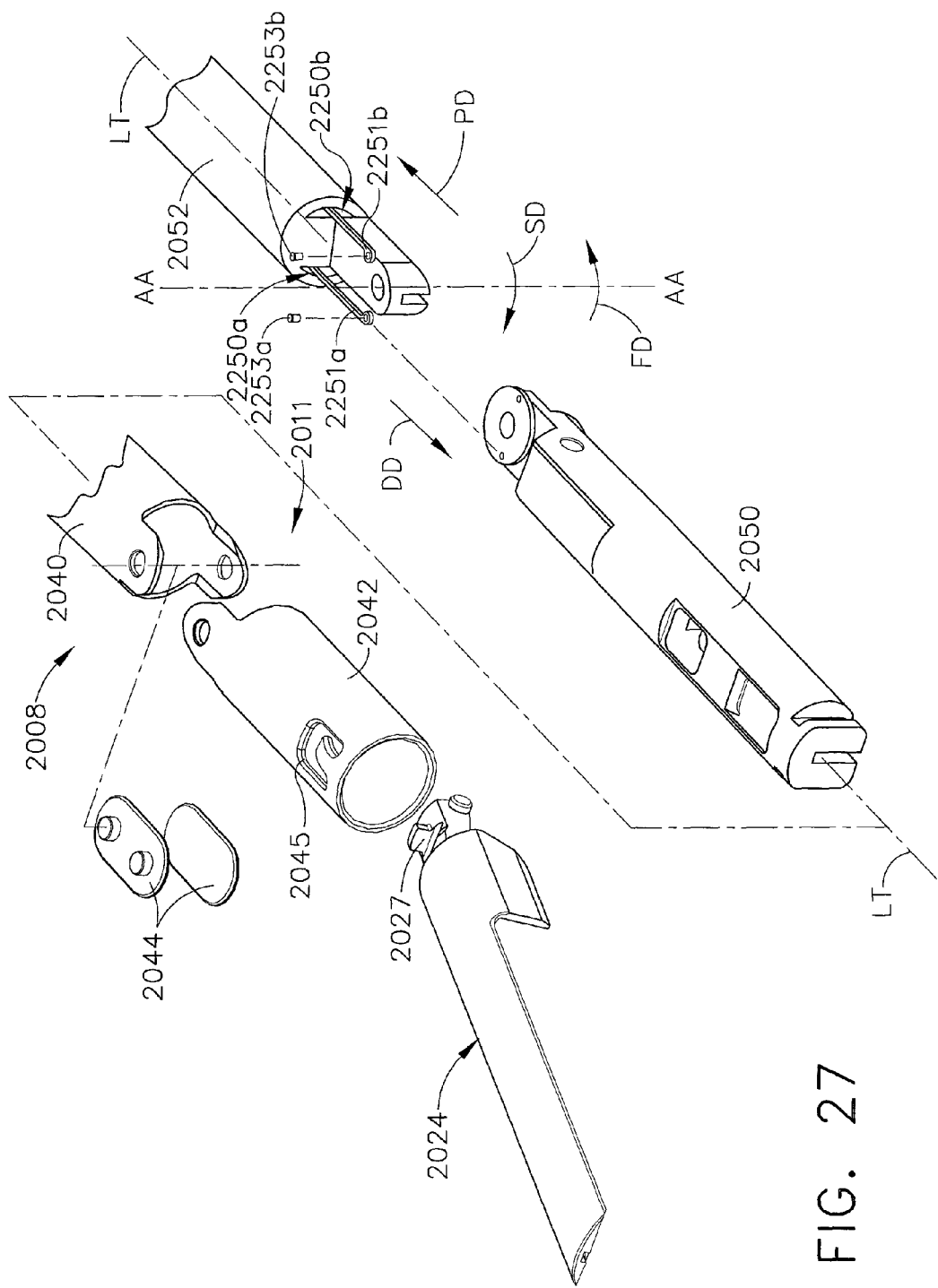
FIG. 27 is a partial exploded view of a portion of an articulatable surgical end effector embodiment of the present invention.
Figure 28:
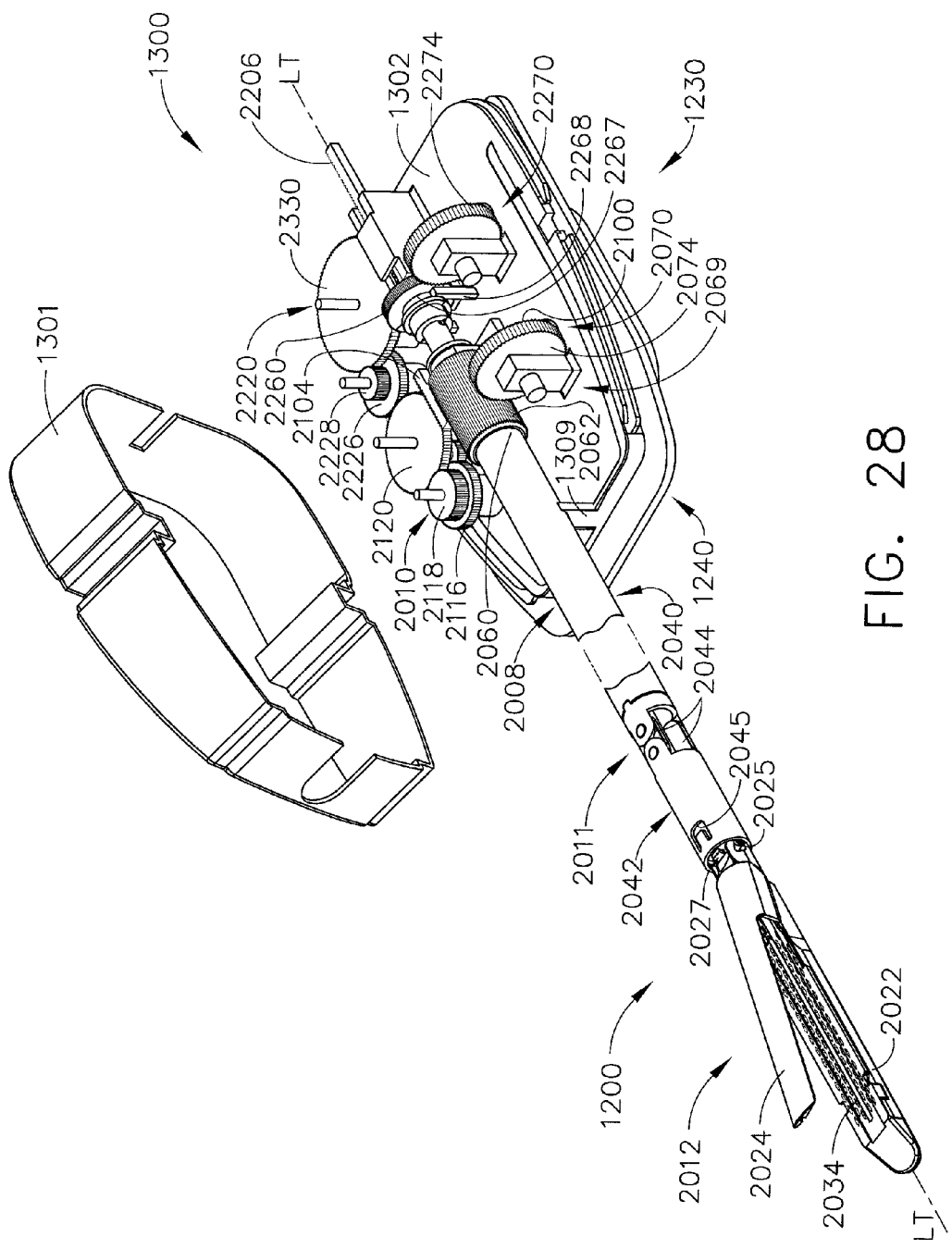
FIG. 28 is a perspective view of the surgical tool embodiment of FIG. 26 with the tool mounting housing removed.

An exemplary non-limiting surgical tool 1200 that is well-adapted for use with a robotic system 1000 that has a tool drive assembly 1010 (FIG. 22) that is operatively coupled to a master controller 1001 that is operable by inputs from an operator (i.e., a surgeon) is depicted in FIG. 21. As can be seen in that Figure, the surgical tool 1200 includes a surgical end effector 2012 that comprises an endocutter. In at least one form, the surgical tool 1200 generally includes an elongated shaft assembly 2008 that has a proximal closure tube 2040 and a distal closure tube 2042 that are coupled together by an articulation joint 2011. The surgical tool 1200 is operably coupled to the manipulator by a tool mounting portion, generally designated as 1300. The surgical tool 1200 further includes an interface 1230 which mechanically and electrically couples the tool mounting portion 1300 to the manipulator. One form of interface 1230 is illustrated in FIGS. 22-26. In various embodiments, the tool mounting portion 1300 includes a tool mounting plate 1302 that operably supports a plurality of (four are shown in FIG. 26) rotatable body portions, driven discs or elements 1304, that each include a pair of pins 1306 that extend from a surface of the driven element 1304. One pin 1306 is closer to an axis of rotation of each driven elements 1304 than the other pin 1306 on the same driven element 1304, which helps to ensure positive angular alignment of the driven element 1304. Interface 1230 includes an adaptor portion 1240 that is configured to mountingly engage the mounting plate 1302 as will be further discussed below. The adaptor portion 1240 may include an array of electrical connecting pins 1242 (FIG. 24) which may be coupled to a memory structure by a circuit board within the tool mounting portion 1300. While interface 1230 is described herein with reference to mechanical, electrical, and magnetic coupling elements, it should be understood that a wide variety of telemetry modalities might be used, including infrared, inductive coupling, or the like.

As can be seen in FIGS. 22-25, the adapter portion 1240 generally includes a tool side 1244 and a holder side 1246. In various forms, a plurality of rotatable bodies 1250 are mounted to a floating plate 1248 which has a limited range of movement relative to the surrounding adaptor structure normal to the major surfaces of the adaptor 1240. Axial movement of the floating plate 1248 helps decouple the rotatable bodies 1250 from the tool mounting portion 1300 when the levers 1303 along the sides of the tool mounting portion housing 1301 are actuated (See FIG. 21). Other mechanisms/arrangements may be employed for releasably coupling the tool mounting portion 1300 to the adaptor 1240. In at least one form, rotatable bodies 1250 are resiliently mounted to floating plate 1248 by resilient radial members which extend into a circumferential indentation about the rotatable bodies 1250. The rotatable bodies 1250 can move axially relative to plate 1248 by deflection of these resilient structures. When disposed in a first axial position (toward tool side 1244) the rotatable bodies 1250 are free to rotate without angular limitation. However, as the rotatable bodies 1250 move axially toward tool side 1244, tabs 1252 (extending radially from the rotatable bodies 1250) laterally engage detents on the floating plates so as to limit angular rotation of the rotatable bodies 1250 about their axes. This limited rotation can be used to help drivingly engage the rotatable bodies 1250 with drive pins 1272 of a corresponding tool holder portion 1270 of the robotic system 1000, as the drive pins 1272 will push the rotatable bodies 1250 into the limited rotation position until the pins 1234 are aligned with (and slide into) openings 1256'. Openings 1256 on the tool side 1244 and openings 1256' on the holder side 1246 of rotatable bodies 1250 are configured to accurately align the driven elements 1304 (FIG. 26) of the tool mounting portion 1300 with the drive elements 1271 of the tool holder 1270. As described above regarding inner and outer pins 1306 of driven elements 1304, the openings 1256, 1256' are at differing distances from the axis of rotation on their respective rotatable bodies 1250 so as to ensure that the alignment is not 180 degrees from its intended position. Additionally, each of the openings 1256 is slightly radially elongated so as to fittingly receive the pins 1306 in the circumferential orientation. This allows the pins 1306 to slide radially within the openings 1256, 1256' and accommodate some axial misalignment between the tool 1200 and tool holder 1270, while minimizing any angular misalignment and backlash between the drive and driven elements. Openings 1256 on the tool side 1244 are offset by about 90 degrees from the openings 1256' (shown in broken lines) on the holder side 1246, as can be seen most clearly in FIG. 25.

Various embodiments may further include an array of electrical connector pins 1242 located on holder side 1246 of adaptor 1240, and the tool side 1244 of the adaptor 1240 may include slots 1258 (FIG. 25) for receiving a pin array (not shown) from the tool mounting portion 1300. In addition to transmitting electrical signals between the surgical tool 1200 and the tool holder 1270, at least some of these electrical connections may be coupled to an adaptor memory device 1260 (FIG. 24) by a circuit board of the adaptor 1240.

Figure 22:
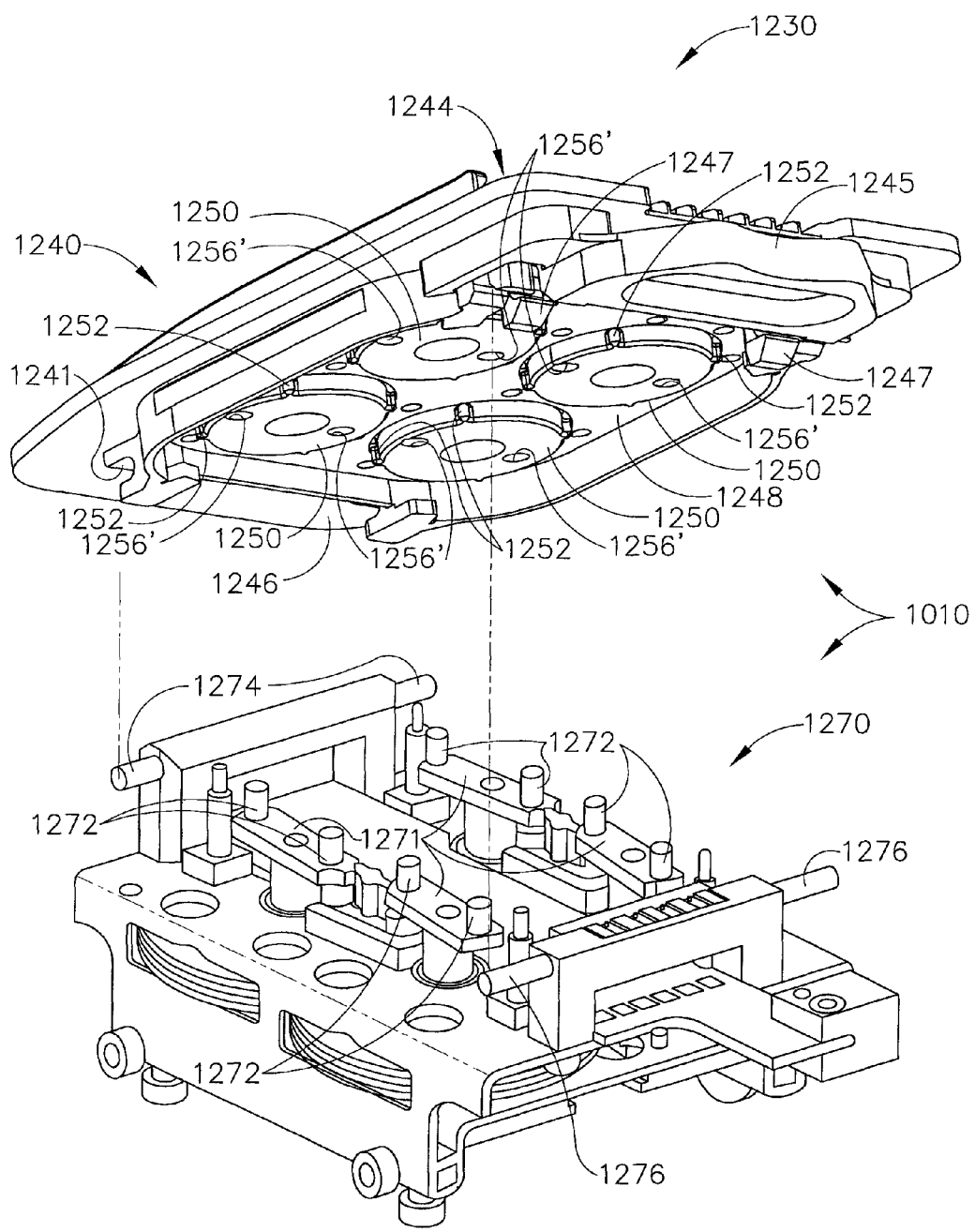
FIG. 22 is an exploded assembly view of an adapter and tool holder arrangement for attaching various surgical tool embodiments to a robotic system.
Figure 23:
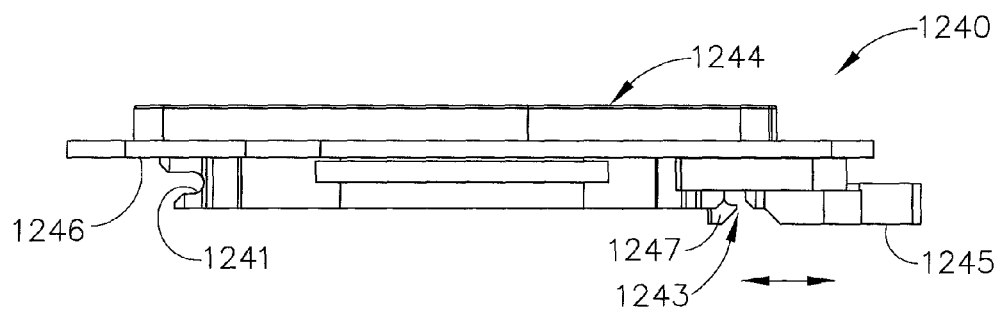
FIG. 23 is a side view of the adapter shown in FIG. 22.
Figure 24:
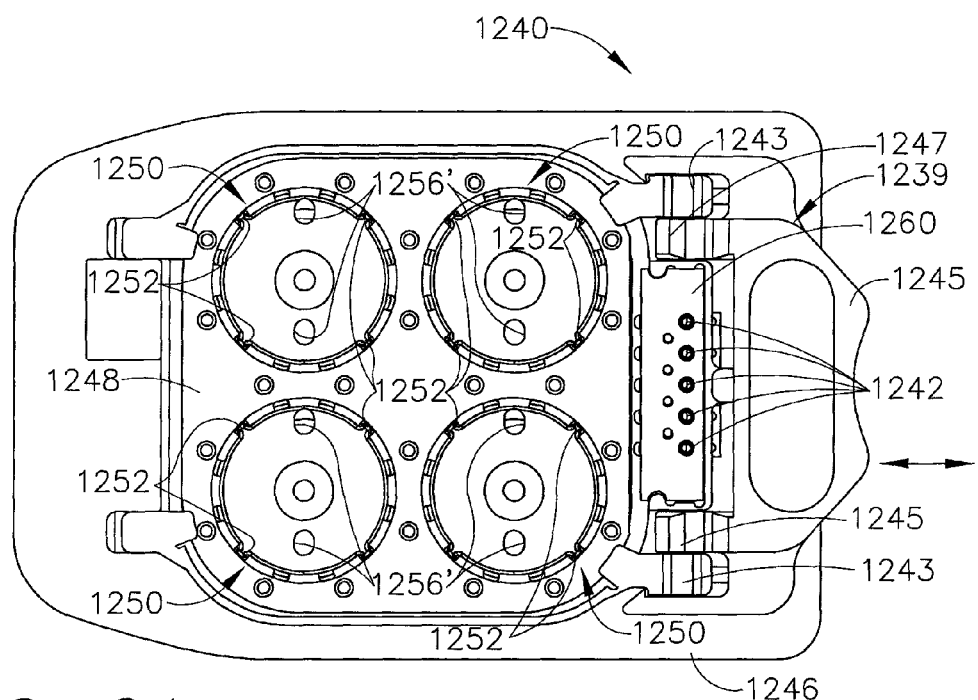
FIG. 24 is a bottom view of the adapter shown in FIG. 22.
Figure 25:
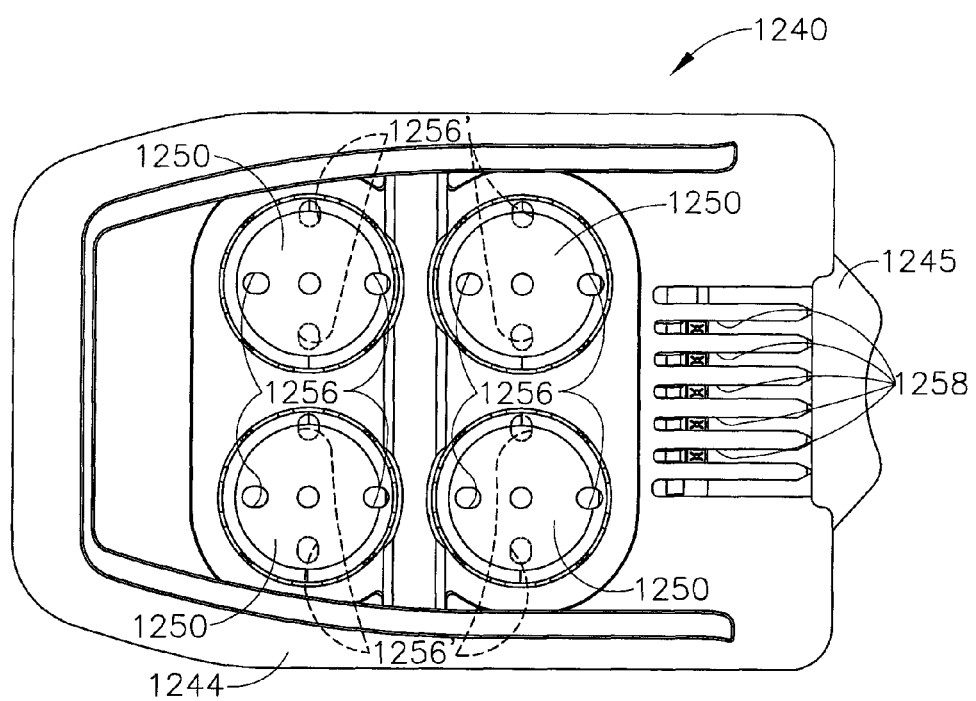
FIG. 25 is a top view of the adapter of FIGS. 22 and 23.

A detachable latch arrangement 1239 may be employed to releasably affix the adaptor 1240 to the tool holder 1270. As used herein, the term "tool drive assembly" when used in the context of the robotic system 1000, at least encompasses various embodiments of the adapter 1240 and tool holder 1270 and which has been generally designated as 1010 in FIG. 22. For example, as can be seen in FIG. 22, the tool holder 1270 may include a first latch pin arrangement 1274 that is sized to be received in corresponding clevis slots 1241 provided in the adaptor 1240. In addition, the tool holder 1270 may further have second latch pins 1276 that are sized to be retained in corresponding latch clevises 1243 in the adaptor 1240. See FIG. 24. In at least one form, a latch assembly 1245 is movably supported on the adapter 1240 and is biasable between a first latched position wherein the latch pins 1276 are retained within their respective latch clevis 1243 and an unlatched position wherein the second latch pins 1276 may be into or removed from the latch clevises 1243. A spring or springs (not shown) are employed to bias the latch assembly into the latched position. A lip on the tool side 1244 of adaptor 1240 may slidably receive laterally extending tabs of tool mounting housing 1301.

Figure 37:
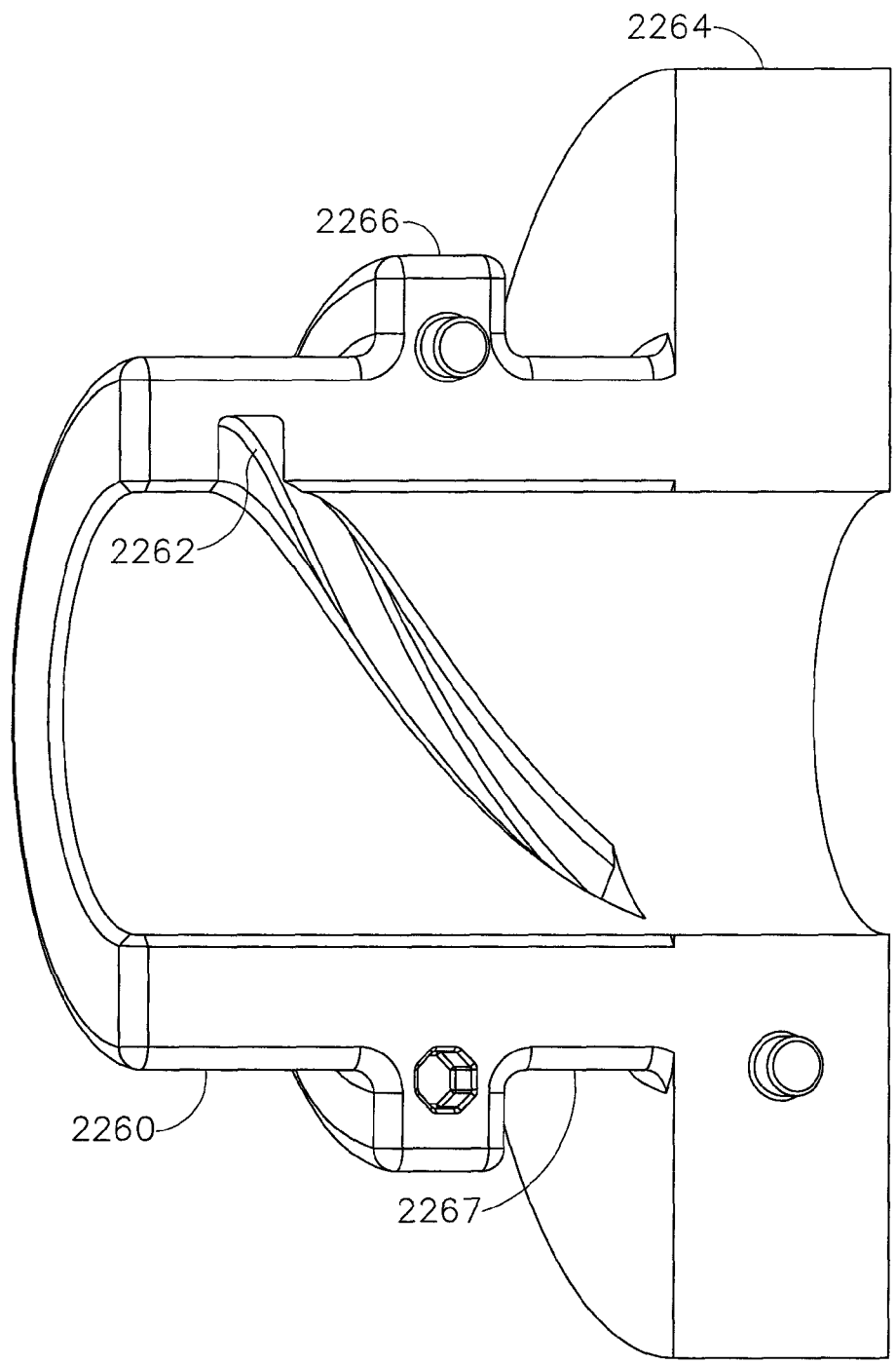
FIG. 37 is a side view of a half portion of a closure nut embodiment of a surgical tool embodiment of the present invention.
Figure 38:
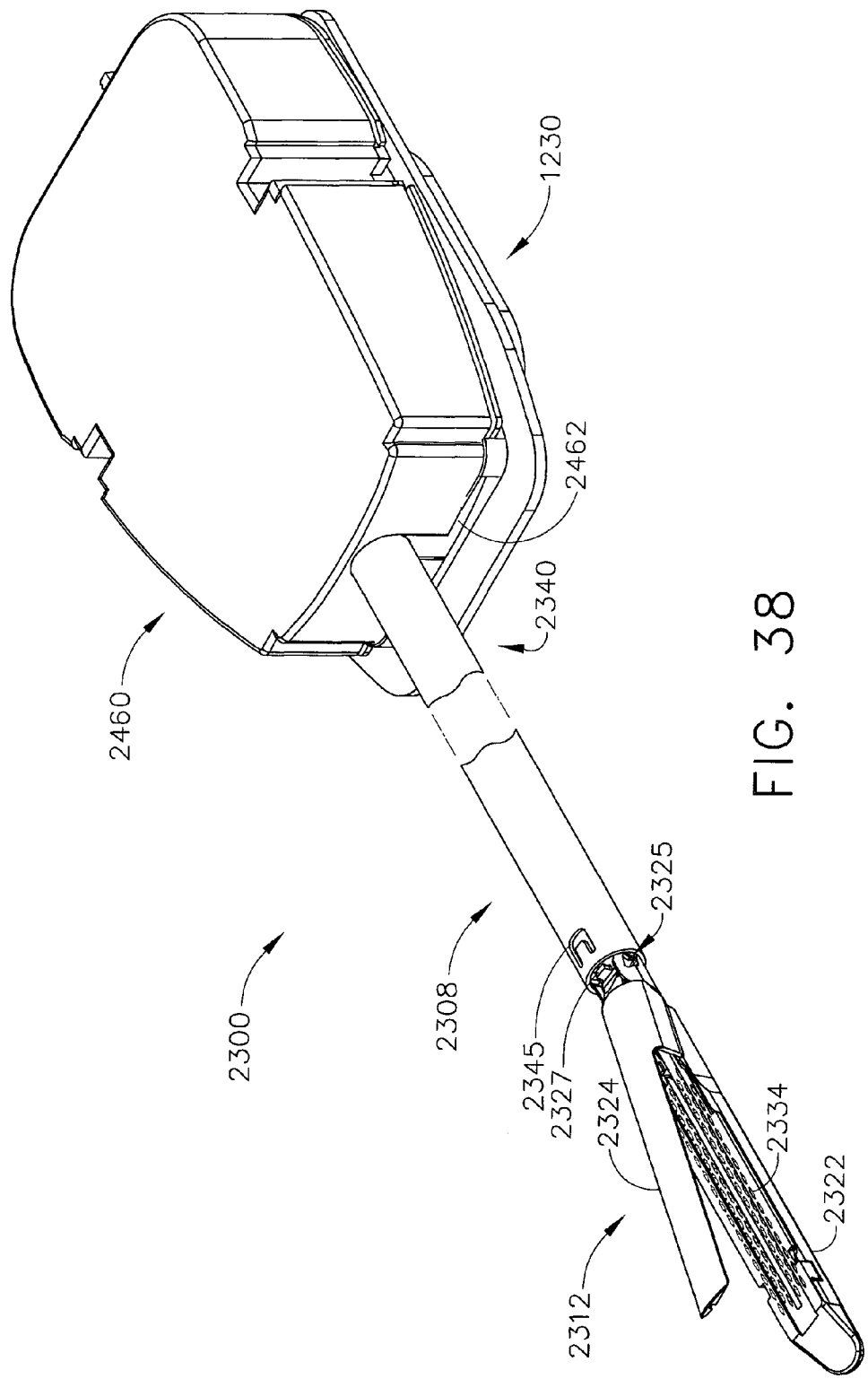
FIG. 38 is a perspective view of another surgical tool embodiment of the present invention.

Turning next to FIGS. 26-33, in at least one embodiment, the surgical tool 1200 includes a surgical end effector 2012 that comprises in this example, among other things, at least one component 2024 that is selectively movable between first and second positions relative to at least one other component 2022 in response to various control motions applied thereto as will be discussed in further detail below. In various embodiments, component 2022 comprises an elongated channel 2022 configured to operably support a surgical staple cartridge 2034 therein and component 2024 comprises a pivotally translatable clamping member, such as an anvil 2024. Various embodiments of the surgical end effector 2012 are configured to maintain the anvil 2024 and elongated channel 2022 at a spacing that assures effective stapling and severing of tissue clamped in the surgical end effector 2012. As can be seen in FIG. 37, the surgical end effector 2012 further includes a cutting instrument 2032 and a sled 2033. The cutting instrument 2032 may be, for example, a knife. The surgical staple cartridge 2034 operably houses a plurality of surgical staples (not show) therein that are supported on movable staple drivers (not shown). As the cutting instrument 2032 is driven distally through a centrally-disposed slot (not shown) in the surgical staple cartridge 2034, it forces the sled 2033 distally as well. As the sled 2033 is driven distally, its "wedge-shaped" configuration contacts the movable staple drivers and drives them vertically toward the closed anvil 2024. The surgical staples are formed as they are driven into the forming surface located on the underside of the anvil 2024. The sled 2033 may be part of the surgical staple cartridge 2034, such that when the cutting instrument 2032 is retracted following the cutting operation, the sled 2033 does not retract. The anvil 2024 may be pivotably opened and closed at a pivot point 2025 located at the proximal end of the elongated channel 2022. The anvil 2024 may also include a tab 2027 at its proximal end that interacts with a component of the mechanical closure system (described further below) to facilitate the opening of the anvil 2024. The elongated channel 2022 and the anvil 2024 may be made of an electrically conductive material (such as metal) so that they may serve as part of an antenna that communicates with sensor(s) in the end effector, as described above. The surgical staple cartridge 2034 could be made of a nonconductive material (such as plastic) and the sensor may be connected to or disposed in the surgical staple cartridge 2034, as was also described above.

As can be seen in FIGS. 26-33, the surgical end effector 2012 is attached to the tool mounting portion 1300 by an elongated shaft assembly 2008 according to various embodiments. As shown in the illustrated embodiment, the shaft assembly 2008 includes an articulation joint generally indicated as 2011 that enables the surgical end effector 2012 to be selectively articulated about an articulation axis AA-AA that is substantially transverse to a longitudinal tool axis LT-LT. See FIG. 27. In other embodiments, the articulation joint is omitted. In various embodiments, the shaft assembly 2008 may include a closure tube assembly 2009 that comprises a proximal closure tube 2040 and a distal closure tube 2042 that are pivotably linked by a pivot links 2044 and operably supported on a spine assembly generally depicted as 2049. In the illustrated embodiment, the spine assembly 2049 comprises a distal spine portion 2050 that is attached to the elongated channel 2022 and is pivotally coupled to the proximal spine portion 2052. The closure tube assembly 2009 is configured to axially slide on the spine assembly 2049 in response to actuation motions applied thereto. The distal closure tube 2042 includes an opening 2045 into which the tab 2027 on the anvil 2024 is inserted in order to facilitate opening of the anvil 2024 as the distal closure tube 2042 is moved axially in the proximal direction "PD". The closure tubes 2040, 2042 may be made of electrically conductive material (such as metal) so that they may serve as part of the antenna, as described above. Components of the main drive shaft assembly (e.g., the drive shafts 2048, 2050) may be made of a nonconductive material (such as plastic).

Figure 29:
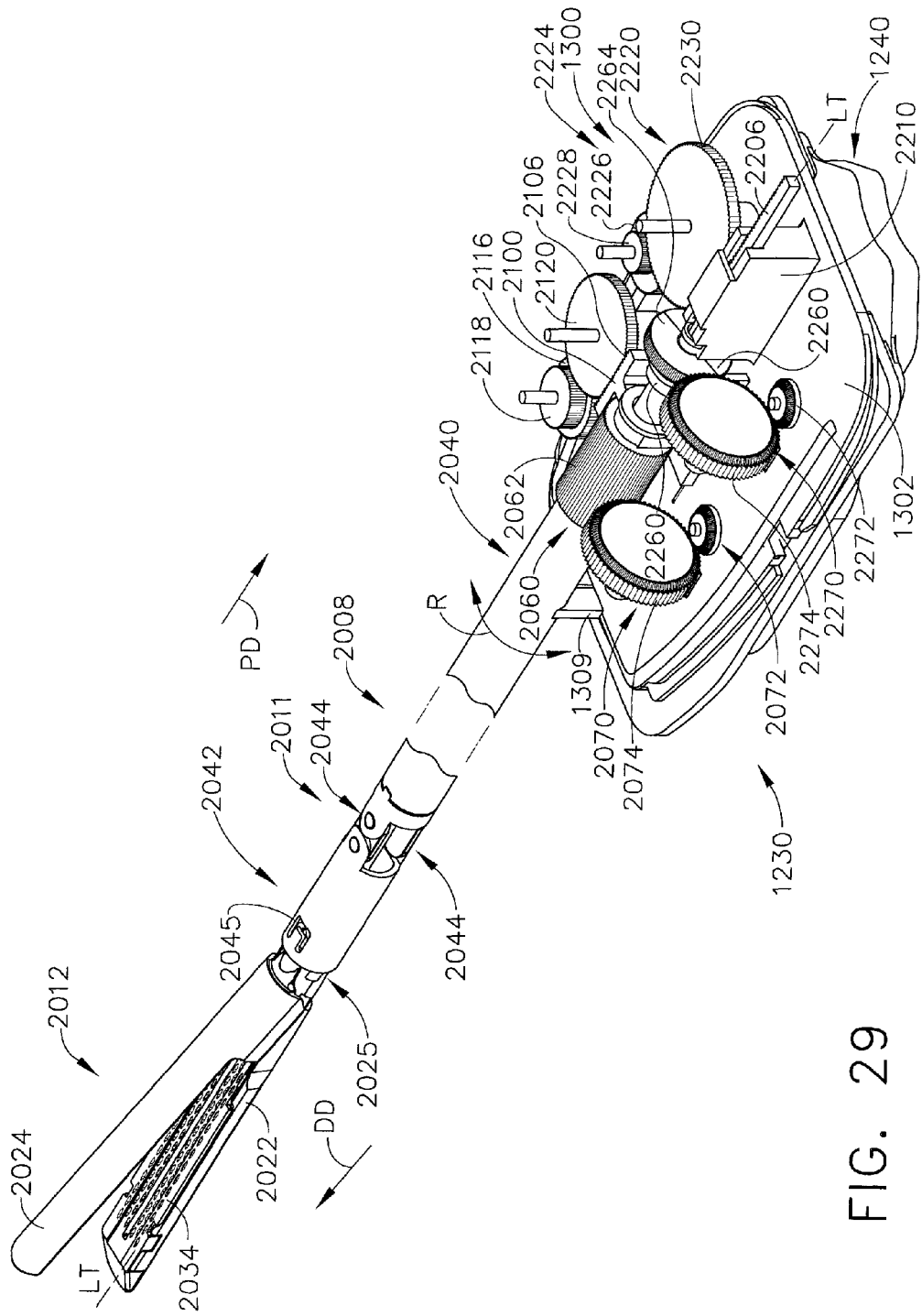
FIG. 29 is a rear perspective view of the surgical tool embodiment of FIG. 26 with the tool mounting housing removed.

In use, it may be desirable to rotate the surgical end effector 2012 about the longitudinal tool axis LT-LT. In at least one embodiment, the tool mounting portion 1300 includes a rotational transmission assembly 2069 that is configured to receive a corresponding rotary output motion from the tool drive assembly 1010 of the robotic system 1000 and convert that rotary output motion to a rotary control motion for rotating the elongated shaft assembly 2008 (and surgical end effector 2012) about the longitudinal tool axis LT-LT. In various embodiments, for example, the proximal end 2060 of the proximal closure tube 2040 is rotatably supported on the tool mounting plate 1302 of the tool mounting portion 1300 by a forward support cradle 1309 and a closure sled 2100 that is also movably supported on the tool mounting plate 1302. In at least one form, the rotational transmission assembly 2069 includes a tube gear segment 2062 that is formed on (or attached to) the proximal end 2060 of the proximal closure tube 2040 for operable engagement by a rotational gear assembly 2070 that is operably supported on the tool mounting plate 1302. As can be seen in FIG. 29, the rotational gear assembly 2070, in at least one embodiment, comprises a rotation drive gear 2072 that is coupled to a corresponding first one of the driven discs or elements 1304 on the adapter side 1307 of the tool mounting plate 1302 when the tool mounting portion 1300 is coupled to the tool drive assembly 1010. See FIG. 26. The rotational gear assembly 2070 further comprises a rotary driven gear 2074 that is rotatably supported on the tool mounting plate 1302 in meshing engagement with the tube gear segment 2062 and the rotation drive gear 2072. Application of a first rotary output motion from the tool drive assembly 1010 of the robotic system 1000 to the corresponding driven element 1304 will thereby cause rotation of the rotation drive gear 2072. Rotation of the rotation drive gear 2072 ultimately results in the rotation of the elongated shaft assembly 2008 (and the surgical end effector 2012) about the longitudinal tool axis LT-LT (represented by arrow "R" in FIG. 29). It will be appreciated that the application of a rotary output motion from the tool drive assembly 1010 in one direction will result in the rotation of the elongated shaft assembly 2008 and surgical end effector 2012 about the longitudinal tool axis LT-LT in a first direction and an application of the rotary output motion in an opposite direction will result in the rotation of the elongated shaft assembly 2008 and surgical end effector 2012 in a second direction that is opposite to the first direction.

Figure 31:
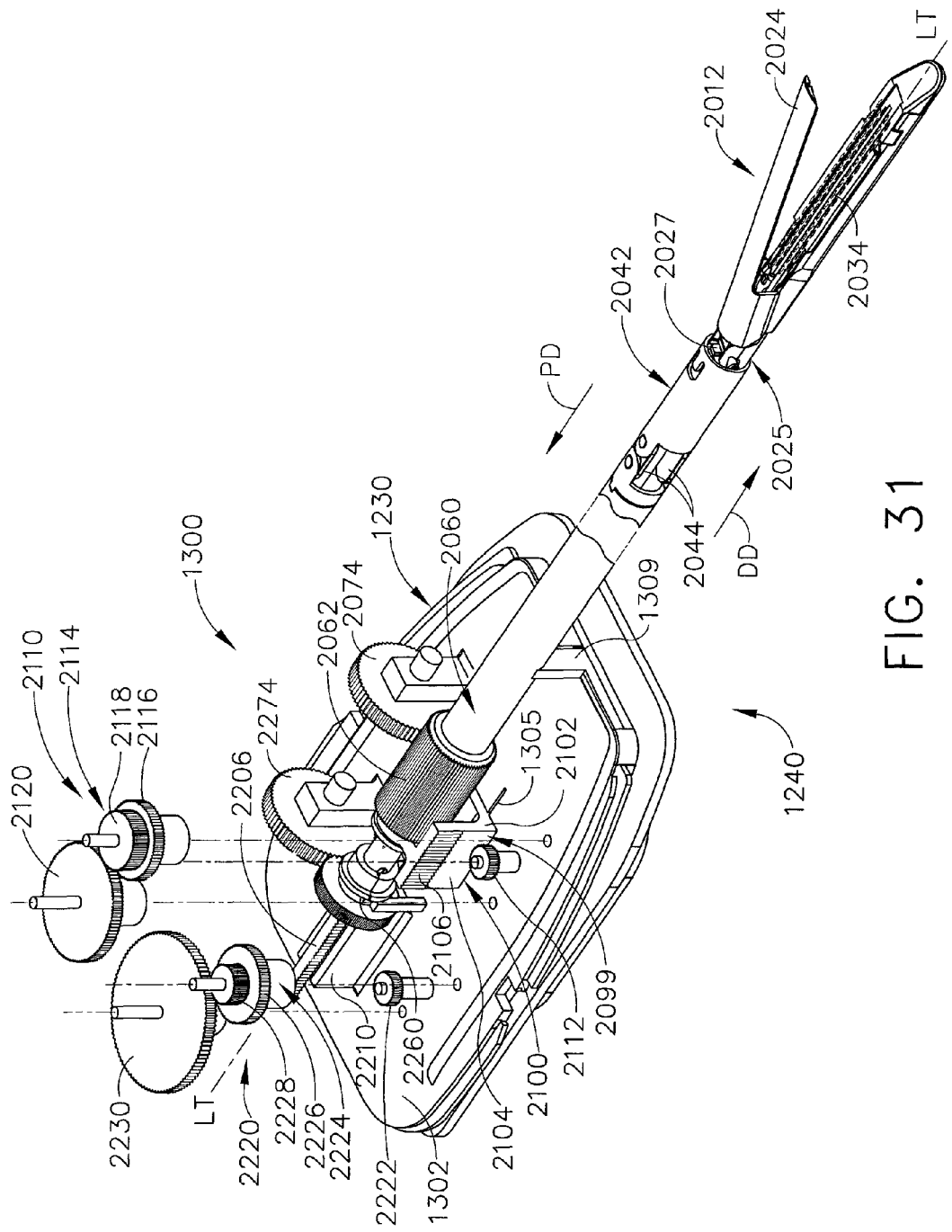
FIG. 31 is a partial exploded perspective view of the surgical tool embodiment of FIG. 30.
Figure 34:
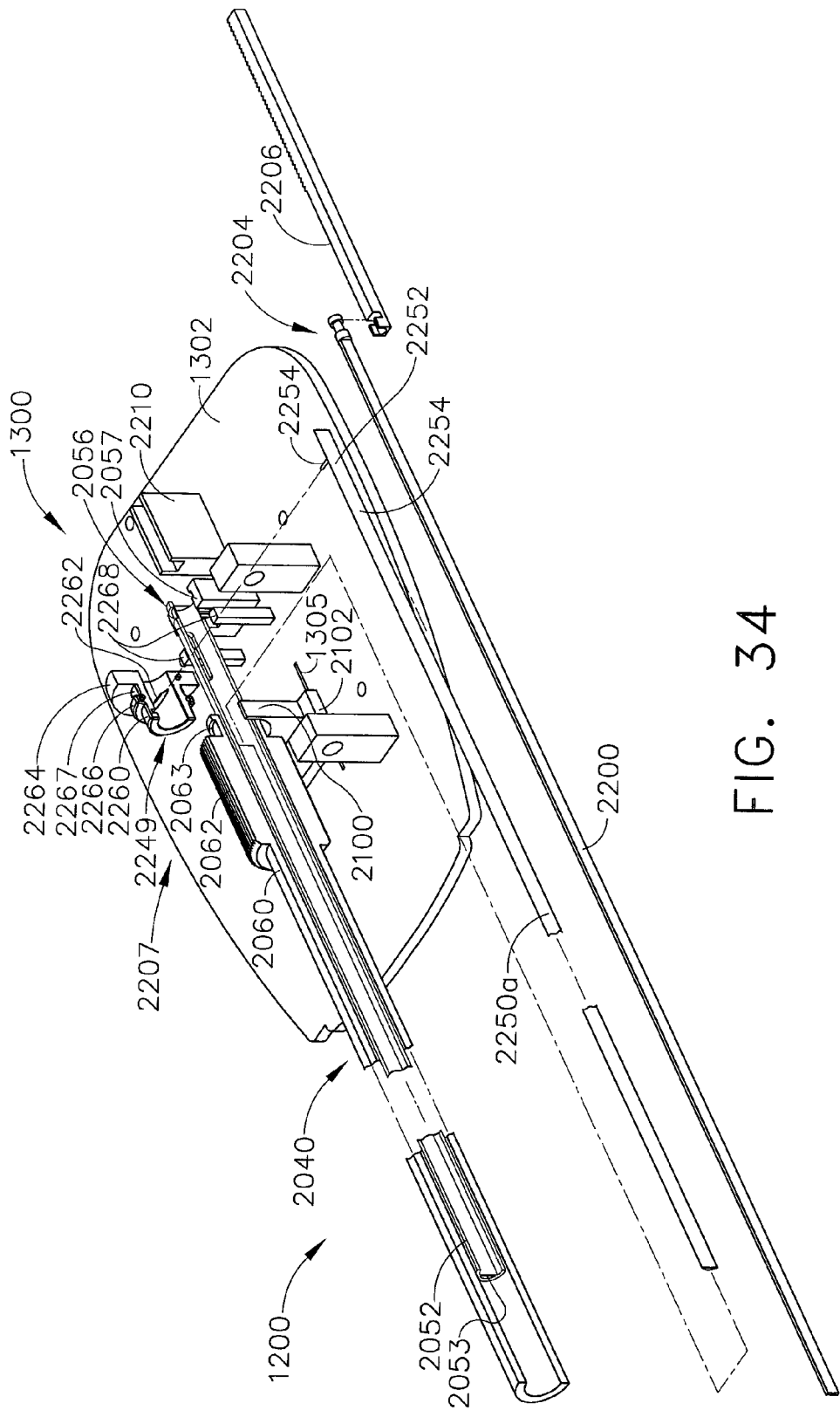
FIG. 34 is an exploded perspective view of a portion of the tool mounting portion of the surgical tool embodiment depicted in FIG. 26.

In at least one embodiment, the closure of the anvil 2024 relative to the staple cartridge 2034 is accomplished by axially moving the closure tube assembly 2009 in the distal direction "DD" on the spine assembly 2049. As indicated above, in various embodiments, the proximal end 2060 of the proximal closure tube 2040 is supported by the closure sled 2100 which comprises a portion of a closure transmission, generally depicted as 2099. In at least one form, the closure sled 2100 is configured to support the closure tube 2009 on the tool mounting plate 1320 such that the proximal closure tube 2040 can rotate relative to the closure sled 2100, yet travel axially with the closure sled 2100. In particular, as can be seen in FIG. 34, the closure sled 2100 has an upstanding tab 2101 that extends into a radial groove 2063 in the proximal end portion of the proximal closure tube 2040. In addition, as can be seen in FIGS. 31 and 34, the closure sled 2100 has a tab portion 2102 that extends through a slot 1305 in the tool mounting plate 1302. The tab portion 2102 is configured to retain the closure sled 2100 in sliding engagement with the tool mounting plate 1302. In various embodiments, the closure sled 2100 has an upstanding portion 2104 that has a closure rack gear 2106 formed thereon. The closure rack gear 2106 is configured for driving engagement with a closure gear assembly 2110. See FIG. 31.

Figure 30:
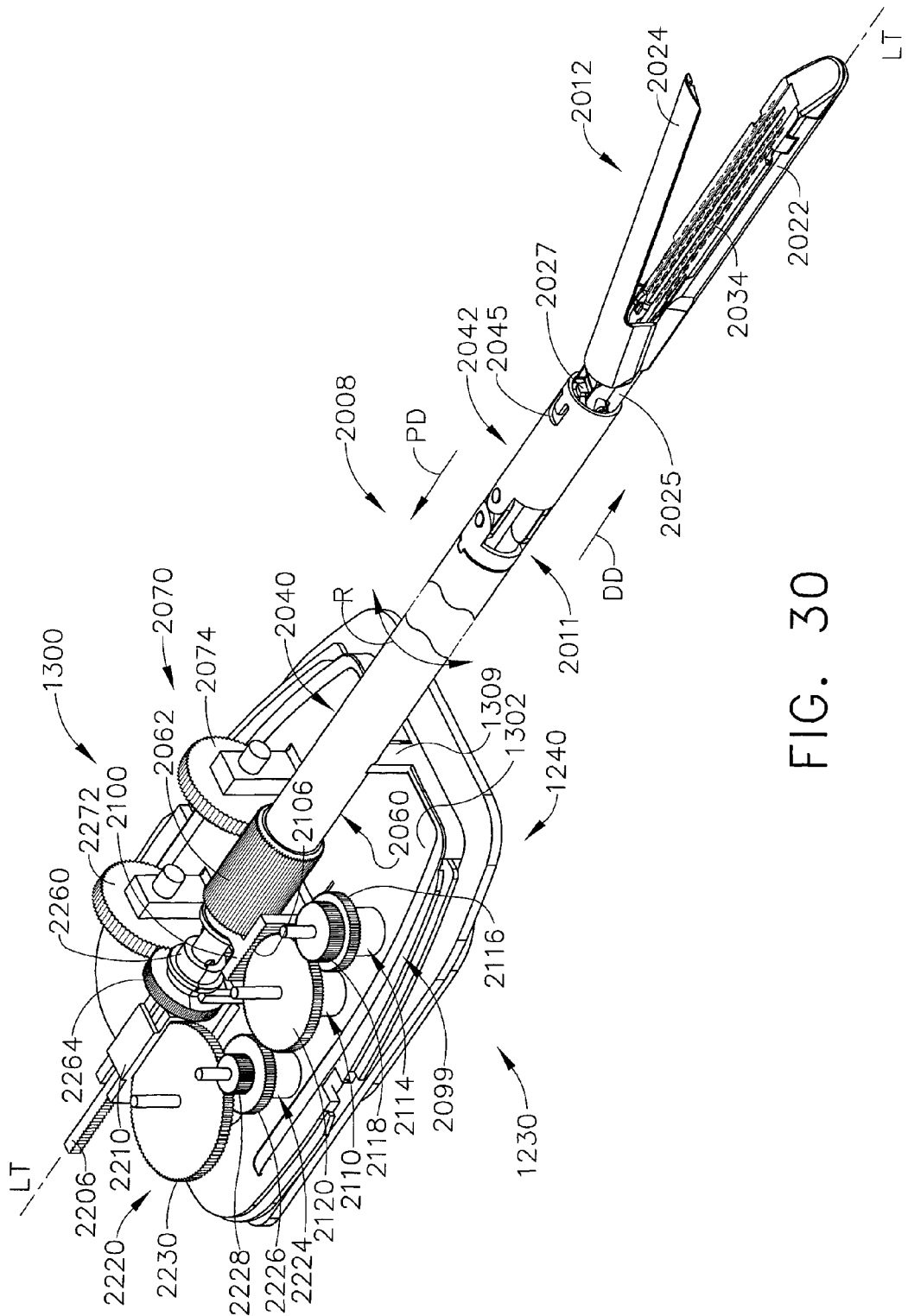
FIG. 30 is a front perspective view of the surgical tool embodiment of FIG. 26 with the tool mounting housing removed.

In various forms, the closure gear assembly 2110 includes a closure spur gear 2112 that is coupled to a corresponding second one of the driven discs or elements 1304 on the adapter side 1307 of the tool mounting plate 1302. See FIG. 26. Thus, application of a second rotary output motion from the tool drive assembly 1010 of the robotic system 1000 to the corresponding second driven element 1304 will cause rotation of the closure spur gear 2112 when the tool mounting portion 1300 is coupled to the tool drive assembly 1010. The closure gear assembly 2110 further includes a closure reduction gear set 2114 that is supported in meshing engagement with the closure spur gear 2112. As can be seen in FIGS. 30 and 31, the closure reduction gear set 2114 includes a driven gear 2116 that is rotatably supported in meshing engagement with the closure spur gear 2112. The closure reduction gear set 2114 further includes a first closure drive gear 2118 that is in meshing engagement with a second closure drive gear 2120 that is rotatably supported on the tool mounting plate 1302 in meshing engagement with the closure rack gear 2106. Thus, application of a second rotary output motion from the tool drive assembly 1010 of the robotic system 1000 to the corresponding second driven element 1304 will cause rotation of the closure spur gear 2112 and the closure transmission 2110 and ultimately drive the closure sled 2100 and closure tube assembly 2009 axially. The axial direction in which the closure tube assembly 2009 moves ultimately depends upon the direction in which the second driven element 1304 is rotated. For example, in response to one rotary output motion received from the tool drive assembly 1010 of the robotic system 1000, the closure sled 2100 will be driven in the distal direction "DD" and ultimately drive the closure tube assembly 1009 in the distal direction. As the distal closure tube 2042 is driven distally, the end of the closure tube segment 2042 will engage a portion of the anvil 2024 and cause the anvil 2024 to pivot to a closed position. Upon application of an "opening" out put motion from the tool drive assembly 1010 of the robotic system 1000, the closure sled 2100 and shaft assembly 2008 will be driven in the proximal direction "PD". As the distal closure tube 2042 is driven in the proximal direction, the opening 2045 therein interacts with the tab 2027 on the anvil 2024 to facilitate the opening thereof. In various embodiments, a spring (not shown) may be employed to bias the anvil to the open position when the distal closure tube 2042 has been moved to its starting position. In various embodiments, the various gears of the closure gear assembly 2110 are sized to generate the necessary closure forces needed to satisfactorily close the anvil 2024 onto the tissue to be cut and stapled by the surgical end effector 2012. For example, the gears of the closure transmission 2110 may be sized to generate approximately 70-120 pounds.

Figure 35:
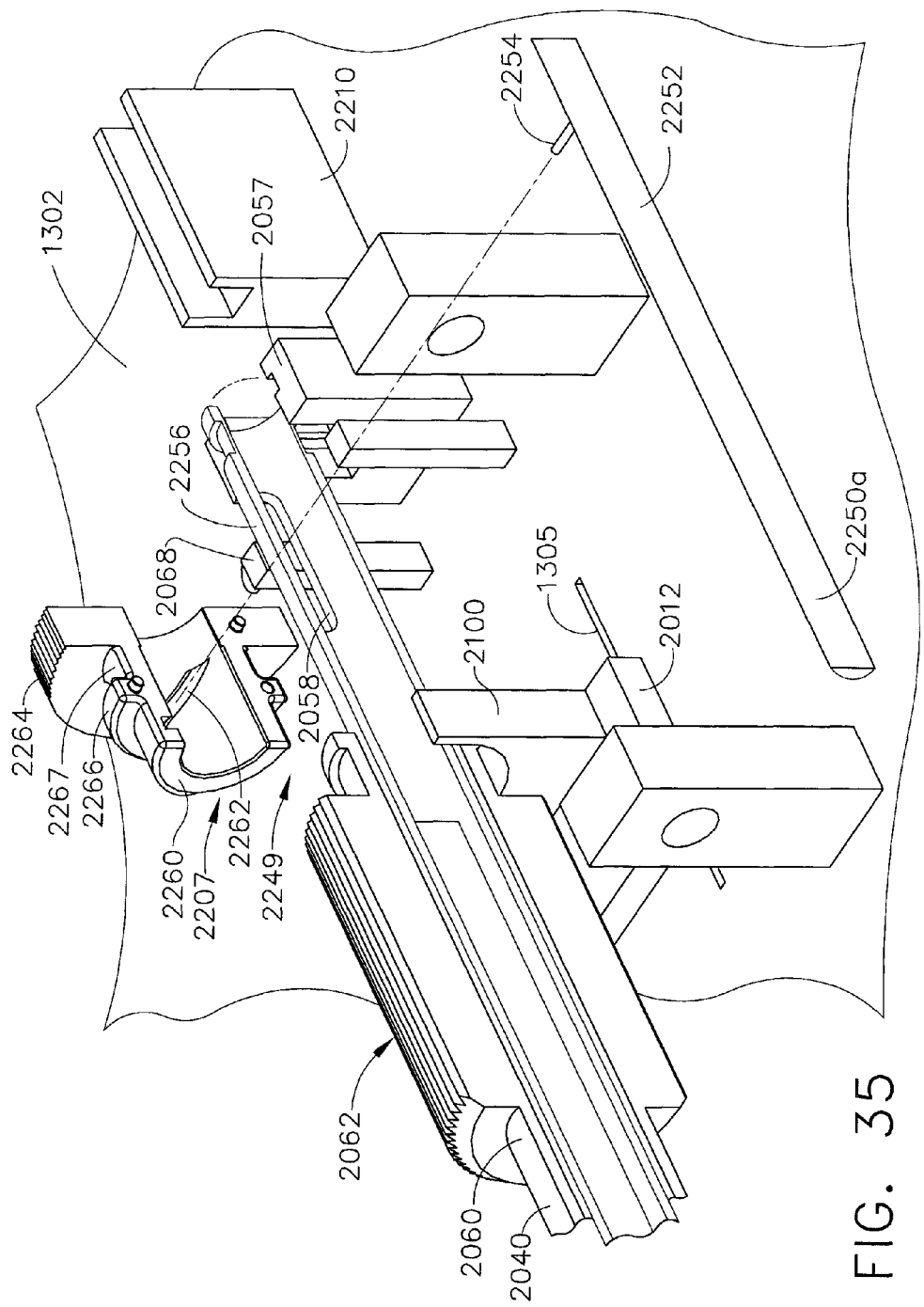
FIG. 35 is an enlarged exploded perspective view of a portion of the tool mounting portion of FIG. 34.
Figure 36:
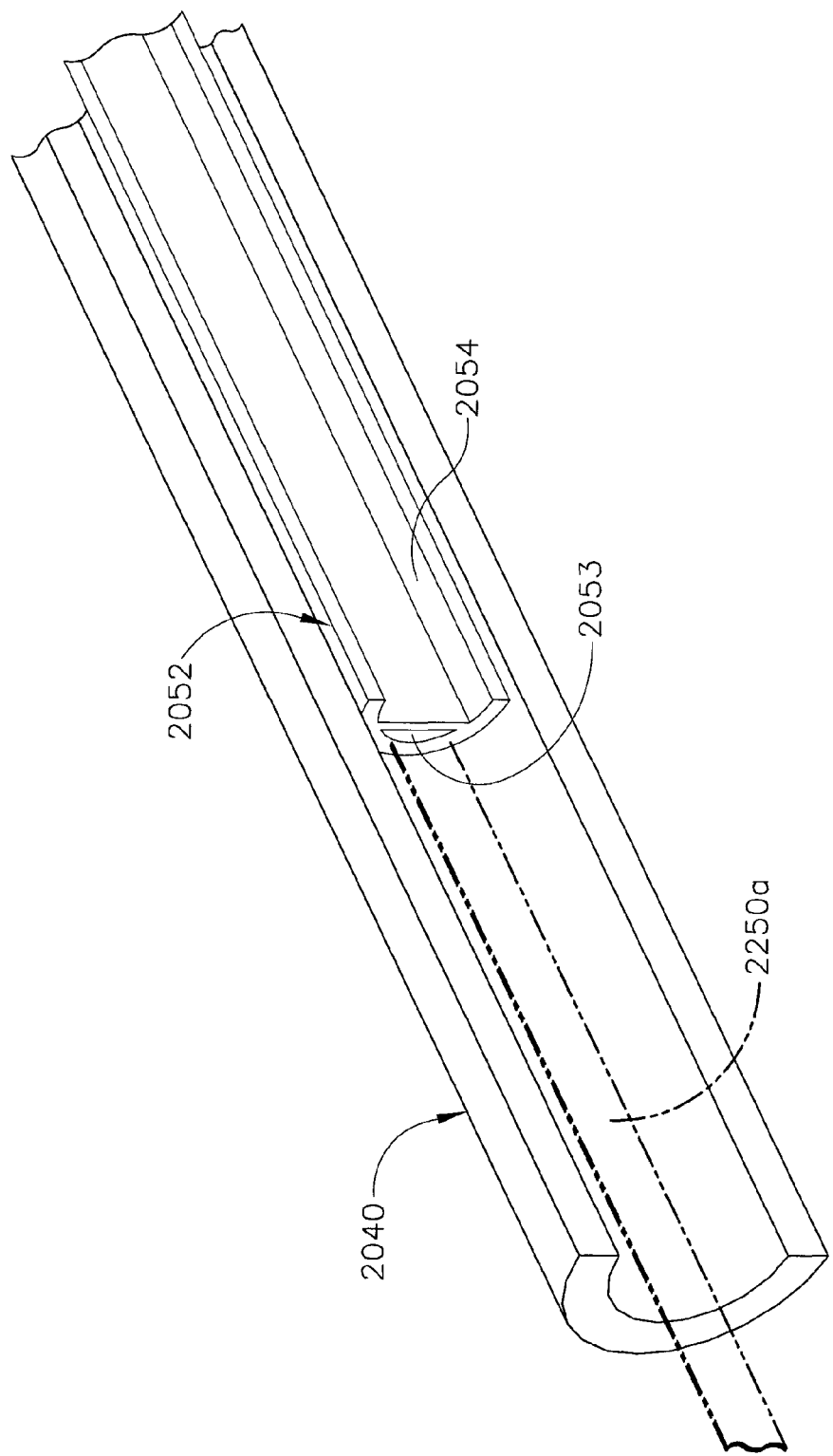
FIG. 36 is a partial cross-sectional view of a portion of the elongated shaft assembly of the surgical tool of FIG. 26.

In various embodiments, the cutting instrument 2032 is driven through the surgical end effector 2012 by a knife bar 2200. See FIGS. 32 and 34. In at least one form, the knife bar 2200 may be fabricated from, for example, stainless steel or other similar material and has a substantially rectangular cross-sectional shape. Such knife bar configuration is sufficiently rigid to push the cutting instrument 2032 through tissue clamped in the surgical end effector 2012, while still being flexible enough to enable the surgical end effector 2012 to articulate relative to the proximal closure tube 2040 and the proximal spine portion 2052 about the articulation axis AA-AA as will be discussed in further detail below. As can be seen in FIGS. 35 and 36, the proximal spine portion 2052 has a rectangular-shaped passage 2054 extending therethrough to provide support to the knife bar 2200 as it is axially pushed therethrough. The proximal spine portion 2052 has a proximal end 2056 that is rotatably mounted to a spine mounting bracket 2057 attached to the tool mounting plate 1032. See FIG. 34. Such arrangement permits the proximal spine portion 2052 to rotate, but not move axially, within the proximal closure tube 2040.

As shown in FIG. 32, the distal end 2202 of the knife bar 2200 is attached to the cutting instrument 2032. The proximal end 2204 of the knife bar 2200 is rotatably affixed to a knife rack gear 2206 such that the knife bar 2200 is free to rotate relative to the knife rack gear 2206. See FIG. 34. As can be seen in FIGS. 28-33, the knife rack gear 2206 is slidably supported within a rack housing 2210 that is attached to the tool mounting plate 1302 such that the knife rack gear 2206 is retained in meshing engagement with a knife gear assembly 2220. More specifically and with reference to FIG. 31, in at least one embodiment, the knife gear assembly 2220 includes a knife spur gear 2222 that is coupled to a corresponding third one of the driven discs or elements 1304 on the adapter side 1307 of the tool mounting plate 1302. See FIG. 26. Thus, application of another rotary output motion from the robotic system 1000 through the tool drive assembly 1010 to the corresponding third driven element 1304 will cause rotation of the knife spur gear 2222. The knife gear assembly 2220 further includes a knife gear reduction set 2224 that includes a first knife driven gear 2226 and a second knife drive gear 2228. The knife gear reduction set 2224 is rotatably mounted to the tool mounting plate 1302 such that the firs knife driven gear 2226 is in meshing engagement with the knife spur gear 2222. Likewise, the second knife drive gear 2228 is in meshing engagement with a third knife drive gear 2230 that is rotatably supported on the tool mounting plate 1302 in meshing engagement with the knife rack gear 2206. In various embodiments, the gears of the knife gear assembly 2220 are sized to generate the forces needed to drive the cutting element 2032 through the tissue clamped in the surgical end effector 2012 and actuate the staples therein. For example, the gears of the knife drive assembly 2230 may be sized to generate approximately 40 to 100 pounds. It will be appreciated that the application of a rotary output motion from the tool drive assembly 1010 in one direction will result in the axial movement of the cutting instrument 2032 in a distal direction and application of the rotary output motion in an opposite direction will result in the axial travel of the cutting instrument 2032 in a proximal direction.

In various embodiments, the surgical tool 1200 employs and articulation system 2007 that includes an articulation joint 2011 that enables the surgical end effector 2012 to be articulated about an articulation axis AA-AA that is substantially transverse to the longitudinal tool axis LT-LT. In at least one embodiment, the surgical tool 1200 includes first and second articulation bars 2250a, 2250b that are slidably supported within corresponding passages 2053 provided through the proximal spine portion 2052. See FIGS. 39 and 41. In at least one form, the first and second articulation bars 2250a, 2250b are actuated by an articulation transmission generally designated as 2249 that is operably supported on the tool mounting plate 1032. Each of the articulation bars 2250a, 2250b has a proximal end 2252 that has a guide rod protruding therefrom which extend laterally through a corresponding slot in the proximal end portion of the proximal spine portion 2052 and into a corresponding arcuate slot in an articulation nut 2260 which comprises a portion of the articulation transmission. FIG. 35 illustrates articulation bar 2250a. It will be understood that articulation bar 2250b is similarly constructed. As can be seen in FIG. 35, for example, the articulation bar 2250a has a guide rod 2254 which extends laterally through a corresponding slot 2058 in the proximal end portion 2056 of the distal spine portion 2050 and into a corresponding arcuate slot 2262 in the articulation nut 2260. In addition, the articulation bar 2250a has a distal end 2251a that is pivotally coupled to the distal spine portion 2050 by, for example, a pin 2253a and articulation bar 2250b has a distal end 2251b that is pivotally coupled to the distal spine portion 2050 by, for example, a pin 2253b. In particular, the articulation bar 2250a is laterally offset in a first lateral direction from the longitudinal tool axis LT-LT and the articulation bar 2250b is laterally offset in a second lateral direction from the longitudinal tool axis LT-LT. Thus, axial movement of the articulation bars 2250a and 2250b in opposing directions will result in the articulation of the distal spine portion 2050 as well as the surgical end effector 2012 attached thereto about the articulation axis AA-AA as will be discussed in further detail below.

Articulation of the surgical end effector 2012 is controlled by rotating the articulation nut 2260 about the longitudinal tool axis LT-LT. The articulation nut 2260 is rotatably journaled on the proximal end portion 2056 of the distal spine portion 2050 and is rotatably driven thereon by an articulation gear assembly 2270. More specifically and with reference to FIG. 29, in at least one embodiment, the articulation gear assembly 2270 includes an articulation spur gear 2272 that is coupled to a corresponding fourth one of the driven discs or elements 1304 on the adapter side 1307 of the tool mounting plate 1302. See FIG. 26. Thus, application of another rotary input motion from the robotic system 1000 through the tool drive assembly 1010 to the corresponding fourth driven element 1304 will cause rotation of the articulation spur gear 2272 when the interface 1230 is coupled to the tool holder 1270. An articulation drive gear 2274 is rotatably supported on the tool mounting plate 1302 in meshing engagement with the articulation spur gear 2272 and a gear portion 2264 of the articulation nut 2260 as shown. As can be seen in FIGS. 34 and 35, the articulation nut 2260 has a shoulder 2266 formed thereon that defines an annular groove 2267 for receiving retaining posts 2268 therein. Retaining posts 2268 are attached to the tool mounting plate 1302 and serve to prevent the articulation nut 2260 from moving axially on the proximal spine portion 2052 while maintaining the ability to be rotated relative thereto. Thus, rotation of the articulation nut 2260 in a first direction, will result in the axial movement of the articulation bar 2250a in a distal direction "DD" and the axial movement of the articulation bar 2250b in a proximal direction "PD" because of the interaction of the guide rods 2254 with the spiral slots 2262 in the articulation gear 2260. Similarly, rotation of the articulation nut 2260 in a second direction that is opposite to the first direction will result in the axial movement of the articulation bar 2250a in the proximal direction "PD" as well as cause articulation bar 2250b to axially move in the distal direction "DD". Thus, the surgical end effector 2012 may be selectively articulated about articulation axis "AA-AA" in a first direction "FD" by simultaneously moving the articulation bar 2250a in the distal direction "DD" and the articulation bar 2250b in the proximal direction "PD". Likewise, the surgical end effector 2012 may be selectively articulated about the articulation axis "AA-AA" in a second direction "SD" by simultaneously moving the articulation bar 2250a in the proximal direction "PD" and the articulation bar 2250b in the distal direction "DD." See FIG. 27.

The tool embodiment described above employs an interface arrangement that is particularly well-suited for mounting the robotically controllable medical tool onto at least one form of robotic arm arrangement that generates at least four different rotary control motions. Those of ordinary skill in the art will appreciate that such rotary output motions may be selectively controlled through the programmable control systems employed by the robotic system/controller. For example, the tool arrangement described above may be well-suited for use with those robotic systems manufactured by Intuitive Surgical, Inc. of Sunnyvale, Calif., U.S.A., many of which may be described in detail in various patents incorporated herein by reference. The unique and novel aspects of various embodiments of the present invention serve to utilize the rotary output motions supplied by the robotic system to generate specific control motions having sufficient magnitudes that enable end effectors to cut and staple tissue. Thus, the unique arrangements and principles of various embodiments of the present invention may enable a variety of different forms of the tool systems disclosed and claimed herein to be effectively employed in connection with other types and forms of robotic systems that supply programmed rotary or other output motions. In addition, as will become further apparent as the present Detailed Description proceeds, various end effector embodiments of the present invention that require other forms of actuation motions may also be effectively actuated utilizing one or more of the control motions generated by the robotic system.

FIGS. 38-42 illustrate yet another surgical tool 2300 that may be effectively employed in connection with the robotic system 1000 that has a tool drive assembly that is operably coupled to a controller of the robotic system that is operable by inputs from an operator and which is configured to provide at least one rotary output motion to at least one rotatable body portion supported on the tool drive assembly. In various forms, the surgical tool 2300 includes a surgical end effector 2312 that includes an elongated channel 2322 and a pivotally translatable clamping member, such as an anvil 2324, which are maintained at a spacing that assures effective stapling and severing of tissue clamped in the surgical end effector 2312. As shown in the illustrated embodiment, the surgical end effector 2312 may include, in addition to the previously-mentioned elongated channel 2322 and anvil 2324, a cutting instrument 2332 that has a sled portion 2333 formed thereon, a surgical staple cartridge 2334 that is seated in the elongated channel 2322, and a rotary end effector drive shaft 2336 that has a helical screw thread formed thereon. The cutting instrument 2332 may be, for example, a knife. As will be discussed in further detail below, rotation of the end effector drive shaft 2336 will cause the cutting instrument 2332 and sled portion 2333 to axially travel through the surgical staple cartridge 2334 to move between a starting position and an ending position. The direction of axial travel of the cutting instrument 2332 depends upon the direction in which the end effector drive shaft 2336 is rotated. The anvil 2324 may be pivotably opened and closed at a pivot point 2325 connected to the proximate end of the elongated channel 2322. The anvil 2324 may also include a tab 2327 at its proximate end that operably interfaces with a component of the mechanical closure system (described further below) to open and close the anvil 2324. When the end effector drive shaft 2336 is rotated, the cutting instrument 2332 and sled 2333 will travel longitudinally through the surgical staple cartridge 2334 from the starting position to the ending position, thereby cutting tissue clamped within the surgical end effector 2312. The movement of the sled 2333 through the surgical staple cartridge 2334 causes the staples therein to be driven through the severed tissue and against the closed anvil 2324, which turns the staples to fasten the severed tissue. In one form, the elongated channel 2322 and the anvil 2324 may be made of an electrically conductive material (such as metal) so that they may serve as part of the antenna that communicates with sensor(s) in the end effector, as described above. The surgical staple cartridge 2334 could be made of a nonconductive material (such as plastic) and the sensor may be connected to or disposed in the surgical staple cartridge 2334, as described above.

It should be noted that although the embodiments of the surgical tool 2300 described herein employ a surgical end effector 2312 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the surgical end effector 2312 is coupled to an elongated shaft assembly 2308 that is coupled to a tool mounting portion 2460 and defines a longitudinal tool axis LT-LT. In this embodiment, the elongated shaft assembly 2308 does not include an articulation joint. Those of ordinary skill in the art will understand that other embodiments may have an articulation joint therein. In at least one embodiment, the elongated shaft assembly 2308 comprises a hollow outer tube 2340 that is rotatably supported on a tool mounting plate 2462 of a tool mounting portion 2460 as will be discussed in further detail below. In various embodiments, the elongated shaft assembly 2308 further includes a distal spine shaft 2350. Distal spine shaft 2350 has a distal end portion 2354 that is coupled to, or otherwise integrally formed with, a distal stationary base portion 2360 that is non-movably coupled to the channel 2322. See FIGS. 39-41.

As shown in FIG. 39, the distal spine shaft 2350 has a proximal end portion 2351 that is slidably received within a slot 2355 in a proximal spine shaft 2353 that is non-movably supported within the hollow outer tube 2340 by at least one support collar 2357. As can be further seen in FIGS. 39 and 40, the surgical tool 2300 includes a closure tube 2370 that is constrained to only move axially relative to the distal stationary base portion 2360. The closure tube 2370 has a proximal end 2372 that has an internal thread 2374 formed therein that is in threaded engagement with a transmission arrangement, generally depicted as 2375 that is operably supported on the tool mounting plate 2462. In various forms, the transmission arrangement 2375 includes a rotary drive shaft assembly, generally designated as 2381. When rotated, the rotary drive shaft assembly 2381 will cause the closure tube 2370 to move axially as will be describe in further detail below. In at least one form, the rotary drive shaft assembly 2381 includes a closure drive nut 2382 of a closure clutch assembly generally designated as 2380. More specifically, the closure drive nut 2382 has a proximal end portion 2384 that is rotatably supported relative to the outer tube 2340 and is in threaded engagement with the closure tube 2370. For assembly purposes, the proximal end portion 2384 may be threadably attached to a retention ring 2386. Retention ring 2386, in cooperation with an end 2387 of the closure drive nut 2382, defines an annular slot 2388 into which a shoulder 2392 of a locking collar 2390 extends. The locking collar 2390 is non-movably attached (e.g., welded, glued, etc.) to the end of the outer tube 2340. Such arrangement serves to affix the closure drive nut 2382 to the outer tube 2340 while enabling the closure drive nut 2382 to rotate relative to the outer tube 2340. The closure drive nut 2382 further has a distal end 2383 that has a threaded portion 2385 that threadably engages the internal thread 2374 of the closure tube 2370. Thus, rotation of the closure drive nut 2382 will cause the closure tube 2370 to move axially as represented by arrow "D" in FIG. 40.

Closure of the anvil 2324 and actuation of the cutting instrument 2332 are accomplished by control motions that are transmitted by a hollow drive sleeve 2400. As can be seen in FIGS. 39 and 40, the hollow drive sleeve 2400 is rotatably and slidably received on the distal spine shaft 2350. The drive sleeve 2400 has a proximal end portion 2401 that is rotatably mounted to the proximal spine shaft 2353 that protrudes from the tool mounting portion 2460 such that the drive sleeve 2400 may rotate relative thereto. See FIG. 39. As can also be seen in FIGS. 39-41, the drive sleeve 2400 is rotated about the longitudinal tool axis "LT-LT" by a drive shaft 2440. The drive shaft 2440 has a drive gear 2444 that is attached to its distal end 2442 and is in meshing engagement with a driven gear 2450 that is attached to the drive sleeve 2400.

The drive sleeve 2400 further has a distal end portion 2402 that is coupled to a closure clutch 2410 portion of the closure clutch assembly 2380 that has a proximal face 2412 and a distal face 2414. The proximal face 2412 has a series of proximal teeth 2416 formed thereon that are adapted for selective engagement with corresponding proximal teeth cavities 2418 formed in the proximal end portion 2384 of the closure drive nut 2382. Thus, when the proximal teeth 2416 are in meshing engagement with the proximal teeth cavities 2418 in the closure drive nut 2382, rotation of the drive sleeve 2400 will result in rotation of the closure drive nut 2382 and ultimately cause the closure tube 2370 to move axially as will be discussed in further detail below.

Figure 44:
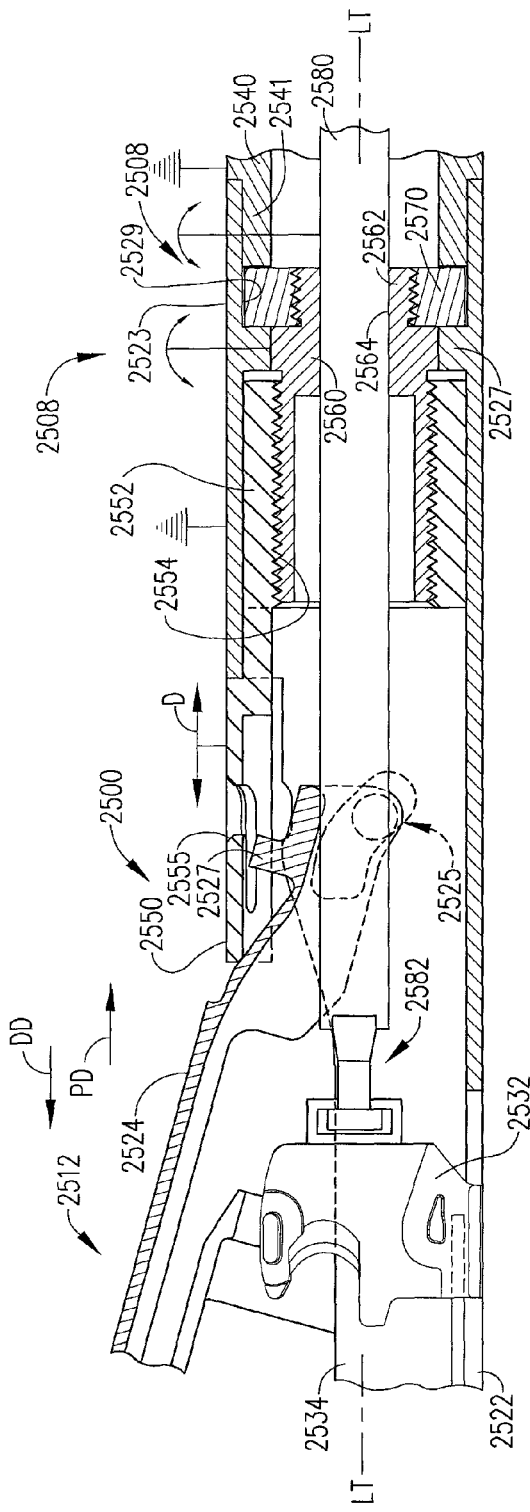
FIG. 44 is a cross-sectional side view of a portion of the surgical end effector and elongated shaft assembly of the surgical tool embodiment of FIG. 43 with the anvil in the open position.
Figure 45:
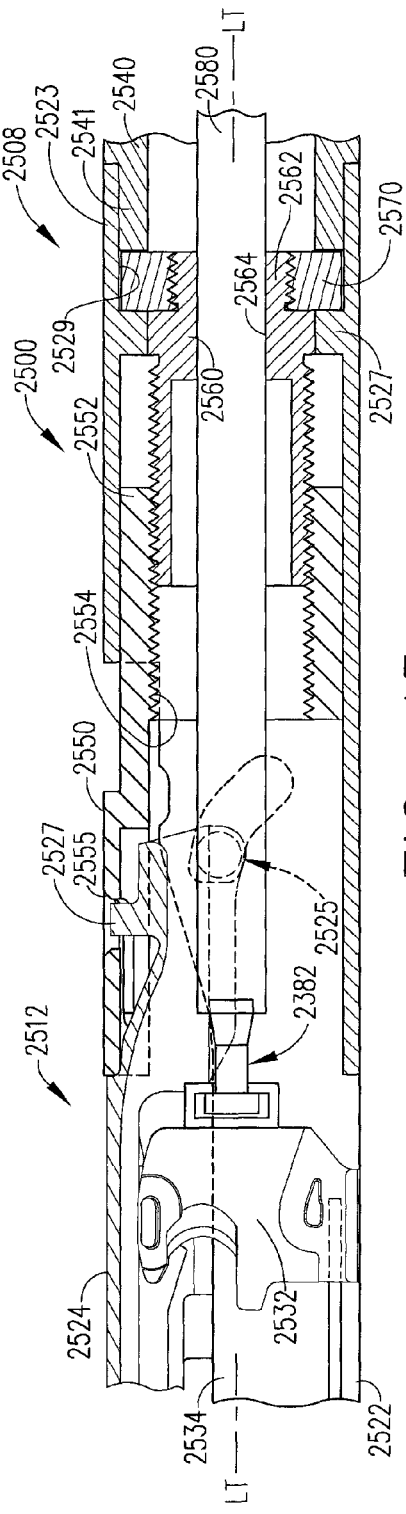
FIG. 45 is another cross-sectional side view of a portion of the surgical end effector and elongated shaft assembly of the surgical tool embodiment of FIG. 43 with the anvil in the closed position.
Figure 46:
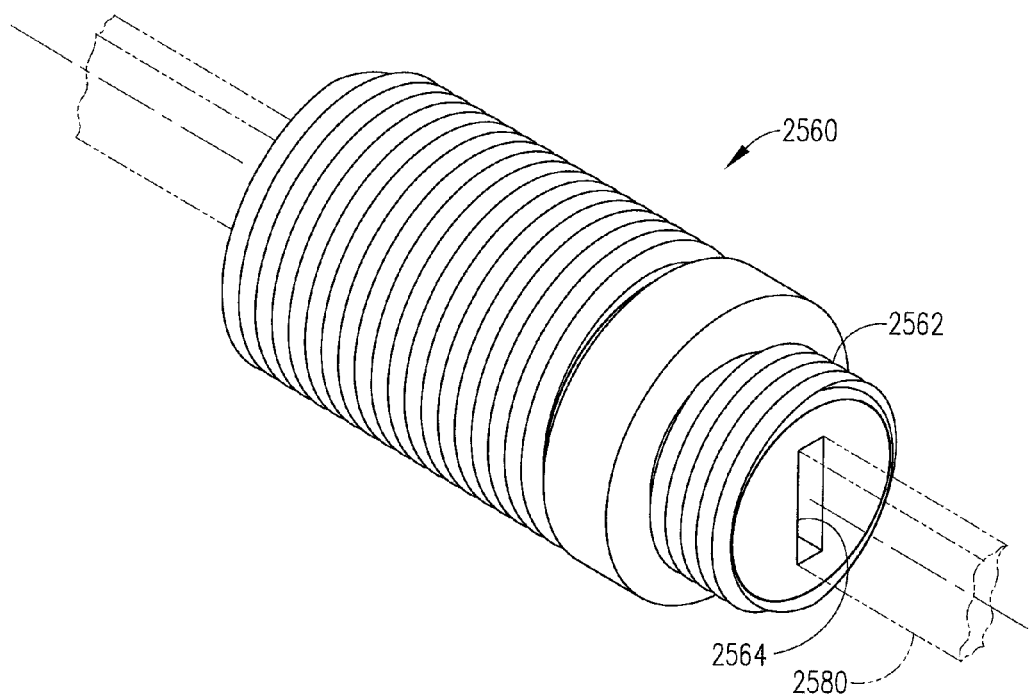
FIG. 46 is a perspective view of a closure drive nut and portion of a knife bar embodiment of the present invention.

As can be most particularly seen in FIGS. 39 and 40, the distal face 2414 of the drive clutch portion 2410 has a series of distal teeth 2415 formed thereon that are adapted for selective engagement with corresponding distal teeth cavities 2426 formed in a face plate portion 2424 of a knife drive shaft assembly 2420. In various embodiments, the knife drive shaft assembly 2420 comprises a hollow knife shaft segment 2430 that is rotatably received on a corresponding portion of the distal spine shaft 2350 that is attached to or protrudes from the stationary base 2360. When the distal teeth 2415 of the closure clutch portion 2410 are in meshing engagement with the distal teeth cavities 2426 in the face plate portion 2424, rotation of the drive sleeve 2400 will result in rotation of the drive shaft segment 2430 about the stationary shaft 2350. As can be seen in FIGS. 44-46, a knife drive gear 2432 is attached to the drive shaft segment 2430 and is meshing engagement with a drive knife gear 2434 that is attached to the end effector drive shaft 2336. Thus, rotation of the drive shaft segment 2430 will result in the rotation of the end effector drive shaft 2336 to drive the cutting instrument 2332 and sled 2333 distally through the surgical staple cartridge 2334 to cut and staple tissue clamped within the surgical end effector 2312. The sled 2333 may be made of, for example, plastic, and may have a sloped distal surface. As the sled 2333 traverses the elongated channel 2322, the sloped forward surface of the sled 2333 pushes up or "drive" the staples in the surgical staple cartridge 2334 through the clamped tissue and against the anvil 2324. The anvil 2324 turns or "forms" the staples, thereby stapling the severed tissue. As used herein, the term "fire" refers to the initiation of actions required to drive the cutting instrument and sled portion in a distal direction through the surgical staple cartridge to cut the tissue clamped in the surgical end effector and drive the staples through the severed tissue.

Figure 42:
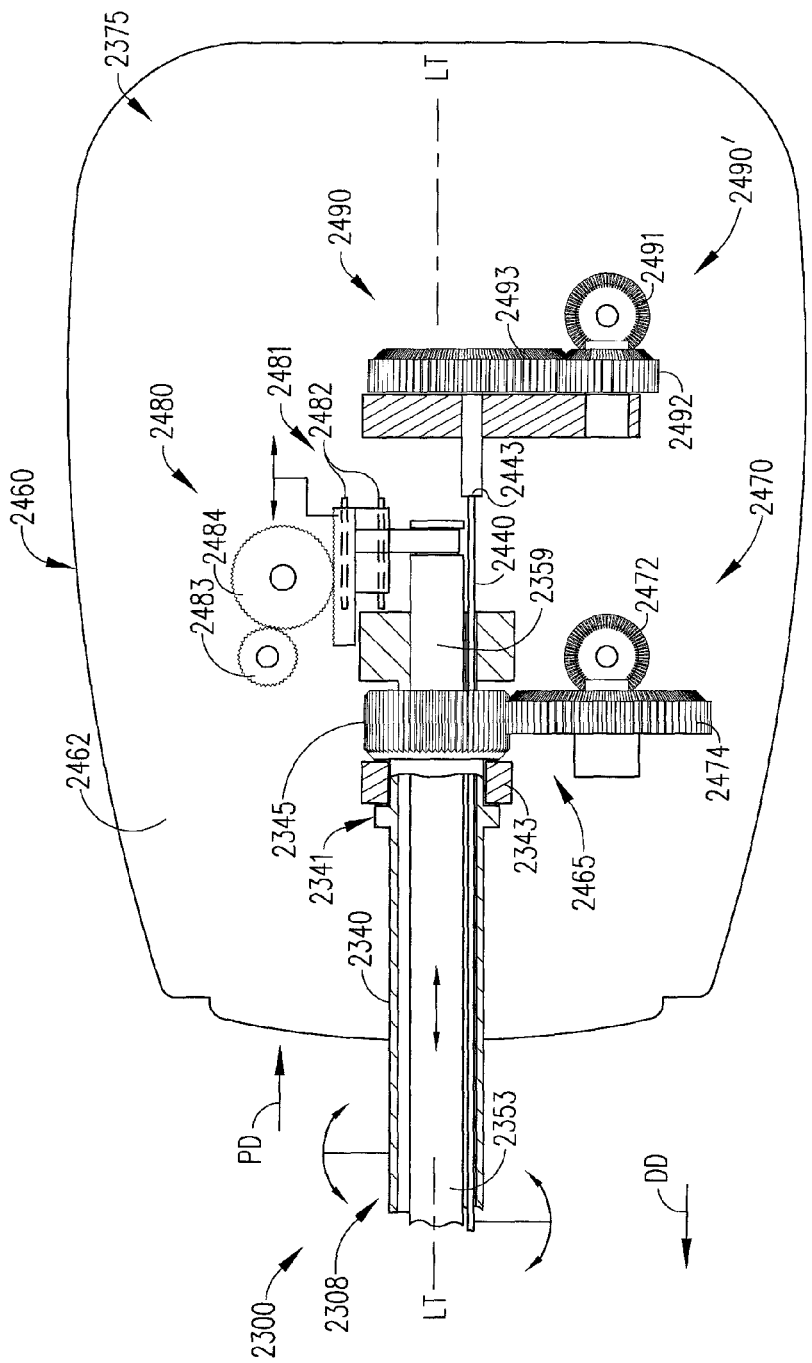
FIG. 42 is a top view of a portion of a tool mounting portion embodiment of the present invention.
Figure 43:
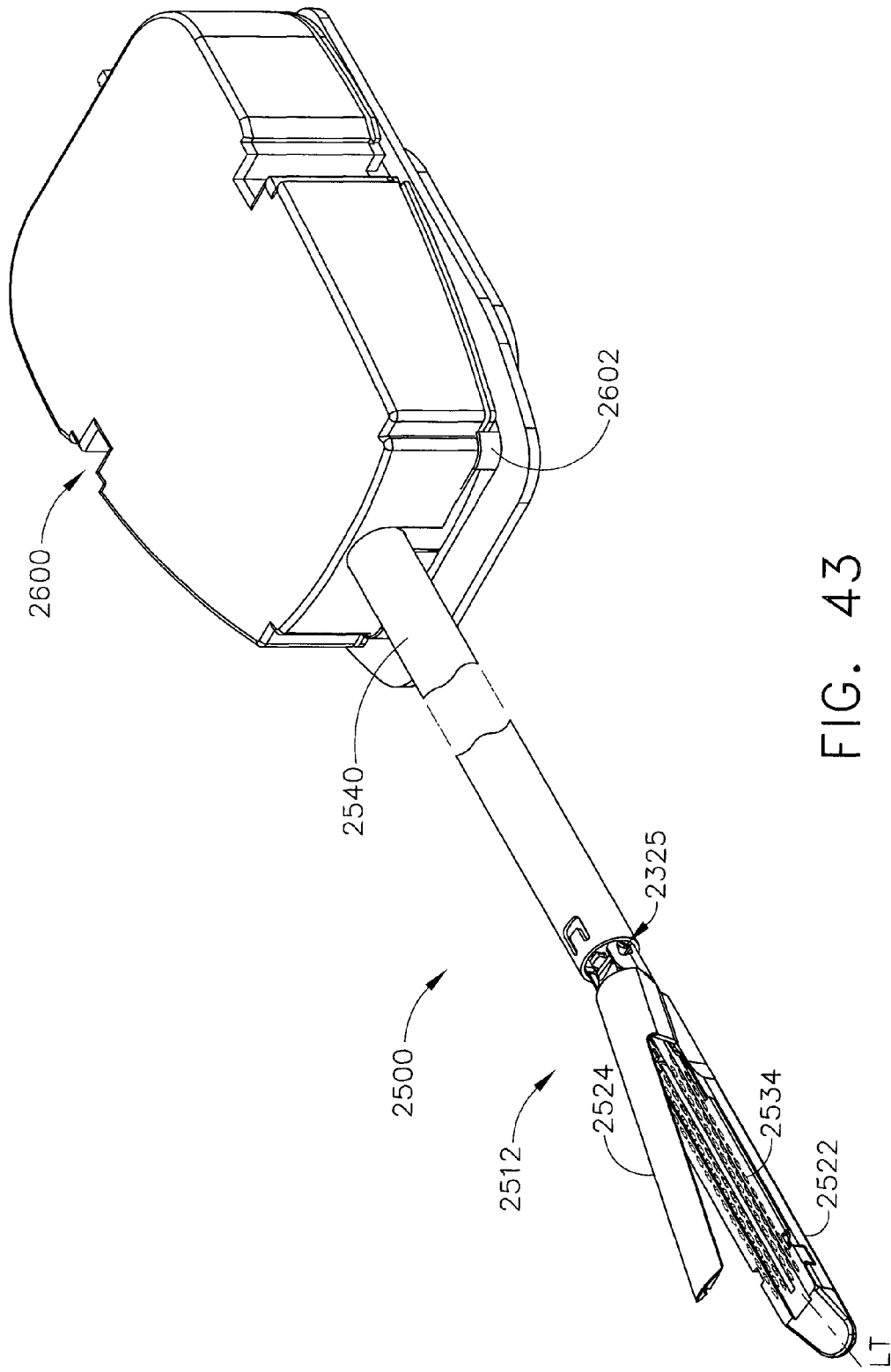
FIG. 43 is a perspective view of another surgical tool embodiment of the present invention.

In use, it may be desirable to rotate the surgical end effector 2312 about the longitudinal tool axis LT-LT. In at least one embodiment, the transmission arrangement 2375 includes a rotational transmission assembly 2465 that is configured to receive a corresponding rotary output motion from the tool drive assembly 1010 of the robotic system 1000 and convert that rotary output motion to a rotary control motion for rotating the elongated shaft assembly 2308 (and surgical end effector 2312) about the longitudinal tool axis LT-LT. As can be seen in FIG. 42, a proximal end 2341 of the outer tube 2340 is rotatably supported within a cradle arrangement 2343 attached to the tool mounting plate 2462 of the tool mounting portion 2460. A rotation gear 2345 is formed on or attached to the proximal end 2341 of the outer tube 2340 of the elongated shaft assembly 2308 for meshing engagement with a rotation gear assembly 2470 operably supported on the tool mounting plate 2462. In at least one embodiment, a rotation drive gear 2472 is coupled to a corresponding first one of the driven discs or elements 1304 on the adapter side of the tool mounting plate 2462 when the tool mounting portion 2460 is coupled to the tool drive assembly 1010. See FIGS. 26 and 42. The rotation drive assembly 2470 further comprises a rotary driven gear 2474 that is rotatably supported on the tool mounting plate 2462 in meshing engagement with the rotation gear 2345 and the rotation drive gear 2472. Application of a first rotary output motion from the robotic system 1000 through the tool drive assembly 1010 to the corresponding driven element 1304 will thereby cause rotation of the rotation drive gear 2472 by virtue of being operably coupled thereto. Rotation of the rotation drive gear 2472 ultimately results in the rotation of the elongated shaft assembly 2308 (and the end effector 2312) about the longitudinal tool axis LT-LT (primary rotary motion).

Closure of the anvil 2324 relative to the staple cartridge 2034 is accomplished by axially moving the closure tube 2370 in the distal direction "DD". Axial movement of the closure tube 2370 in the distal direction "DD" is accomplished by applying a rotary control motion to the closure drive nut 2382. To apply the rotary control motion to the closure drive nut 2382, the closure clutch 2410 must first be brought into meshing engagement with the proximal end portion 2384 of the closure drive nut 2382. In various embodiments, the transmission arrangement 2375 further includes a shifter drive assembly 2480 that is operably supported on the tool mounting plate 2462. More specifically and with reference to FIG. 42, it can be seen that a proximal end portion 2359 of the proximal spine portion 2353 extends through the rotation gear 2345 and is rotatably coupled to a shifter gear rack 2481 that is slidably affixed to the tool mounting plate 2462 through slots 2482. The shifter drive assembly 2480 further comprises a shifter drive gear 2483 that is coupled to a corresponding second one of the driven discs or elements 1304 on the adapter side of the tool mounting plate 2462 when the tool mounting portion 2460 is coupled to the tool holder 1270. See FIGS. 26 and 42. The shifter drive assembly 2480 further comprises a shifter driven gear 2478 that is rotatably supported on the tool mounting plate 2462 in meshing engagement with the shifter drive gear 2483 and the shifter rack gear 2482. Application of a second rotary output motion from the robotic system 1000 through the tool drive assembly 1010 to the corresponding driven element 1304 will thereby cause rotation of the shifter drive gear 2483 by virtue of being operably coupled thereto. Rotation of the shifter drive gear 2483 ultimately results in the axial movement of the shifter gear rack 2482 and the proximal spine portion 2353 as well as the drive sleeve 2400 and the closure clutch 2410 attached thereto. The direction of axial travel of the closure clutch 2410 depends upon the direction in which the shifter drive gear 2483 is rotated by the robotic system 1000. Thus, rotation of the shifter drive gear 2483 in a first rotary direction will result in the axial movement of the closure clutch 2410 in the proximal direction "PD" to bring the proximal teeth 2416 into meshing engagement with the proximal teeth cavities 2418 in the closure drive nut 2382. Conversely, rotation of the shifter drive gear 2483 in a second rotary direction (opposite to the first rotary direction) will result in the axial movement of the closure clutch 2410 in the distal direction "DD" to bring the distal teeth 2415 into meshing engagement with corresponding distal teeth cavities 2426 formed in the face plate portion 2424 of the knife drive shaft assembly 2420.

Once the closure clutch 2410 has been brought into meshing engagement with the closure drive nut 2382, the closure drive nut 2382 is rotated by rotating the closure clutch 2410. Rotation of the closure clutch 2410 is controlled by applying rotary output motions to a rotary drive transmission portion 2490 of transmission arrangement 2375 that is operably supported on the tool mounting plate 2462 as shown in FIG. 42. In at least one embodiment, the rotary drive transmission 2490 includes a rotary drive assembly 2490' that includes a gear 2491 that is coupled to a corresponding third one of the driven discs or elements 1304 on the adapter side of the tool mounting plate 2462 when the tool mounting portion 2460 is coupled to the tool holder 1270. See FIGS. 26 and 42. The rotary drive transmission 2490 further comprises a first rotary driven gear 2492 that is rotatably supported on the tool mounting plate 2462 in meshing engagement with a second rotary driven gear 2493 and the rotary drive gear 2491. The second rotary driven gear 2493 is coupled to a proximal end portion 2443 of the drive shaft 2440.

Rotation of the rotary drive gear 2491 in a first rotary direction will result in the rotation of the drive shaft 2440 in a first direction. Conversely, rotation of the rotary drive gear 2491 in a second rotary direction (opposite to the first rotary direction) will cause the drive shaft 2440 to rotate in a second direction. As indicated above, the drive shaft 2440 has a drive gear 2444 that is attached to its distal end 2442 and is in meshing engagement with a driven gear 2450 that is attached to the drive sleeve 2400. Thus, rotation of the drive shaft 2440 results in rotation of the drive sleeve 2400.

Figure 41:
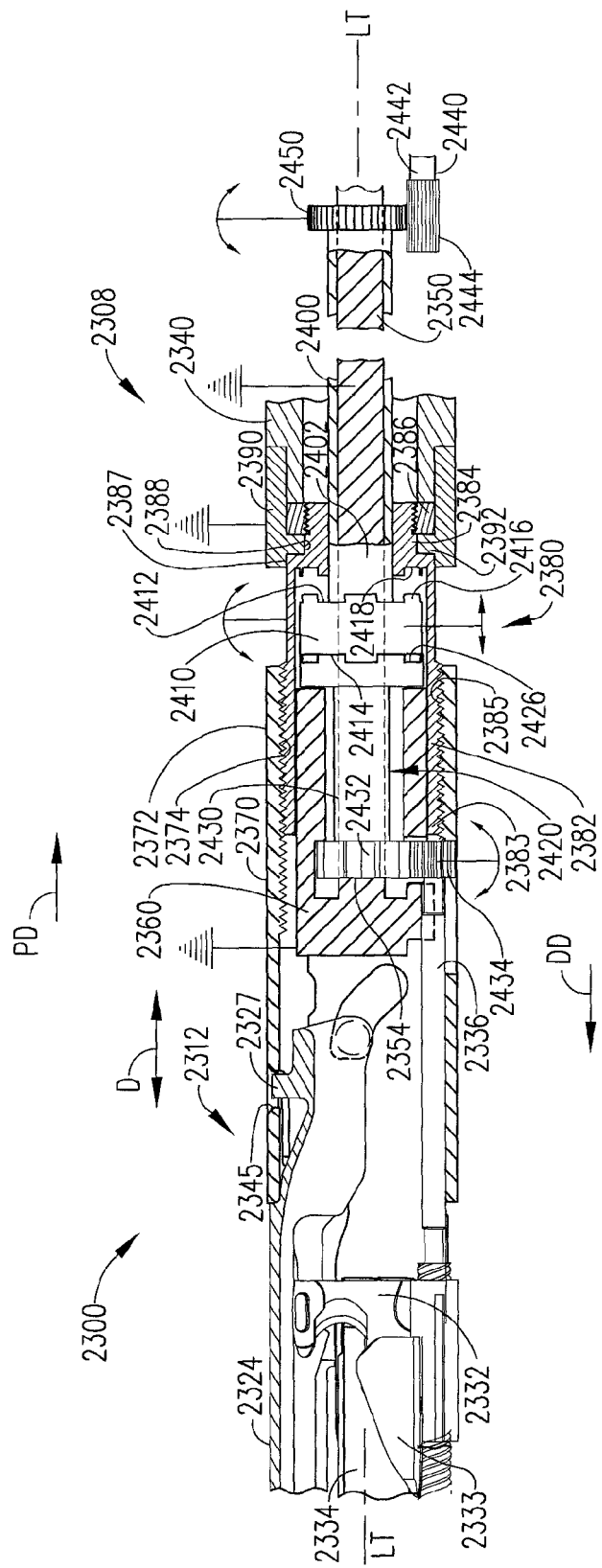
FIG. 41 is another cross-sectional side view of the surgical end effector and elongated shaft assembly shown in FIG. 39 with the clutch assembly engaged in a firing position.

A method of operating the surgical tool 2300 will now be described. Once the tool mounting portion 2462 has been operably coupled to the tool holder 1270 of the robotic system 1000 and oriented into position adjacent the target tissue to be cut and stapled, if the anvil 2334 is not already in the open position (FIG. 39), the robotic system 1000 may apply the first rotary output motion to the shifter drive gear 2483 which results in the axial movement of the closure clutch 2410 into meshing engagement with the closure drive nut 2382 (if it is not already in meshing engagement therewith). See FIG. 40. Once the controller 1001 of the robotic system 1000 has confirmed that the closure clutch 2410 is meshing engagement with the closure drive nut 2382 (e.g., by means of sensor(s)) in the surgical end effector 2312 that are in communication with the robotic control system), the robotic controller 1001 may then apply a second rotary output motion to the rotary drive gear 2492 which, as was described above, ultimately results in the rotation of the rotary drive nut 2382 in the first direction which results in the axial travel of the closure tube 2370 in the distal direction "DD". As the closure tube 2370 moved in the distal direction, it contacts a portion of the anvil 2323 and causes the anvil 2324 to pivot to the closed position to clamp the target tissue between the anvil 2324 and the surgical staple cartridge 2334. Once the robotic controller 1001 determines that the anvil 2334 has been pivoted to the closed position by corresponding sensor(s) in the surgical end effector 2312 in communication therewith, the robotic system 1000 discontinues the application of the second rotary output motion to the rotary drive gear 2491. The robotic controller 1001 may also provide the surgeon with an indication that the anvil 2334 has been fully closed. The surgeon may then initiate the firing procedure. In alternative embodiments, the firing procedure may be automatically initiated by the robotic controller 1001. The robotic controller 1001 then applies the primary rotary control motion 2483 to the shifter drive gear 2483 which results in the axial movement of the closure clutch 2410 into meshing engagement with the face plate portion 2424 of the knife drive shaft assembly 2420. See FIG. 41. Once the controller 1001 of the robotic system 1000 has confirmed that the closure clutch 2410 is meshing engagement with the face plate portion 2424 (by means of sensor(s)) in the end effector 2312 that are in communication with the robotic controller 1001), the robotic controller 1001 may then apply the second rotary output motion to the rotary drive gear 2492 which, as was described above, ultimately results in the axial movement of the cutting instrument 2332 and sled portion 2333 in the distal direction "DD" through the surgical staple cartridge 2334. As the cutting instrument 2332 moves distally through the surgical staple cartridge 2334, the tissue clamped therein is severed. As the sled portion 2333 is driven distally, it causes the staples within the surgical staple cartridge to be driven through the severed tissue into forming contact with the anvil 2324. Once the robotic controller 1001 has determined that the cutting instrument 2324 has reached the end position within the surgical staple cartridge 2334 (by means of sensor(s)) in the end effector 2312 that are in communication with the robotic controller 1001), the robotic controller 1001 discontinues the application of the second rotary output motion to the rotary drive gear 2491. Thereafter, the robotic controller 1001 applies the secondary rotary output motion to the rotary drive gear 2491 which ultimately results in the axial travel of the cutting instrument 2332 and sled portion 2333 in the proximal direction "PD" to the starting position. Once the robotic controller 1001 has determined that the cutting instrument 2324 has reached the starting position by means of sensor(s) in the surgical end effector 2312 that are in communication with the robotic controller 1001, the robotic controller 1001 discontinues the application of the secondary rotary output motion to the rotary drive gear 2491. Thereafter, the robotic controller 1001 applies the primary rotary output motion to the shifter drive gear 2483 to cause the closure clutch 2410 to move into engagement with the rotary drive nut 2382. Once the closure clutch 2410 has been moved into meshing engagement with the rotary drive nut 2382, the robotic controller 1001 then applies the secondary output motion to the rotary drive gear 2491 which ultimately results in the rotation of the rotary drive nut 2382 in the second direction to cause the closure tube 2370 to move in the proximal direction "PD". As can be seen in FIGS. 39-41, the closure tube 2370 has an opening 2345 therein that engages the tab 2327 on the anvil 2324 to cause the anvil 2324 to pivot to the open position. In alternative embodiments, a spring may also be employed to pivot the anvil 2324 to the open position when the closure tube 2370 has been returned to the starting position (FIG. 39).

FIGS. 43-47 illustrate yet another surgical tool 2500 that may be effectively employed in connection with the robotic system 1000. In various forms, the surgical tool 2500 includes a surgical end effector 2512 that includes a "first portion" in the form of an elongated channel 2522 and a "second movable portion" in the form of a pivotally translatable clamping member, such as an anvil 2524, which are maintained at a spacing that assures effective stapling and severing of tissue clamped in the surgical end effector 2512. As shown in the illustrated embodiment, the surgical end effector 2512 may include, in addition to the previously-mentioned elongated channel 2522 and anvil 2524, a "third movable portion" in the form of a cutting instrument 2532, a sled (not shown), and a surgical staple cartridge 2534 that is removably seated in the elongated channel 2522. The cutting instrument 2532 may be, for example, a knife. The anvil 2524 may be pivotably opened and closed at a pivot point 2525 connected to the proximate end of the elongated channel 2522. The anvil 2524 may also include a tab 2527 at its proximate end that is configured to operably interface with a component of the mechanical closure system (described further below) to open and close the anvil 2524. When actuated, the knife 2532 and sled travel longitudinally along the elongated channel 2522, thereby cutting tissue clamped within the surgical end effector 2512. The movement of the sled along the elongated channel 2522 causes the staples of the surgical staple cartridge 2534 to be driven through the severed tissue and against the closed anvil 2524, which turns the staples to fasten the severed tissue. In one form, the elongated channel 2522 and the anvil 2524 may be made of an electrically conductive material (such as metal) so that they may serve as part of the antenna that communicates with sensor(s) in the surgical end effector, as described above. The surgical staple cartridge 2534 could be made of a nonconductive material (such as plastic) and the sensor may be connected to or disposed in the surgical staple cartridge 2534, as described above.

It should be noted that although the embodiments of the surgical tool 2500 described herein employ a surgical end effector 2512 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688, 270, entitled "Electrosurgical Hemostatic Device With Recessed And/Or Offset Electrodes" to Yates et al., which are incorporated herein by reference, discloses cutting instruments that use RF, energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the elongated channel 2522 of the surgical end effector 2512 is coupled to an elongated shaft assembly 2508 that is coupled to a tool mounting portion 2600. In at least one embodiment, the elongated shaft assembly 2508 comprises a hollow spine tube 2540 that is nonmovably coupled to a tool mounting plate 2602 of the tool mounting portion 2600. As can be seen in FIGS. 44 and 45, the proximal end 2523 of the elongated channel 2522 comprises a hollow tubular structure configured to be attached to the distal end 2541 of the spine tube 2540. In one embodiment, for example, the proximal end 2523 of the elongated channel 2522 is welded or glued to the distal end of the spine tube 2540.

As can be further seen in FIGS. 44 and 45, in at least one non-limiting embodiment, the surgical tool 2500 further includes an axially movable actuation member in the form of a closure tube 2550 that is constrained to move axially relative to the elongated channel 2522 and the spine tube 1540. The closure tube 2550 has a proximal end 2552 that has an internal thread 2554 formed therein that is in threaded engagement with a rotatably movable portion in the form of a closure drive nut 2560. More specifically, the closure drive nut 2560 has a proximal end portion 2562 that is rotatably supported relative to the elongated channel 2522 and the spine tube 2540. For assembly purposes, the proximal end portion 2562 is threadably attached to a retention ring 2570. The retention ring 2570 is received in a groove 2529 formed between a shoulder 2527 on the proximal end 2523 of the elongated channel 2522 and the distal end 2541 of the spine tube 1540. Such arrangement serves to rotatably support the closure drive nut 2560 within the elongated channel 2522. Rotation of the closure drive nut 2560 will cause the closure tube 2550 to move axially as represented by arrow "D" in FIG. 44.

Extending through the spine tube 2540 and the closure drive nut 2560 is a drive member which, in at least one embodiment, comprises a knife bar 2580 that has a distal end portion 2582 that is rotatably coupled to the cutting instrument 2532 such that the knife bar 2580 may rotate relative to the cutting instrument 2582. As can be seen in FIG. 44-46, the closure drive nut 2560 has a slot 2564 therein through which the knife bar 2580 can slidably extend. Such arrangement permits the knife bar 2580 to move axially relative to the closure drive nut 2560. However, rotation of the knife bar 2580 about the longitudinal tool axis LT-LT will also result in the rotation of the closure drive nut 2560. The axial direction in which the closure tube 2550 moves ultimately depends upon the direction in which the knife bar 2580 and the closure drive nut 2560 are rotated. As the closure tube 2550 is driven distally, the distal end thereof will contact the anvil 2524 and cause the anvil 2524 to pivot to a closed position. Upon application of an opening rotary output motion from the robotic system 1000, the closure tube 2550 will be driven in the proximal direction "PD" and pivot the anvil 2524 to the open position by virtue of the engagement of the tab 2527 with the opening 2555 in the closure tube 2550.

In use, it may be desirable to rotate the surgical end effector 2512 about the longitudinal tool axis LT-LT. In at least one embodiment, the tool mounting portion 2600 is configured to receive a corresponding first rotary output motion from the robotic system 1000 and convert that first rotary output motion to a rotary control motion for rotating the elongated shaft assembly 2508 about the longitudinal tool axis LT-LT. As can be seen in FIG. 42, a proximal end 2542 of the hollow spine tube 2540 is rotatably supported within a cradle arrangement 2603 attached to a tool mounting plate 2602 of the tool mounting portion 2600. Various embodiments of the surgical tool 2500 further include a transmission arrangement, generally depicted as 2605, that is operably supported on the tool mounting plate 2602. In various forms the transmission arrangement 2605 include a rotation gear 2544 that is formed on or attached to the proximal end 2542 of the spine tube 2540 for meshing engagement with a rotation drive assembly 2610 that is operably supported on the tool mounting plate 2602. In at least one embodiment, a rotation drive gear 2612 is coupled to a corresponding first one of the rotational bodies, driven discs or elements 1304 on the adapter side of the tool mounting plate 2602 when the tool mounting portion 2600 is coupled to the tool holder 1270. See FIGS. 26 and 47. The rotation drive assembly 2610 further comprises a rotary driven gear 2614 that is rotatably supported on the tool mounting plate 2602 in meshing engagement with the rotation gear 2544 and the rotation drive gear 2612. Application of a first rotary output motion from the robotic system 1000 through the tool drive assembly 1010 to the corresponding driven rotational body 1304 will thereby cause rotation of the rotation drive gear 2612 by virtue of being operably coupled thereto. Rotation of the rotation drive gear 2612 ultimately results in the rotation of the elongated shaft assembly 2508 (and the end effector 2512) about the longitudinal tool axis LT-LT.

Figure 47:
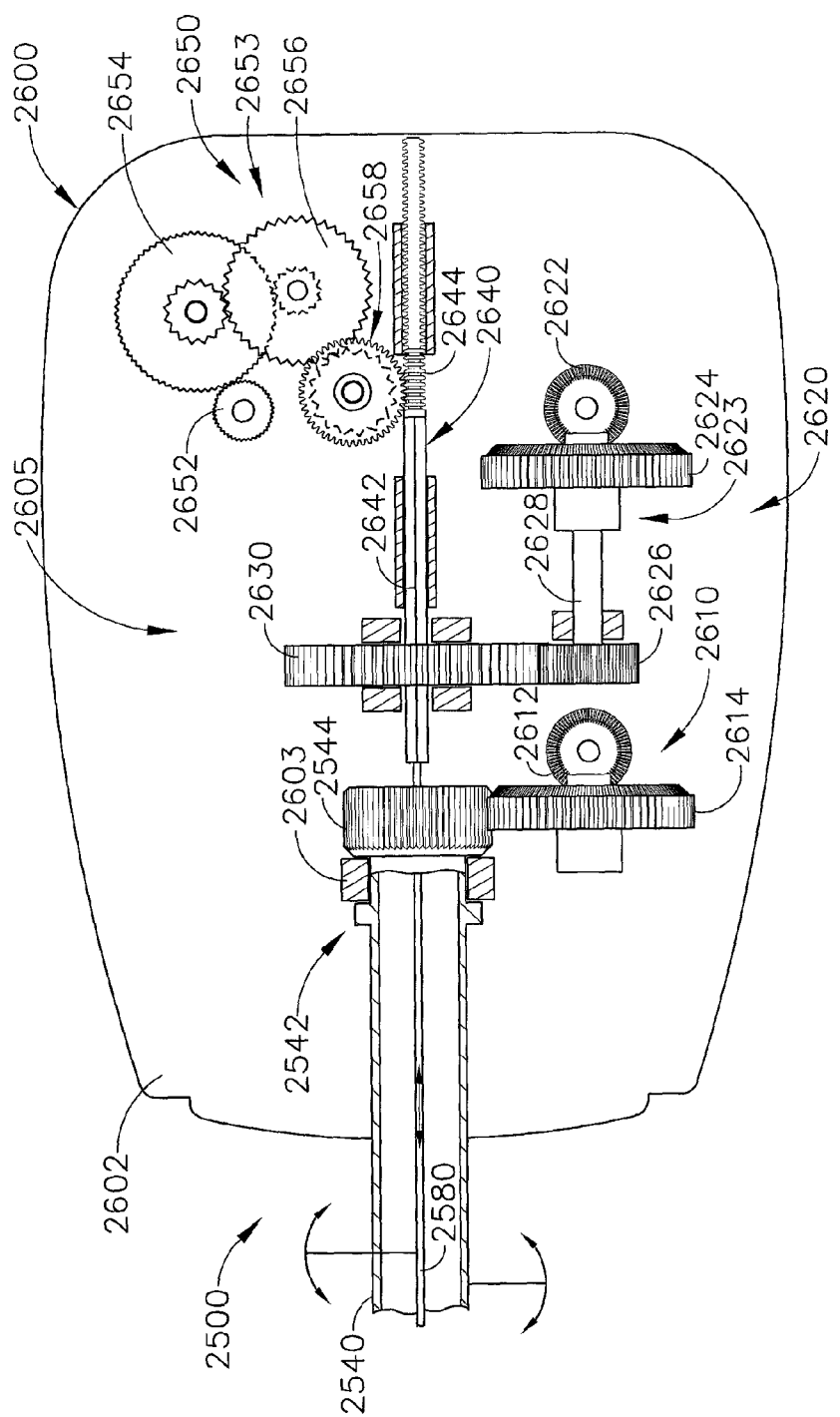
FIG. 47 is a top view of another tool mounting portion embodiment of the present invention.
Figure 48:
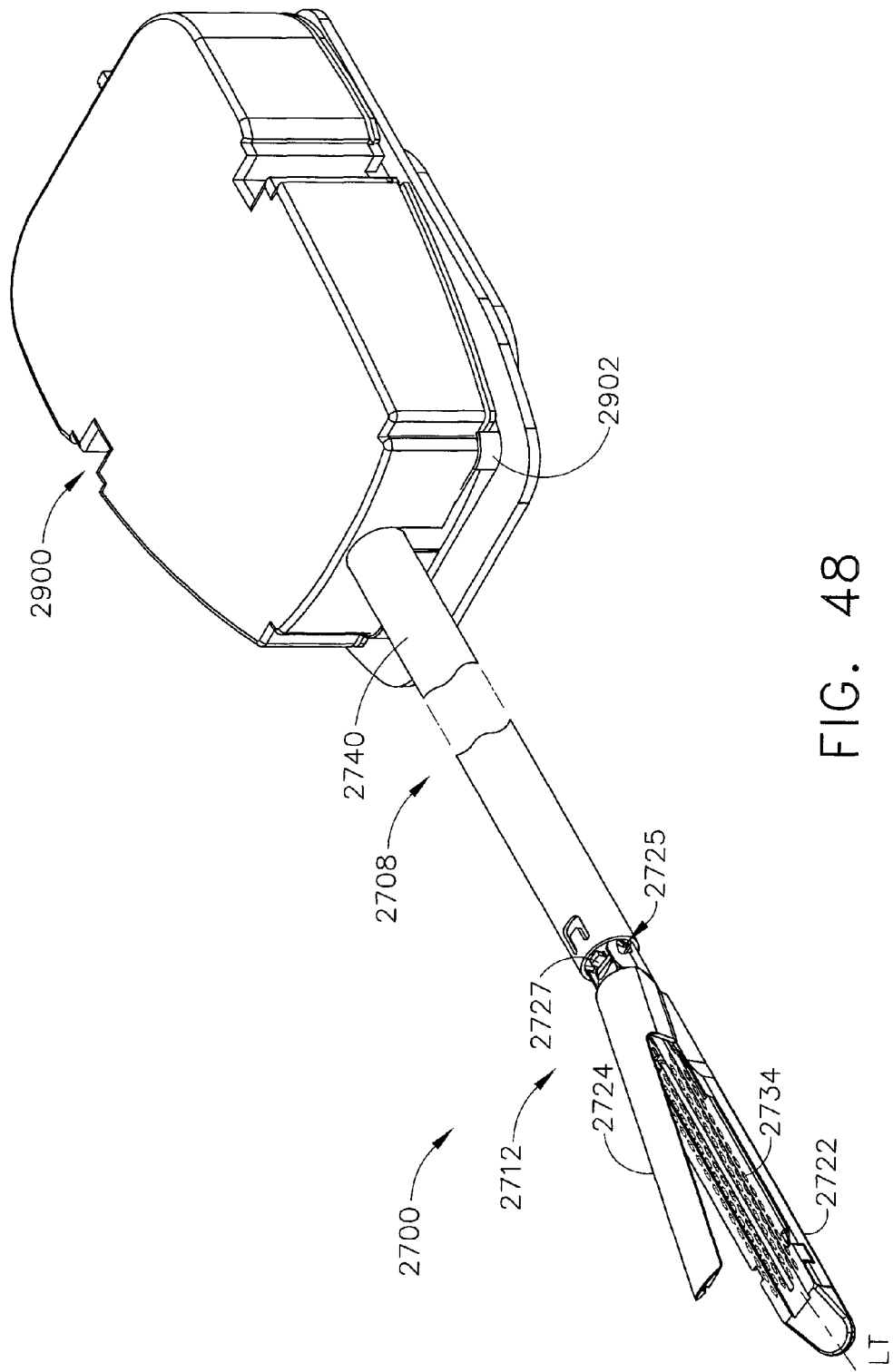
FIG. 48 is a perspective view of another surgical tool embodiment of the present invention.

Closure of the anvil 2524 relative to the surgical staple cartridge 2534 is accomplished by axially moving the closure tube 2550 in the distal direction "DD". Axial movement of the closure tube 2550 in the distal direction "DD" is accomplished by applying a rotary control motion to the closure drive nut 2382. In various embodiments, the closure drive nut 2560 is rotated by applying a rotary output motion to the knife bar 2580. Rotation of the knife bar 2580 is controlled by applying rotary output motions to a rotary closure system 2620 that is operably supported on the tool mounting plate 2602 as shown in FIG. 47. In at least one embodiment, the rotary closure system 2620 includes a closure drive gear 2622 that is coupled to a corresponding second one of the driven rotatable body portions discs or elements 1304 on the adapter side of the tool mounting plate 2462 when the tool mounting portion 2600 is coupled to the tool holder 1270. See FIGS. 26 and 47. The closure drive gear 2622, in at least one embodiment, is in meshing driving engagement with a closure gear train, generally depicted as 2623. The closure gear drive rain 2623 comprises a first driven closure gear 2624 that is rotatably supported on the tool mounting plate 2602. The first closure driven gear 2624 is attached to a second closure driven gear 2626 by a drive shaft 2628. The second closure driven gear 2626 is in meshing engagement with a third closure driven gear 2630 that is rotatably supported on the tool mounting plate 2602. Rotation of the closure drive gear 2622 in a second rotary direction will result in the rotation of the third closure driven gear 2630 in a second direction. Conversely, rotation of the closure drive gear 2483 in a secondary rotary direction (opposite to the second rotary direction) will cause the third closure driven gear 2630 to rotate in a secondary direction.

As can be seen in FIG. 47, a drive shaft assembly 2640 is coupled to a proximal end of the knife bar 2580. In various embodiments, the drive shaft assembly 2640 includes a proximal portion 2642 that has a square cross-sectional shape. The proximal portion 2642 is configured to slideably engage a correspondingly shaped aperture in the third driven gear 2630. Such arrangement results in the rotation of the drive shaft assembly 2640 (and knife bar 2580) when the third driven gear 2630 is rotated. The drive shaft assembly 2640 is axially advanced in the distal and proximal directions by a knife drive assembly 2650. One form of the knife drive assembly 2650 comprises a rotary drive gear 2652 that is coupled to a corresponding third one of the driven rotatable body portions, discs or elements 1304 on the adapter side of the tool mounting plate 2462 when the tool mounting portion 2600 is coupled to the tool holder 1270. See FIGS. 26 and 47. The rotary driven gear 2652 is in meshing driving engagement with a gear train, generally depicted as 2653. In at least one form, the gear train 2653 further comprises a first rotary driven gear assembly 2654 that is rotatably supported on the tool mounting plate 2602. The first rotary driven gear assembly 2654 is in meshing engagement with a third rotary driven gear assembly 2656 that is rotatably supported on the tool mounting plate 2602 and which is in meshing engagement with a fourth rotary driven gear assembly 2658 that is in meshing engagement with a threaded portion 2644 of the drive shaft assembly 2640. Rotation of the rotary drive gear 2652 in a third rotary direction will result in the axial advancement of the drive shaft assembly 2640 and knife bar 2580 in the distal direction "DD". Conversely, rotation of the rotary drive gear 2652 in a tertiary rotary direction (opposite to the third rotary direction) will cause the drive shaft assembly 2640 and the knife bar 2580 to move in the proximal direction.

A method of operating the surgical tool 2500 will now be described. Once the tool mounting portion 2600 has been operably coupled to the tool holder 1270 of the robotic system 1000, the robotic system 1000 can orient the surgical end effector 2512 in position adjacent the target tissue to be cut and stapled. If the anvil 2524 is not already in the open position (FIG. 44), the robotic system 1000 may apply the second rotary output motion to the closure drive gear 2622 which results in the rotation of the knife bar 2580 in a second direction. Rotation of the knife bar 2580 in the second direction results in the rotation of the closure drive nut 2560 in a second direction. As the closure drive nut 2560 rotates in the second direction, the closure tube 2550 moves in the proximal direction "PD". As the closure tube 2550 moves in the proximal direction "PD", the tab 2527 on the anvil 2524 interfaces with the opening 2555 in the closure tube 2550 and causes the anvil 2524 to pivot to the open position. In addition or in alternative embodiments, a spring (not shown) may be employed to pivot the anvil 2354 to the open position when the closure tube 2550 has been returned to the starting position (FIG. 44). The opened surgical end effector 2512 may then be manipulated by the robotic system 1000 to position the target tissue between the open anvil 2524 and the surgical staple cartridge 2534. Thereafter, the surgeon may initiate the closure process by activating the robotic control system 1000 to apply the second rotary output motion to the closure drive gear 2622 which, as was described above, ultimately results in the rotation of the closure drive nut 2382 in the second direction which results in the axial travel of the closure tube 2250 in the distal direction "DD". As the closure tube 2550 moves in the distal direction, it contacts a portion of the anvil 2524 and causes the anvil 2524 to pivot to the closed position to clamp the target tissue between the anvil 2524 and the staple cartridge 2534. Once the robotic controller 1001 determines that the anvil 2524 has been pivoted to the closed position by corresponding sensor(s) in the end effector 2512 that are in communication therewith, the robotic controller 1001 discontinues the application of the second rotary output motion to the closure drive gear 2622. The robotic controller 1001 may also provide the surgeon with an indication that the anvil 2524 has been fully closed. The surgeon may then initiate the firing procedure. In alternative embodiments, the firing procedure may be automatically initiated by the robotic controller 1001.

After the robotic controller 1001 has determined that the anvil 2524 is in the closed position, the robotic controller 1001 then applies the third rotary output motion to the rotary drive gear 2652 which results in the axial movement of the drive shaft assembly 2640 and knife bar 2580 in the distal direction "DD". As the cutting instrument 2532 moves distally through the surgical staple cartridge 2534, the tissue clamped therein is severed. As the sled portion (not shown) is driven distally, it causes the staples within the surgical staple cartridge 2534 to be driven through the severed tissue into forming contact with the anvil 2524. Once the robotic controller 1001 has determined that the cutting instrument 2532 has reached the end position within the surgical staple cartridge 2534 by means of sensor(s) in the surgical end effector 2512 that are in communication with the robotic controller 1001, the robotic controller 1001 discontinues the application of the second rotary output motion to the rotary drive gear 2652. Thereafter, the robotic controller 1001 applies the secondary rotary control motion to the rotary drive gear 2652 which ultimately results in the axial travel of the cutting instrument 2532 and sled portion in the proximal direction "PD" to the starting position. Once the robotic controller 1001 has determined that the cutting instrument 2524 has reached the starting position by means of sensor(s) in the end effector 2512 that are in communication with the robotic controller 1001, the robotic controller 1001 discontinues the application of the secondary rotary output motion to the rotary drive gear 2652. Thereafter, the robotic controller 1001 may apply the secondary rotary output motion to the closure drive gear 2622 which results in the rotation of the knife bar 2580 in a secondary direction. Rotation of the knife bar 2580 in the secondary direction results in the rotation of the closure drive nut 2560 in a secondary direction. As the closure drive nut 2560 rotates in the secondary direction, the closure tube 2550 moves in the proximal direction "PD" to the open position.

FIGS. 48-53B illustrate yet another surgical tool 2700 that may be effectively employed in connection with the robotic system 1000. In various forms, the surgical tool 2700 includes a surgical end effector 2712 that includes a "first portion" in the form of an elongated channel 2722 and a "second movable portion" in on form comprising a pivotally translatable clamping member, such as an anvil 2724, which are maintained at a spacing that assures effective stapling and severing of tissue clamped in the surgical end effector 2712. As shown in the illustrated embodiment, the surgical end effector 2712 may include, in addition to the previously-mentioned channel 2722 and anvil 2724, a "third movable portion" in the form of a cutting instrument 2732, a sled (not shown), and a surgical staple cartridge 2734 that is removably seated in the elongated channel 2722. The cutting instrument 2732 may be, for example, a knife. The anvil 2724 may be pivotably opened and closed at a pivot point 2725 connected to the proximal end of the elongated channel 2722. The anvil 2724 may also include a tab 2727 at its proximal end that interfaces with a component of the mechanical closure system (described further below) to open and close the anvil 2724. When actuated, the knife 2732 and sled to travel longitudinally along the elongated channel 2722, thereby cutting tissue clamped within the surgical end effector 2712. The movement of the sled along the elongated channel 2722 causes the staples of the surgical staple cartridge 2734 to be driven through the severed tissue and against the closed anvil 2724, which turns the staples to fasten the severed tissue. In one form, the elongated channel 2722 and the anvil 2724 may be made of an electrically conductive material (such as metal) so that they may serve as part of the antenna that communicates with sensor(s) in the surgical end effector, as described above. The surgical staple cartridge 2734 could be made of a nonconductive material (such as plastic) and the sensor may be connected to or disposed in the surgical staple cartridge 2734, as described above.

It should be noted that although the embodiments of the surgical tool 2500 described herein employ a surgical end effector 2712 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 51:
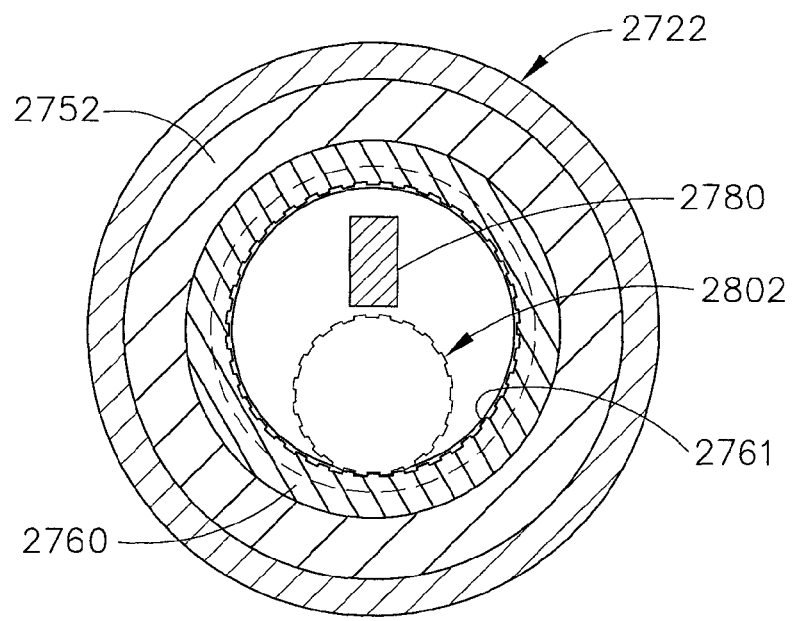
FIG. 51 is a cross-sectional view of a mounting collar embodiment of a surgical tool embodiment of the present invention showing the knife bar and distal end portion of the closure drive shaft.
Figure 52:
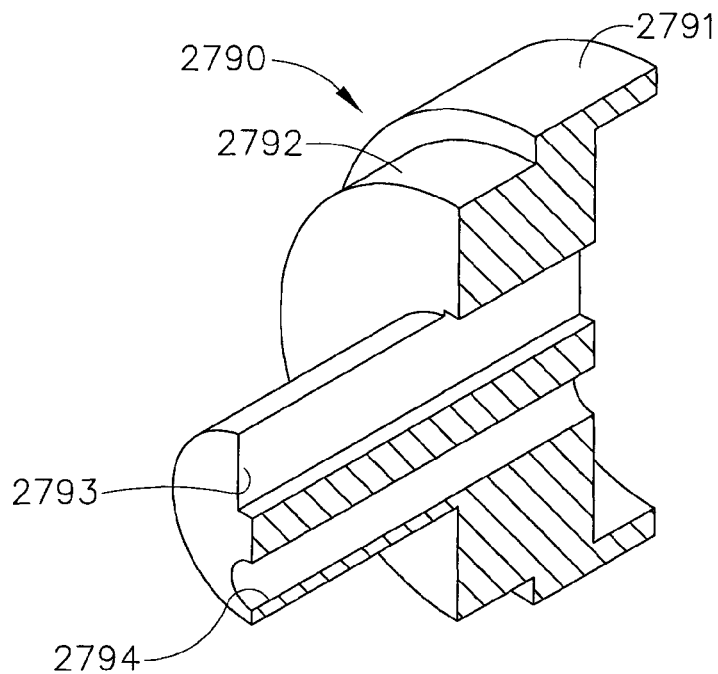
FIG. 52 is a cross-sectional view of the mounting collar embodiment of FIG. 51.

In the illustrated embodiment, the elongated channel 2722 of the surgical end effector 2712 is coupled to an elongated shaft assembly 2708 that is coupled to a tool mounting portion 2900. Although not shown, the elongated shaft assembly 2708 may include an articulation joint to permit the surgical end effector 2712 to be selectively articulated about an axis that is substantially transverse to the tool axis LT-LT. In at least one embodiment, the elongated shaft assembly 2708 comprises a hollow spine tube 2740 that is non-movably coupled to a tool mounting plate 2902 of the tool mounting portion 2900. As can be seen in FIGS. 49 and 50, the proximal end 2723 of the elongated channel 2722 comprises a hollow tubular structure that is attached to the spine tube 2740 by means of a mounting collar 2790. A cross-sectional view of the mounting collar 2790 is shown in FIG. 51. In various embodiments, the mounting collar 2790 has a proximal flanged end 2791 that is configured for attachment to the distal end of the spine tube 2740. In at least one embodiment, for example, the proximal flanged end 2791 of the mounting collar 2790 is welded or glued to the distal end of the spine tube 2740. As can be further seen in FIGS. 54 and 55, the mounting collar 2790 further has a mounting hub portion 2792 that is sized to receive the proximal end 2723 of the elongated channel 2722 thereon. The proximal end 2723 of the elongated channel 2722 is non-movably attached to the mounting hub portion 2792 by, for example, welding, adhesive, etc.

As can be further seen in FIGS. 49 and 50, the surgical tool 2700 further includes an axially movable actuation member in the form of a closure tube 2750 that is constrained to move axially relative to the elongated channel 2722. The closure tube 2750 has a proximal end 2752 that has an internal thread 2754 formed therein that is in threaded engagement with a rotatably movable portion in the form of a closure drive nut 2760. More specifically, the closure drive nut 2760 has a proximal end portion 2762 that is rotatably supported relative to the elongated channel 2722 and the spine tube 2740. For assembly purposes, the proximal end portion 2762 is threadably attached to a retention ring 2770. The retention ring 2770 is received in a groove 2729 formed between a shoulder 2727 on the proximal end 2723 of the channel 2722 and the mounting hub 2729 of the mounting collar 2790. Such arrangement serves to rotatably support the closure drive nut 2760 within the channel 2722. Rotation of the closure drive nut 2760 will cause the closure tube 2750 to move axially as represented by arrow "D" in FIG. 49.

Extending through the spine tube 2740, the mounting collar 2790, and the closure drive nut 2760 is a drive member, which in at least one embodiment, comprises a knife bar 2780 that has a distal end portion 2782 that is coupled to the cutting instrument 2732. As can be seen in FIGS. 49 and 50, the mounting collar 2790 has a passage 2793 therethrough for permitting the knife bar 2780 to slidably pass therethrough. Similarly, the closure drive nut 2760 has a slot 2764 therein through which the knife bar 2780 can slidably extend. Such arrangement permits the knife bar 2780 to move axially relative to the closure drive nut 2760.

Actuation of the anvil 2724 is controlled by a rotary driven closure shaft 2800. As can be seen in FIGS. 49 and 50, a distal end portion 2802 of the closure drive shaft 2800 extends through a passage 2794 in the mounting collar 2790 and a closure gear 2804 is attached thereto. The closure gear 2804 is configured for driving engagement with the inner surface 2761 of the closure drive nut 2760. Thus, rotation of the closure shaft 2800 will also result in the rotation of the closure drive nut 2760. The axial direction in which the closure tube 2750 moves ultimately depends upon the direction in which the closure shaft 2800 and the closure drive nut 2760 are rotated. For example, in response to one rotary closure motion received from the robotic system 1000, the closure tube 2750 will be driven in the distal direction "DD". As the closure tube 2750 is driven distally, the opening 2745 will engage the tab 2727 on the anvil 2724 and cause the anvil 2724 to pivot to a closed position. Upon application of an opening rotary motion from the robotic system 1000, the closure tube 2750 will be driven in the proximal direction "PD" and pivot the anvil 2724 to the open position. In various embodiments, a spring (not shown) may be employed to bias the anvil 2724 to the open position (FIG. 49).

Figure 53:
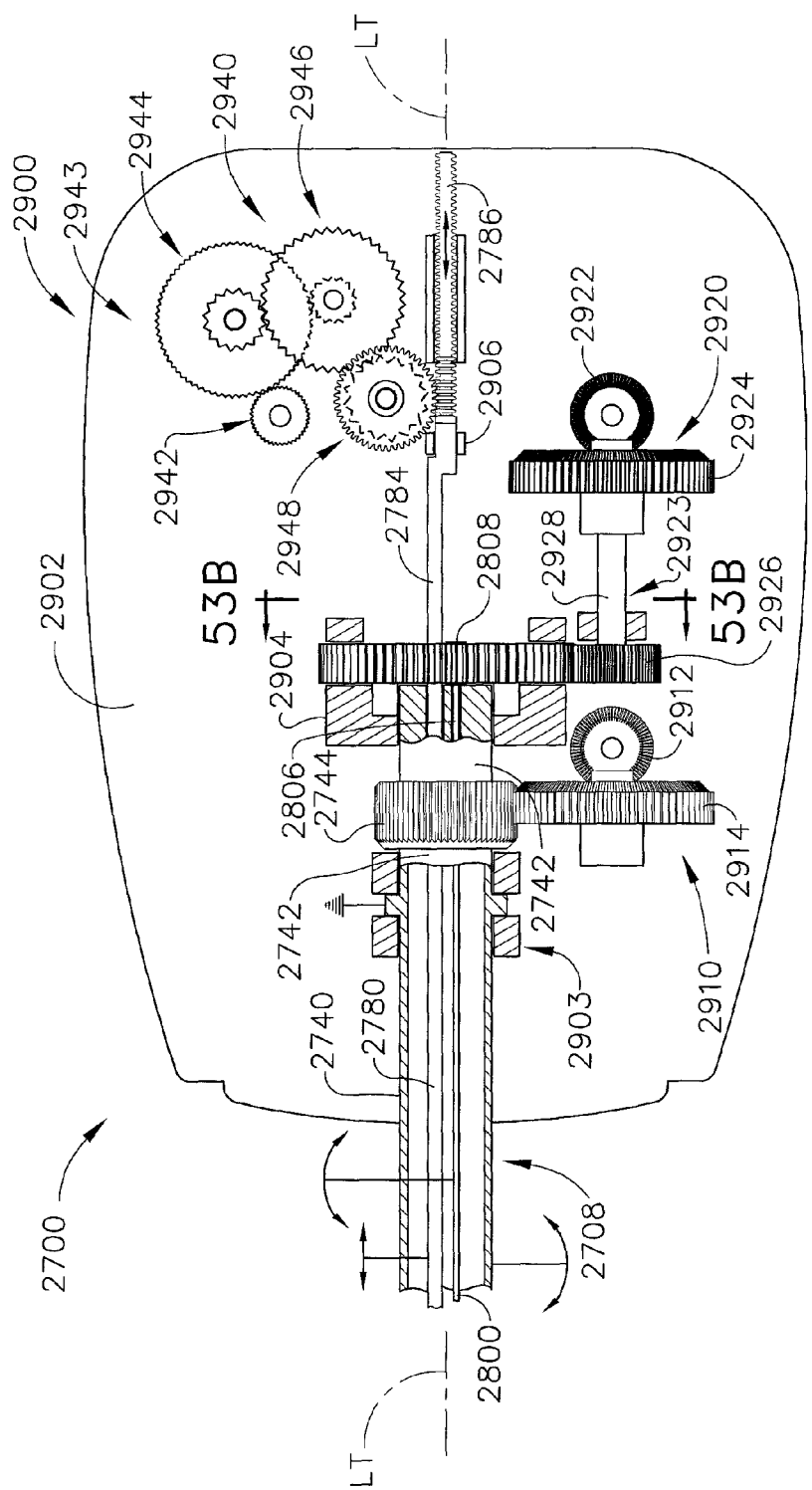
FIG. 53 is a top view of another tool mounting portion embodiment of another surgical tool embodiment of the present invention.

In use, it may be desirable to rotate the surgical end effector 2712 about the longitudinal tool axis LT-LT. In at least one embodiment, the tool mounting portion 2900 is configured to receive a corresponding first rotary output motion from the robotic system 1000 for rotating the elongated shaft assembly 2708 about the tool axis LT-LT. As can be seen in FIG. 53, a proximal end 2742 of the hollow spine tube 2740 is rotatably supported within a cradle arrangement 2903 and a bearing assembly 2904 that are attached to a tool mounting plate 2902 of the tool mounting portion 2900. A rotation gear 2744 is formed on or attached to the proximal end 2742 of the spine tube 2740 for meshing engagement with a rotation drive assembly 2910 that is operably supported on the tool mounting plate 2902. In at least one embodiment, a rotation drive gear 2912 is coupled to a corresponding first one of the driven discs or elements 1304 on the adapter side of the tool mounting plate 2602 when the tool mounting portion 2600 is coupled to the tool holder 1270. See FIGS. 26 and 53. The rotation drive assembly 2910 further comprises a rotary driven gear 2914 that is rotatably supported on the tool mounting plate 2902 in meshing engagement with the rotation gear 2744 and the rotation drive gear 2912. Application of a first rotary control motion from the robotic system 1000 through the tool holder 1270 and the adapter 1240 to the corresponding driven element 1304 will thereby cause rotation of the rotation drive gear 2912 by virtue of being operably coupled thereto. Rotation of the rotation drive gear 2912 ultimately results in the rotation of the elongated shaft assembly 2708 (and the end effector 2712) about the longitudinal tool axis LT-LT (primary rotary motion).

Figure 53A:
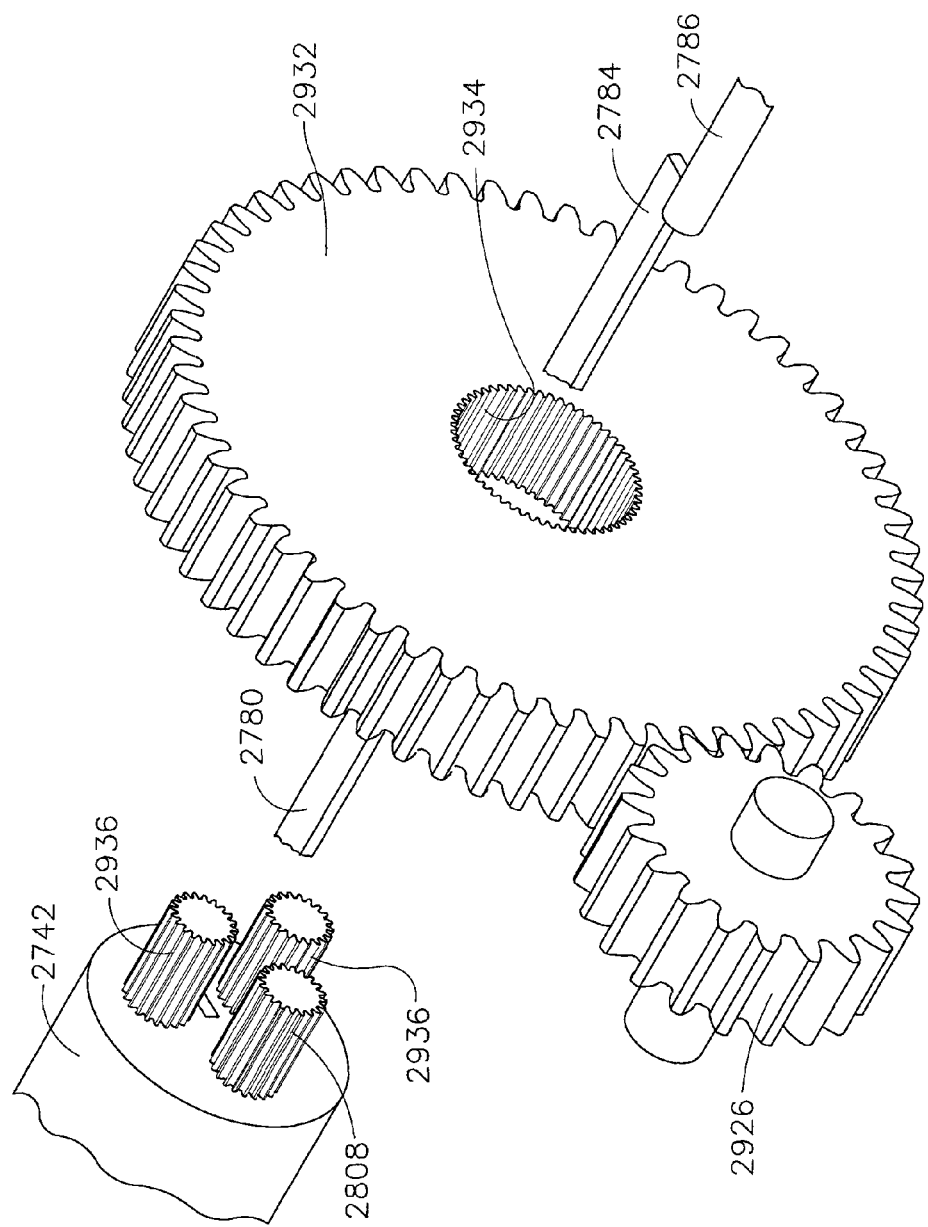
FIG. 53A is an exploded perspective view of a portion of a gear arrangement of another surgical tool embodiment of the present invention.
Figure 53B:
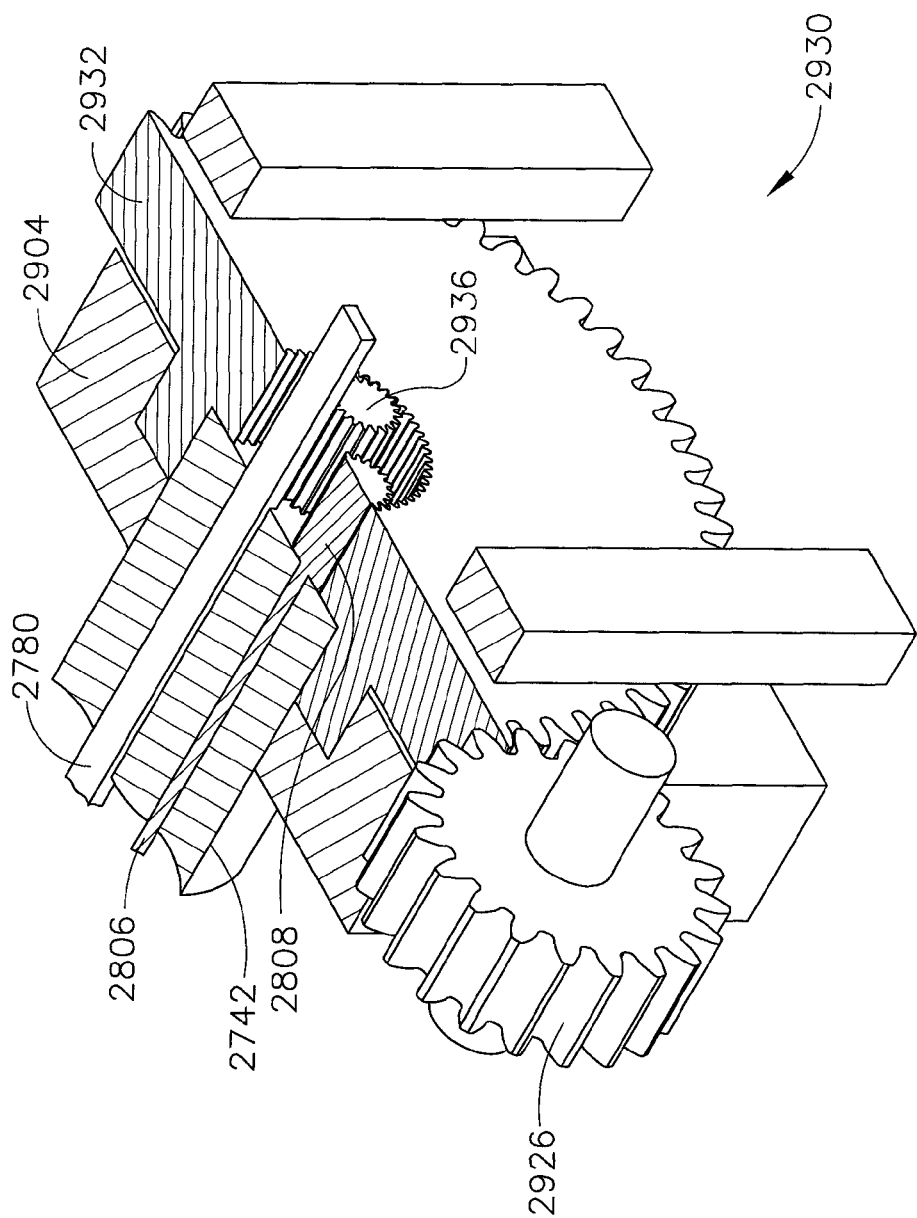
FIG. 53B is a cross-sectional perspective view of the gear arrangement shown in FIG. 53A.

Closure of the anvil 2724 relative to the staple cartridge 2734 is accomplished by axially moving the closure tube 2750 in the distal direction "DD". Axial movement of the closure tube 2750 in the distal direction "DD" is accomplished by applying a rotary control motion to the closure drive nut 2760. In various embodiments, the closure drive nut 2760 is rotated by applying a rotary output motion to the closure drive shaft 2800. As can be seen in FIG. 53, a proximal end portion 2806 of the closure drive shaft 2800 has a driven gear 2808 thereon that is in meshing engagement with a closure drive assembly 2920. In various embodiments, the closure drive system 2920 includes a closure drive gear 2922 that is coupled to a corresponding second one of the driven rotational bodies or elements 1304 on the adapter side of the tool mounting plate 2462 when the tool mounting portion 2900 is coupled to the tool holder 1270. See FIGS. 26 and 53. The closure drive gear 2922 is supported in meshing engagement with a closure gear train, generally depicted as 2923. In at least one form, the closure gear rain 2923 comprises a first driven closure gear 2924 that is rotatably supported on the tool mounting plate 2902. The first closure driven gear 2924 is attached to a second closure driven gear 2926 by a drive shaft 2928. The second closure driven gear 2926 is in meshing engagement with a planetary gear assembly 2930. In various embodiments, the planetary gear assembly 2930 includes a driven planetary closure gear 2932 that is rotatably supported within the bearing assembly 2904 that is mounted on tool mounting plate 2902. As can be seen in FIGS. 53 and 53B, the proximal end portion 2806 of the closure drive shaft 2800 is rotatably supported within the proximal end portion 2742 of the spine tube 2740 such that the driven gear 2808 is in meshing engagement with central gear teeth 2934 formed on the planetary gear 2932. As can also be seen in FIG. 53A, two additional support gears 2936 are attached to or rotatably supported relative to the proximal end portion 2742 of the spine tube 2740 to provide bearing support thereto. Such arrangement with the planetary gear assembly 2930 serves to accommodate rotation of the spine shaft 2740 by the rotation drive assembly 2910 while permitting the closure driven gear 2808 to remain in meshing engagement with the closure drive system 2920. In addition, rotation of the closure drive gear 2922 in a first direction will ultimately result in the rotation of the closure drive shaft 2800 and closure drive nut 2760 which will ultimately result in the closure of the anvil 2724 as described above. Conversely, rotation of the closure drive gear 2922 in a second opposite direction will ultimately result in the rotation of the closure drive nut 2760 in an opposite direction which results in the opening of the anvil 2724.

As can be seen in FIG. 53, the proximal end 2784 of the knife bar 2780 has a threaded shaft portion 2786 attached thereto which is in driving engagement with a knife drive assembly 2940. In various embodiments, the threaded shaft portion 2786 is rotatably supported by a bearing 2906 attached to the tool mounting plate 2902. Such arrangement permits the threaded shaft portion 2786 to rotate and move axially relative to the tool mounting plate 2902. The knife bar 2780 is axially advanced in the distal and proximal directions by the knife drive assembly 2940. One form of the knife drive assembly 2940 comprises a rotary drive gear 2942 that is coupled to a corresponding third one of the rotatable bodies, driven discs or elements 1304 on the adapter side of the tool mounting plate 2902 when the tool mounting portion 2900 is coupled to the tool holder 1270. See FIGS. 26 and 53. The rotary drive gear 2942 is in meshing engagement with a knife gear train, generally depicted as 2943. In various embodiments, the knife gear train 2943 comprises a first rotary driven gear assembly 2944 that is rotatably supported on the tool mounting plate 2902. The first rotary driven gear assembly 2944 is in meshing engagement with a third rotary driven gear assembly 2946 that is rotatably supported on the tool mounting plate 2902 and which is in meshing engagement with a fourth rotary driven gear assembly 2948 that is in meshing engagement with the threaded portion 2786 of the knife bar 2780. Rotation of the rotary drive gear 2942 in one direction will result in the axial advancement of the knife bar 2780 in the distal direction "DD". Conversely, rotation of the rotary drive gear 2942 in an opposite direction will cause the knife bar 2780 to move in the proximal direction. Tool 2700 may otherwise be used as described above.

FIGS. 54 and 55 illustrate a surgical tool embodiment 2700 that is substantially identical to tool 2700 that was described in detail above. However tool 2700' includes a pressure sensor 2950 that is configured to provide feedback to the robotic controller 1001 concerning the amount of clamping pressure experienced by the anvil 2724. In various embodiments, for example, the pressure sensor may comprise a spring biased contact switch. For a continuous signal, it would use either a cantilever beam with a strain gage on it or a dome button top with a strain gage on the inside. Another version may comprise an off switch that contacts only at a known desired load. Such arrangement would include a dome on the based wherein the dome is one electrical pole and the base is the other electrical pole. Such arrangement permits the robotic controller 1001 to adjust the amount of clamping pressure being applied to the tissue within the surgical end effector 2712 by adjusting the amount of closing pressure applied to the anvil 2724. Those of ordinary skill in the art will understand that such pressure sensor arrangement may be effectively employed with several of the surgical tool embodiments described herein as well as their equivalent structures.

FIG. 56 illustrates a portion of another surgical tool 3000 that may be effectively used in connection with a robotic system 1000. The surgical tool 3003 employs on-board motor (s) for powering various components of a surgical end effector cutting instrument. In at least one non-limiting embodiment for example, the surgical tool 3000 includes a surgical end effector in the form of an endocutter (not shown) that has an anvil (not shown) and surgical staple cartridge arrangement (not shown) of the types and constructions described above. The surgical tool 3000 also includes an elongated shaft (not shown) and anvil closure arrangement (not shown) of the types described above. Thus, this portion of the Detailed Description will not repeat the description of those components beyond that which is necessary to appreciate the unique and novel attributes of the various embodiments of surgical tool 3000.

In the depicted embodiment, the end effector includes a cutting instrument 3002 that is coupled to a knife bar 3003. As can be seen in FIG. 56, the surgical tool 3000 includes a tool mounting portion 3010 that includes a tool mounting plate 3012 that is configured to mountingly interface with the adaptor portion 1240' which is coupled to the robotic system 1000 in the various manners described above. The tool mounting portion 3010 is configured to operably support a transmission arrangement 3013 thereon. In at least one embodiment, the adaptor portion 1240' may be identical to the adaptor portion 1240 described in detail above without the powered rotation bodies and disc members employed by adapter 1240. In other embodiments, the adaptor portion 1240' may be identical to adaptor portion 1240. Still other modifications which are considered to be within the spirit and scope of the various forms of the present invention may employ one or more of the mechanical motions (i.e., rotary motion(s)) from the tool holder portion 1270 (as described hereinabove) to power/actuate the transmission arrangement 3013 while also employing one or more motors within the tool mounting portion 3010 to power one or more other components of the surgical end effector. In addition, while the end effector of the depicted embodiment comprises an endocutter, those of ordinary skill in the art will understand that the unique and novel attributes of the depicted embodiment may be effectively employed in connection with other types of surgical end effectors without departing from the spirit and scope of various forms of the present invention.

In various embodiments, the tool mounting plate 3012 is configured to at least house a first firing motor 3011 for supplying firing and retraction motions to the knife bar 3003 which is coupled to or otherwise operably interfaces with the cutting instrument 3002. The tool mounting plate 3012 has an array of electrical connecting pins 3014 which are configured to interface with the slots 1258 (FIG. 25) in the adapter 1240'. Such arrangement permits the controller 1001 of the robotic system 1000 to provide control signals to the electronic control circuit 3020 of the surgical tool 3000. While the interface is described herein with reference to mechanical, electrical, and magnetic coupling elements, it should be understood that a wide variety of telemetry modalities might be used, including infrared, inductive coupling, or the like.

Control circuit 3020 is shown in schematic form in FIG. 56. In one form or embodiment, the control circuit 3020 includes a power supply in the form of a battery 3022 that is coupled to an on-off solenoid powered switch 3024. Control circuit 3020 further includes an on/off firing solenoid 3026 that is coupled to a double pole switch 3028 for controlling the rotational direction of the motor 3011. Thus, when the controller 1001 of the robotic system 1000 supplies an appropriate control signal, switch 3024 will permit battery 3022 to supply power to the double pole switch 3028. The controller 1001 of the robotic system 1000 will also supply an appropriate signal to the double pole switch 3028 to supply power to the motor 3011. When it is desired to fire the surgical end effector (i.e., drive the cutting instrument 3002 distally through tissue clamped in the surgical end effector, the double pole switch 3028 will be in a first position. When it is desired to retract the cutting instrument 3002 to the starting position, the double pole switch 3028 will be moved to the second position by the controller 1001.

Various embodiments of the surgical tool 3000 also employ a gear box 3030 that is sized, in cooperation with a firing gear train 3031 that, in at least one non-limiting embodiment, comprises a firing drive gear 3032 that is in meshing engagement with a firing driven gear 3034 for generating a desired amount of driving force necessary to drive the cutting instrument 3002 through tissue and to drive and form staples in the various manners described herein. In the embodiment depicted in FIG. 56, the driven gear 3034 is coupled to a screw shaft 3036 that is in threaded engagement with a screw nut arrangement 3038 that is constrained to move axially (represented by arrow "D"). The screw nut arrangement 3038 is attached to the firing bar 3003. Thus, by rotating the screw shaft 3036 in a first direction, the cutting instrument 3002 is driven in the distal direction "DD" and rotating the screw shaft in an opposite second direction, the cutting instrument 3002 may be retracted in the proximal direction "PD".

FIG. 57 illustrates a portion of another surgical tool 3000' that is substantially identical to tool 3000 described above, except that the driven gear 3034 is attached to a drive shaft 3040. The drive shaft 3040 is attached to a second driver gear 3042 that is in meshing engagement with a third driven gear 3044 that is in meshing engagement with a screw 3046 coupled to the firing bar 3003.

Figure 58:
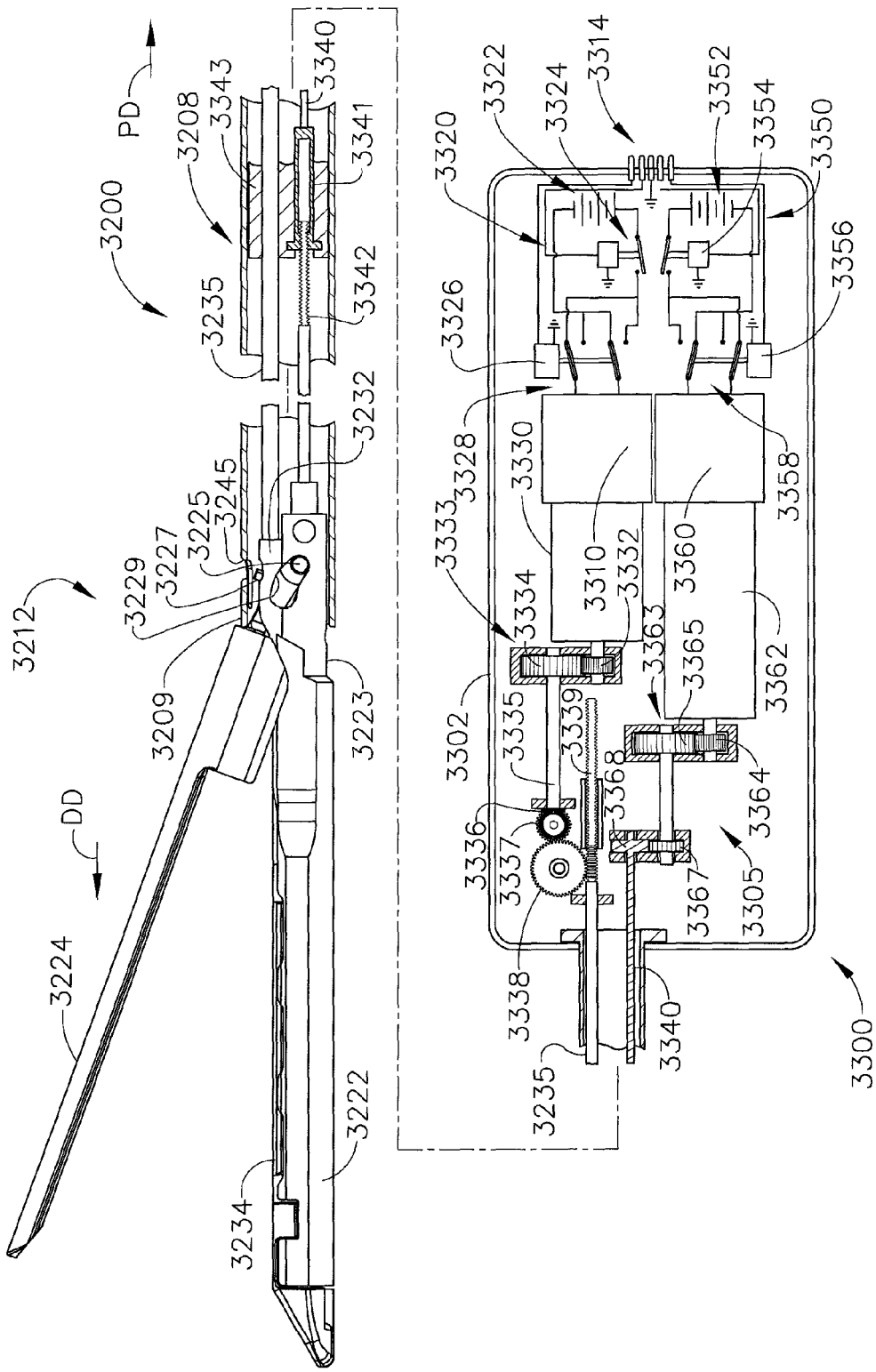
FIG. 58 is a side view of a portion of another surgical tool embodiment of the present invention with some of the components thereof shown in cross-section.

FIG. 58 illustrates another surgical tool 3200 that may be effectively used in connection with a robotic system 1000. In this embodiment, the surgical tool 3200 includes a surgical end effector 3212 that in one non-limiting form, comprises a component portion that is selectively movable between first and second positions relative to at least one other end effector component portion. As will be discussed in further detail below, the surgical tool 3200 employs on-board motors for powering various components of a transmission arrangement 3305. The surgical end effector 3212 includes an elongated channel 3222 that operably supports a surgical staple cartridge 3234. The elongated channel 3222 has a proximal end 3223 that slidably extends into a hollow elongated shaft assembly 3208 that is coupled to a tool mounting portion 3300. In addition, the surgical end effector 3212 includes an anvil 3224 that is pivotally coupled to the elongated channel 3222 by a pair of trunnions 3225 that are received within corresponding openings 3229 in the elongated channel 3222. A distal end portion 3209 of the shaft assembly 3208 includes an opening 3245 into which a tab 3227 on the anvil 3224 is inserted in order to open the anvil 3224 as the elongated channel 3222 is moved axially in the proximal direction "PD" relative to the distal end portion 3209 of the shaft assembly 3208. In various embodiments, a spring (not shown) may be employed to bias the anvil 3224 to the open position.

As indicated above, the surgical tool 3200 includes a tool mounting portion 3300 that includes a tool mounting plate 3302 that is configured to operably support the transmission arrangement 3305 and to mountingly interface with the adaptor portion 1240' which is coupled to the robotic system 1000 in the various manners described above. In at least one embodiment, the adaptor portion 1240' may be identical to the adaptor portion 1240 described in detail above without the powered disc members employed by adapter 1240. In other embodiments, the adaptor portion 1240' may be identical to adaptor portion 1240. However, in such embodiments, because the various components of the surgical end effector 3212 are all powered by motor(s) in the tool mounting portion 3300, the surgical tool 3200 will not employ or require any of the mechanical (i.e., non-electrical) actuation motions from the tool holder portion 1270 to power the surgical end effector 3200 components. Still other modifications which are considered to be within the spirit and scope of the various forms of the present invention may employ one or more of the mechanical motions from the tool holder portion 1270 (as described hereinabove) to power/actuate one or more of the surgical end effector components while also employing one or more motors within the tool mounting portion to power one or more other components of the surgical end effector.

In various embodiments, the tool mounting plate 3302 is configured to support a first firing motor 3310 for supplying firing and retraction motions to the transmission arrangement 3305 to drive a knife bar 3335 that is coupled to a cutting instrument 3332 of the type described above. As can be seen in FIG. 58, the tool mounting plate 3212 has an array of electrical connecting pins 3014 which are configured to interface with the slots 1258 (FIG. 25) in the adapter 1240'. Such arrangement permits the controller 1001 of the robotic system 1000 to provide control signals to the electronic control circuits 3320, 3340 of the surgical tool 3200. While the interface is described herein with reference to mechanical, electrical, and magnetic coupling elements, it should be understood that a wide variety of telemetry modalities might be used, including infrared, inductive coupling, or the like.

In one form or embodiment, the first control circuit 3320 includes a first power supply in the form of a first battery 3322 that is coupled to a first on-off solenoid powered switch 3324. The first firing control circuit 3320 further includes a first on/off firing solenoid 3326 that is coupled to a first double pole switch 3328 for controlling the rotational direction of the first firing motor 3310. Thus, when the robotic controller 1001 supplies an appropriate control signal, the first switch 3324 will permit the first battery 3322 to supply power to the first double pole switch 3328. The robotic controller 1001 will also supply an appropriate signal to the first double pole switch 3328 to supply power to the first firing motor 3310. When it is desired to fire the surgical end effector (i.e., drive the cutting instrument 3232 distally through tissue clamped in the surgical end effector 3212, the first switch 3328 will be positioned in a first position by the robotic controller 1001. When it is desired to retract the cutting instrument 3232 to the starting position, the robotic controller 1001 will send the appropriate control signal to move the first switch 3328 to the second position.

Various embodiments of the surgical tool 3200 also employ a first gear box 3330 that is sized, in cooperation with a firing drive gear 3332 coupled thereto that operably interfaces with a firing gear train 3333. In at least one non-limiting embodiment, the firing gear train 333 comprises a firing driven gear 3334 that is in meshing engagement with drive gear 3332, for generating a desired amount of driving force necessary to drive the cutting instrument 3232 through tissue and to drive and form staples in the various manners described herein. In the embodiment depicted in FIG. 58, the driven gear 3334 is coupled to a drive shaft 3335 that has a second driven gear 3336 coupled thereto. The second driven gear 3336 is supported in meshing engagement with a third driven gear 3337 that is in meshing engagement with a fourth driven gear 3338. The fourth driven gear 3338 is in meshing engagement with a threaded proximal portion 3339 of the knife bar 3235 that is constrained to move axially. Thus, by rotating the drive shaft 3335 in a first direction, the cutting instrument 3232 is driven in the distal direction "DD" and rotating the drive shaft 3335 in an opposite second direction, the cutting instrument 3232 may be retracted in the proximal direction "PD".

As indicated above, the opening and closing of the anvil 3224 is controlled by axially moving the elongated channel 3222 relative to the elongated shaft assembly 3208. The axial movement of the elongated channel 3222 is controlled by a closure control system 3339. In various embodiments, the closure control system 3339 includes a closure shaft 3340 which has a hollow threaded end portion 3341 that threadably engages a threaded closure rod 3342. The threaded end portion 3341 is rotatably supported in a spine shaft 3343 that operably interfaces with the tool mounting portion 3300 and extends through a portion of the shaft assembly 3208 as shown. The closure system 3339 further comprises a closure control circuit 3350 that includes a second power supply in the form of a second battery 3352 that is coupled to a second on-off solenoid powered switch 3354. Closure control circuit 3350 further includes a second on/off firing solenoid 3356 that is coupled to a second double pole switch 3358 for controlling the rotation of a second closure motor 3360. Thus, when the robotic controller 1001 supplies an appropriate control signal, the second switch 3354 will permit the second battery 3352 to supply power to the second double pole switch 3354. The robotic controller 1001 will also supply an appropriate signal to the second double pole switch 3358 to supply power to the second motor 3360. When it is desired to close the anvil 3224, the second switch 3348 will be in a first position. When it is desired to open the anvil 3224, the second switch 3348 will be moved to a second position.

Various embodiments of tool mounting portion 3300 also employ a second gear box 3362 that is coupled to a closure drive gear 3364. The closure drive gear 3364 is in meshing engagement with a closure gear train 3363. In various non-limiting forms, the closure gear train 3363 includes a closure driven gear 3365 that is attached to a closure drive shaft 3366. Also attached to the closure drive shaft 3366 is a closure drive gear 3367 that is in meshing engagement with a closure shaft gear 3360 attached to the closure shaft 3340. FIG. 63 depicts the end effector 3212 in the open position. As indicated above, when the threaded closure rod 3342 is in the position depicted in FIG. 58, a spring (not shown) biases the anvil 3224 to the open position. When it is desired to close the anvil 3224, the robotic controller 1001 will activate the second motor 3360 to rotate the closure shaft 3340 to draw the threaded closure rod 3342 and the channel 3222 in the proximal direction 'PD'. As the anvil 3224 contacts the distal end portion 3209 of the shaft 3208, the anvil 3224 is pivoted to the closed position.

A method of operating the surgical tool 3200 will now be described. Once the tool mounting portion 3302 has be operably coupled to the tool holder 1270 of the robotic system 1000, the robotic system 1000 can orient the end effector 3212 in position adjacent the target tissue to be cut and stapled. If the anvil 3224 is not already in the open position, the robotic controller 1001 may activate the second closure motor 3360 to drive the channel 3222 in the distal direction to the position depicted in FIG. 58. Once the robotic controller 1001 determines that the surgical end effector 3212 is in the open position by sensor(s) in the and effector and/or the tool mounting portion 3300, the robotic controller 1001 may provide the surgeon with a signal to inform the surgeon that the anvil 3224 may then be closed. Once the target tissue is positioned between the open anvil 3224 and the surgical staple cartridge 3234, the surgeon may then commence the closure process by activating the robotic controller 1001 to apply a closure control signal to the second closure motor 3360. The second closure motor 3360 applies a rotary motion to the closure shaft 3340 to draw the channel 3222 in the proximal direction "PD" until the anvil 3224 has been pivoted to the closed position. Once the robotic controller 1001 determines that the anvil 3224 has been moved to the closed position by sensor(s) in the surgical end effector 3212 and/or in the tool mounting portion 3300 that are in communication with the robotic control system, the motor 3360 may be deactivated. Thereafter, the firing process may be commenced either manually by the surgeon activating a trigger, button, etc. on the controller 1001 or the controller 1001 may automatically commence the firing process.

To commence the firing process, the robotic controller 1001 activates the firing motor 3310 to drive the firing bar 3235 and the cutting instrument 3232 in the distal direction "DD". Once robotic controller 1001 has determined that the cutting instrument 3232 has moved to the ending position within the surgical staple cartridge 3234 by means of sensors in the surgical end effector 3212 and/or the motor drive portion 3300, the robotic controller 1001 may provide the surgeon with an indication signal. Thereafter the surgeon may manually activate the first motor 3310 to retract the cutting instrument 3232 to the starting position or the robotic controller 1001 may automatically activate the first motor 3310 to retract the cutting element 3232.

The embodiment depicted in FIG. 58 does not include an articulation joint. FIGS. 64 and 65 illustrate surgical tools 3200' and 3200" that have end effectors 3212', 3212", respectively that may be employed with an elongated shaft embodiment that has an articulation joint of the various types disclosed herein. For example, as can be seen in FIG. 59, a threaded closure shaft 3342 is coupled to the proximal end 3223 of the elongated channel 3222 by a flexible cable or other flexible member 3345. The location of an articulation joint (not shown) within the elongated shaft assembly 3208 will coincide with the flexible member 3345 to enable the flexible member 3345 to accommodate such articulation. In addition, in the above-described embodiment, the flexible member 33345 is rotatably affixed to the proximal end portion 3223 of the elongated channel 3222 to enable the flexible member 3345 to rotate relative thereto to prevent the flexible member 3229 from "winding up" relative to the channel 3222. Although not shown, the cutting element may be driven in one of the above described manners by a knife bar that can also accommodate articulation of the elongated shaft assembly. FIG. 60 depicts a surgical end effector 3212" that is substantially identical to the surgical end effector 3212 described above, except that the threaded closure rod 3342 is attached to a closure nut 3347 that is constrained to only move axially within the elongated shaft assembly 3208. The flexible member 3345 is attached to the closure nut 3347. Such arrangement also prevents the threaded closure rod 3342 from winding-up the flexible member 3345. A flexible knife bar 3235' may be employed to facilitate articulation of the surgical end effector 3212".

The surgical tools 3200, 3200', and 3200" described above may also employ anyone of the cutting instrument embodiments described herein. As described above, the anvil of each of the end effectors of these tools is closed by drawing the elongated channel into contact with the distal end of the elongated shaft assembly. Thus, once the target tissue has been located between the staple cartridge 3234 and the anvil 3224, the robotic controller 1001 can start to draw the channel 3222 inward into the shaft assembly 3208. In various embodiments, however, to prevent the end effector 3212, 3212', 3212" from moving the target tissue with the end effector during this closing process, the controller 1001 may simultaneously move the tool holder and ultimately the tool such to compensate for the movement of the elongated channel 3222 so that, in effect, the target tissue is clamped between the anvil and the elongated channel without being otherwise moved.

FIGS. 61-63 depict another surgical tool embodiment 3201 that is substantially identical to surgical tool 3200" described above, except for the differences discussed below. In this embodiment, the threaded closure rod 3342' has variable pitched grooves. More specifically, as can be seen in FIG. 62, the closure rod 3342' has a distal groove section 3380 and a proximal groove section 3382. The distal and proximal groove sections 3380, 3382 are configured for engagement with a lug 3390 supported within the hollow threaded end portion 3341'. As can be seen in FIG. 62, the distal groove section 3380 has a finer pitch than the groove section 3382. Thus, such variable pitch arrangement permits the elongated channel 3222 to be drawn into the shaft 3208 at a first speed or rate by virtue of the engagement between the lug 3390 and the proximal groove segment 3382. When the lug 3390 engages the distal groove segment, the channel 3222 will be drawn into the shaft 3208 at a second speed or rate. Because the proximal groove segment 3382 is coarser than the distal groove segment 3380, the first speed will be greater than the second speed. Such arrangement serves to speed up the initial closing of the end effector for tissue manipulation and then after the tissue has been properly positioned therein, generate the amount of closure forces to properly clamp the tissue for cutting and sealing. Thus, the anvil 3234 initially closes fast with a lower force and then applies a higher closing force as the anvil closes more slowly.

The surgical end effector opening and closing motions are employed to enable the user to use the end effector to grasp and manipulate tissue prior to fully clamping it in the desired location for cutting and sealing. The user may, for example, open and close the surgical end effector numerous times during this process to orient the end effector in a proper position which enables the tissue to be held in a desired location. Thus, in at least some embodiments, to produce the high loading for firing, the fine thread may require as many as 5-10 full rotations to generate the necessary load. In some cases, for example, this action could take as long as 2-5 seconds. If it also took an equally long time to open and close the end effector each time during the positioning/tissue manipulation process, just positioning the end effector may take an undesirably long time. If that happens, it is possible that a user may abandon such use of the end effector for use of a conventional grasper device. Use of graspers, etc. may undesirably increase the costs associated with completing the surgical procedure.

The above-described embodiments employ a battery or batteries to power the motors used to drive the end effector components. Activation of the motors is controlled by the robotic system 1000. In alternative embodiments, the power supply may comprise alternating current "AC" that is supplied to the motors by the robotic system 1000. That is, the AC power would be supplied from the system powering the robotic system 1000 through the tool holder and adapter. In still other embodiments, a power cord or tether may be attached to the tool mounting portion 3300 to supply the requisite power from a separate source of alternating or direct current.

In use, the controller 1001 may apply an initial rotary motion to the closure shaft 3340 (FIG. 58) to draw the elongated channel 3222 axially inwardly into the elongated shaft assembly 3208 and move the anvil from a first position to an intermediate position at a first rate that corresponds with the point wherein the distal groove section 3380 transitions to the proximal groove section 3382. Further application of rotary motion to the closure shaft 3340 will cause the anvil to move from the intermediate position to the closed position relative to the surgical staple cartridge. When in the closed position, the tissue to be cut and stapled is properly clamped between the anvil and the surgical staple cartridge.

FIGS. 64-68 illustrate another surgical tool embodiment 3400 of the present invention. This embodiment includes an elongated shaft assembly 3408 that extends from a tool mounting portion 3500. The elongated shaft assembly 3408 includes a rotatable proximal closure tube segment 3410 that is rotatably journaled on a proximal spine member 3420 that is rigidly coupled to a tool mounting plate 3502 of the tool mounting portion 3500. The proximal spine member 3420 has a distal end 3422 that is coupled to an elongated channel portion 3522 of a surgical end effector 3412. For example, in at least one embodiment, the elongated channel portion 3522 has a distal end portion 3523 that "hookingly engages" the distal end 3422 of the spine member 3420. The elongated channel 3522 is configured to support a surgical staple cartridge 3534 therein. This embodiment may employ one of the various cutting instrument embodiments disclosed herein to sever tissue that is clamped in the surgical end effector 3412 and fire the staples in the staple cartridge 3534 into the severed tissue.

Surgical end effector 3412 has an anvil 3524 that is pivotally coupled to the elongated channel 3522 by a pair of trunnions 3525 that are received in corresponding openings 3529 in the elongated channel 3522. The anvil 3524 is moved between the open (FIG. 64) and closed positions (FIGS. 65-67) by a distal closure tube segment 3430. A distal end portion 3432 of the distal closure tube segment 3430 includes an opening 3445 into which a tab 3527 on the anvil 3524 is inserted in order to open and close the anvil 3524 as the distal closure tube segment 3430 moves axially relative thereto. In various embodiments, the opening 3445 is shaped such that as the closure tube segment 3430 is moved in the proximal direction, the closure tube segment 3430 causes the anvil 3524 to pivot to an open position. In addition or in the alternative, a spring (not shown) may be employed to bias the anvil 3524 to the open position.

As can be seen in FIGS. 64-67, the distal closure tube segment 3430 includes a lug 3442 that extends from its distal end 3440 into threaded engagement with a variable pitch groove/thread 3414 formed in the distal end 3412 of the rotatable proximal closure tube segment 3410. The variable pitch groove/thread 3414 has a distal section 3416 and a proximal section 3418. The pitch of the distal groove/thread section 3416 is finer than the pitch of the proximal groove/thread section 3418. As can also be seen in FIGS. 64-67, the distal closure tube segment 3430 is constrained for axial movement relative to the spine member 3420 by an axial retainer pin 3450 that is received in an axial slot 3424 in the distal end of the spine member 3420.

As indicated above, the anvil 2524 is open and closed by rotating the proximal closure tube segment 3410. The variable pitch thread arrangement permits the distal closure tube segment 3430 to be driven in the distal direction "DD" at a first speed or rate by virtue of the engagement between the lug 3442 and the proximal groove/thread section 3418. When the lug 3442 engages the distal groove/thread section 3416, the distal closure tube segment 3430 will be driven in the distal direction at a second speed or rate. Because the proximal groove/thread section 3418 is coarser than the distal groove/thread segment 3416, the first speed will be greater than the second speed.

Figure 68:
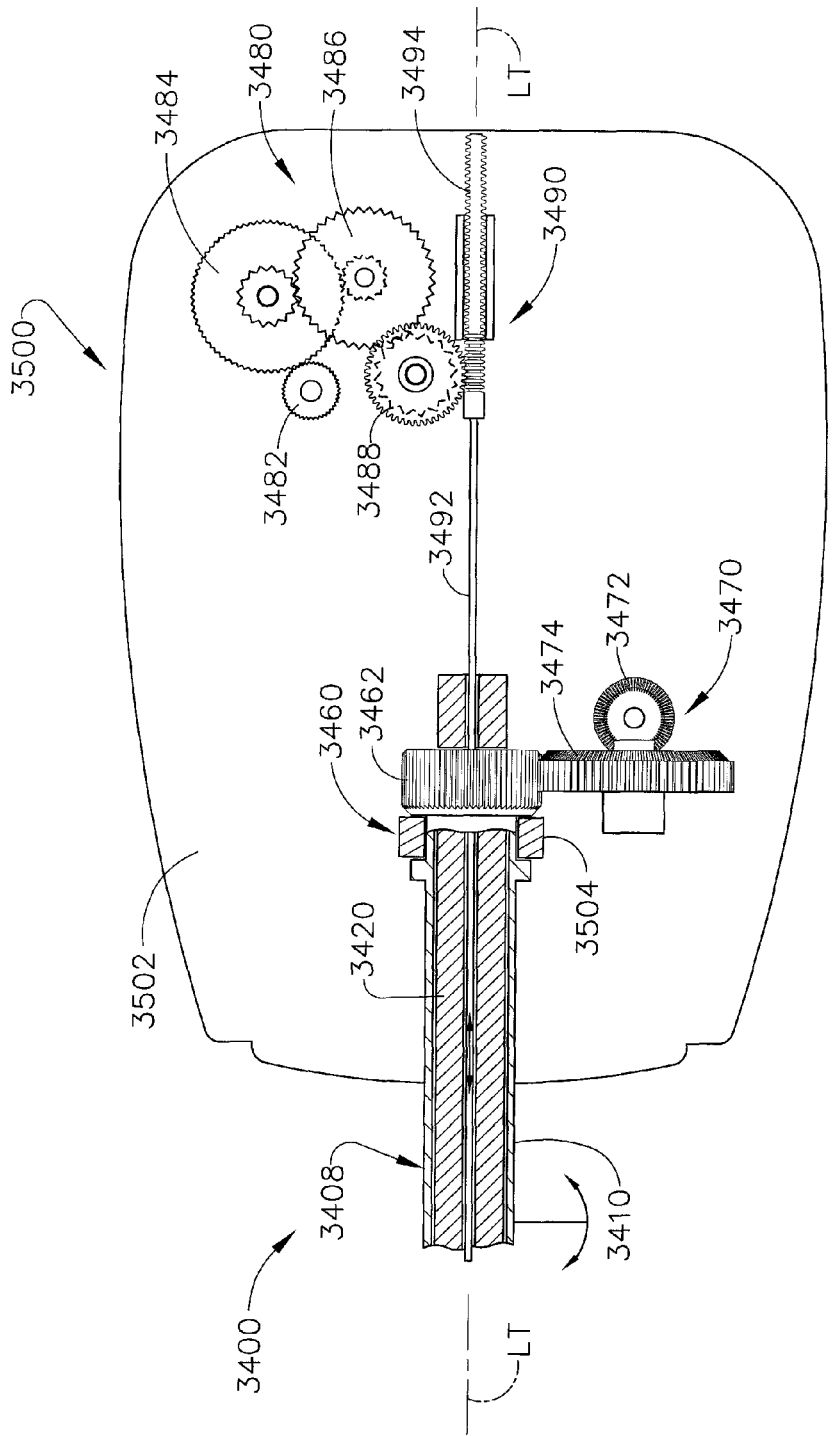
FIG. 68 is a top view of a tool mounting portion embodiment of a surgical tool embodiment of the present invention.

In at least one embodiment, the tool mounting portion 3500 is configured to receive a corresponding first rotary motion from the robotic controller 1001 and convert that first rotary motion to a primary rotary motion for rotating the rotatable proximal closure tube segment 3410 about a longitudinal tool axis LT-LT. As can be seen in FIG. 68, a proximal end 3460 of the proximal closure tube segment 3410 is rotatably supported within a cradle arrangement 3504 attached to a tool mounting plate 3502 of the tool mounting portion 3500. A rotation gear 3462 is formed on or attached to the proximal end 3460 of the closure tube segment 3410 for meshing engagement with a rotation drive assembly 3470 that is operably supported on the tool mounting plate 3502. In at least one embodiment, a rotation drive gear 3472 is coupled to a corresponding first one of the driven discs or elements 1304 on the adapter side of the tool mounting plate 3502 when the tool mounting portion 3500 is coupled to the tool holder 1270. See FIGS. 26 and 68. The rotation drive assembly 3470 further comprises a rotary driven gear 3474 that is rotatably supported on the tool mounting plate 3502 in meshing engagement with the rotation gear 3462 and the rotation drive gear 3472. Application of a first rotary control motion from the robotic controller 1001 through the tool holder 1270 and the adapter 1240 to the corresponding driven element 1304 will thereby cause rotation of the rotation drive gear 3472 by virtue of being operably coupled thereto. Rotation of the rotation drive gear 3472 ultimately results in the rotation of the closure tube segment 3410 to open and close the anvil 3524 as described above.

As indicated above, the surgical end effector 3412 employs a cutting instrument of the type and constructions described above. FIG. 68 illustrates one form of knife drive assembly 3480 for axially advancing a knife bar 3492 that is attached to such cutting instrument. One form of the knife drive assembly 3480 comprises a rotary drive gear 3482 that is coupled to a corresponding third one of the driven discs or elements 1304 on the adapter side of the tool mounting plate 3502 when the tool drive portion 3500 is coupled to the tool holder 1270. See FIGS. 26 and 68. The knife drive assembly 3480 further comprises a first rotary driven gear assembly 3484 that is rotatably supported on the tool mounting plate 5200. The first rotary driven gear assembly 3484 is in meshing engagement with a third rotary driven gear assembly 3486 that is rotatably supported on the tool mounting plate 3502 and which is in meshing engagement with a fourth rotary driven gear assembly 3488 that is in meshing engagement with a threaded portion 3494 of drive shaft assembly 3490 that is coupled to the knife bar 3492. Rotation of the rotary drive gear 3482 in a second rotary direction will result in the axial advancement of the drive shaft assembly 3490 and knife bar 3492 in the distal direction "DD". Conversely, rotation of the rotary drive gear 3482 in a secondary rotary direction (opposite to the second rotary direction) will cause the drive shaft assembly 3490 and the knife bar 3492 to move in the proximal direction.

Figure 69:
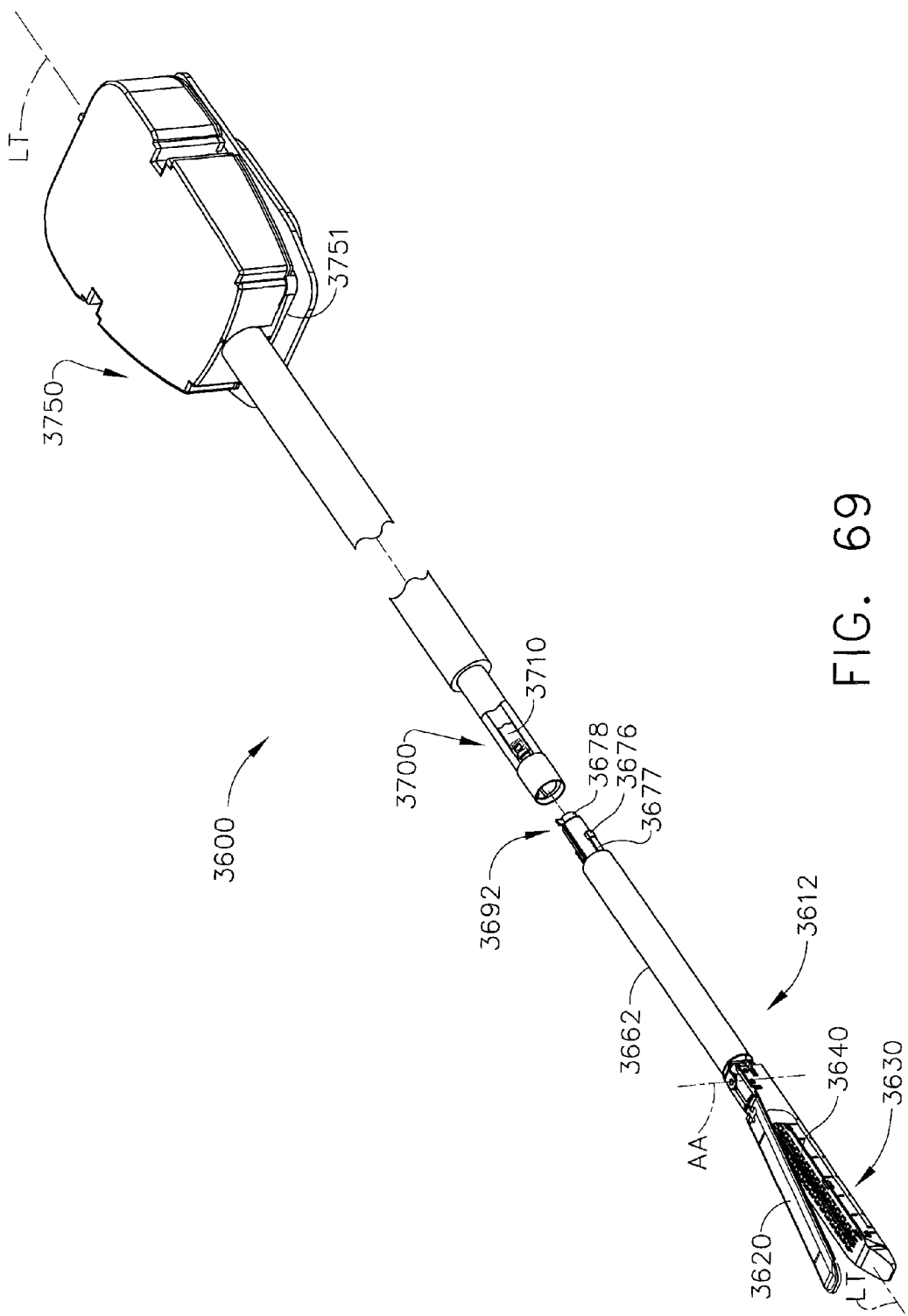
FIG. 69 is a perspective assembly view of another surgical tool embodiment of the present invention.

FIGS. 69-78 illustrate another surgical tool 3600 embodiment of the present invention that may be employed in connection with a robotic system 1000. As can be seen in FIG. 69, the tool 3600 includes an end effector in the form of a disposable loading unit 3612. Various forms of disposable loading units that may be employed in connection with tool 3600 are disclosed, for example, in U.S. Patent Application Publication No. US 2009/0206131 A1, entitled "End Effector Arrangements For a Surgical Cutting and Stapling Instrument", the disclosure of which is herein incorporated by reference in its entirety.

Figure 74:
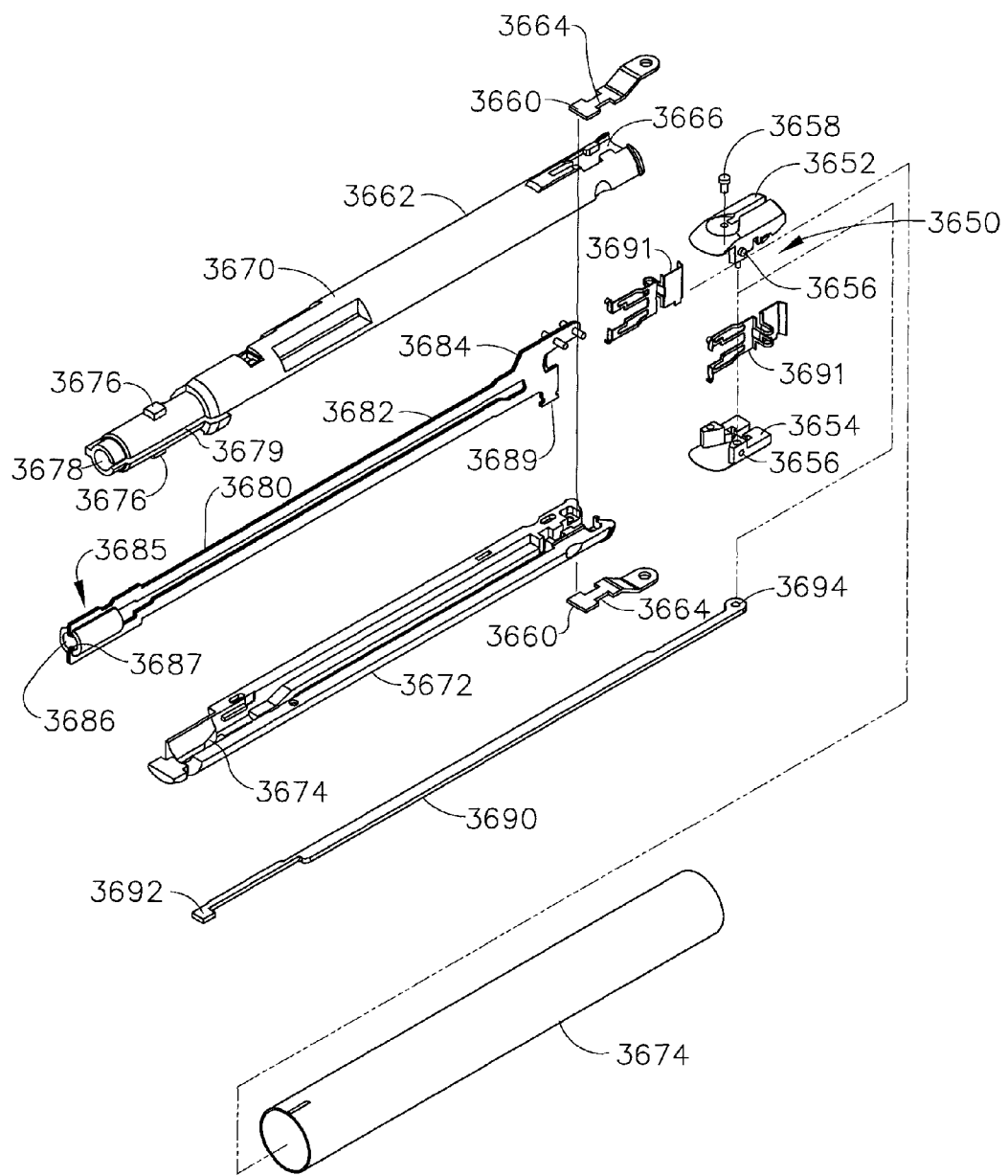
FIG. 74 is an exploded perspective view of a mounting portion of a disposable loading unit depicted in FIGS. 70-72.
Figure 77:
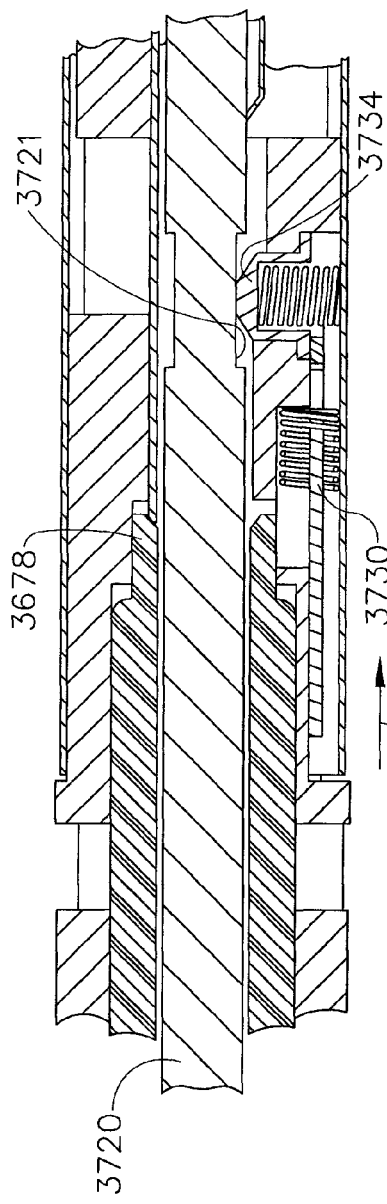
FIG. 77 is a cross-sectional view of a portion of the disposable loading unit and elongated shaft assembly embodiment depicted in FIGS. 75 and 76.
Figure 78:
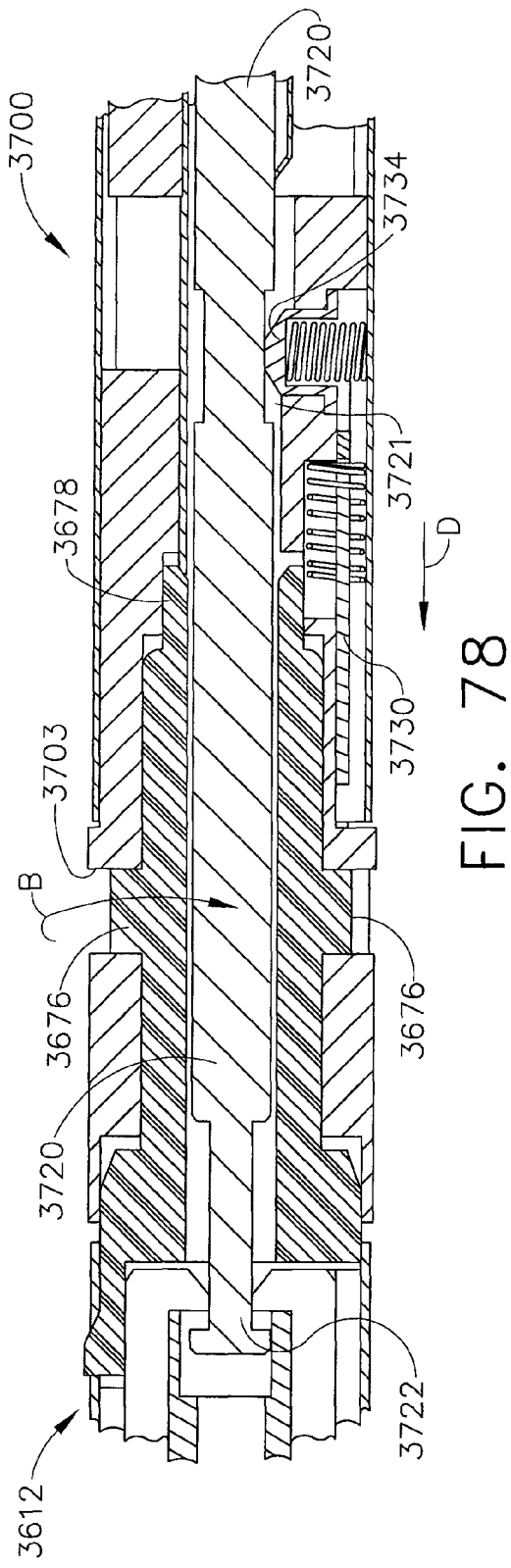
FIG. 78 is another cross-sectional view of the disposable loading unit and elongated shaft assembly embodiment depicted in FIGS. 75-77.

In at least one form, the disposable loading unit 3612 includes an anvil assembly 3620 that is supported for pivotal travel relative to a carrier 3630 that operably supports a staple cartridge 3640 therein. A mounting assembly 3650 is pivotally coupled to the cartridge carrier 3630 to enable the carrier 3630 to pivot about an articulation axis AA-AA relative to a longitudinal tool axis LT-LT. Referring to FIG. 74, mounting assembly 3650 includes upper and lower mounting portions 3652 and 3654. Each mounting portion includes a threaded bore 3656 on each side thereof dimensioned to receive threaded bolts (not shown) for securing the proximal end of carrier 3630 thereto. A pair of centrally located pivot members 3658 extends between upper and lower mounting portions via a pair of coupling members 3660 which engage a distal end of a housing portion 3662. Coupling members 3660 each include an interlocking proximal portion 3664 configured to be received in grooves 3666 formed in the proximal end of housing portion 3662 to retain mounting assembly 3650 and housing portion 3662 in a longitudinally fixed position in relation thereto.

In various forms, housing portion 3662 of disposable loading unit 3614 includes an upper housing half 3670 and a lower housing half 3672 contained within an outer casing 3674. The proximal end of housing half 3670 includes engagement nubs 3676 for releasably engaging an elongated shaft 3700 and an insertion tip 3678. Nubs 3676 form a bayonet-type coupling with the distal end of the elongated shaft 3700 which will be discussed in further detail below. Housing halves 3670, 3672 define a channel 3674 for slidably receiving axial drive assembly 3680. A second articulation link 3690 is dimensioned to be slidably positioned within a slot 3679 formed between housing halves 3670, 3672. A pair of blow out plates 3691 are positioned adjacent the distal end of housing portion 3662 adjacent the distal end of axial drive assembly 3680 to prevent outward bulging of drive assembly 3680 during articulation of carrier 3630.

In various embodiments, the second articulation link 3690 includes at least one elongated metallic plate. Preferably, two or more metallic plates are stacked to form link 3690. The proximal end of articulation link 3690 includes a hook portion 3692 configured to engage first articulation link 3710 extending through the elongated shaft 3700. The distal end of the second articulation link 3690 includes a loop 3694 dimensioned to engage a projection formed on mounting assembly 3650. The projection is laterally offset from pivot pin 3658 such that linear movement of second articulation link 3690 causes mounting assembly 3650 to pivot about pivot pins 3658 to articulate the carrier 3630.

In various forms, axial drive assembly 3680 includes an elongated drive beam 3682 including a distal working head 3684 and a proximal engagement section 3685. Drive beam 3682 may be constructed from a single sheet of material or, preferably, multiple stacked sheets. Engagement section 3685 includes a pair of engagement fingers which are dimensioned and configured to mountingly engage a pair of corresponding retention slots formed in drive member 3686. Drive member 3686 includes a proximal porthole 3687 configured to receive the distal end 3722 of control rod 2720 (See FIG. 78) when the proximal end of disposable loading unit 3614 is engaged with elongated shaft 3700 of surgical tool 3600.

Referring to FIGS. 69 and 76-78, to use the surgical tool 3600, a disposable loading unit 3612 is first secured to the distal end of elongated shaft 3700. It will be appreciated that the surgical tool 3600 may include an articulating or a non-articulating disposable loading unit. To secure the disposable loading unit 3612 to the elongated shaft 3700, the distal end 3722 of control rod 3720 is inserted into insertion tip 3678 of disposable loading unit 3612, and insertion tip 3678 is slid longitudinally into the distal end of the elongated shaft 3700 in the direction indicated by arrow "A" in FIG. 76 such that hook portion 3692 of second articulation link 3690 slides within a channel 3702 in the elongated shaft 3700. Nubs 3676 will each be aligned in a respective channel (not shown) in elongated shaft 3700. When hook portion 3692 engages the proximal wall 3704 of channel 3702, disposable loading unit 3612 is rotated in the direction indicated by arrow "B" in FIGS. 75 and 78 to move hook portion 3692 of second articulation link 3690 into engagement with finger 3712 of first articulation link 3710. Nubs 3676 also form a "bayonet-type" coupling within annular channel 3703 in the elongated shaft 3700. During rotation of loading unit 3612, nubs 3676 engage cam surface 3732 (FIG. 76) of block plate 3730 to initially move plate 3730 in the direction indicated by arrow "C" in FIG. 81 to lock engagement member 3734 in recess 3721 of control rod 3720 to prevent longitudinal movement of control rod 3720 during attachment of disposable loading unit 3612. During the final degree of rotation, nubs 3676 disengage from cam surface 3732 to allow blocking plate 3730 to move in the direction indicated by arrow "D" in FIGS. 75 and 78 from behind engagement member 3734 to once again permit longitudinal movement of control rod 3720. While the above-described attachment method reflects that the disposable loading unit 3612 is manipulated relative to the elongated shaft 3700, the person of ordinary skill in the art will appreciate that the disposable loading unit 3612 may be supported in a stationary position and the robotic system 1000 may manipulate the elongated shaft portion 3700 relative to the disposable loading unit 3612 to accomplish the above-described coupling procedure.

Figure 79:
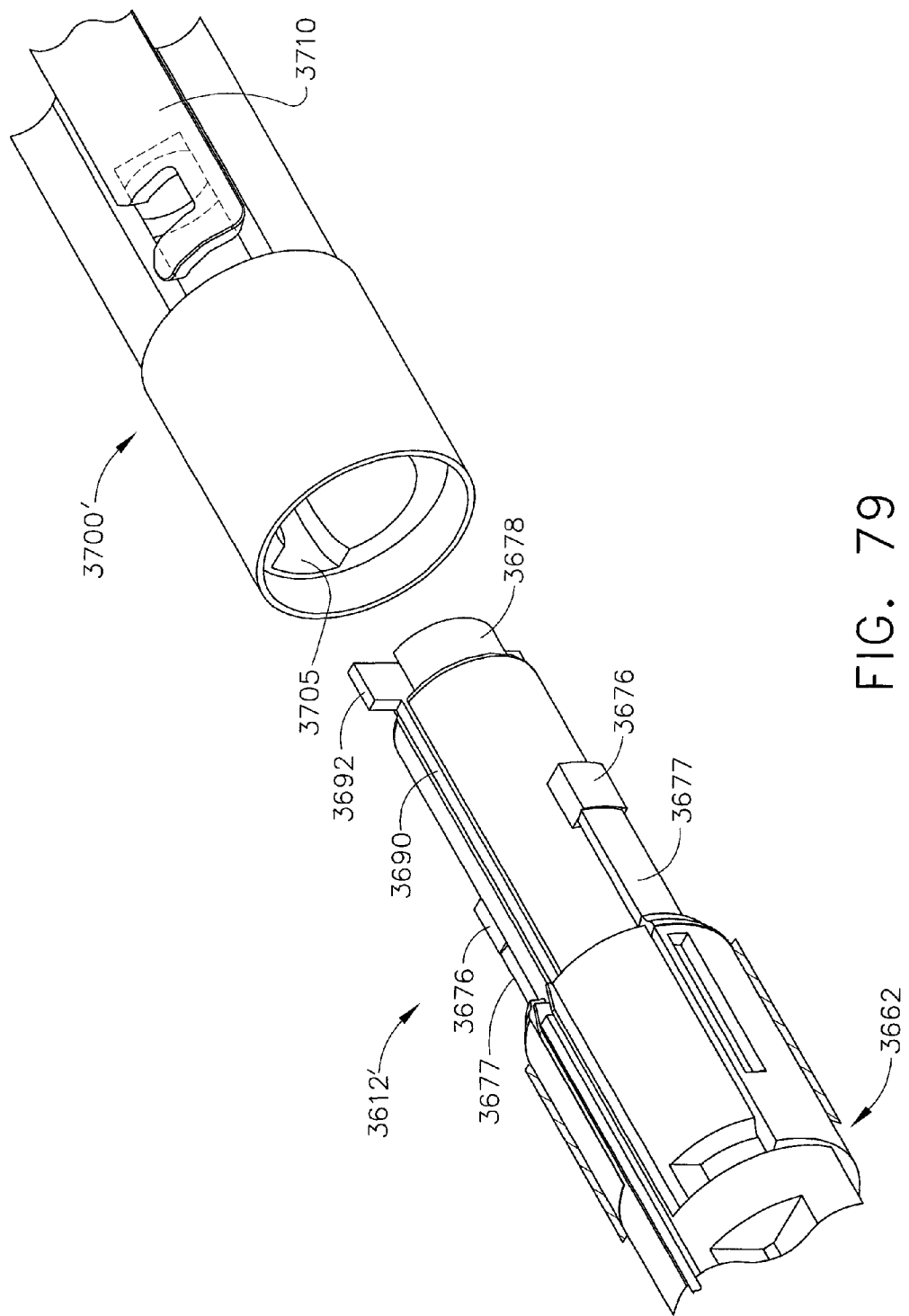
FIG. 79 is a partial exploded perspective view of a portion of another disposable loading unit embodiment and an elongated shaft assembly embodiment of a surgical tool embodiment of the present invention.

FIG. 79 illustrates another disposable loading unit 3612' that is attachable in a bayonet-type arrangement with the elongated shaft 3700' that is substantially identical to shaft 3700 except for the differences discussed below. As can be seen in FIG. 79, the elongated shaft 3700' has slots 3705 that extend for at least a portion thereof and which are configured to receive nubs 3676 therein. In various embodiments, the disposable loading unit 3612' includes arms 3677 extending therefrom which, prior to the rotation of disposable loading unit 3612', can be aligned, or at least substantially aligned, with nubs 3676 extending from housing portion 3662. In at least one embodiment, arms 3677 and nubs 3676 can be inserted into slots 3705 in elongated shaft 3700', for example, when disposable loading unit 3612' is inserted into elongated shaft 3700'. When disposable loading unit 3612' is rotated, arms 3677 can be sufficiently confined within slots 3705 such that slots 3705 can hold them in position, whereas nubs 3676 can be positioned such that they are not confined within slots 3705 and can be rotated relative to arms 3677. When rotated, the hook portion 3692 of the articulation link 3690 is engaged with the first articulation link 3710 extending through the elongated shaft 3700'.

Figure 80:
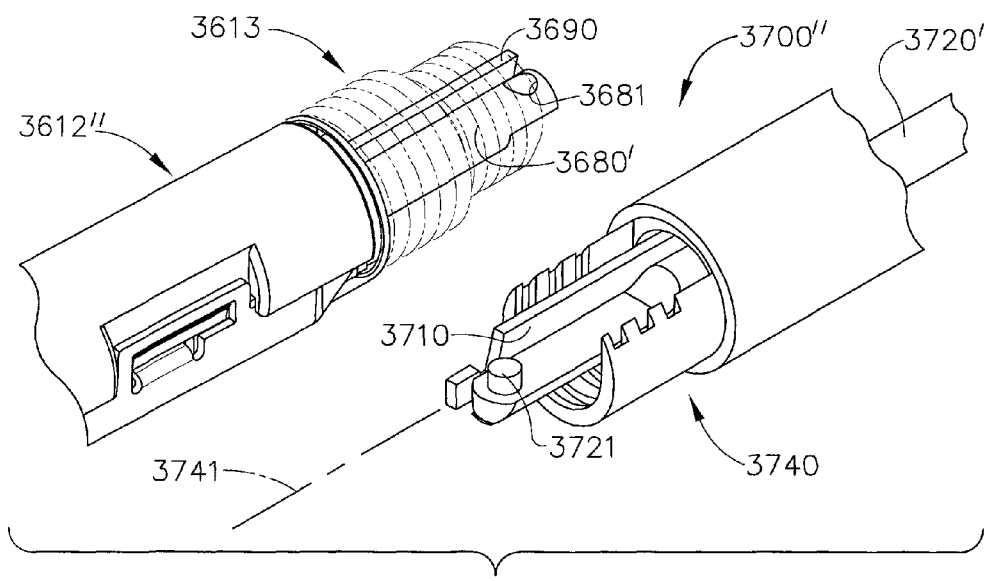
FIG. 80 is a partial exploded perspective view of a portion of another disposable loading unit embodiment and an elongated shaft assembly embodiment of a surgical tool embodiment of the present invention.
Figure 81:
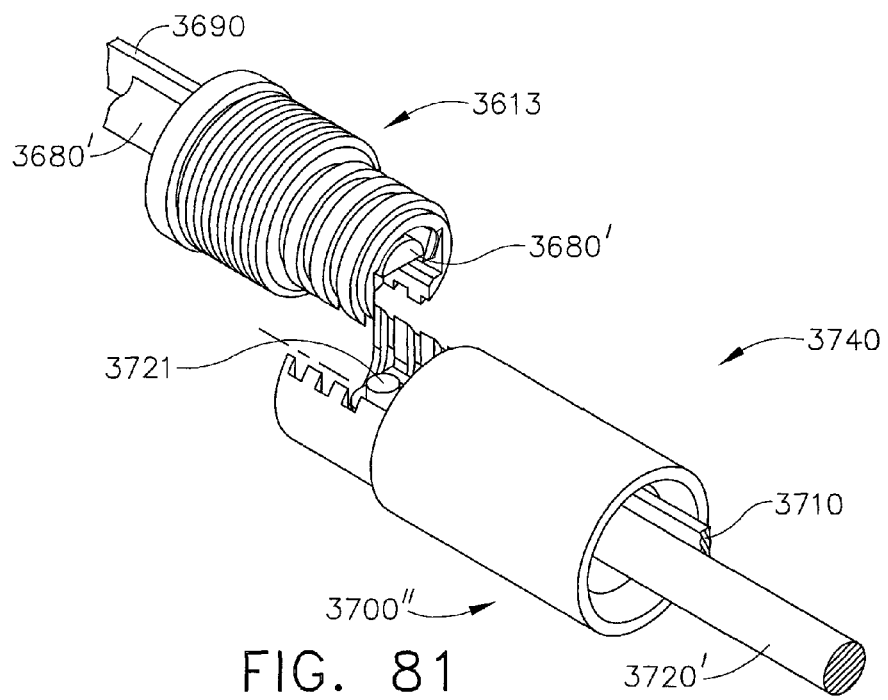
FIG. 81 is another partial exploded perspective view of the disposable loading unit embodiment and an elongated shaft assembly embodiment of FIG. 80.

Other methods of coupling the disposable loading units to the end of the elongated shaft may be employed. For example, as shown in FIGS. 80 and 81, disposable loading unit 3612" can include connector portion 3613 which can be configured to be engaged with connector portion 3740 of the elongated shaft 3700". In at least one embodiment, connector portion 3613 can include at least one projection and/or groove which can be mated with at least one projection and/or groove of connector portion 3740. In at least one such embodiment, the connector portions can include co-operating dovetail portions. In various embodiments, the connector portions can be configured to interlock with one another and prevent, or at least inhibit, distal and/or proximal movement of disposable loading unit 3612" along axis 3741. In at least one embodiment, the distal end of the axial drive assembly 3680' can include aperture 3681 which can be configured to receive projection 3721 extending from control rod 3720'. In various embodiments, such an arrangement can allow disposable loading unit 3612" to be assembled to elongated shaft 3700 in a direction which is not collinear with or parallel to axis 3741. Although not illustrated, axial drive assembly 3680' and control rod 3720 can include any other suitable arrangement of projections and apertures to operably connect them to each other. Also in this embodiment, the first articulation link 3710 which can be operably engaged with second articulation link 3690.

Figure 82:
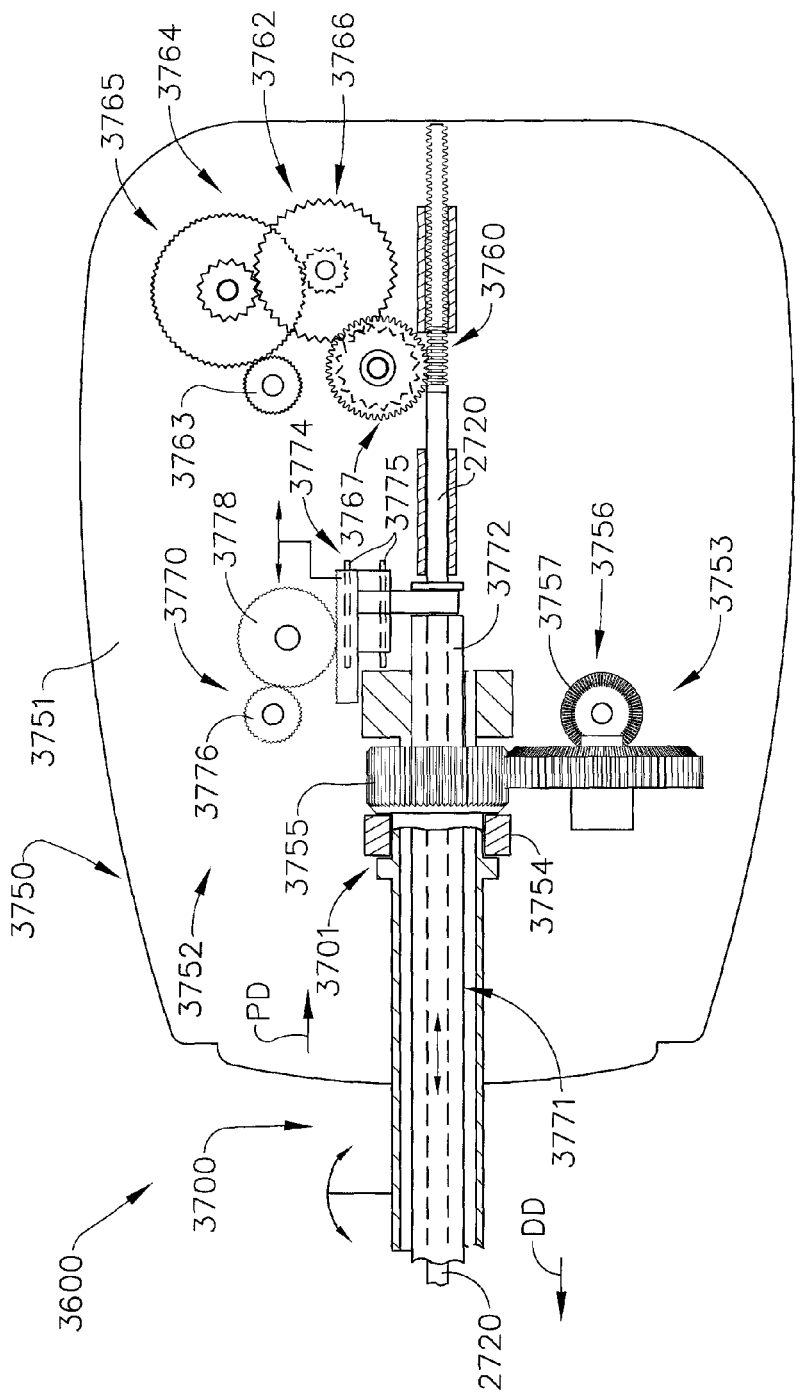
FIG. 82 is a top view of another tool mounting portion embodiment of a surgical tool embodiment of the present invention.

As can be seen in FIGS. 69 and 82, the surgical tool 3600 includes a tool mounting portion 3750. The tool mounting portion 3750 includes a tool mounting plate 3751 that is configured for attachment to the tool drive assembly 1010. The tool mounting portion operably supported a transmission arrangement 3752 thereon. In use, it may be desirable to rotate the disposable loading unit 3612 about the longitudinal tool axis defined by the elongated shaft 3700. In at least one embodiment, the transmission arrangement 3752 includes a rotational transmission assembly 3753 that is configured to receive a corresponding rotary output motion from the tool drive assembly 1010 of the robotic system 1000 and convert that rotary output motion to a rotary control motion for rotating the elongated shaft 3700 (and the disposable loading unit 3612) about the longitudinal tool axis LT-LT. As can be seen in FIG. 82, a proximal end 3701 of the elongated shaft 3700 is rotatably supported within a cradle arrangement 3754 that is attached to the tool mounting plate 3751 of the tool mounting portion 3750. A rotation gear 3755 is formed on or attached to the proximal end 3701 of the elongated shaft 3700 for meshing engagement with a rotation gear assembly 3756 operably supported on the tool mounting plate 3751. In at least one embodiment, a rotation drive gear 3757 drivingly coupled to a corresponding first one of the driven discs or elements 1304 on the adapter side of the tool mounting plate 3751 when the tool mounting portion 3750 is coupled to the tool drive assembly 1010. The rotation transmission assembly 3753 further comprises a rotary driven gear 3758 that is rotatably supported on the tool mounting plate 3751 in meshing engagement with the rotation gear 3755 and the rotation drive gear 3757. Application of a first rotary output motion from the robotic system 1000 through the tool drive assembly 1010 to the corresponding driven element 1304 will thereby cause rotation of the rotation drive gear 3757 by virtue of being operably coupled thereto. Rotation of the rotation drive gear 3757 ultimately results in the rotation of the elongated shaft 3700 (and the disposable loading unit 3612) about the longitudinal tool axis LT-LT (primary rotary motion).

As can be seen in FIG. 82, a drive shaft assembly 3760 is coupled to a proximal end of the control rod 2720. In various embodiments, the control rod 2720 is axially advanced in the distal and proximal directions by a knife/closure drive transmission 3762. One form of the knife/closure drive assembly 3762 comprises a rotary drive gear 3763 that is coupled to a corresponding second one of the driven rotatable body portions, discs or elements 1304 on the adapter side of the tool mounting plate 3751 when the tool mounting portion 3750 is coupled to the tool holder 1270. The rotary driven gear 3763 is in meshing driving engagement with a gear train, generally depicted as 3764. In at least one form, the gear train 3764 further comprises a first rotary driven gear assembly 3765 that is rotatably supported on the tool mounting plate 3751. The first rotary driven gear assembly 3765 is in meshing engagement with a second rotary driven gear assembly 3766 that is rotatably supported on the tool mounting plate 3751 and which is in meshing engagement with a third rotary driven gear assembly 3767 that is in meshing engagement with a threaded portion 3768 of the drive shaft assembly 3760. Rotation of the rotary drive gear 3763 in a second rotary direction will result in the axial advancement of the drive shaft assembly 3760 and control rod 2720 in the distal direction "DD". Conversely, rotation of the rotary drive gear 3763 in a secondary rotary direction which is opposite to the second rotary direction will cause the drive shaft assembly 3760 and the control rod 2720 to move in the proximal direction. When the control rod 2720 moves in the distal direction, it drives the drive beam 3682 and the working head 3684 thereof distally through the surgical staple cartridge 3640. As the working head 3684 is driven distally, it operably engages the anvil 3620 to pivot it to a closed position.

The cartridge carrier 3630 may be selectively articulated about articulation axis AA-AA by applying axial articulation control motions to the first and second articulation links 3710 and 3690. In various embodiments, the transmission arrangement 3752 further includes an articulation drive 3770 that is operably supported on the tool mounting plate 3751. More specifically and with reference to FIG. 82, it can be seen that a proximal end portion 3772 of an articulation drive shaft 3771 configured to operably engage with the first articulation link 3710 extends through the rotation gear 3755 and is rotatably coupled to a shifter rack gear 3774 that is slidably affixed to the tool mounting plate 3751 through slots 3775. The articulation drive 3770 further comprises a shifter drive gear 3776 that is coupled to a corresponding third one of the driven discs or elements 1304 on the adapter side of the tool mounting plate 3751 when the tool mounting portion 3750 is coupled to the tool holder 1270. The articulation drive assembly 3770 further comprises a shifter driven gear 3778 that is rotatably supported on the tool mounting plate 3751 in meshing engagement with the shifter drive gear 3776 and the shifter rack gear 3774. Application of a third rotary output motion from the robotic system 1000 through the tool drive assembly 1010 to the corresponding driven element 1304 will thereby cause rotation of the shifter drive gear 3776 by virtue of being operably coupled thereto. Rotation of the shifter drive gear 3776 ultimately results in the axial movement of the shifter gear rack 3774 and the articulation drive shaft 3771. The direction of axial travel of the articulation drive shaft 3771 depends upon the direction in which the shifter drive gear 3776 is rotated by the robotic system 1000. Thus, rotation of the shifter drive gear 3776 in a first rotary direction will result in the axial movement of the articulation drive shaft 3771 in the proximal direction "PD" and cause the cartridge carrier 3630 to pivot in a first direction about articulation axis AA-AA. Conversely, rotation of the shifter drive gear 3776 in a second rotary direction (opposite to the first rotary direction) will result in the axial movement of the articulation drive shaft 3771 in the distal direction "DD" to thereby cause the cartridge carrier 3630 to pivot about articulation axis AA-AA in an opposite direction.

Figure 83:
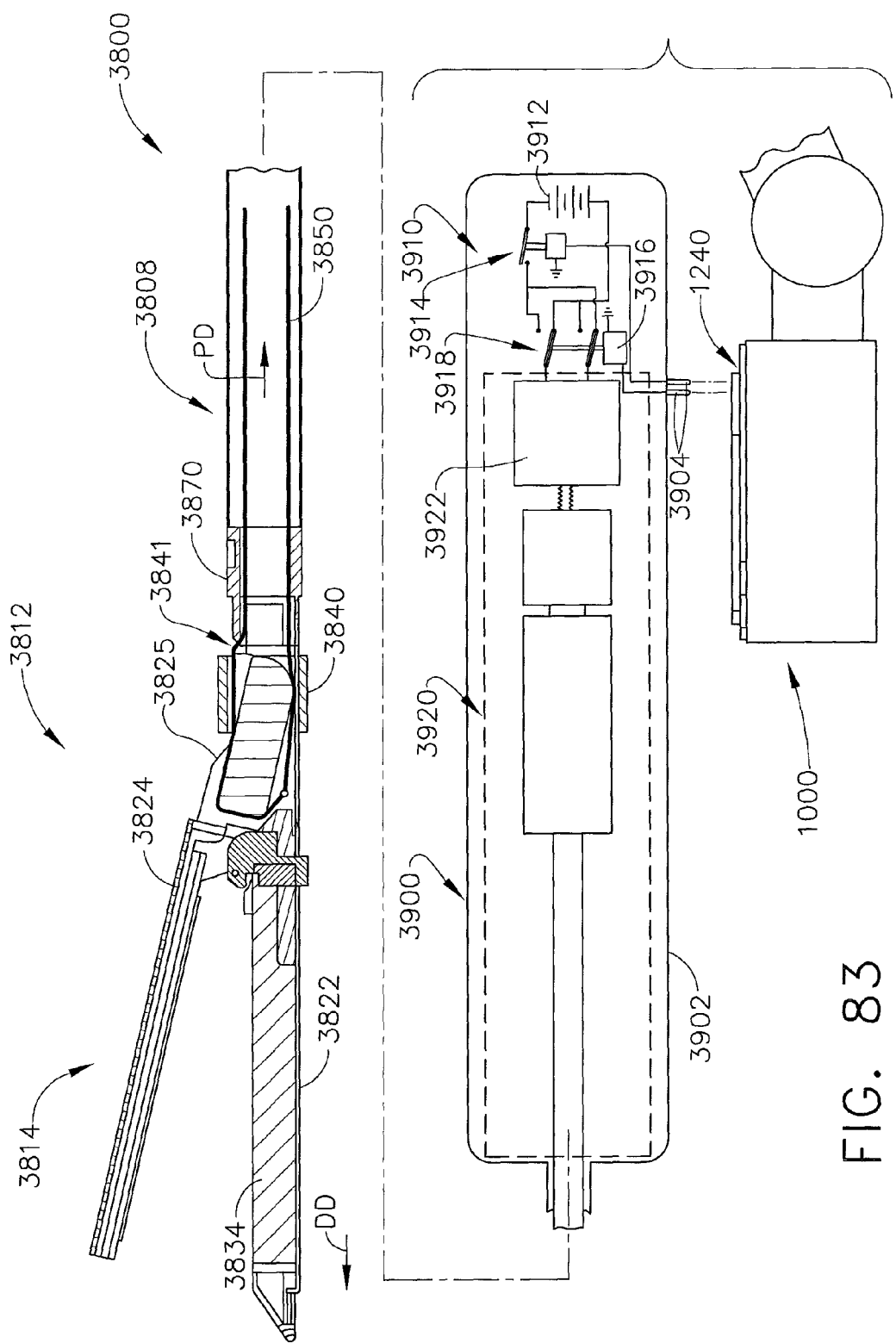
FIG. 83 is a side view of another surgical tool embodiment of the present invention with some of the components thereof shown in cross-section and in relation to a robotic tool holder of a robotic system.

FIG. 83 illustrates yet another surgical tool 3800 embodiment of the present invention that may be employed with a robotic system 1000. As can be seen in FIG. 83, the surgical tool 3800 includes a surgical end effector 3812 in the form of an endocutter 3814 that employs various cable-driven components. Various forms of cable driven endocutters are disclosed, for example, in U.S. Pat. No. 7,726,537, entitled "Surgical Stapler With Universal Articulation and Tissue Pre-Clamp" and U.S. Patent Application Publication No. US 2008/0308603A1, entitled "Cable Driven Surgical Stapling and Cutting Instrument With Improved Cable Attachment Arrangements", the disclosures of each are herein incorporated by reference in their respective entireties. Such endocutters 3814 may be referred to as a "disposable loading unit" because they are designed to be disposed of after a single use. However, the various unique and novel arrangements of various embodiments of the present invention may also be employed in connection with cable driven end effectors that are reusable.

As can be seen in FIG. 83, in at least one form, the endocutter 3814 includes an elongated channel 3822 that operably supports a surgical staple cartridge 3834 therein. An anvil 3824 is pivotally supported for movement relative to the surgical staple cartridge 3834. The anvil 3824 has a cam surface 3825 that is configured for interaction with a pre-clamping collar 3840 that is supported for axial movement relative thereto. The end effector 3814 is coupled to an elongated shaft assembly 3808 that is attached to a tool mounting portion 3900. In various embodiments, a closure cable 3850 is employed to move pre-clamping collar 3840 distally onto and over cam surface 3825 to close the anvil 3824 relative to the surgical staple cartridge 3834 and compress the tissue therebetween. Preferably, closure cable 3850 attaches to the pre-clamping collar 3840 at or near point 3841 and is fed through a passageway in anvil 3824 (or under a proximal portion of anvil 3824) and fed proximally through shaft 3808. Actuation of closure cable 3850 in the proximal direction "PD" forces pre-clamping collar 3840 distally against cam surface 3825 to close anvil 3824 relative to staple cartridge assembly 3834. A return mechanism, e.g., a spring, cable system or the like, may be employed to return pre-clamping collar 3840 to a pre-clamping orientation which re-opens the anvil 3824.

The elongated shaft assembly 3808 may be cylindrical in shape and define a channel 3811 which may be dimensioned to receive a tube adapter 3870. See FIG. 84. In various embodiments, the tube adapter 3870 may be slidingly received in friction-fit engagement with the internal channel of elongated shaft 3808. The outer surface of the tube adapter 3870 may further include at least one mechanical interface, e.g., a cutout or notch 3871, oriented to mate with a corresponding mechanical interface, e.g., a radially inwardly extending protrusion or detent (not shown), disposed on the inner periphery of internal channel 3811 to lock the tube adapter 3870 to the elongated shaft 3808. In various embodiments, the distal end of tube adapter 3870 may include a pair of opposing flanges 3872a and 3872b which define a cavity for pivotably receiving a pivot block 3873 therein. Each flange 3872a and 3872b may include an aperture 3874a and 3874b that is oriented to receive a pivot pin 3875 that extends through an aperture in pivot block 3873 to allow pivotable movement of pivot block 3873 about an axis that is perpendicular to longitudinal tool axis "LT-LT". The channel 3822 may be formed with two upwardly extending flanges 3823a, 3823b that have apertures therein, which are dimensioned to receive a pivot pin 3827. In turn, pivot pin 3875 mounts through apertures in pivot block 3873 to permit rotation of the surgical end effector 3814 about the "Y" axis as needed during a given surgical procedure. Rotation of pivot block 3873 about pin 3875 along "Z" axis rotates the surgical end effector 3814 about the "Z" axis. See FIG. 84. Other methods of fastening the elongated channel 3822 to the pivot block 3873 may be effectively employed without departing from the spirit and scope of the present invention.

The surgical staple cartridge 3834 can be assembled and mounted within the elongated channel 3822 during the manufacturing or assembly process and sold as part of the surgical end effector 3812, or the surgical staple cartridge 3834 may be designed for selective mounting within the elongated channel 3822 as needed and sold separately, e.g., as a single use replacement, replaceable or disposable staple cartridge assembly. It is within the scope of this disclosure that the surgical end effector 3812 may be pivotally, operatively, or integrally attached, for example, to distal end 3809 of the elongated shaft assembly 3808 of a disposable surgical stapler. As is known, a used or spent disposable loading unit 3814 can be removed from the elongated shaft assembly 3808 and replaced with an unused disposable unit. The endocutter 3814 may also preferably include an actuator, preferably a dynamic clamping member 3860, a sled 3862, as well as staple pushers (not shown) and staples (not shown) once an unspent or unused cartridge 3834 is mounted in the elongated channel 3822. See FIG. 84.

In various embodiments, the dynamic clamping member 3860 is associated with, e.g., mounted on and rides on, or with or is connected to or integral with and/or rides behind sled 3862. It is envisioned that dynamic clamping member 3860 can have cam wedges or cam surfaces attached or integrally formed or be pushed by a leading distal surface thereof. In various embodiments, dynamic clamping member 3860 may include an upper portion 3863 having a transverse aperture 3864 with a pin 3865 mountable or mounted therein, a central support or upward extension 3866 and substantially T-shaped bottom flange 3867 which cooperate to slidingly retain dynamic clamping member 3860 along an ideal cutting path during longitudinal, distal movement of sled 3862. The leading cutting edge 3868, here, knife blade 3869, is dimensioned to ride within slot 3835 of staple cartridge assembly 3834 and separate tissue once stapled. As used herein, the term "knife assembly" may include the aforementioned dynamic clamping member 3860, knife 3869, and sled 3862 or other knife/beam/sled drive arrangements and cutting instrument arrangements. In addition, the various embodiments of the present invention may be employed with knife assembly/cutting instrument arrangements that may be entirely supported in the staple cartridge 3834 or partially supported in the staple cartridge 3834 and elongated channel 3822 or entirely supported within the elongated channel 3822.

In various embodiments, the dynamic clamping member 3860 may be driven in the proximal and distal directions by a cable drive assembly 3870. In one non-limiting form, the cable drive assembly comprises a pair of advance cables 3880, 3882 and a firing cable 3884. FIGS. 85 and 86 illustrate the cables 3880, 3882, 3884 in diagrammatic form. As can be seen in those Figures, a first advance cable 3880 is operably supported on a first distal cable transition support 3885 which may comprise, for example, a pulley, rod, capstan, etc. that is attached to the distal end of the elongated channel 3822 and a first proximal cable transition support 3886 which may comprise, for example, a pulley, rod, capstan, etc. that is operably supported by the elongated channel 3822. A distal end 3881 of the first advance cable 3880 is affixed to the dynamic clamping assembly 3860. The second advance cable 3882 is operably supported on a second distal cable transition support 3887 which may, for example, comprise a pulley, rod, capstan etc. that is mounted to the distal end of the elongated channel 3822 and a second proximal cable transition support 3888 which may, for example, comprise a pulley, rod, capstan, etc. mounted to the proximal end of the elongated channel 3822. The proximal end 3883 of the second advance cable 3882 may be attached to the dynamic clamping assembly 3860. Also in these embodiments, an endless firing cable 3884 is employed and journaled on a support 3889 that may comprise a pulley, rod, capstan, etc. mounted within the elongated shaft 3808. In one embodiment, the retract cable 3884 may be formed in a loop and coupled to a connector 3889' that is fixedly attached to the first and second advance cables 3880, 3882.

Various non-limiting embodiments of the present invention include a cable drive transmission 3920 that is operably supported on a tool mounting plate 3902 of the tool mounting portion 3900. The tool mounting portion 3900 has an array of electrical connecting pins 3904 which are configured to interface with the slots 1258 (FIG. 25) in the adapter 1240'. Such arrangement permits the robotic system 1000 to provide control signals to a control circuit 3910 of the tool 3800. While the interface is described herein with reference to mechanical, electrical, and magnetic coupling elements, it should be understood that a wide variety of telemetry modalities might be used, including infrared, inductive coupling, or the like.

Control circuit 3910 is shown in schematic form in FIG. 83. In one form or embodiment, the control circuit 3910 includes a power supply in the form of a battery 3912 that is coupled to an on-off solenoid powered switch 3914. In other embodiments, however, the power supply may comprise a source of alternating current. Control circuit 3910 further includes an on/off solenoid 3916 that is coupled to a double pole switch 3918 for controlling motor rotation direction. Thus, when the robotic system 1000 supplies an appropriate control signal, switch 3914 will permit battery 3912 to supply power to the double pole switch 3918. The robotic system 1000 will also supply an appropriate signal to the double pole switch 3918 to supply power to a shifter motor 3922.

Turning to FIGS. 87-92, at least one embodiment of the cable drive transmission 3920 comprises a drive pulley 3930 that is operably mounted to a drive shaft 3932 that is attached to a driven element 1304 of the type and construction described above that is designed to interface with a corresponding drive element 1250 of the adapter 1240. See FIGS. 25 and 90. Thus, when the tool mounting portion 3900 is operably coupled to the tool holder 1270, the robot system 1000 can apply rotary motion to the drive pulley 3930 in a desired direction. A first drive member or belt 3934 drivingly engages the drive pulley 3930 and a second drive shaft 3936 that is rotatably supported on a shifter yoke 3940. The shifter yoke 3940 is operably coupled to the shifter motor 3922 such that rotation of the shaft 3923 of the shifter motor 3922 in a first direction will shift the shifter yoke in a first direction "FD" and rotation of the shifter motor shaft 3923 in a second direction will shift the shifter yoke 3940 in a second direction "SD". Other embodiments of the present invention may employ a shifter solenoid arrangement for shifting the shifter yoke in said first and second directions.

As can be seen in FIGS. 87-90, a closure drive gear 3950 mounted to a second drive shaft 3936 and is configured to selectively mesh with a closure drive assembly, generally designated as 3951. Likewise a firing drive gear 3960 is also mounted to the second drive shaft 3936 and is configured to selectively mesh with a firing drive assembly generally designated as 3961. Rotation of the second drive shaft 3936 causes the closure drive gear 3950 and the firing drive gear 3960 to rotate. In one non-limiting embodiment, the closure drive assembly 3951 comprises a closure driven gear 3952 that is coupled to a first closure pulley 3954 that is rotatably supported on a third drive shaft 3956. The closure cable 3850 is drivingly received on the first closure pulley 3954 such that rotation of the closure driven gear 3952 will drive the closure cable 3850. Likewise, the firing drive assembly 3961 comprises a firing driven gear 3962 that is coupled to a first firing pulley 3964 that is rotatably supported on the third drive shaft 3956. The first and second driving pulleys 3954 and 3964 are independently rotatable on the third drive shaft 3956. The firing cable 3884 is drivingly received on the first firing pulley 3964 such that rotation of the firing driven gear 3962 will drive the firing cable 3884.

Also in various embodiments, the cable drive transmission 3920 further includes a braking assembly 3970. In at least one embodiment, for example, the braking assembly 3970 includes a closure brake 3972 that comprises a spring arm 3973 that is attached to a portion of the transmission housing 3971. The closure brake 3972 has a gear lug 3974 that is sized to engage the teeth of the closure driven gear 3952 as will be discussed in further detail below. The braking assembly 3970 further includes a firing brake 3976 that comprises a spring arm 3977 that is attached to another portion of the transmission housing 3971. The firing brake 3976 has a gear lug 3978 that is sized to engage the teeth of the firing driven gear 3962.

Figure 87:
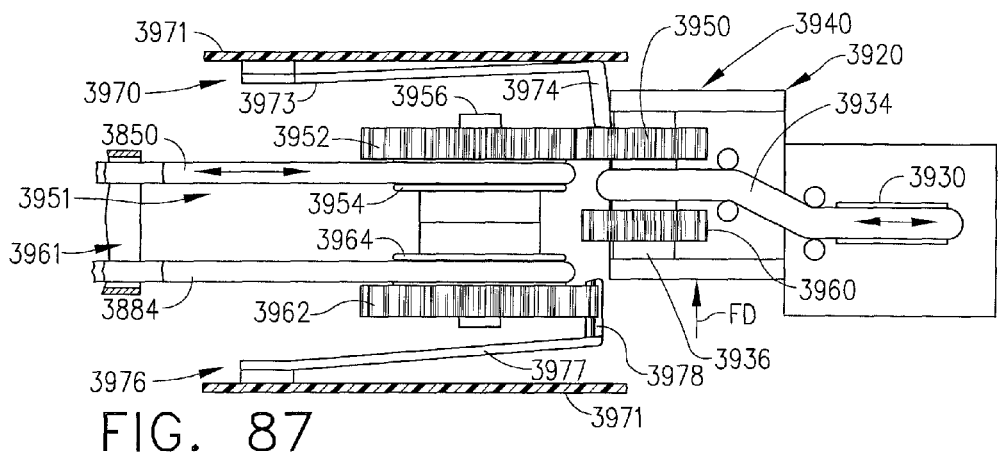
FIG. 87 is a top view of a cable drive transmission embodiment of the present invention in a closure position.
Figure 88:
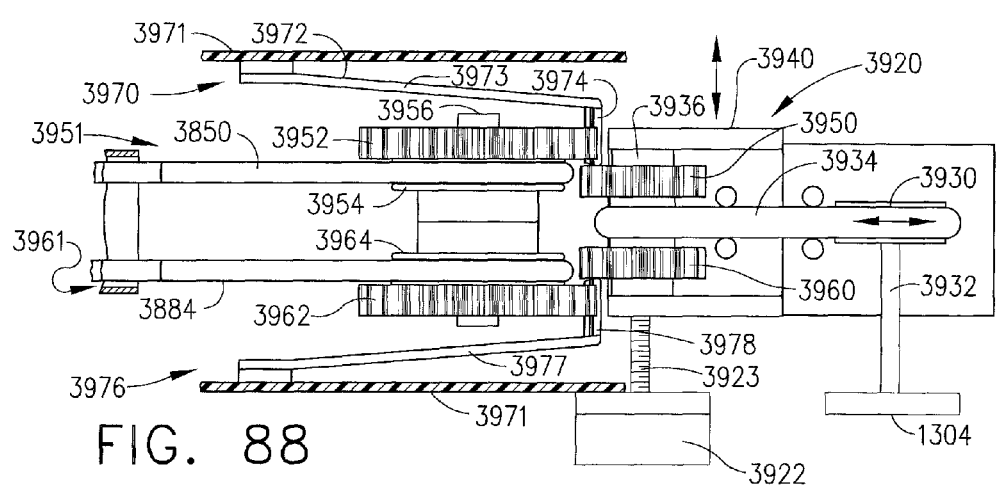
FIG. 88 is another top view of the cable drive transmission embodiment of FIG. 87 in a neutral position.
Figure 89:
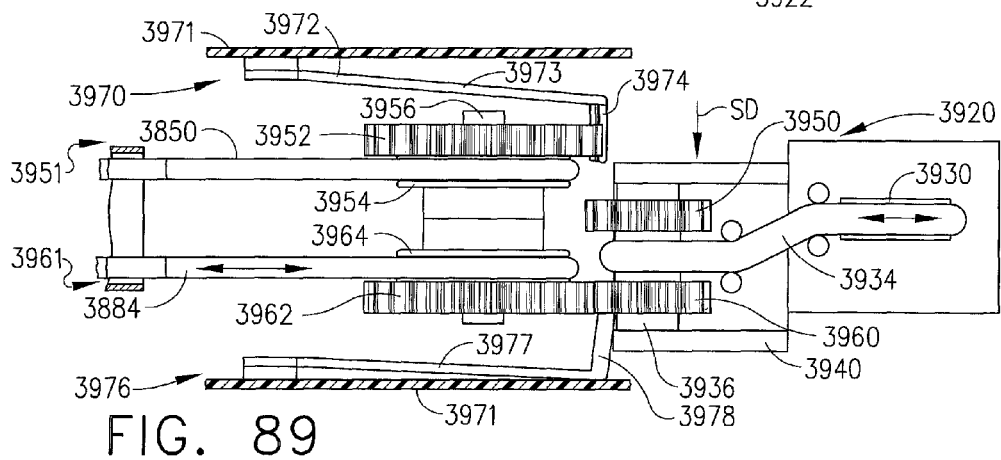
FIG. 89 is another top view of the cable drive transmission embodiment of FIGS. 87 and 88 in a firing position.
Figure 90:
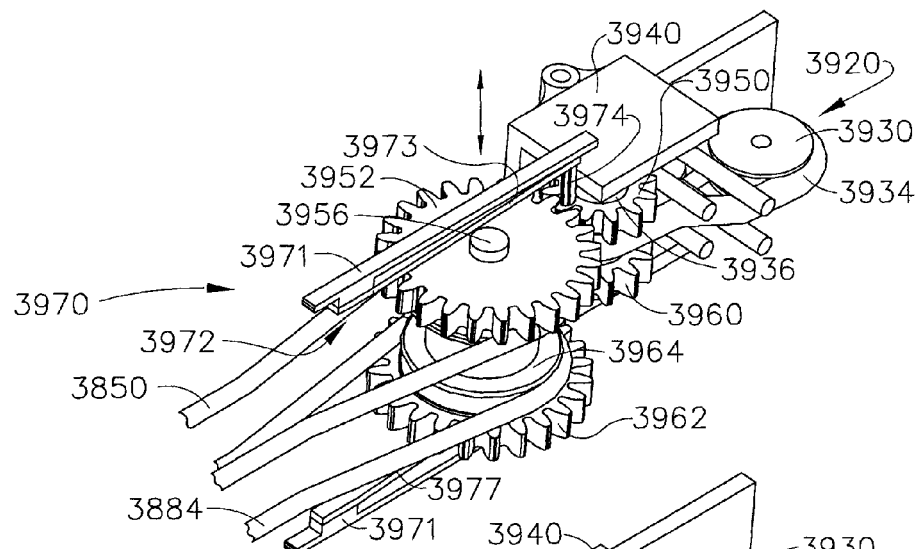
FIG. 90 is a perspective view of the cable drive transmission embodiment in the position depicted in FIG. 87.
Figure 91:
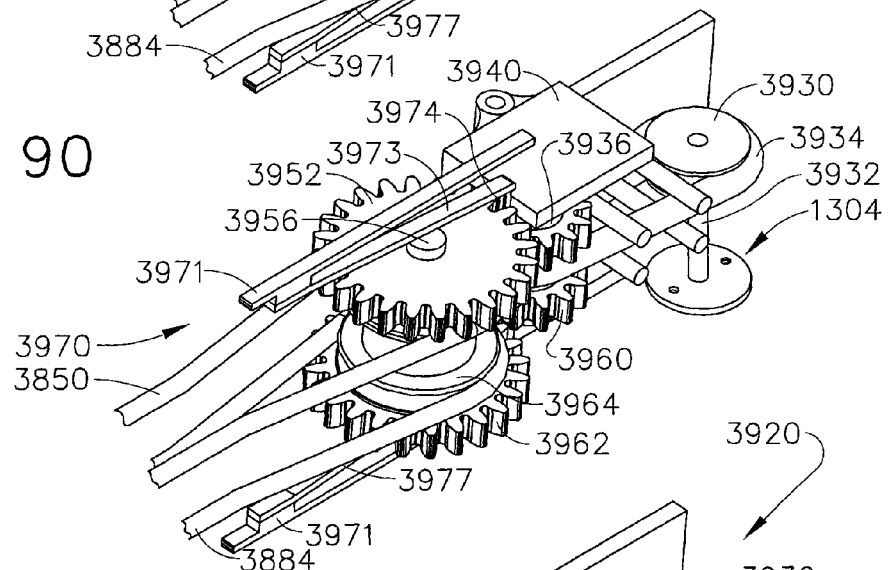
FIG. 91 is a perspective view of the cable drive transmission embodiment in the position depicted in FIG. 88.
Figure 92:
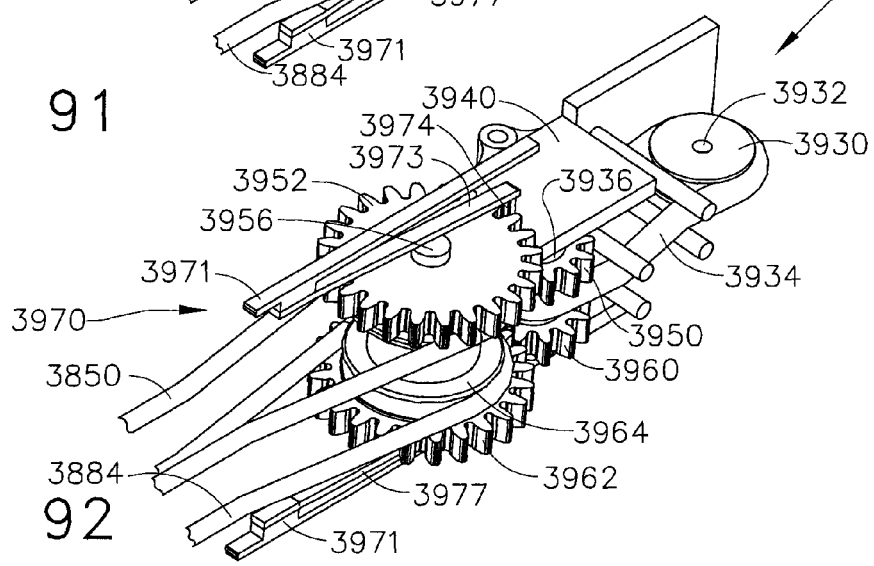
FIG. 92 is a perspective view of the cable drive transmission embodiment in the position depicted in FIG. 89.
Figure 94:
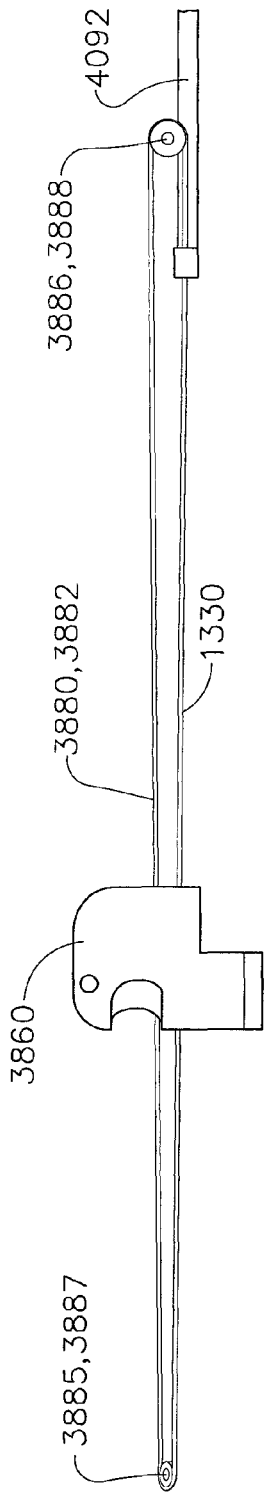
FIG. 94 is a side view of a portion of another cable-driven system embodiment for driving a cutting instrument employed in various surgical end effector embodiments of the present invention.

At least one embodiment of the surgical tool 3800 may be used as follows. The tool mounting portion 3900 is operably coupled to the interface 1240 of the robotic system 1000. The controller or control unit of the robotic system is operated to locate the tissue to be cut and stapled between the open anvil 3824 and the staple cartridge 3834. When in that initial position, the braking assembly 3970 has locked the closure driven gear 3952 and the firing driven gear 3962 such that they cannot rotate. That is, as shown in FIG. 88, the gear lug 3974 is in locking engagement with the closure driven gear 3952 and the gear lug 3978 is in locking engagement with the firing driven gear 3962. Once the surgical end effector 3814 has been properly located, the controller 1001 of the robotic system 1000 will provide a control signal to the shifter motor 3922 (or shifter solenoid) to move the shifter yoke 3940 in the first direction. As the shifter yoke 3940 is moved in the first direction, the closure drive gear 3950 moves the gear lug 3974 out of engagement with the closure driven gear 3952 as it moves into meshing engagement with the closure driven gear 3952. As can be seen in FIG. 87, when in that position, the gear lug 3978 remains in locking engagement with the firing driven gear 3962 to prevent actuation of the firing system. Thereafter, the robotic controller 1001 provides a first rotary actuation motion to the drive pulley 3930 through the interface between the driven element 1304 and the corresponding components of the tool holder 1240. As the drive pulley 3930 is rotated in the first direction, the closure cable 3850 is rotated to drive the preclamping collar 3840 into closing engagement with the cam surface 3825 of the anvil 3824 to move it to the closed position thereby clamping the target tissue between the anvil 3824 and the staple cartridge 3834. See FIG. 83. Once the anvil 3824 has been moved to the closed position, the robotic controller 1001 stops the application of the first rotary motion to the drive pulley 3930. Thereafter, the robotic controller 1001 may commence the firing process by sending another control signal to the shifter motor 3922 (or shifter solenoid) to cause the shifter yoke to move in the second direction "SD" as shown in FIG. 94. As the shifter yoke 3940 is moved in the second direction, the firing drive gear 3960 moves the gear lug 3978 out of engagement with the firing driven gear 3962 as it moves into meshing engagement with the firing driven gear 3962. As can be seen in FIG. 89, when in that position, the gear lug 3974 remains in locking engagement with the closure driven gear 3952 to prevent actuation of the closure system. Thereafter, the robotic controller 1001 is activated to provide the first rotary actuation motion to the drive pulley 3930 through the interface between the driven element 1304 and the corresponding components of the tool holder 1240. As the drive pulley 3930 is rotated in the first direction, the firing cable 3884 is rotated to drive the dynamic clamping member 3860 in the distal direction "DD" thereby firing the stapes and cutting the tissue clamped in the end effector 3814. Once the robotic system 1000 determines that the dynamic clamping member 3860 has reached its distal most position—either through sensors or through monitoring the amount of rotary input applied to the drive pulley 3930, the controller 1001 may then apply a second rotary motion to the drive pulley 3930 to rotate the closure cable 3850 in an opposite direction to cause the dynamic clamping member 3860 to be retracted in the proximal direction "PD". Once the dynamic clamping member has been retracted to the starting position, the application of the second rotary motion to the drive pulley 3930 is discontinued. Thereafter, the shifter motor 3922 (or shifter solenoid) is powered to move the shifter yoke 3940 to the closure position (FIG. 92). Once the closure drive gear 3950 is in meshing engagement with the closure driven gear 3952, the robotic controller 1001 may once again apply the second rotary motion to the drive pulley 3930. Rotation of the drive pulley 3930 in the second direction causes the closure cable 3850 to retract the preclamping collar 3840 out of engagement with the cam surface 3825 of the anvil 3824 to permit the anvil 3824 to move to an open position (by a spring or other means) to release the stapled tissue from the surgical end effector 3814.

Figure 93:
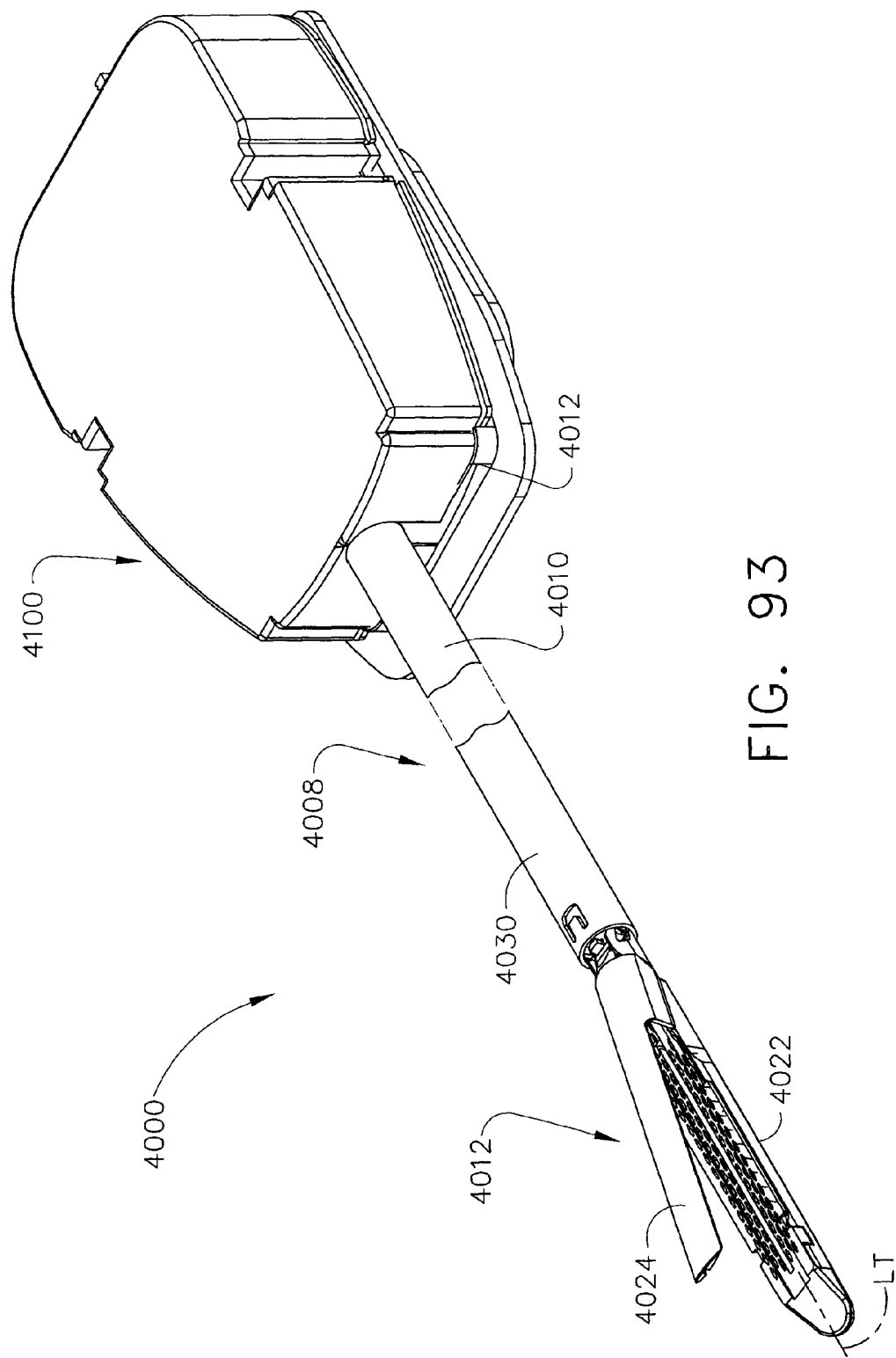
FIG. 93 is a perspective view of another surgical tool embodiment of the present invention.
Figure 95:
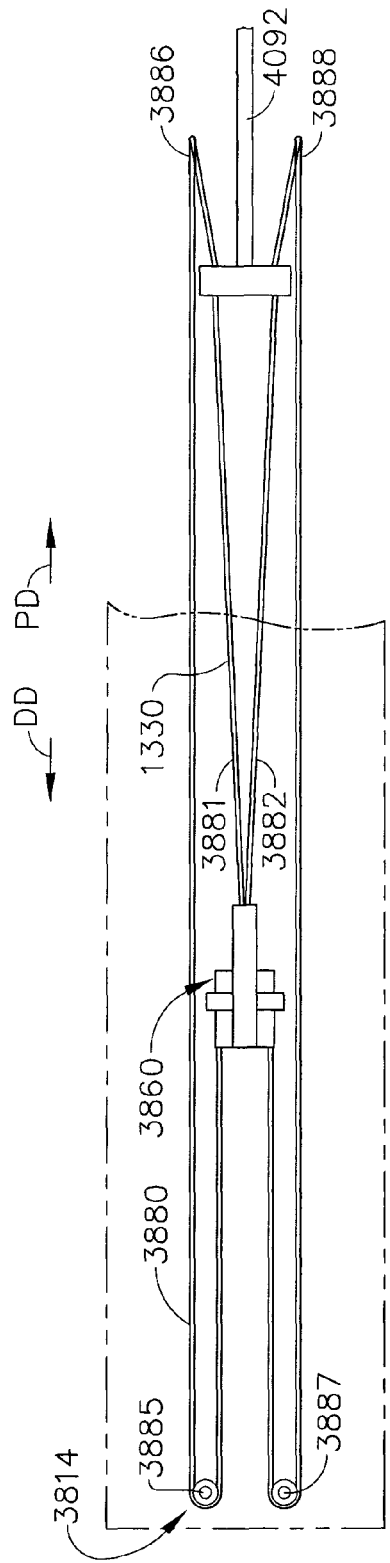
FIG. 95 is a top view of the cable-driven system embodiment of FIG. 94.
Figure 96:
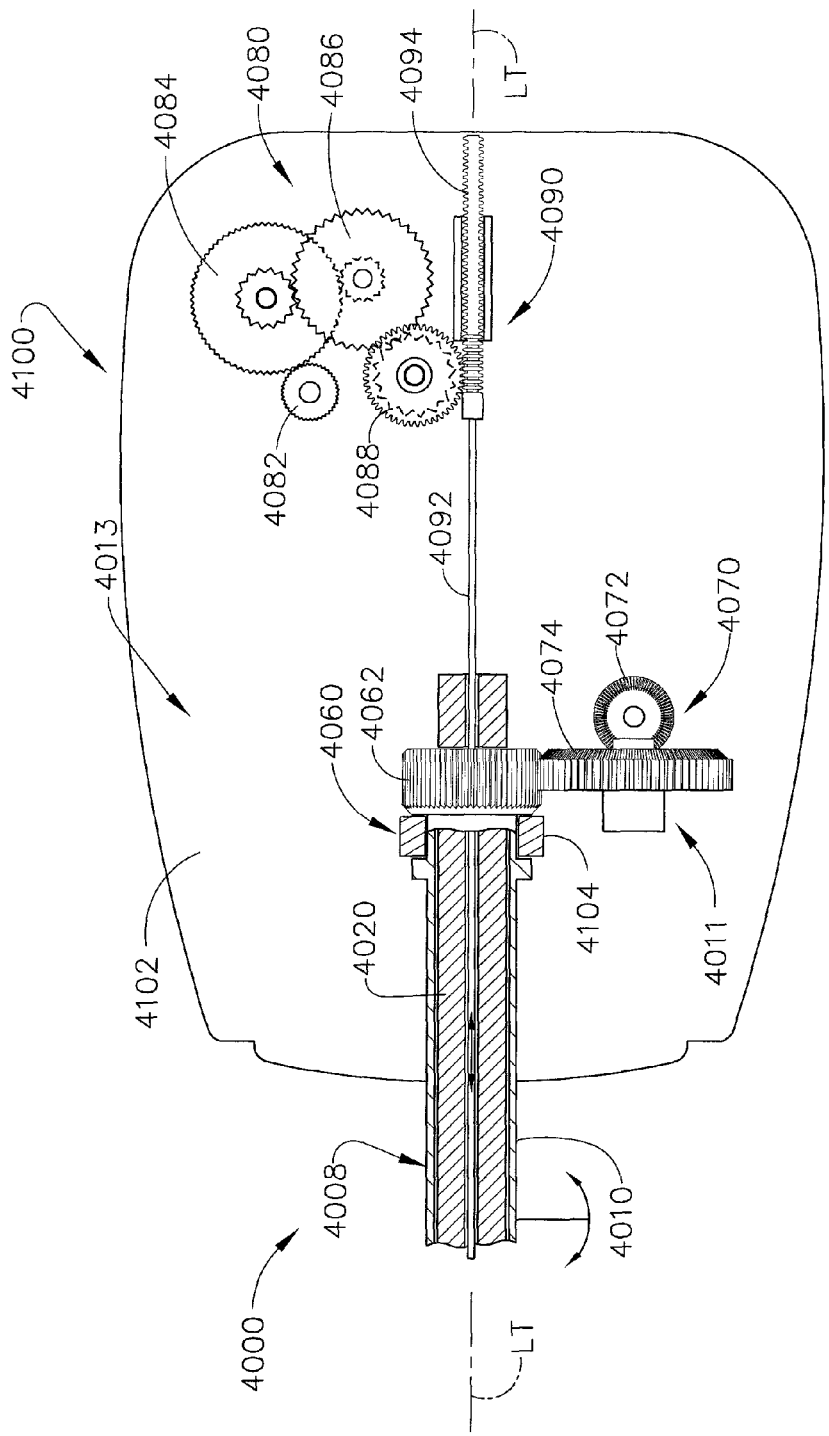
FIG. 96 is a top view of a tool mounting portion embodiment of another surgical tool embodiment of the present invention.

FIG. 93 illustrates a surgical tool 4000 that employs a gear driven firing bar 4092 as shown in FIGS. 94-96. This embodiment includes an elongated shaft assembly 4008 that extends from a tool mounting portion 4100. The tool mounting portion 4100 includes a tool mounting plate 4102 that operable supports a transmission arrangement 4103 thereon. The elongated shaft assembly 4008 includes a rotatable proximal closure tube 4010 that is rotatably journaled on a proximal spine member 4020 that is rigidly coupled to the tool mounting plate 4102. The proximal spine member 4020 has a distal end that is coupled to an elongated channel portion 4022 of a surgical end effector 4012. The surgical effector 4012 may be substantially similar to surgical end effector 3412 described above. In addition, the anvil 4024 of the surgical end effector 4012 may be opened and closed by a distal closure tube 4030 that operably interfaces with the proximal closure tube 4010. Distal closure tube 4030 is identical to distal closure tube 3430 described above. Similarly, proximal closure tube 4010 is identical to proximal closure tube segment 3410 described above.

Anvil 4024 is opened and closed by rotating the proximal closure tube 4010 in manner described above with respect to distal closure tube 3410. In at least one embodiment, the transmission arrangement comprises a closure transmission, generally designated as 4011. As will be further discussed below, the closure transmission 4011 is configured to receive a corresponding first rotary motion from the robotic system 1000 and convert that first rotary motion to a primary rotary motion for rotating the rotatable proximal closure tube 4010 about the longitudinal tool axis LT-LT. As can be seen in FIG. 96, a proximal end 4060 of the proximal closure tube 4010 is rotatably supported within a cradle arrangement 4104 that is attached to a tool mounting plate 4102 of the tool mounting portion 4100. A rotation gear 4062 is formed on or attached to the proximal end 4060 of the closure tube segment 4010 for meshing engagement with a rotation drive assembly 4070 that is operably supported on the tool mounting plate 4102. In at least one embodiment, a rotation drive gear 4072 is coupled to a corresponding first one of the driven discs or elements 1304 on the adapter side of the tool mounting plate 4102 when the tool mounting portion 4100 is coupled to the tool holder 1270. See FIGS. 26 and 96. The rotation drive assembly 4070 further comprises a rotary driven gear 4074 that is rotatably supported on the tool mounting plate 4102 in meshing engagement with the rotation gear 4062 and the rotation drive gear 4072. Application of a first rotary control motion from the robotic system 1000 through the tool holder 1270 and the adapter 1240 to the corresponding driven element 1304 will thereby cause rotation of the rotation drive gear 4072 by virtue of being operably coupled thereto. Rotation of the rotation drive gear 4072 ultimately results in the rotation of the closure tube segment 4010 to open and close the anvil 4024 as described above.

As indicated above, the end effector 4012 employs a cutting element 3860 as shown in FIGS. 94 and 95. In at least one non-limiting embodiment, the transmission arrangement 4103 further comprises a knife drive transmission that includes a knife drive assembly 4080. FIG. 96 illustrates one form of knife drive assembly 4080 for axially advancing the knife bar 4092 that is attached to such cutting element using cables as described above with respect to surgical tool 3800. In particular, the knife bar 4092 replaces the firing cable 3884 employed in an embodiment of surgical tool 3800. One form of the knife drive assembly 4080 comprises a rotary drive gear 4082 that is coupled to a corresponding second one of the driven discs or elements 1304 on the adapter side of the tool mounting plate 4102 when the tool mounting portion 4100 is coupled to the tool holder 1270. See FIGS. 26 and 96. The knife drive assembly 4080 further comprises a first rotary driven gear assembly 4084 that is rotatably supported on the tool mounting plate 4102. The first rotary driven gear assembly 4084 is in meshing engagement with a third rotary driven gear assembly 4086 that is rotatably supported on the tool mounting plate 4102 and which is in meshing engagement with a fourth rotary driven gear assembly 4088 that is in meshing engagement with a threaded portion 4094 of drive shaft assembly 4090 that is coupled to the knife bar 4092. Rotation of the rotary drive gear 4082 in a second rotary direction will result in the axial advancement of the drive shaft assembly 4090 and knife bar 4092 in the distal direction "DD". Conversely, rotation of the rotary drive gear 4082 in a secondary rotary direction (opposite to the second rotary direction) will cause the drive shaft assembly 4090 and the knife bar 4092 to move in the proximal direction. Movement of the firing bar 4092 in the proximal direction "PD" will drive the cutting element 3860 in the distal direction "DD". Conversely, movement of the firing bar 4092 in the distal direction "DD" will result in the movement of the cutting element 3860 in the proximal direction "PD".

Figure 99:
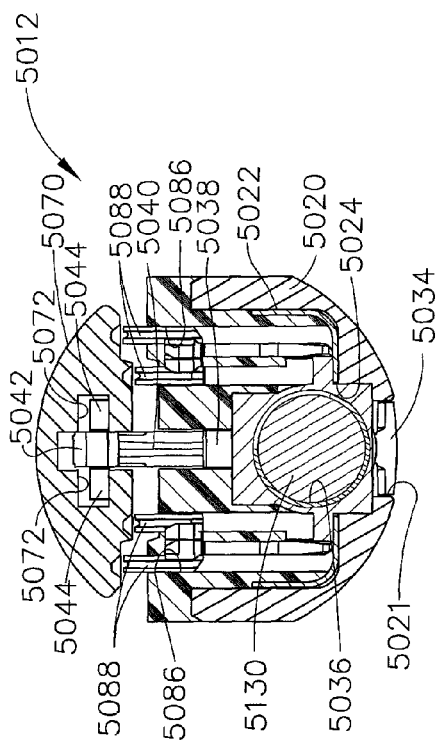
FIG. 99 is a cross-sectional end view of the surgical end effector of FIG. 103 taken along line 99-99 in FIG. 98.

FIGS. 97-103 illustrate yet another surgical tool 5000 that may be effectively employed in connection with a robotic system 1000. In various forms, the surgical tool 5000 includes a surgical end effector 5012 in the form of a surgical stapling instrument that includes an elongated channel 5020 and a pivotally translatable clamping member, such as an anvil 5070, which are maintained at a spacing that assures effective stapling and severing of tissue clamped in the surgical end effector 5012. As can be seen in FIG. 99, the elongated channel 5020 may be substantially U-shaped in cross-section and be fabricated from, for example, titanium, 203 stainless steel, 304 stainless steel, 416 stainless steel, 17-4 stainless steel, 17-7 stainless steel, 6061 or 7075 aluminum, chromium steel, ceramic, etc. A substantially U-shaped metal channel pan 5022 may be supported in the bottom of the elongated channel 5020 as shown.

Various embodiments include an actuation member in the form of a sled assembly 5030 that is operably supported within the surgical end effector 5012 and axially movable therein between a starting position and an ending position in response to control motions applied thereto. In some forms, the metal channel pan 5022 has a centrally-disposed slot 5024 therein to movably accommodate a base portion 5032 of the sled assembly 5030. The base portion 5032 includes a foot portion 5034 that is sized to be slidably received in a slot 5021 in the elongated channel 5020. See FIG. 104. As can be seen in FIGS. 98, 99, 102, and 103, the base portion 5032 of sled assembly 5030 includes an axially extending threaded bore 5036 that is configured to be threadedly received on a threaded drive shaft 5130 as will be discussed in further detail below. In addition, the sled assembly 5030 includes an upstanding support portion 5038 that supports a tissue cutting blade or tissue cutting instrument 5040. The upstanding support portion 5038 terminates in a top portion 5042 that has a pair of laterally extending retaining fins 5044 protruding therefrom. As shown in FIG. 99, the fins 5044 are positioned to be received within corresponding slots 5072 in anvil 5070. The fins 5044 and the foot 5034 serve to retain the anvil 5070 in a desired spaced closed position as the sled assembly 5030 is driven distally through the tissue clamped within the surgical end effector 5014. As can also be seen in FIGS. 101 and 103, the sled assembly 5030 further includes a reciprocatably or sequentially activatable drive assembly 5050 for driving staple pushers toward the closed anvil 5070.

Figure 100:
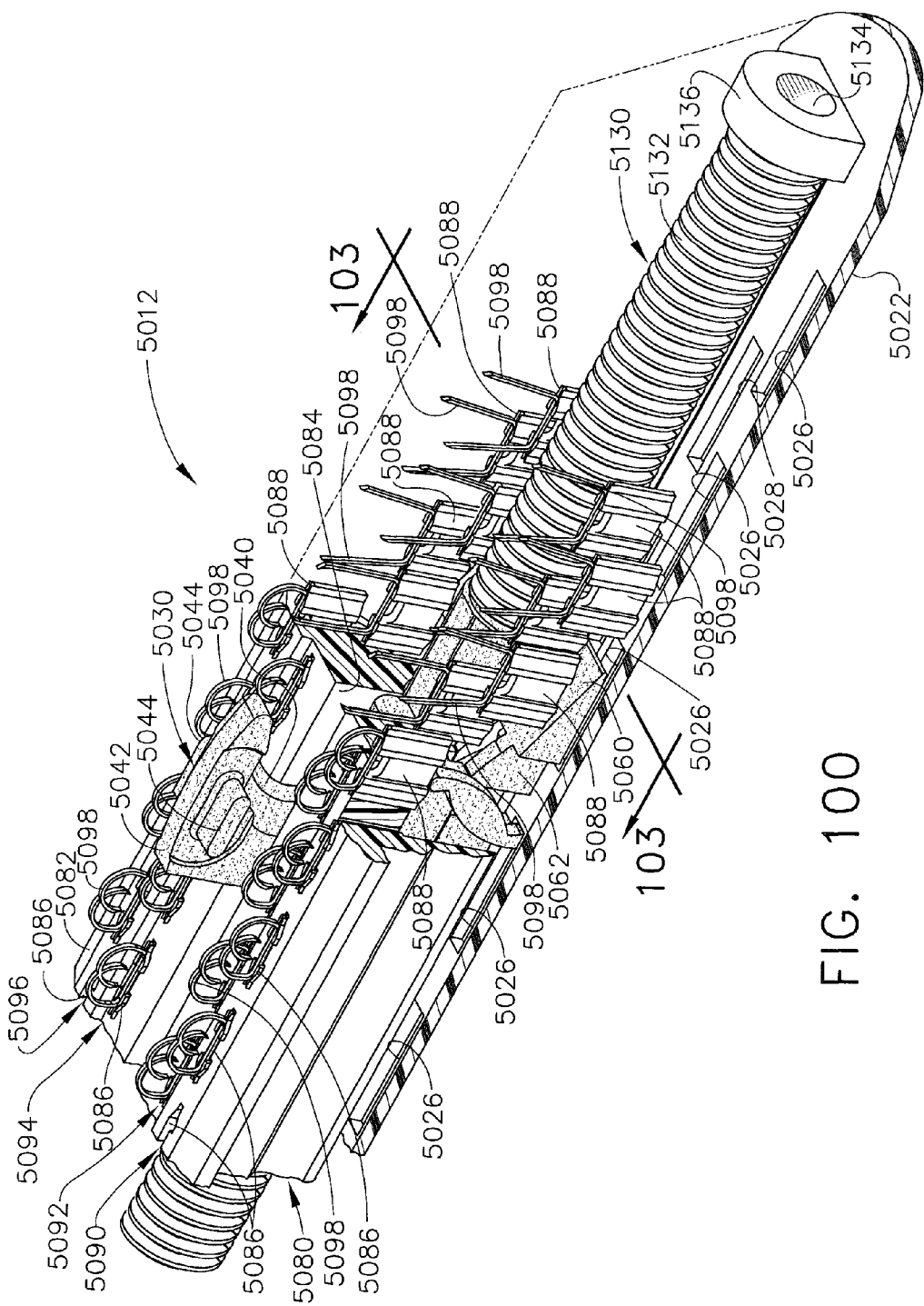
FIG. 100 is a perspective view of the surgical end effector of FIGS. 98 and 99 with portions thereof shown in cross-section.
Figure 101:
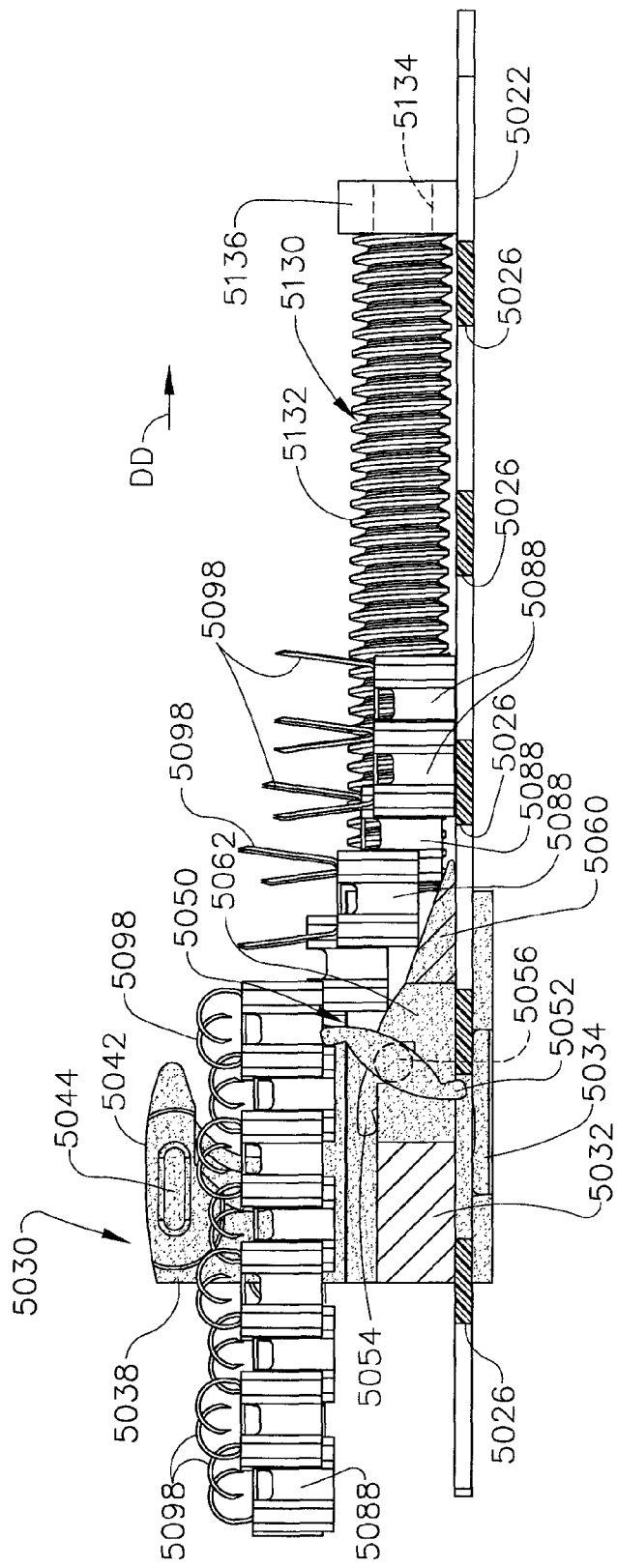
FIG. 101 is a side view of a portion of the surgical end effector of FIGS. 98-100.
Figure 103:
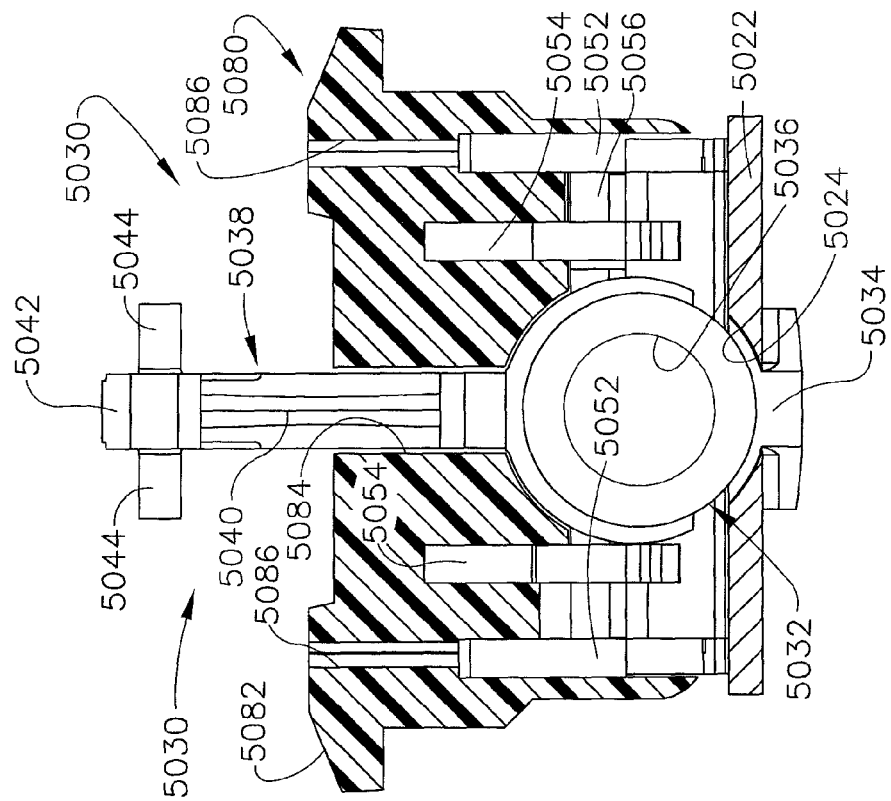
FIG. 103 is a cross-sectional view of the sled assembly embodiment of FIG. 102 and a portion of the elongated channel of FIG. 101.
Figure 102:
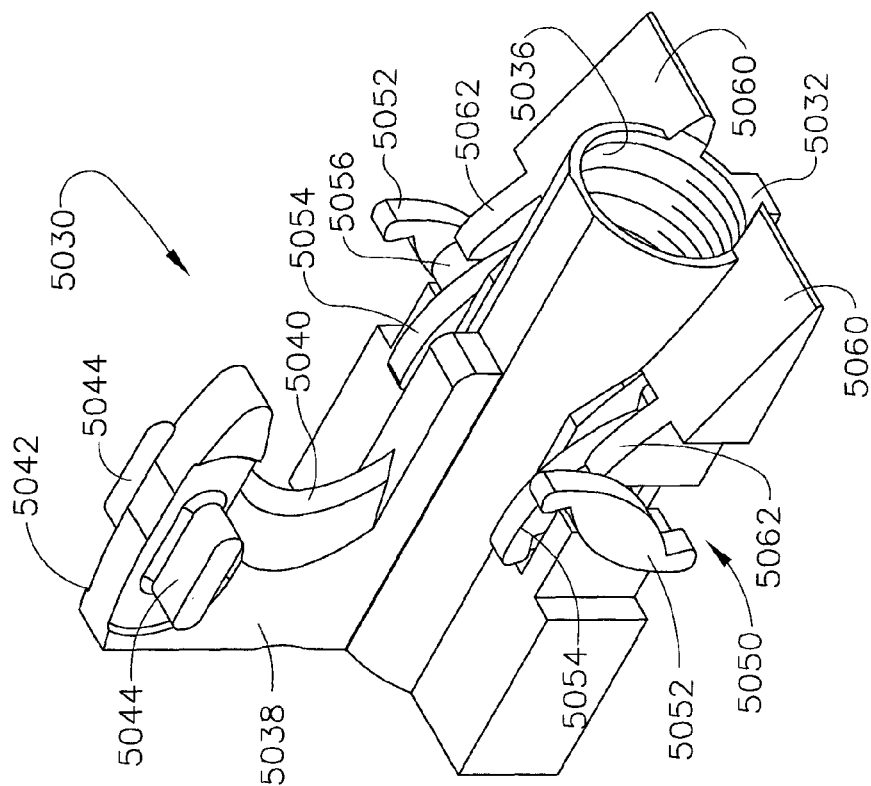
FIG. 102 is a perspective view of a sled assembly embodiment of various surgical tool embodiments of the present invention.

More specifically and with reference to FIGS. 99 and 100, the elongated channel 5020 is configured to operably support a surgical staple cartridge 5080 therein. In at least one form, the surgical staple cartridge 5080 comprises a body portion 5082 that may be fabricated from, for example, Vectra, Nylon (6/6 or 6/12) and include a centrally disposed slot 5084 for accommodating the upstanding support portion 5038 of the sled assembly 5030. See FIG. 99. These materials could also be filled with glass, carbon, or mineral fill of 10%-40%. The surgical staple cartridge 5080 further includes a plurality of cavities 5086 for movably supporting lines or rows of staple-supporting pushers 5088 therein. The cavities 5086 may be arranged in spaced longitudinally extending lines or rows 5090, 5092, 5094, 5096. For example, the rows 5090 may be referred to herein as first outboard rows. The rows 5092 may be referred to herein as first inboard rows. The rows 5094 may be referred to as second inboard rows and the rows 5096 may be referred to as second outboard rows. The first inboard row 5090 and the first outboard row 5092 are located on a first lateral side of the longitudinal slot 5084 and the second inboard row 5094 and the second outboard row 5096 are located on a second lateral side of the longitudinal slot 5084. The first staple pushers 5088 in the first inboard row 5092 are staggered in relationship to the first staple pushers 5088 in the first outboard row 5090. Similarly, the second staple pushers 5088 in the second outboard row 5096 are staggered in relationship to the second pushers 5088 in the second inboard row 5094. Each pusher 5088 operably supports a surgical staple 5098 thereon.

In various embodiments, the sequentially-activatable or reciprocatably—activatable drive assembly 5050 includes a pair of outboard drivers 5052 and a pair of inboard drivers 5054 that are each attached to a common shaft 5056 that is rotatably mounted within the base 5032 of the sled assembly 5030. The outboard drivers 5052 are oriented to sequentially or reciprocatingly engage a corresponding plurality of outboard activation cavities 5026 provided in the channel pan 5022. Likewise, the inboard drivers 5054 are oriented to sequentially or reciprocatingly engage a corresponding plurality of inboard activation cavities 5028 provided in the channel pan 5022. The inboard activation cavities 5028 are arranged in a staggered relationship relative to the adjacent outboard activation cavities 5026. See FIG. 100. As can also be seen in FIGS. 100 and 102, in at least one embodiment, the sled assembly 5030 further includes distal wedge segments 5060 and intermediate wedge segments 5062 located on each side of the bore 5036 to engage the pushers 5088 as the sled assembly 5030 is driven distally in the distal direction "DD". As indicated above, the sled assembly 5030 is threadedly received on a threaded portion 5132 of a drive shaft 5130 that is rotatably supported within the end effector 5012. In various embodiments, for example, the drive shaft 5130 has a distal end 5134 that is supported in a distal bearing 5136 mounted in the surgical end effector 5012. See FIGS. 99 and 100.

In various embodiments, the surgical end effector 5012 is coupled to a tool mounting portion 5200 by an elongated shaft assembly 5108. In at least one embodiment, the tool mounting portion 5200 operably supports a transmission arrangement generally designated as 5204 that is configured to receive rotary output motions from the robotic system. The elongated shaft assembly 5108 includes an outer closure tube 5110 that is rotatable and axially movable on a spine member 5120 that is rigidly coupled to a tool mounting plate 5201 of the tool mounting portion 5200. The spine member 5120 also has a distal end 5122 that is coupled to the elongated channel portion 5020 of the surgical end effector 5012.

Figure 97:
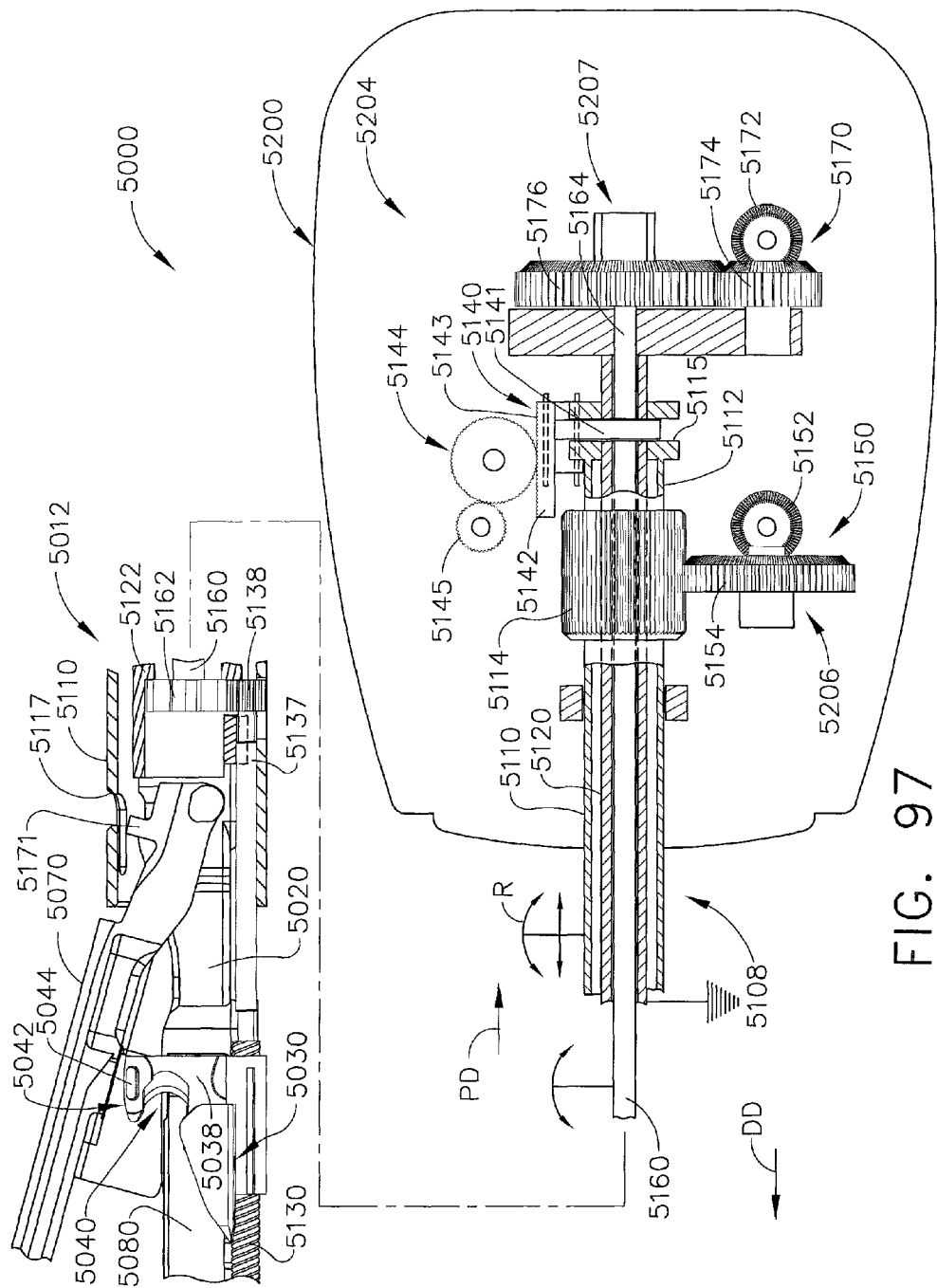
FIG. 97 is a top cross-sectional view of another surgical tool embodiment of the present invention.
Figure 98:
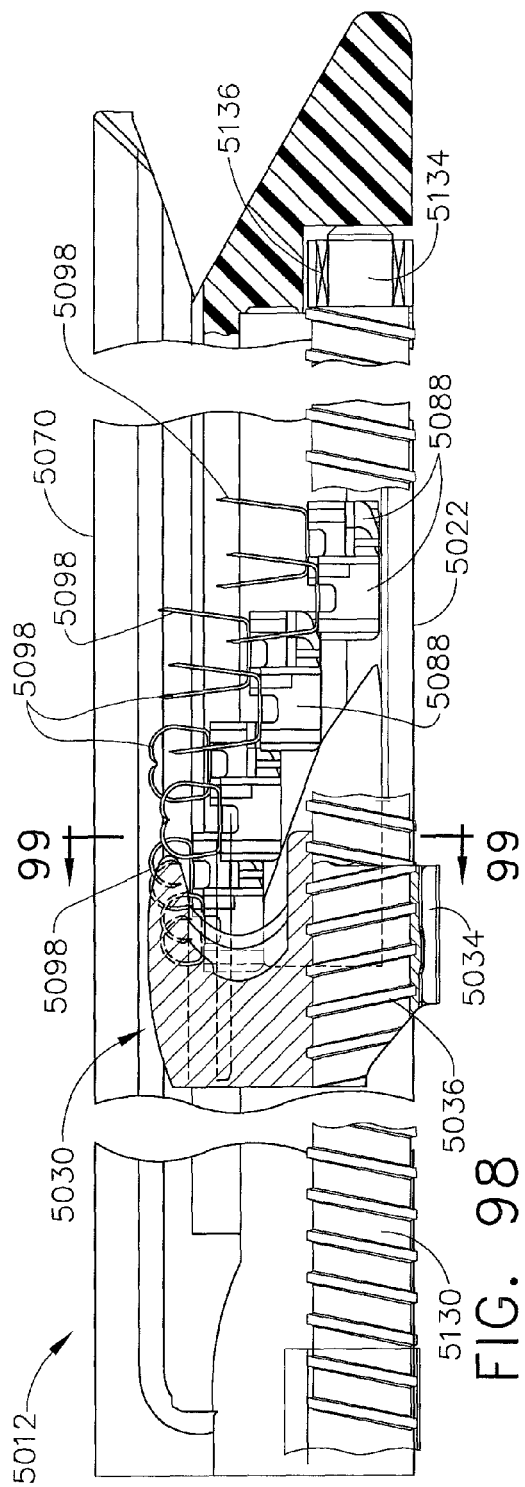
FIG. 98 is a cross-sectional view of a portion of a surgical end effector embodiment of a surgical tool embodiment of the present invention.

In use, it may be desirable to rotate the surgical end effector 5012 about a longitudinal tool axis LT-LT defined by the elongated shaft assembly 5008. In various embodiments, the outer closure tube 5110 has a proximal end 5112 that is rotatably supported on the tool mounting plate 5201 of the tool drive portion 5200 by a forward support cradle 5203. The proximal end 5112 of the outer closure tube 5110 is configured to operably interface with a rotation transmission portion 5206 of the transmission arrangement 5204. In various embodiments, the proximal end 5112 of the outer closure tube 5110 is also supported on a closure sled 5140 that is also movably supported on the tool mounting plate 5201. A closure tube gear segment 5114 is formed on the proximal end 5112 of the outer closure tube 5110 for meshing engagement with a rotation drive assembly 5150 of the rotation transmission 5206. As can be seen in FIG. 97, the rotation drive assembly 5150, in at least one embodiment, comprises a rotation drive gear 5152 that is coupled to a corresponding first one of the driven discs or elements 1304 on the adapter side 1307 of the tool mounting plate 5201 when the tool drive portion 5200 is coupled to the tool holder 1270. The rotation drive assembly 5150 further comprises a rotary driven gear 5154 that is rotatably supported on the tool mounting plate 5201 in meshing engagement with the closure tube gear segment 5114 and the rotation drive gear 5152. Application of a first rotary control motion from the robotic system 1000 through the tool holder 1270 and the adapter 1240 to the corresponding driven element 1304 will thereby cause rotation of the rotation drive gear 5152. Rotation of the rotation drive gear 5152 ultimately results in the rotation of the elongated shaft assembly 5108 (and the end effector 5012) about the longitudinal tool axis LT-LT (represented by arrow "R" in FIG. 97).

Closure of the anvil 5070 relative to the surgical staple cartridge 5080 is accomplished by axially moving the outer closure tube 5110 in the distal direction "DD". Such axial movement of the outer closure tube 5110 may be accomplished by a closure transmission portion 5144 of the transmission arrangement 5204. As indicated above, in various embodiments, the proximal end 5112 of the outer closure tube 5110 is supported by the closure sled 5140 which enables the proximal end 5112 to rotate relative thereto, yet travel axially with the closure sled 5140. In particular, as can be seen in FIG. 97, the closure sled 5140 has an upstanding tab 5141 that extends into a radial groove 5115 in the proximal end portion 5112 of the outer closure tube 5110. In addition, as was described above, the closure sled 5140 is slidably mounted to the tool mounting plate 5201. In various embodiments, the closure sled 5140 has an upstanding portion 5142 that has a closure rack gear 5143 formed thereon. The closure rack gear 5143 is configured for driving engagement with the closure transmission 5144.

In various forms, the closure transmission 5144 includes a closure spur gear 5145 that is coupled to a corresponding second one of the driven discs or elements 1304 on the adapter side 1307 of the tool mounting plate 5201. Thus, application of a second rotary control motion from the robotic system 1000 through the tool holder 1270 and the adapter 1240 to the corresponding second driven element 1304 will cause rotation of the closure spur gear 5145 when the interface 1230 is coupled to the tool mounting portion 5200. The closure transmission 5144 further includes a driven closure gear set 5146 that is supported in meshing engagement with the closure spur gear 5145 and the closure rack gear 5143. Thus, application of a second rotary control motion from the robotic system 1000 through the tool holder 1270 and the adapter 1240 to the corresponding second driven element 1304 will cause rotation of the closure spur gear 5145 and ultimately drive the closure sled 5140 and the outer closure tube 5110 axially. The axial direction in which the closure tube 5110 moves ultimately depends upon the direction in which the second driven element 1304 is rotated. For example, in response to one rotary closure motion received from the robotic system 1000, the closure sled 5140 will be driven in the distal direction "DD" and ultimately the outer closure tube 5110 will be driven in the distal direction as well. The outer closure tube 5110 has an opening 5117 in the distal end 5116 that is configured for engagement with a tab 5071 on the anvil 5070 in the manners described above. As the outer closure tube 5110 is driven distally, the proximal end 5116 of the closure tube 5110 will contact the anvil 5070 and pivot it closed. Upon application of an "opening" rotary motion from the robotic system 1000, the closure sled 5140 and outer closure tube 5110 will be driven in the proximal direction "PD" and pivot the anvil 5070 to the open position in the manners described above.

In at least one embodiment, the drive shaft 5130 has a proximal end 5137 that has a proximal shaft gear 5138 attached thereto. The proximal shaft gear 5138 is supported in meshing engagement with a distal drive gear 5162 attached to a rotary drive bar 5160 that is rotatably supported with spine member 5120. Rotation of the rotary drive bar 5160 and ultimately rotary drive shaft 5130 is controlled by a rotary knife transmission 5207 which comprises a portion of the transmission arrangement 5204 supported on the tool mounting plate 5210. In various embodiments, the rotary knife transmission 5207 comprises a rotary knife drive system 5170 that is operably supported on the tool mounting plate 5201. In various embodiments, the knife drive system 5170 includes a rotary drive gear 5172 that is coupled to a corresponding third one of the driven discs or elements 1304 on the adapter side of the tool mounting plate 5201 when the tool drive portion 5200 is coupled to the tool holder 1270. The knife drive system 5170 further comprises a first rotary driven gear 5174 that is rotatably supported on the tool mounting plate 5201 in meshing engagement with a second rotary driven gear 5176 and the rotary drive gear 5172. The second rotary driven gear 5176 is coupled to a proximal end portion 5164 of the rotary drive bar 5160.

Rotation of the rotary drive gear 5172 in a first rotary direction will result in the rotation of the rotary drive bar 5160 and rotary drive shaft 5130 in a first direction. Conversely, rotation of the rotary drive gear 5172 in a second rotary direction (opposite to the first rotary direction) will cause the rotary drive bar 5160 and rotary drive shaft 5130 to rotate in a second direction. 2400. Thus, rotation of the drive shaft 2440 results in rotation of the drive sleeve 2400.

One method of operating the surgical tool 5000 will now be described. The tool drive 5200 is operably coupled to the interface 1240 of the robotic system 1000. The controller 1001 of the robotic system 1000 is operated to locate the tissue to be cut and stapled between the open anvil 5070 and the surgical staple cartridge 5080. Once the surgical end effector 5012 has been positioned by the robot system 1000 such that the target tissue is located between the anvil 5070 and the surgical staple cartridge 5080, the controller 1001 of the robotic system 1000 may be activated to apply the second rotary output motion to the second driven element 1304 coupled to the closure spur gear 5145 to drive the closure sled 5140 and the outer closure tube 5110 axially in the distal direction to pivot the anvil 5070 closed in the manner described above. Once the robotic controller 1001 determines that the anvil 5070 has been closed by, for example, sensors in the surgical end effector 5012 and/or the tool drive portion 5200, the robotic controller 1001 system may provide the surgeon with an indication that signifies the closure of the anvil. Such indication may be, for example, in the form of a light and/or audible sound, tactile feedback on the control members, etc. Then the surgeon may initiate the firing process. In alternative embodiments, however, the robotic controller 1001 may automatically commence the firing process.

To commence the firing process, the robotic controller applies a third rotary output motion to the third driven disc or element 1304 coupled to the rotary drive gear 5172. Rotation of the rotary drive gear 5172 results in the rotation of the rotary drive bar 5160 and rotary drive shaft 5130 in the manner described above. Firing and formation of the surgical staples 5098 can be best understood from reference to FIGS. 98, 100, and 101. As the sled assembly 5030 is driven in the distal direction "DD" through the surgical staple cartridge 5080, the distal wedge segments 5060 first contact the staple pushers 5088 and start to move them toward the closed anvil 5070. As the sled assembly 5030 continues to move distally, the outboard drivers 5052 will drop into the corresponding activation cavity 5026 in the channel pan 5022. The opposite end of each outboard driver 5052 will then contact the corresponding outboard pusher 5088 that has moved up the distal and intermediate wedge segments 5060, 5062. Further distal movement of the sled assembly 5030 causes the outboard drivers 5052 to rotate and drive the corresponding pushers 5088 toward the anvil 5070 to cause the staples 5098 supported thereon to be formed as they are driven into the anvil 5070. It will be understood that as the sled assembly 5030 moves distally, the knife blade 5040 cuts through the tissue that is clamped between the anvil and the staple cartridge. Because the inboard drivers 5054 and outboard drivers 5052 are attached to the same shaft 5056 and the inboard drivers 5054 are radially offset from the outboard drivers 5052 on the shaft 5056, as the outboard drivers 5052 are driving their corresponding pushers 5088 toward the anvil 5070, the inboard drivers 5054 drop into their next corresponding activation cavity 5028 to cause them to rotatably or reciprocatingly drive the corresponding inboard pushers 5088 towards the closed anvil 5070 in the same manner. Thus, the laterally corresponding outboard staples 5098 on each side of the centrally disposed slot 5084 are simultaneously formed together and the laterally corresponding inboard staples 5098 on each side of the slot 5084 are simultaneously formed together as the sled assembly 5030 is driven distally. Once the robotic controller 1001 determines that the sled assembly 5030 has reached its distal most position—either through sensors or through monitoring the amount of rotary input applied to the drive shaft 5130 and/or the rotary drive bar 5160, the controller 1001 may then apply a third rotary output motion to the drive shaft 5130 to rotate the drive shaft 5130 in an opposite direction to retract the sled assembly 5030 back to its starting position. Once the sled assembly 5030 has been retracted to the starting position (as signaled by sensors in the end effector 5012 and/or the tool drive portion 5200), the application of the second rotary motion to the drive shaft 5130 is discontinued. Thereafter, the surgeon may manually activate the anvil opening process or it may be automatically commenced by the robotic controller 1001. To open the anvil 5070, the second rotary output motion is applied to the closure spur gear 5145 to drive the closure sled 5140 and the outer closure tube 5110 axially in the proximal direction. As the closure tube 5110 moves proximally, the opening 5117 in the distal end 5116 of the closure tube 5110 contacts the tab 5071 on the anvil 5070 to pivot the anvil 5070 to the open position. A spring may also be employed to bias the anvil 5070 to the open position when the closure tube 5116 has been returned to the starting position. Again, sensors in the surgical end effector 5012 and/or the tool mounting portion 5200 may provide the robotic controller 1001 with a signal indicating that the anvil 5070 is now open. Thereafter, the surgical end effector 5012 may be withdrawn from the surgical site.

Figure 104:
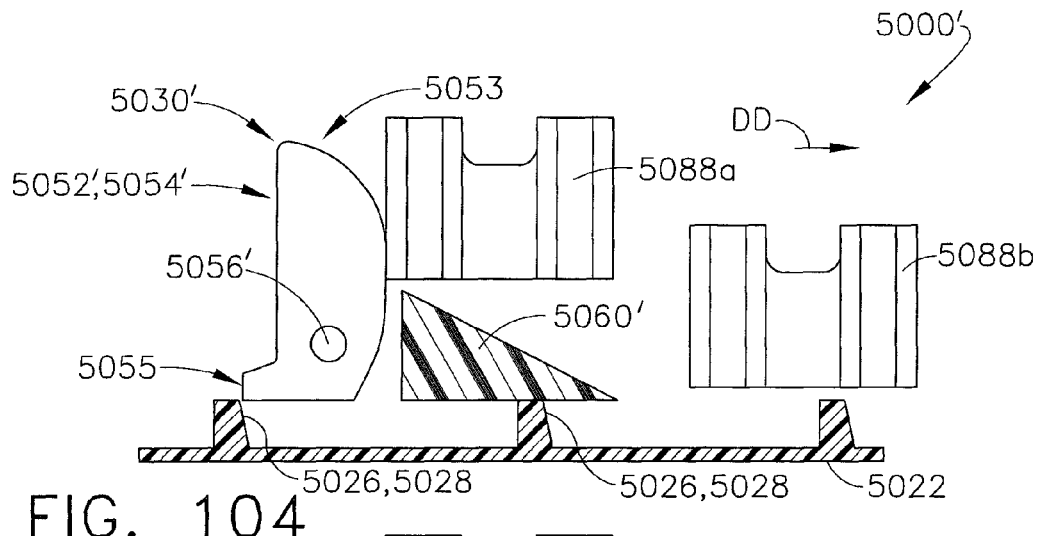
FIGS. 104-109 diagrammatically depict the sequential firing of staples in a surgical tool embodiment of the present invention.
Figure 105:
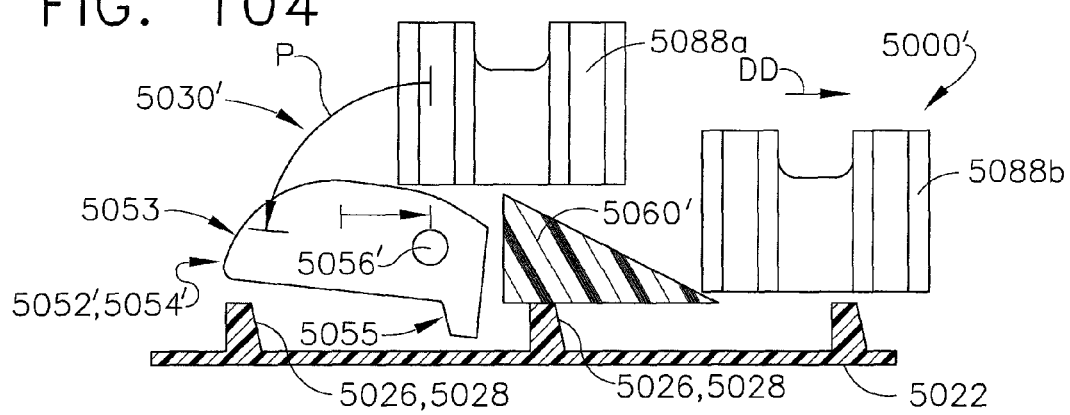
Figure 106:
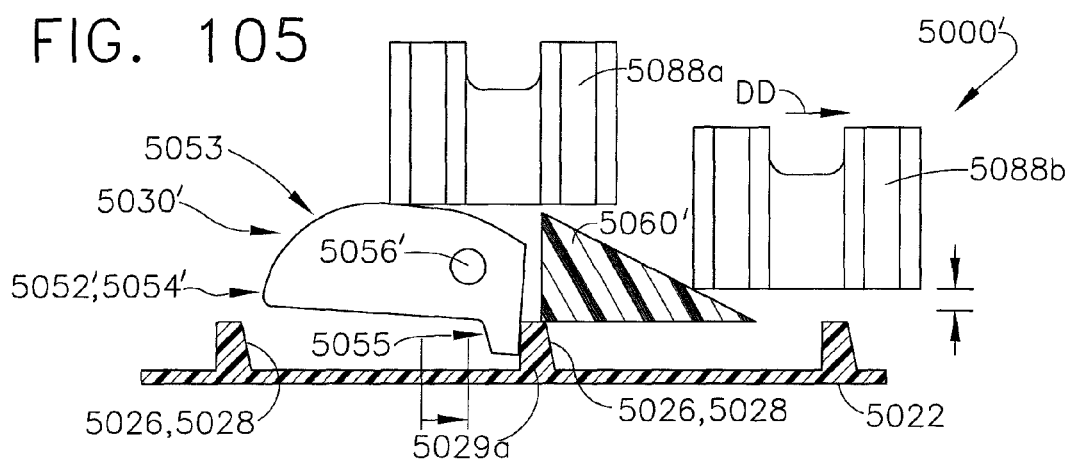
Figure 107:
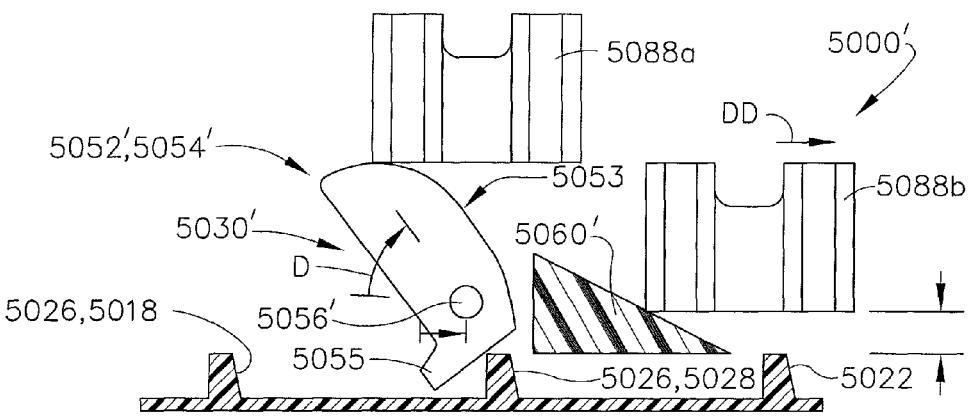
Figure 108:
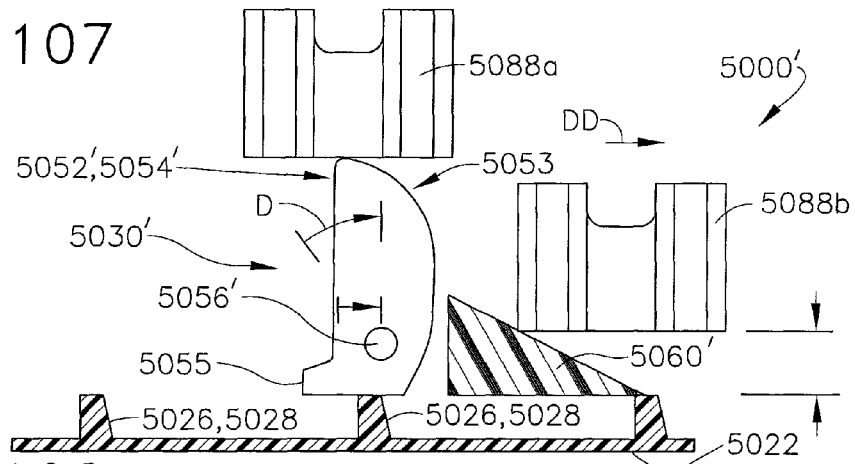
Figure 109:
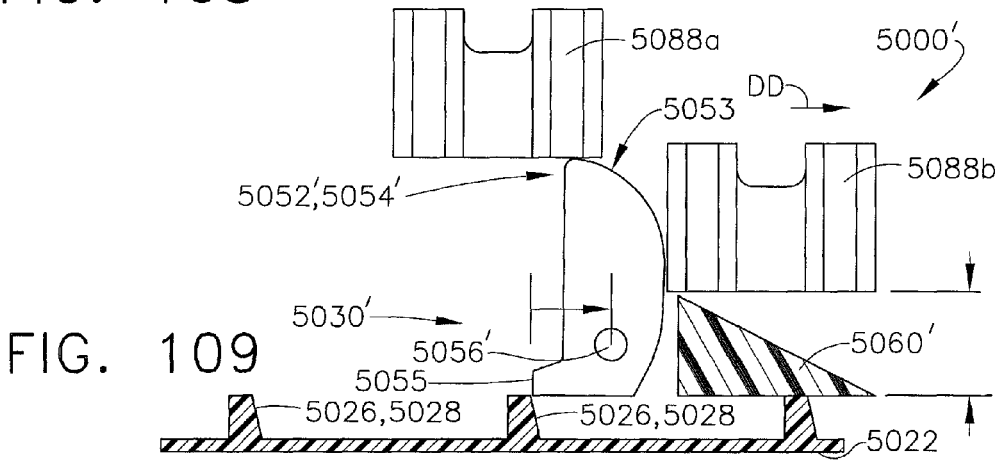
Figure 110:
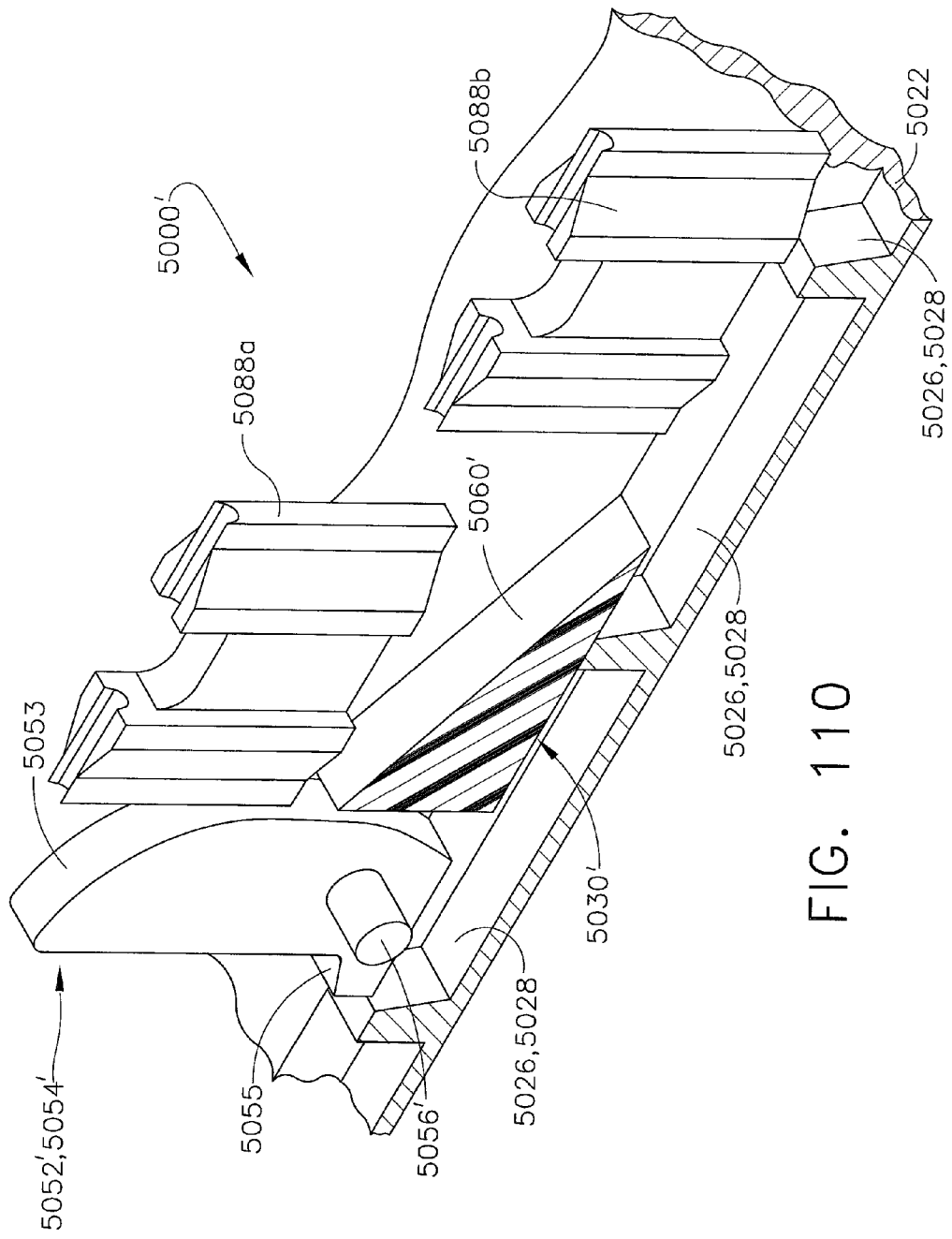
FIG. 110 is a partial perspective view of a portion of a surgical end effector embodiment of the present invention.
Figure 111:
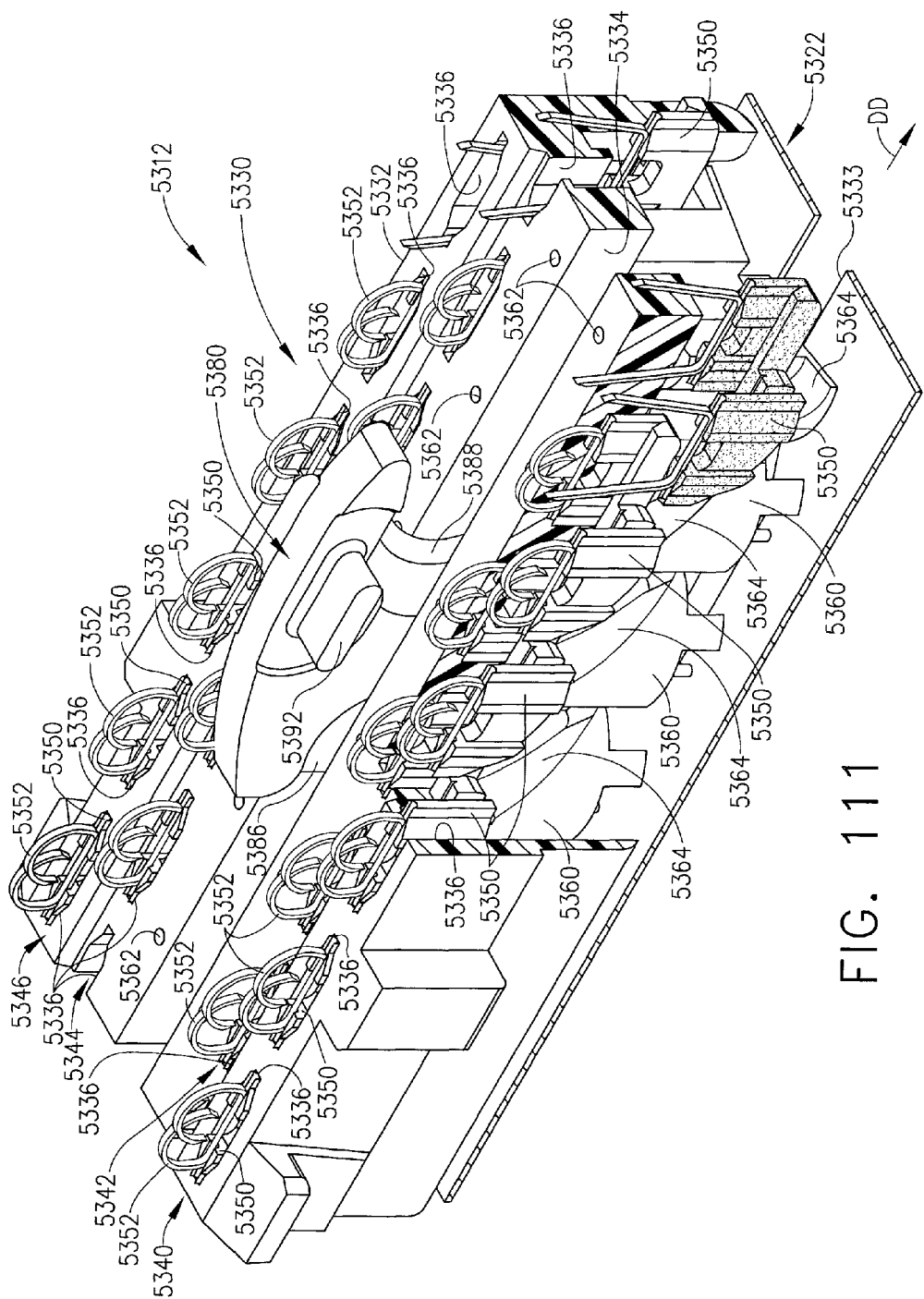

FIGS. 104-109 diagrammatically depict the sequential firing of staples in a surgical tool assembly 5000' that is substantially similar to the surgical tool assembly 5000 described above. In this embodiment, the inboard and outboard drivers 5052', 5054' have a cam-like shape with a cam surface 5053 and an actuator protrusion 5055 as shown in FIGS. 104-110. The drivers 5052', 5054' are journaled on the same shaft 5056' that is rotatably supported by the sled assembly 5030'. In this embodiment, the sled assembly 5030' has distal wedge segments 5060' for engaging the pushers 5088. FIG. 104 illustrates an initial position of two inboard or outboard drivers 5052', 5054' as the sled assembly 5030' is driven in the distal direction "DD". As can be seen in that Figure, the pusher 5088a has advanced up the wedge segment 5060' and has contacted the driver 5052', 5054'. Further travel of the sled assembly 5030' in the distal direction causes the driver 5052', 5054' to pivot in the "P" direction (FIG. 105) until the actuator portion 5055 contacts the end wall 5029a of the activation cavity 5026, 5028 as shown in FIG. 111. Continued advancement of the sled assembly 5030' in the distal direction "DD" causes the driver 5052', 5054' to rotate in the "D" direction as shown in FIG. 107. As the driver 5052', 5054' rotates, the pusher 5088a rides up the cam surface 5053 to the final vertical position shown in FIG. 108. When the pusher 5088a reaches the final vertical position shown in FIGS. 108 and 109, the staple (not shown) supported thereon has been driven into the staple forming surface of the anvil to form the staple.

FIGS. 111-116 illustrate a surgical end effector 5312 that may be employed for example, in connection with the tool mounting portion 1300 and shaft 2008 described in detail above. In various forms, the surgical end effector 5312 includes an elongated channel 5322 that is constructed as described above for supporting a surgical staple cartridge 5330 therein. The surgical staple cartridge 5330 comprises a body portion 5332 that includes a centrally disposed slot 5334 for accommodating an upstanding support portion 5386 of a sled assembly 5380. See FIGS. 111-113. The surgical staple cartridge body portion 5332 further includes a plurality of cavities 5336 for movably supporting staple-supporting pushers 5350 therein. The cavities 5336 may be arranged in spaced longitudinally extending rows 5340, 5342, 5344, 5346. The rows 5340, 5342 are located on one lateral side of the longitudinal slot 5334 and the rows 5344, 5346 are located on the other side of longitudinal slot 5334. In at least one embodiment, the pushers 5350 are configured to support two surgical staples 5352 thereon. In particular, each pusher 5350 located on one side of the elongated slot 5334 supports one staple 5352 in row 5340 and one staple 5352 in row 5342 in a staggered orientation. Likewise, each pusher 5350 located on the other side of the elongated slot 5334 supports one surgical staple 5352 in row 5344 and another surgical staple 5352 in row 5346 in a staggered orientation. Thus, every pusher 5350 supports two surgical staples 5352.

Figure 112:
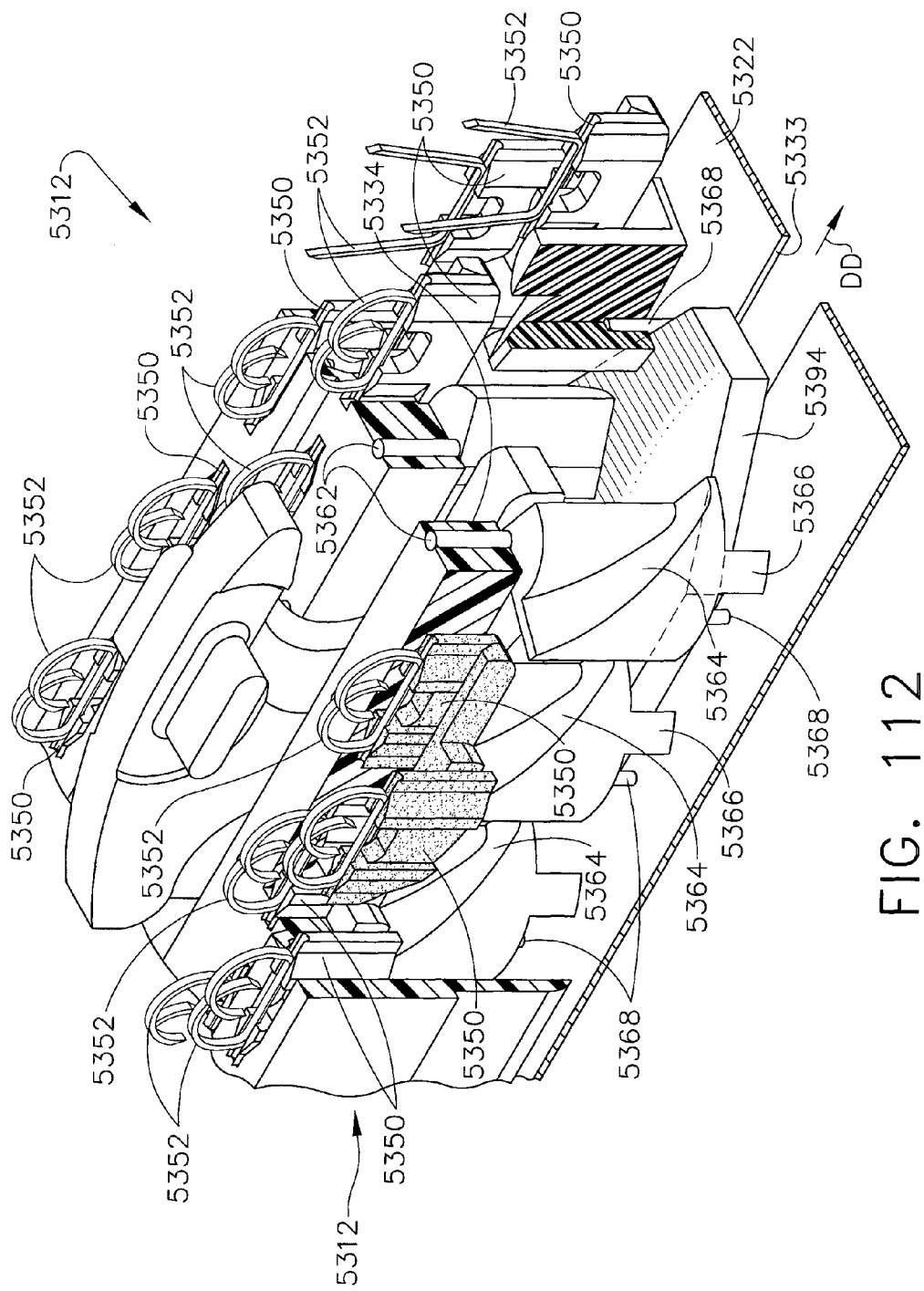
Figure 116:
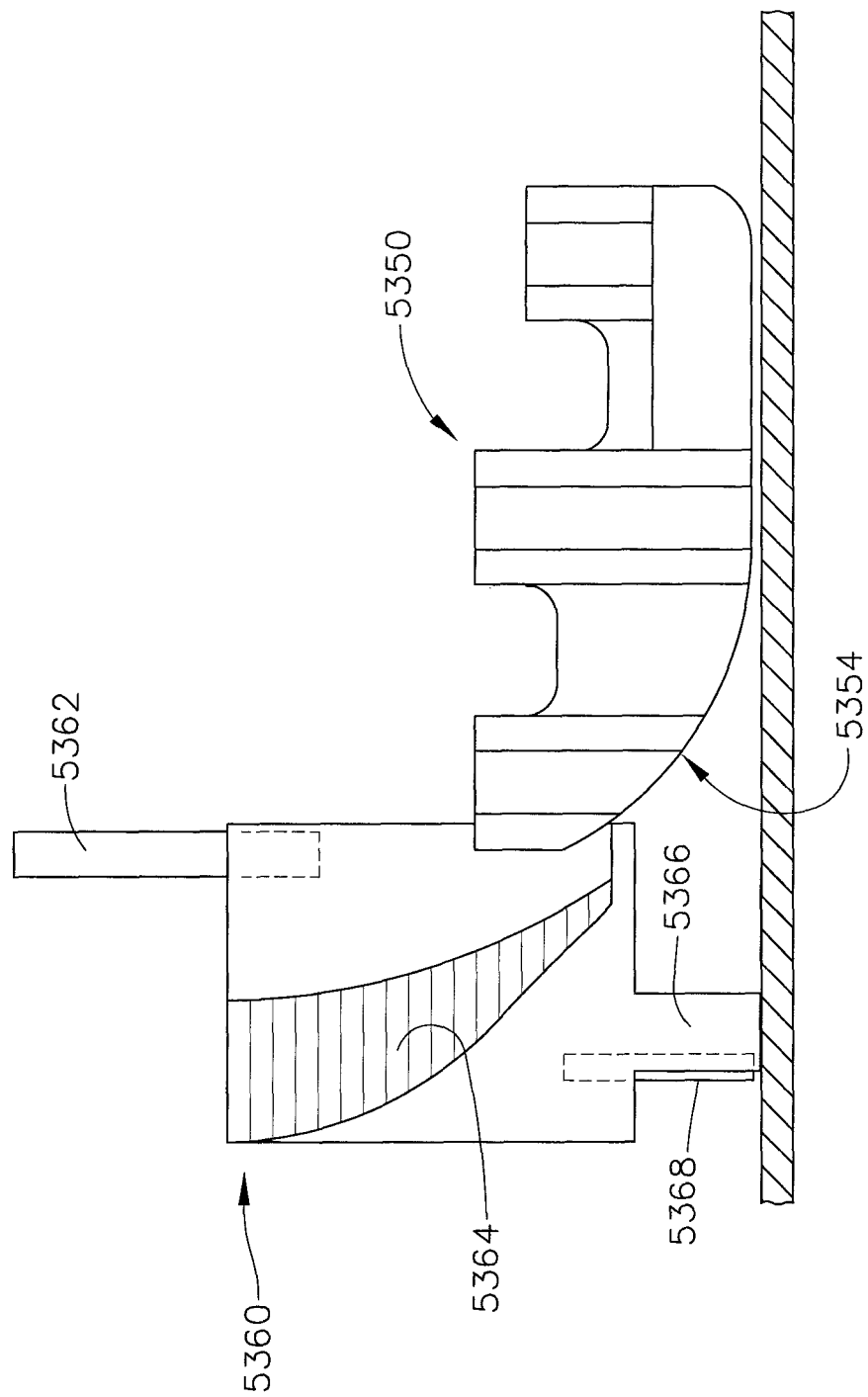

As can be further seen in FIGS. 111, 112, the surgical staple cartridge 5330 includes a plurality of rotary drivers 5360. More particularly, the rotary drivers 5360 on one side of the elongated slot 5334 are arranged in a single line 5370 and correspond to the pushers 5350 in lines 5340, 5342. In addition, the rotary drivers 5360 on the other side of the elongated slot 5334 are arranged in a single line 5372 and correspond to the pushers 5350 in lines 5344, 5346. As can be seen in FIG. 116, each rotary driver 5360 is rotatably supported within the staple cartridge body 5332. More particularly, each rotary driver 5360 is rotatably received on a corresponding driver shaft 5362. Each driver 5360 has an arcuate ramp portion 5364 formed thereon that is configured to engage an arcuate lower surface 5354 formed on each pusher 5350. See FIG.

116. In addition, each driver 5360 has a lower support portion 5366 extend therefrom to slidably support the pusher 5360 on the channel 5322. Each driver 5360 has a downwardly extending actuation rod 5368 that is configured for engagement with a sled assembly 5380.

Figure 113:
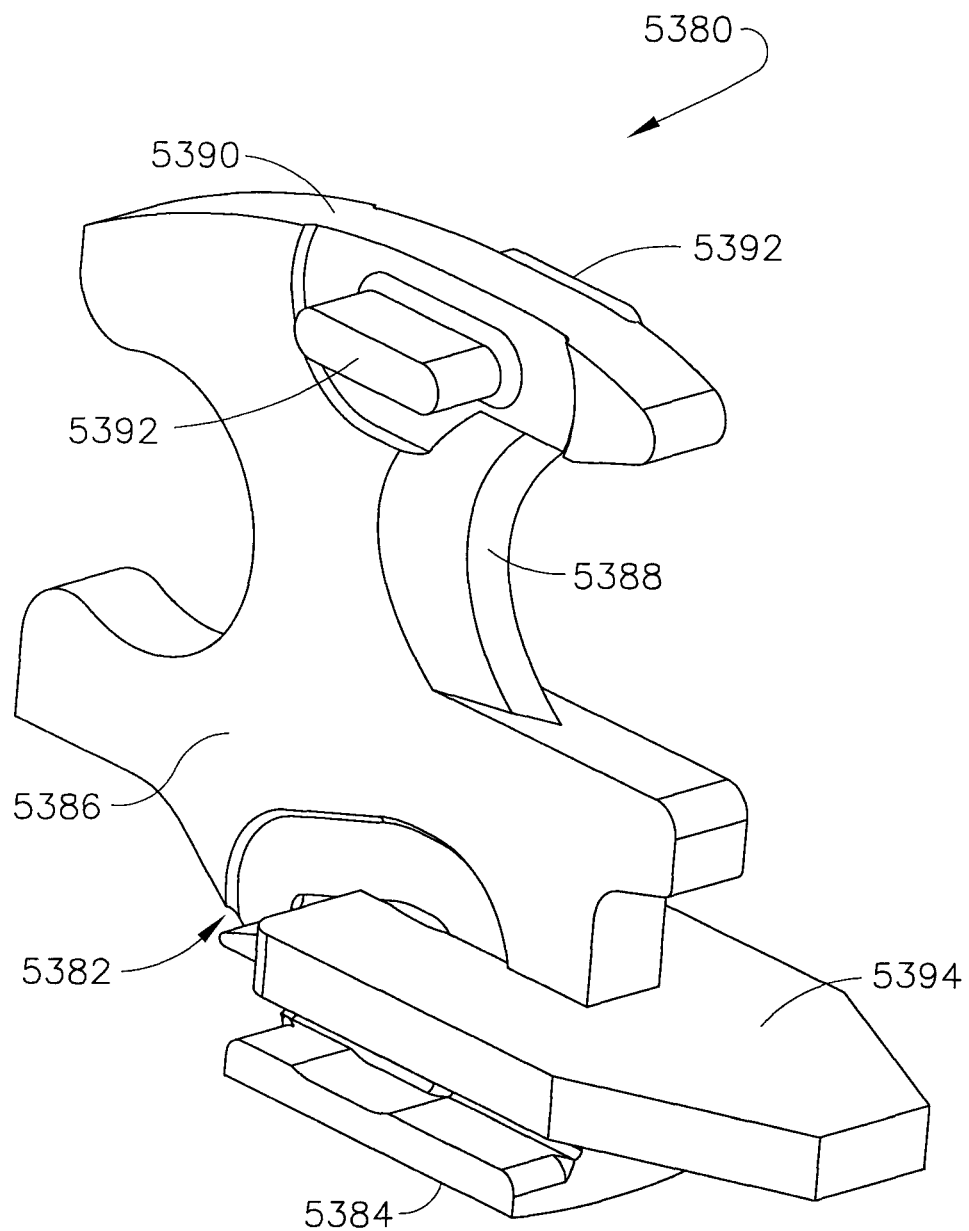
Figure 114:
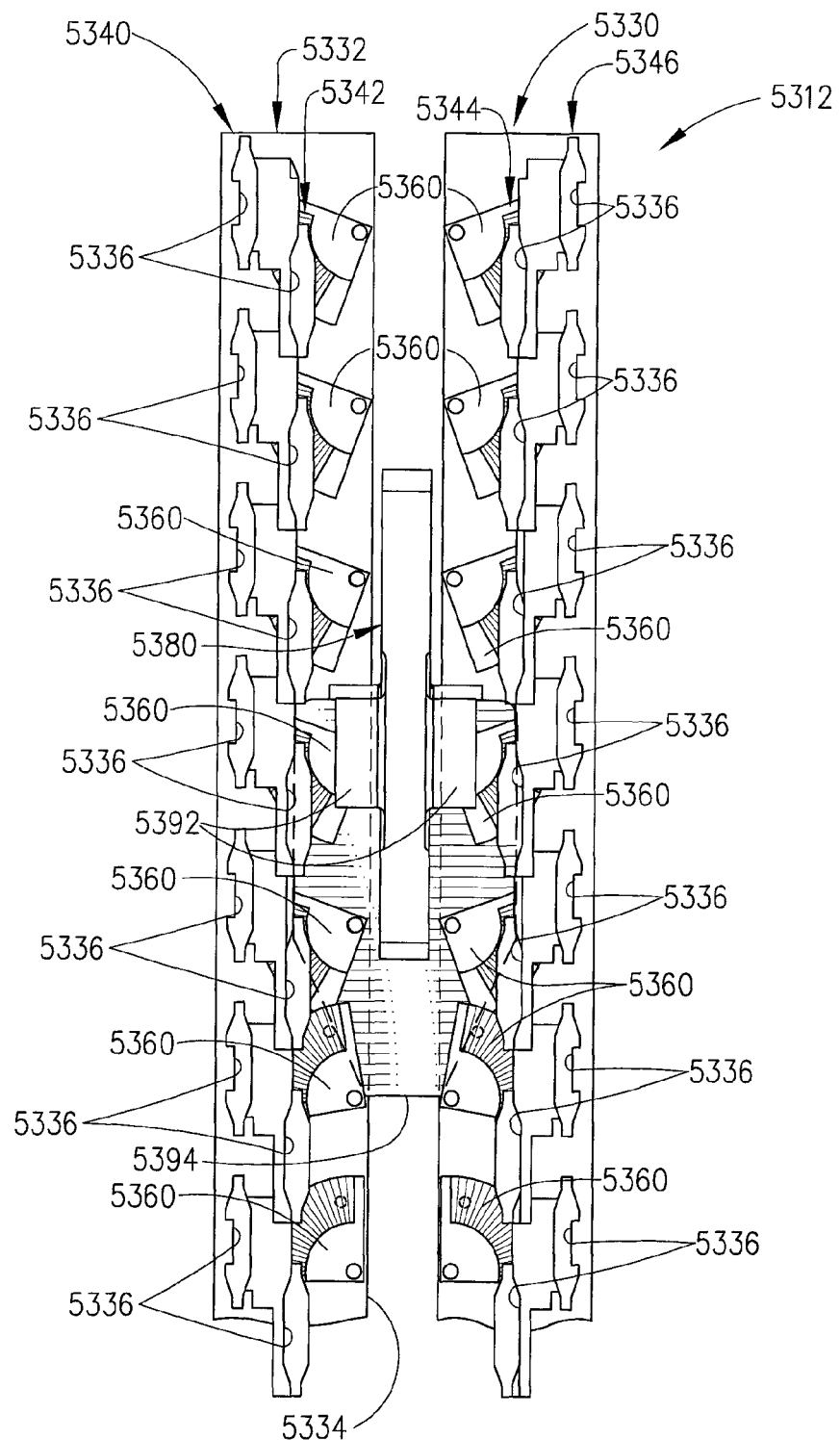
Figure 115:
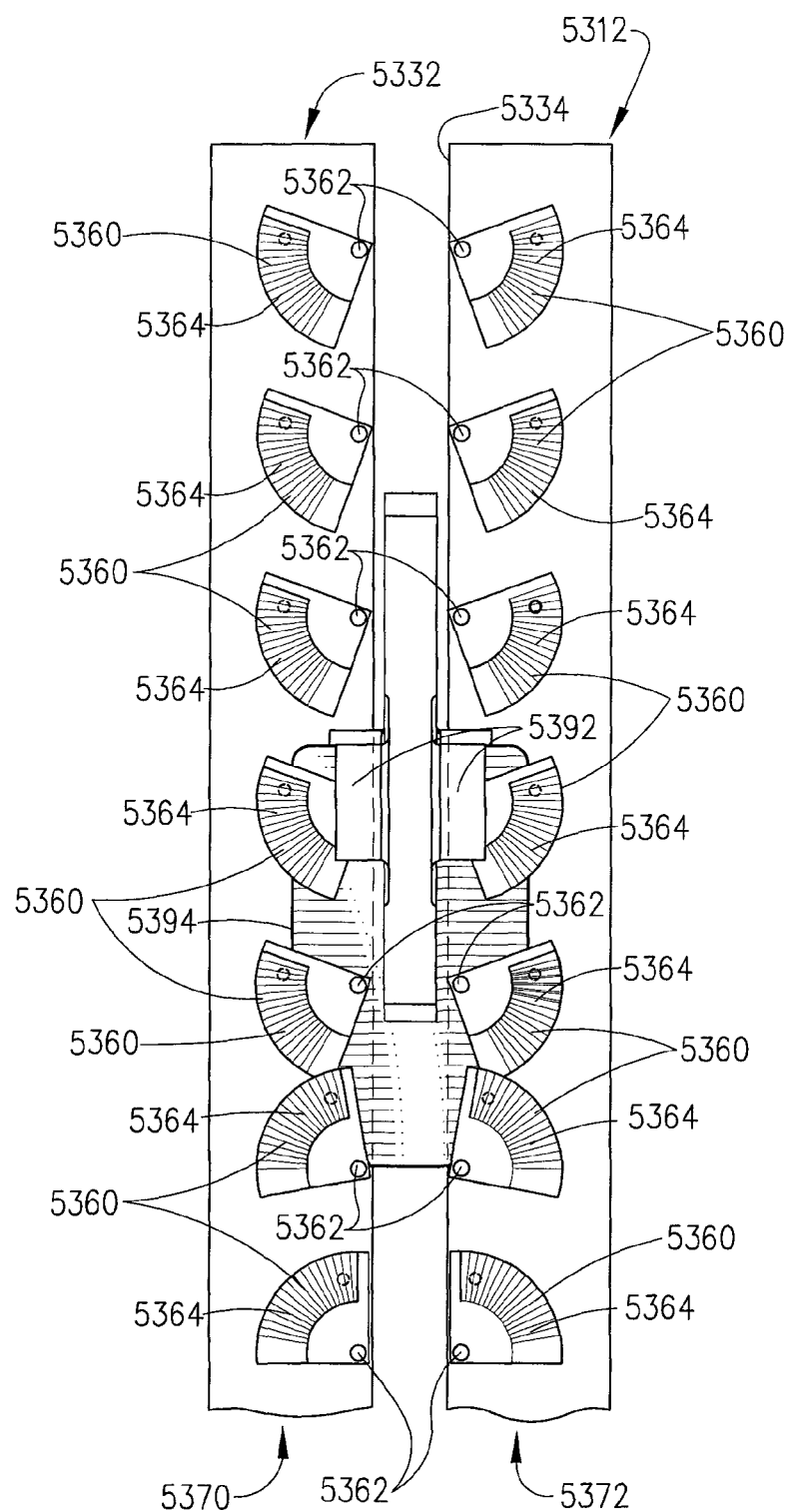

As can be seen in FIG. 113, in at least one embodiment, the sled assembly 5380 includes a base portion 5382 that has a foot portion 5384 that is sized to be slidably received in a slot 5333 in the channel 5322. See FIG. 111. The sled assembly 5380 includes an upstanding support portion 5386 that supports a tissue cutting blade or tissue cutting instrument 5388. The upstanding support portion 5386 terminates in a top portion 5390 that has a pair of laterally extending retaining fins 5392 protruding therefrom. The fins 5392 are positioned to be received within corresponding slots (not shown) in the anvil (not shown). As with the above-described embodiments, the fins 5392 and the foot portion 5384 serve to retain the anvil (not shown) in a desired spaced closed position as the sled assembly 5380 is driven distally through the tissue clamped within the surgical end effector 5312. The upstanding support portion 5386 is configured for attachment to a knife bar 2200 (FIG. 32). The sled assembly 5380 further has a horizontally-extending actuator plate 5394 that is shaped for actuating engagement with each of the actuation rods 5368 on the pushers 5360.

Operation of the surgical end effector 5312 will now be explained with reference to FIGS. 111 and 112. As the sled assembly 5380 is driven in the distal direction "DD" through the staple cartridge 5330, the actuator plate 5394 sequentially contacts the actuation rods 5368 on the pushers 5360. As the sled assembly 5380 continues to move distally, the actuator plate 5394 sequentially contacts the actuator rods 5368 of the drivers 5360 on each side of the elongated slot 5334. Such action causes the drivers 5360 to rotate from a first unactuated position to an actuated portion wherein the pushers 5350 are driven towards the closed anvil. As the pushers 5350 are driven toward the anvil, the surgical staples 5352 thereon are driven into forming contact with the underside of the anvil. Once the robotic system 1000 determines that the sled assembly 5080 has reached its distal most position through sensors or other means, the control system of the robotic system 1000 may then retract the knife bar and sled assembly 5380 back to the starting position. Thereafter, the robotic control system may then activate the procedure for returning the anvil to the open position to release the stapled tissue.

FIGS. 117-121 depict one form of an automated reloading system embodiment of the present invention, generally designated as 5500. In one form, the automated reloading system 5500 is configured to replace a "spent" surgical end effector component in a manipulatable surgical tool portion of a robotic surgical system with a "new" surgical end effector component. As used herein, the term "surgical end effector component" may comprise, for example, a surgical staple cartridge, a disposable loading unit or other end effector components that, when used, are spent and must be replaced with a new component. Furthermore, the term "spent" means that the end effector component has been activated and is no longer useable for its intended purpose in its present state. For example, in the context of a surgical staple cartridge or disposable loading unit, the term "spent" means that at least some of the unformed staples that were previously supported therein have been "fired" therefrom. As used herein, the term "new" surgical end effector component refers to an end effector component that is in condition for its intended use. In the context of a surgical staple cartridge or disposable loading unit, for example, the term "new" refers to such a component that has unformed staples therein and which is otherwise ready for use.

In various embodiments, the automated reloading system 5500 includes a base portion 5502 that may be strategically located within a work envelope 1109 of a robotic arm cart 1100 (FIG. 18) of a robotic system 1000. As used herein, the term "manipulatable surgical tool portion" collectively refers to a surgical tool of the various types disclosed herein and other forms of surgical robotically-actuated tools that are operably attached to, for example, a robotic arm cart 1100 or similar device that is configured to automatically manipulate and actuate the surgical tool. The term "work envelope" as used herein refers to the range of movement of the manipulatable surgical tool portion of the robotic system. FIG. 18 generally depicts an area that may comprise a work envelope of the robotic arm cart 1100. Those of ordinary skill in the art will understand that the shape and size of the work envelope depicted therein is merely illustrative. The ultimate size, shape and location of a work envelope will ultimately depend upon the construction, range of travel limitations, and location of the manipulatable surgical tool portion. Thus, the term "work envelope" as used herein is intended to cover a variety of different sizes and shapes of work envelopes and should not be limited to the specific size and shape of the sample work envelope depicted in FIG. 18.

Figure 117:
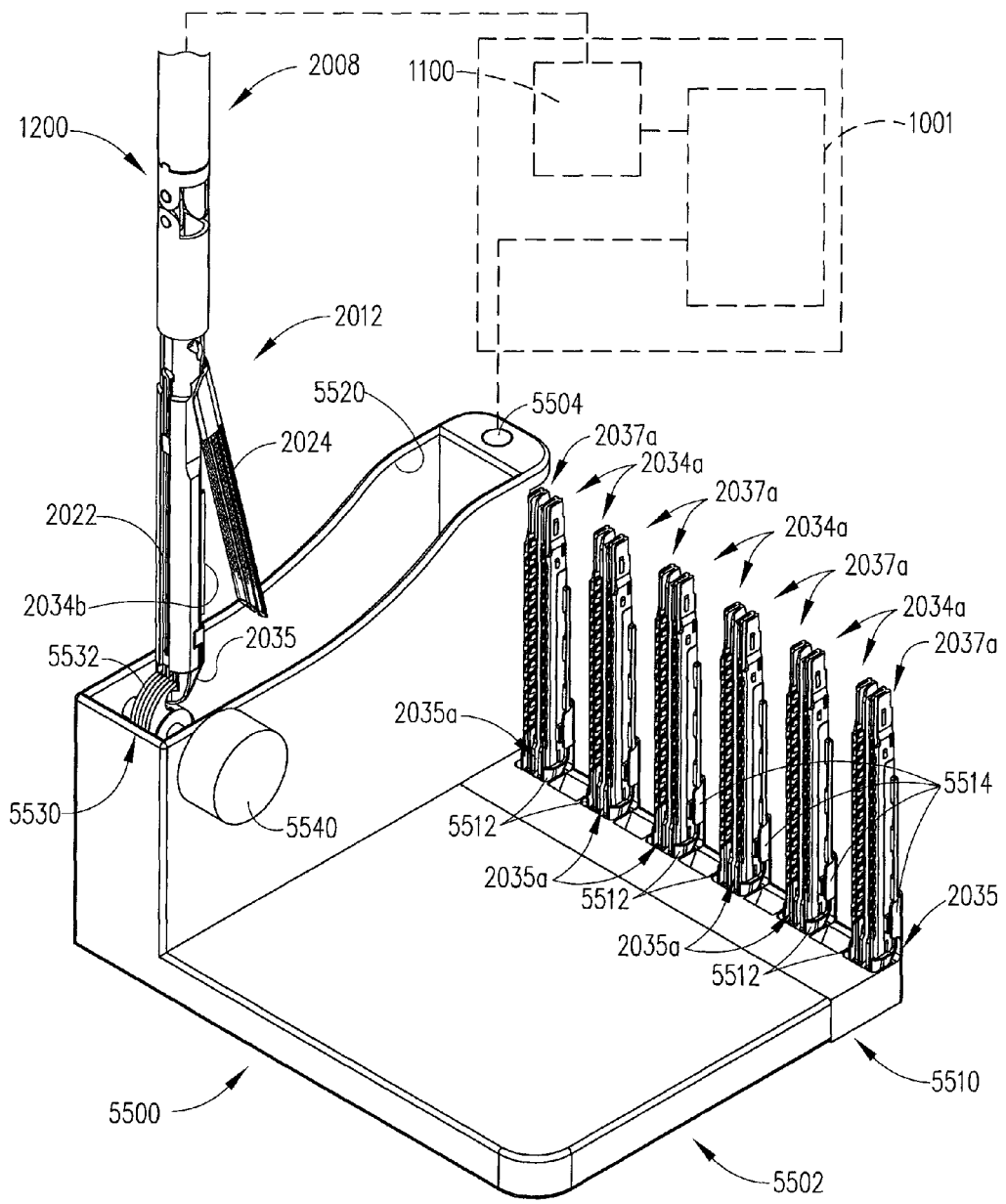

As can be seen in FIG. 117, the base portion 5502 includes a new component support section or arrangement 5510 that is configured to operably support at least one new surgical end effector component in a "loading orientation". As used herein, the term "loading orientation" means that the new end effector component is supported in such away so as to permit the corresponding component support portion of the manipulatable surgical tool portion to be brought into loading engagement with (i.e., operably seated or operably attached to) the new end effector component (or the new end effector component to be brought into loading engagement with the corresponding component support portion of the manipulatable surgical tool portion) without human intervention beyond that which may be necessary to actuate the robotic system. As will be further appreciated as the present Detailed Description proceeds, in at least one embodiment, the preparation nurse will load the new component support section before the surgery with the appropriate length and color cartridges (some surgical staple cartridges may support certain sizes of staples the size of which may be indicated by the color of the cartridge body) required for completing the surgical procedure. However, no direct human interaction is necessary during the surgery to reload the robotic endocutter. In one form, the surgical end effector component comprises a staple cartridge 2034 that is configured to be operably seated within a component support portion (elongated channel) of any of the various other end effector arrangements described above. For explanation purposes, new (unused) cartridges will be designated as "2034a" and spent cartridges will be designated as "2034b". The Figures depict cartridges 2034a, 2034b designed for use with a surgical end effector 2012 that includes a channel 2022 and an anvil 2024, the construction and operation of which were discussed in detail above. Cartridges 2034a, 2034b are identical to cartridges 2034 described above. In various embodiments, the cartridges 2034a, 2034b are configured to be snappingly retained (i.e., loading engagement) within the channel 2022 of a surgical end effector 2012. As the present Detailed Description proceeds, however, those of ordinary skill in the art will appreciate that the unique and novel features of the automated cartridge reloading system 5500 may be effectively employed in connection with the automated removal and installation of other cartridge arrangements without departing from the spirit and scope of the present invention.

In the depicted embodiment, the term "loading orientation" means that the distal tip portion 2035a of the a new surgical staple cartridge 2034a is inserted into a corresponding support cavity 5512 in the new cartridge support section 5510 such that the proximal end portion 2037a of the new surgical staple cartridge 2034a is located in a convenient orientation for enabling the arm cart 1100 to manipulate the surgical end effector 2012 into a position wherein the new cartridge 2034a may be automatically loaded into the channel 2022 of the surgical end effector 2012. In various embodiments, the base 5502 includes at least one sensor 5504 which communicates with the control system 1003 of the robotic controller 1001 to provide the control system 1003 with the location of the base 5502 and/or the reload length and color doe each staged or new cartridge 2034a.

As can also be seen in the Figures, the base 5502 further includes a collection receptacle 5520 that is configured to collect spent cartridges 2034b that have been removed or disengaged from the surgical end effector 2012 that is operably attached to the robotic system 1000. In addition, in one form, the automated reloading system 5500 includes an extraction system 5530 for automatically removing the spent end effector component from the corresponding support portion of the end effector or manipulatable surgical tool portion without specific human intervention beyond that which may be necessary to activate the robotic system. In various embodiments, the extraction system 5530 includes an extraction hook member 5532. In one form, for example, the extraction hook member 5532 is rigidly supported on the base portion 5502. In one embodiment, the extraction hook member has at least one hook 5534 formed thereon that is configured to hookingly engage the distal end 2035 of a spent cartridge 2034b when it is supported in the elongated channel 2022 of the surgical end effector 2012. In various forms, the extraction hook member 5532 is conveniently located within a portion of the collection receptacle 5520 such that when the spent end effector component (cartridge 2034b) is brought into extractive engagement with the extraction hook member 5532, the spent end effector component (cartridge 2034b) is dislodged from the corresponding component support portion (elongated channel 2022), and falls into the collection receptacle 5020. Thus, to use this embodiment, the manipulatable surgical tool portion manipulates the end effector attached thereto to bring the distal end 2035 of the spent cartridge 2034b therein into hooking engagement with the hook 5534 and then moves the end effector in such a way to dislodge the spent cartridge 2034b from the elongated channel 2022.

Figure 119:
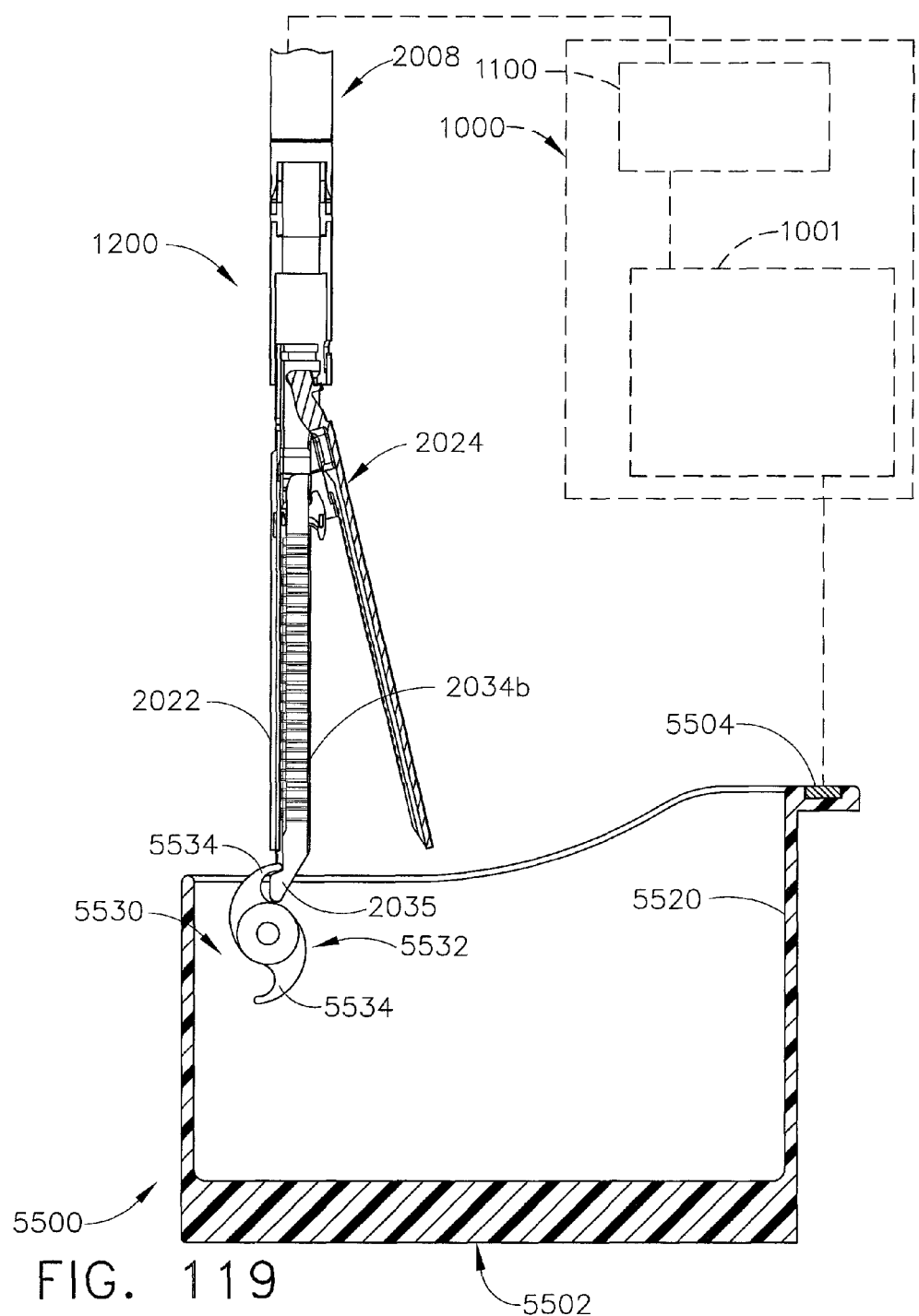
Figure 120:
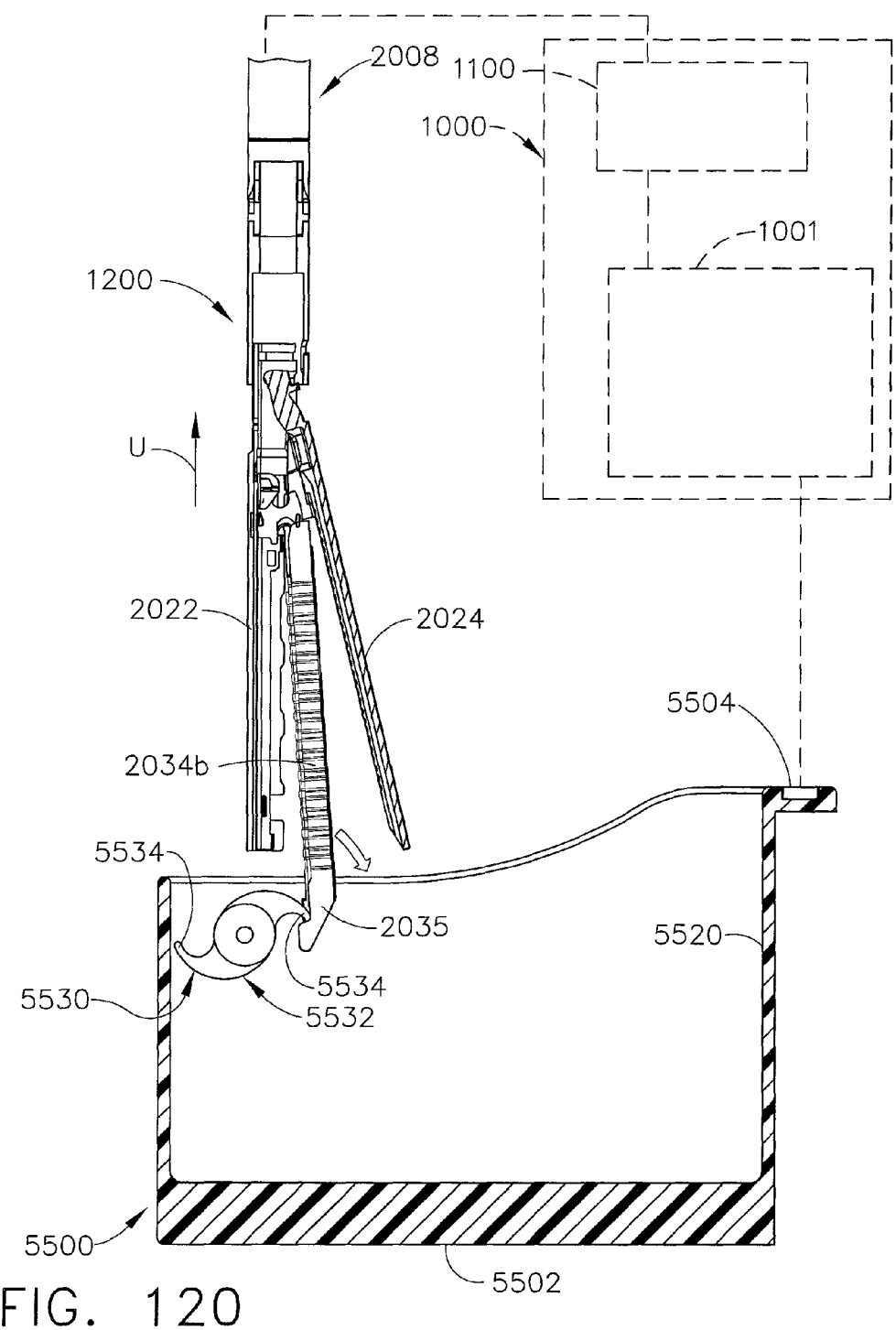

In other arrangements, the extraction hook member 5532 comprises a rotatable wheel configuration that has a pair of diametrically-opposed hooks 5334 protruding therefrom. See FIGS. 122 and 125. The extraction hook member 5532 is rotatably supported within the collection receptacle 5520 and is coupled to an extraction motor 5540 that is controlled by the controller 1001 of the robotic system. This form of the automated reloading system 5500 may be used as follows. FIG. 119 illustrates the introduction of the surgical end effector 2012 that is operably attached to the manipulatable surgical tool portion 1200. As can be seen in that Figure, the arm cart 1100 of the robotic system 1000 locates the surgical end effector 2012 in the shown position wherein the hook end 5534 of the extraction member 5532 hookingly engages the distal end 2035 of the spent cartridge 2034b in the surgical end effector 2012. The anvil 2024 of the surgical end effector 2012 is in the open position. After the distal end 2035 of the spent cartridge 2034b is engaged with the hook end 5532, the extraction motor 5540 is actuated to rotate the extraction wheel 5532 to disengage the spent cartridge 2034b from the channel 2022. To assist with the disengagement of the spent cartridge 2034b from the channel 2022 (or if the extraction member 5530 is stationary), the robotic system 1000 may move the surgical end effector 2012 in an upward direction (arrow "U" in FIG. 120). As the spent cartridge 2034b is dislodged from the channel 2022, the spent cartridge 2034b falls into the collection receptacle 5520. Once the spent cartridge 2034b has been removed from the surgical end effector 2012, the robotic system 1000 moves the surgical end effector 2012 to the position shown in FIG. 121.

In various embodiments, a sensor arrangement 5533 is located adjacent to the extraction member 5532 that is in communication with the controller 1001 of the robotic system 1000. The sensor arrangement 5533 may comprise a sensor that is configured to sense the presence of the surgical end effector 2012 and, more particularly the tip 2035b of the spent surgical staple cartridge 2034b thereof as the distal tip portion 2035b is brought into engagement with the extraction member 5532. In some embodiments, the sensor arrangement 5533 may comprise, for example, a light curtain arrangement. However, other forms of proximity sensors may be employed. In such arrangement, when the surgical end effector 2012 with the spent surgical staple cartridge 2034b is brought into extractive engagement with the extraction member 5532, the sensor senses the distal tip 2035b of the surgical staple cartridge 2034b (e.g., the light curtain is broken). When the extraction member 5532 spins and pops the surgical staple cartridge 2034b loose and it falls into the collection receptacle 5520, the light curtain is again unbroken. Because the surgical end effector 2012 was not moved during this procedure, the robotic controller 1001 is assured that the spent surgical staple cartridge 2034b has been removed therefrom. Other sensor arrangements may also be successfully employed to provide the robotic controller 1001 with an indication that the spent surgical staple cartridge 2034b has been removed from the surgical end effector 2012.

Figure 118:
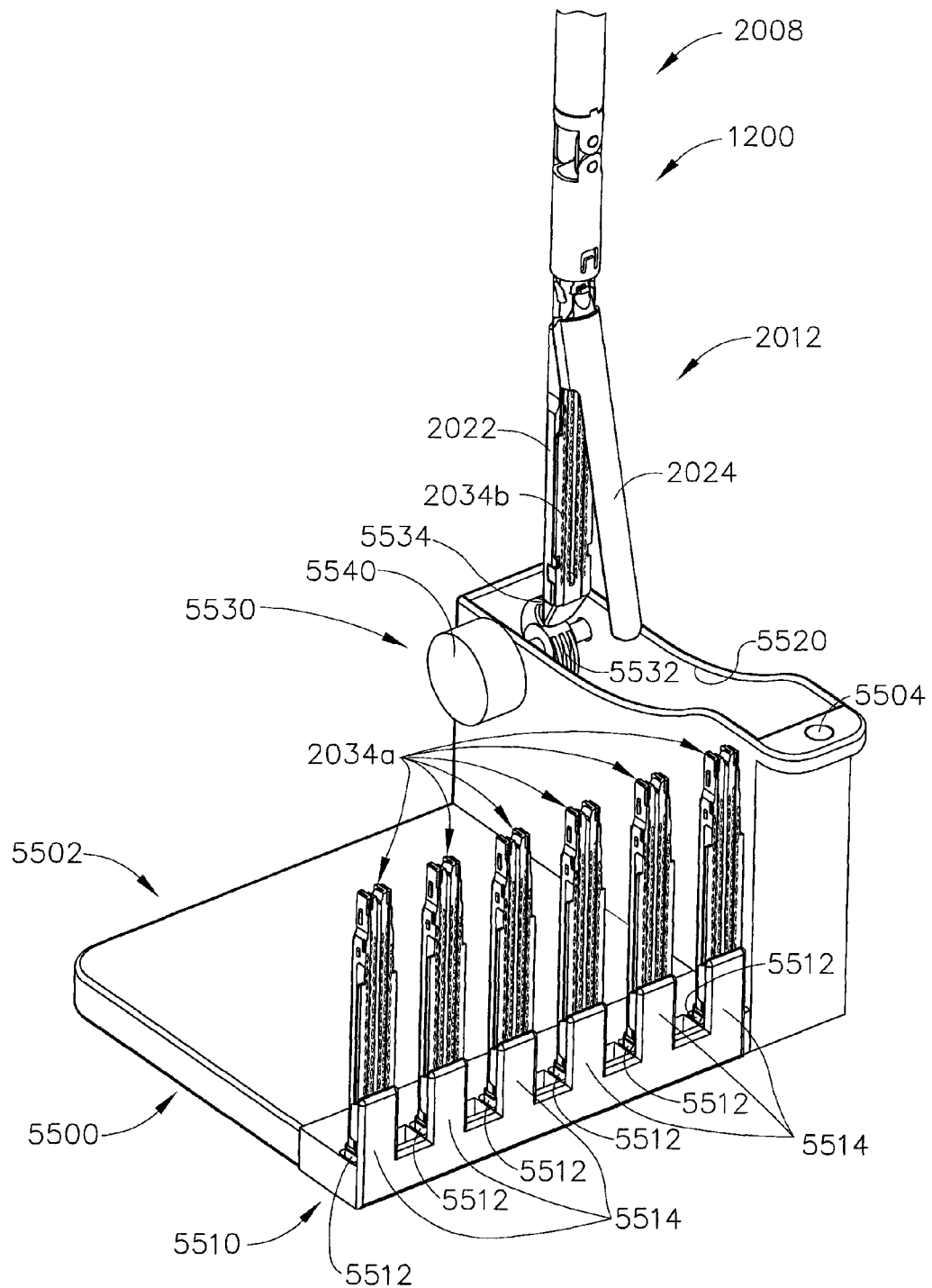
Figure 121:
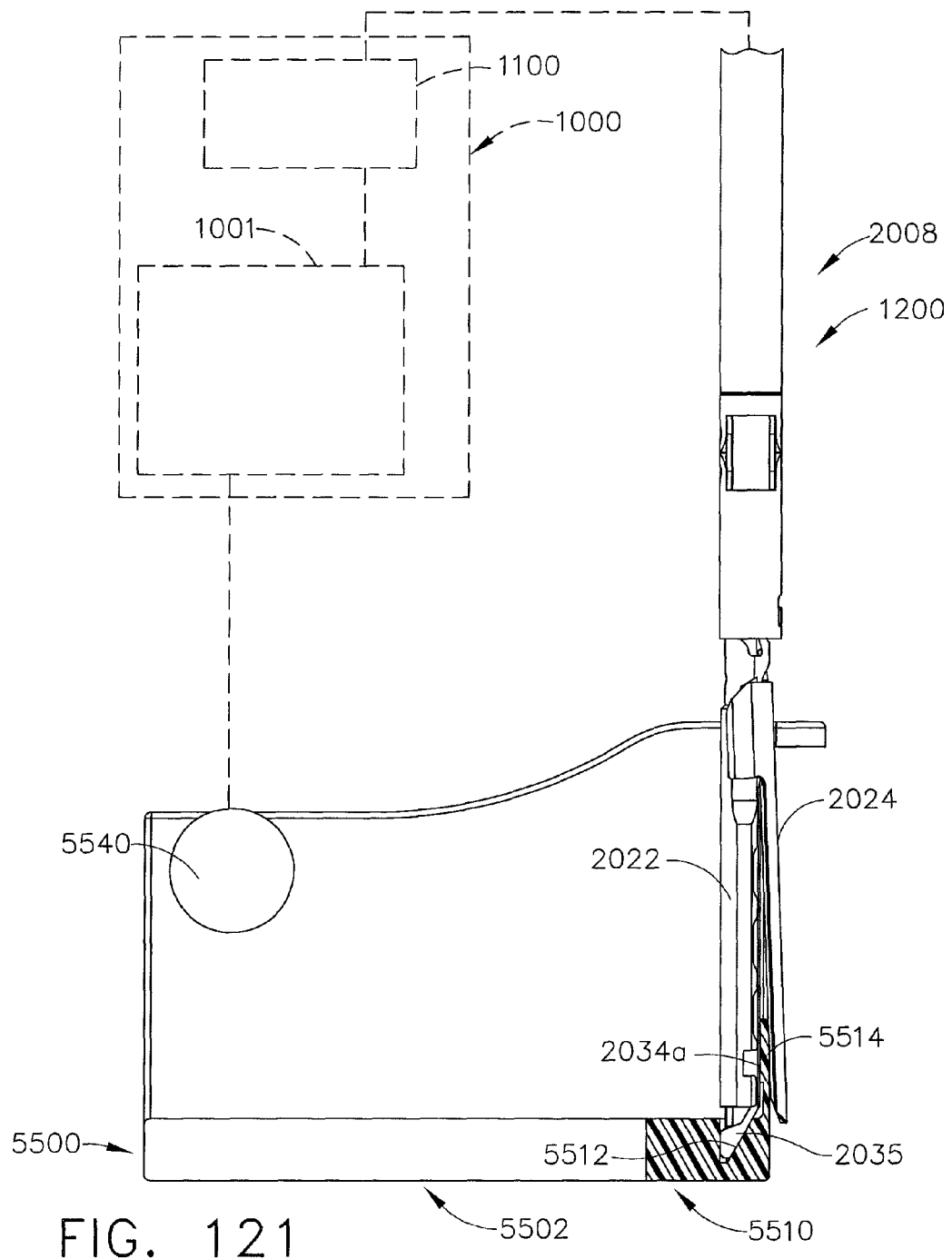

As can be seen in FIG. 121, the surgical end effector 2012 is positioned to grasp a new surgical staple cartridge 2034a between the channel 2022 and the anvil 2024. More specifically, as shown in FIGS. 118 and 121, each cavity 5512 has a corresponding upstanding pressure pad 5514 associated with it. The surgical end effector 2012 is located such that the pressure pad 5514 is located between the new cartridge 2034a and the anvil 2024. Once in that position, the robotic system 1000 closes the anvil 2024 onto the pressure pad 5514 which serves to push the new cartridge 2034a into snapping engagement with the channel 2022 of the surgical end effector 2012. Once the new cartridge 2034a has been snapped into position within the elongated channel 2022, the robotic system 1000 then withdraws the surgical end effector 2012 from the automated cartridge reloading system 5500 for use in connection with performing another surgical procedure.

FIGS. 122-126 depict another automated reloading system 5600 that may be used to remove a spent disposable loading unit 3612 from a manipulatable surgical tool arrangement 3600 (FIGS. 69-82) that is operably attached to an arm cart 1100 or other portion of a robotic system 1000 and reload a new disposable loading unit 3612 therein. As can be seen in FIGS. 122 and 123, one form of the automated reloading system 5600 includes a housing 5610 that has a movable support assembly in the form of a rotary carrousel top plate 5620 supported thereon which cooperates with the housing 5610 to form a hollow enclosed area 5612. The automated reloading system 5600 is configured to be operably supported within the work envelop of the manipulatable surgical tool portion of a robotic system as was described above. In various embodiments, the rotary carrousel plate 5620 has a plurality of holes 5622 for supporting a plurality of orientation tubes 5660 therein. As can be seen in FIGS. 123 and 124, the rotary carrousel plate 5620 is affixed to a spindle shaft 5624. The spindle shaft 5624 is centrally disposed within the enclosed area 5612 and has a spindle gear 5626 attached thereto. The spindle gear 5626 is in meshing engagement with a carrousel drive gear 5628 that is coupled to a carrousel drive motor 5630 that is in operative communication with the robotic controller 1001 of the robotic system 1000.

Various embodiments of the automated reloading system 5600 may also include a carrousel locking assembly, generally designated as 5640. In various forms, the carrousel locking assembly 5640 includes a cam disc 5642 that is affixed to the spindle shaft 5624. The spindle gear 5626 may be attached to the underside of the cam disc 5642 and the cam disc 5642 may be keyed onto the spindle shaft 5624. In alternative arrangements, the spindle gear 5626 and the cam disc 5642 may be independently non-rotatably affixed to the spindle shaft 5624. As can be seen in FIGS. 123 and 124, a plurality of notches 5644 are spaced around the perimeter of the cam disc 5642. A locking arm 5648 is pivotally mounted within the housing 5610 and is biased into engagement with the perimeter of the cam disc 5642 by a locking spring 5649. As can be seen in FIG. 122, the outer perimeter of the cam disc 5642 is rounded to facilitate rotation of the cam disc 5642 relative to the locking arm 5648. The edges of each notch 5644 are also rounded such that when the cam disc 5642 is rotated, the locking arm 5648 is cammed out of engagement with the notches 5644 by the perimeter of the cam disc 5642.

Various forms of the automated reloading system 5600 are configured to support a portable/replaceable tray assembly 5650 that is configured to support a plurality of disposable loading units 3612 in individual orientation tubes 5660. More specifically and with reference to FIGS. 123 and 124, the replaceable tray assembly 5650 comprises a tray 5652 that has a centrally-disposed locator spindle 5654 protruding from the underside thereof. The locator spindle 5654 is sized to be received within a hollow end 5625 of spindle shaft 5624. The tray 5652 has a plurality of holes 5656 therein that are configured to support an orientation tube 5660 therein. Each orientation tube 5660 is oriented within a corresponding hole 5656 in the replaceable tray assembly 5650 in a desired orientation by a locating fin 5666 on the orientation tube 5660 that is designed to be received within a corresponding locating slot 5658 in the tray assembly 5650. In at least one embodiment, the locating fin 5666 has a substantially V-shaped cross-sectional shape that is sized to fit within a V-shaped locating slot 5658. Such arrangement serves to orient the orientation tube 5660 in a desired starting position while enabling it to rotate within the hole 5656 when a rotary motion is applied thereto. That is, when a rotary motion is applied to the orientation tube 5660 the V-shaped locating fin 5666 will pop out of its corresponding locating slot enabling the tube 5660 to rotate relative to the tray 5652 as will be discussed in further detail below. As can also be seen in FIGS. 122-124, the replaceable tray 5652 may be provided with one or more handle portions 5653 to facilitate transport of the tray assembly 5652 when loaded with orientation tubes 5660.

As can be seen in FIG. 126, each orientation tube 5660 comprises a body portion 5662 that has a flanged open end 5664. The body portion 5662 defines a cavity 5668 that is sized to receive a portion of a disposable loading unit 3612 therein. To properly orient the disposable loading unit 3612 within the orientation tube 5660, the cavity 5668 has a flat locating surface 5670 formed therein. As can be seen in FIG. 126, the flat locating surface 5670 is configured to facilitate the insertion of the disposable loading unit into the cavity 5668 in a desired or predetermined non-rotatable orientation. In addition, the end 5669 of the cavity 5668 may include a foam or cushion material 5672 that is designed to cushion the distal end of the disposable loading unit 3612 within the cavity 5668. Also, the length of the locating surface may cooperate with a sliding support member 3689 of the axial drive assembly 3680 of the disposable loading unit 3612 to further locate the disposable loading unit 3612 at a desired position within the orientation tube 5660.

The orientation tubes 5660 may be fabricated from Nylon, polycarbonate, polyethylene, liquid crystal polymer, 6061 or 7075 aluminum, titanium, 300 or 400 series stainless steel, coated or painted steel, plated steel, etc. and, when loaded in the replaceable tray 5662 and the locator spindle 5654 is inserted into the hollow end 5625 of spindle shaft 5624, the orientation tubes 5660 extend through corresponding holes 5662 in the carrousel top plate 5620. Each replaceable tray 5662 is equipped with a location sensor 5663 that communicates with the control system 1003 of the controller 1001 of the robotic system 1000. The sensor 5663 serves to identify the location of the reload system, and the number, length, color and fired status of each reload housed in the tray. In addition, an optical sensor or sensors 5665 that communicate with the robotic controller 1001 may be employed to sense the type/size/length of disposable loading units that are loaded within the tray 5662.

Various embodiments of the automated reloading system 5600 further include a drive assembly 5680 for applying a rotary motion to the orientation tube 5660 holding the disposable loading unit 3612 to be attached to the shaft 3700 of the surgical tool 3600 (collectively the "manipulatable surgical tool portion") that is operably coupled to the robotic system. The drive assembly 5680 includes a support yoke 5682 that is attached to the locking arm 5648. Thus, the support yoke 5682 pivots with the locking arm 5648. The support yoke 5682 rotatably supports a tube idler wheel 5684 and a tube drive wheel 5686 that is driven by a tube motor 5688 attached thereto. Tube motor 5688 communicates with the control system 1003 and is controlled thereby. The tube idler wheel 5684 and tube drive wheel 5686 are fabricated from, for example, natural rubber, sanoprene, isoplast, etc. such that the outer surfaces thereof create sufficient amount of friction to result in the rotation of an orientation tube 5660 in contact therewith upon activation of the tube motor 5688. The idler wheel 5684 and tube drive wheel 5686 are oriented relative to each other to create a cradle area 5687 therebetween for receiving an orientation tube 5060 in driving engagement therein.

In use, one or more of the orientation tubes 5660 loaded in the automated reloading system 5600 are left empty, while the other orientation tubes 5660 may operably support a corresponding new disposable loading unit 3612 therein. As will be discussed in further detail below, the empty orientation tubes 5660 are employed to receive a spent disposable loading unit 3612 therein.

The automated reloading system 5600 may be employed as follows after the system 5600 is located within the work envelope of the manipulatable surgical tool portion of a robotic system. If the manipulatable surgical tool portion has a spent disposable loading unit 3612 operably coupled thereto, one of the orientation tubes 5660 that are supported on the replaceable tray 5662 is left empty to receive the spent disposable loading unit 3612 therein. If, however, the manipulatable surgical tool portion does not have a disposable loading unit 3612 operably coupled thereto, each of the orientation tubes 5660 may be provided with a properly oriented new disposable loading unit 3612.

As described hereinabove, the disposable loading unit 3612 employs a rotary "bayonet-type" coupling arrangement for operably coupling the disposable loading unit 3612 to a corresponding portion of the manipulatable surgical tool portion. That is, to attach a disposable loading unit 3612 to the corresponding portion of the manipulatable surgical tool portion (3700—see FIGS. 75, 76), a rotary installation motion must be applied to the disposable loading unit 3612 and/or the corresponding portion of the manipulatable surgical tool portion when those components have been moved into loading engagement with each other. Such installation motions are collectively referred to herein as "loading motions". Likewise, to decouple a spent disposable loading unit 3612 from the corresponding portion of the manipulatable surgical tool, a rotary decoupling motion must be applied to the spent disposable loading unit 3612 and/or the corresponding portion of the manipulatable surgical tool portion while simultaneously moving the spent disposable loading unit and the corresponding portion of the manipulatable surgical tool away from each other. Such decoupling motions are collectively referred to herein as "extraction motions".

To commence the loading process, the robotic system 1000 is activated to manipulate the manipulatable surgical tool portion and/or the automated reloading system 5600 to bring the manipulatable surgical tool portion into loading engagement with the new disposable loading unit 3612 that is supported in the orientation tube 5660 that is in driving engagement with the drive assembly 5680. Once the robotic controller 1001 (FIG. 17) of the robotic control system 1000 has located the manipulatable surgical tool portion in loading engagement with the new disposable loading unit 3612, the robotic controller 1001 activates the drive assembly 5680 to apply a rotary loading motion to the orientation tube 5660 in which the new disposable loading unit 3612 is supported and/or applies another rotary loading motion to the corresponding portion of the manipulatable surgical tool portion. Upon application of such rotary loading motions(s), the robotic controller 1001 also causes the corresponding portion of the manipulatable surgical tool portion to be moved towards the new disposable loading unit 3612 into loading engagement therewith. Once the disposable loading unit 3612 is in loading engagement with the corresponding portion of the manipulatable tool portion, the loading motions are discontinued and the manipulatable surgical tool portion may be moved away from the automated reloading system 5600 carrying with it the new disposable loading unit 3612 that has been operably coupled thereto.

To decouple a spent disposable loading unit 3612 from a corresponding manipulatable surgical tool portion, the robotic controller 1001 of the robotic system manipulates the manipulatable surgical tool portion so as to insert the distal end of the spent disposable loading unit 3612 into the empty orientation tube 5660 that remains in driving engagement with the drive assembly 5680. Thereafter, the robotic controller 1001 activates the drive assembly 5680 to apply a rotary extraction motion to the orientation tube 5660 in which the spent disposable loading unit 3612 is supported and/or applies a rotary extraction motion to the corresponding portion of the manipulatable surgical tool portion. The robotic controller 1001 also causes the manipulatable surgical tool portion to withdraw away from the spent rotary disposable loading unit 3612. Thereafter the rotary extraction motion(s) are discontinued.

After the spent disposable loading unit 3612 has been removed from the manipulatable surgical tool portion, the robotic controller 1001 may activate the carrousel drive motor 5630 to index the carrousel top plate 5620 to bring another orientation tube 5660 that supports a new disposable loading unit 3612 therein into driving engagement with the drive assembly 5680. Thereafter, the loading process may be repeated to attach the new disposable loading unit 3612 therein to the portion of the manipulatable surgical tool portion. The robotic controller 1001 may record the number of disposable loading units that have been used from a particular replaceable tray 5652. Once the controller 1001 determines that all of the new disposable loading units 3612 have been used from that tray, the controller 1001 may provide the surgeon with a signal (visual and/or audible) indicating that the tray 5652 supporting all of the spent disposable loading units 3612 must be replaced with a new tray 5652 containing new disposable loading units 3612.

FIGS. 127-132 depict another non-limiting embodiment of a surgical tool 6000 of the present invention that is well-adapted for use with a robotic system 1000 that has a tool drive assembly 1010 (FIG. 22) that is operatively coupled to a master controller 1001 that is operable by inputs from an operator (i.e., a surgeon). As can be seen in FIG. 127, the surgical tool 6000 includes a surgical end effector 6012 that comprises an endocutter. In at least one form, the surgical tool 6000 generally includes an elongated shaft assembly 6008 that has a proximal closure tube 6040 and a distal closure tube 6042 that are coupled together by an articulation joint 6100. The surgical tool 6000 is operably coupled to the manipulator by a tool mounting portion, generally designated as 6200. The surgical tool 6000 further includes an interface 6030 which may mechanically and electrically couple the tool mounting portion 6200 to the manipulator in the various manners described in detail above.

In at least one embodiment, the surgical tool 6000 includes a surgical end effector 6012 that comprises, among other things, at least one component 6024 that is selectively movable between first and second positions relative to at least one other component 6022 in response to various control motions applied to component 6024 as will be discussed in further detail below to perform a surgical procedure. In various embodiments, component 6022 comprises an elongated channel 6022 configured to operably support a surgical staple cartridge 6034 therein and component 6024 comprises a pivotally translatable clamping member, such as an anvil 6024. Various embodiments of the surgical end effector 6012 are configured to maintain the anvil 6024 and elongated channel 6022 at a spacing that assures effective stapling and severing of tissue clamped in the surgical end effector 6012. Unless otherwise stated, the end effector 6012 is similar to the surgical end effector 2012 described above and includes a cutting instrument (not shown) and a sled (not shown). The anvil 6024 may include a tab 6027 at its proximal end that interacts with a component of the mechanical closure system (described further below) to facilitate the opening of the anvil 6024. The elongated channel 6022 and the anvil 6024 may be made of an electrically conductive material (such as metal) so that they may serve as part of an antenna that communicates with sensor(s) in the end effector, as described above. The surgical staple cartridge 6034 could be made of a nonconductive material (such as plastic) and the sensor may be connected to or disposed in the surgical staple cartridge 6034, as was also described above.

As can be seen in FIG. 127, the surgical end effector 6012 is attached to the tool mounting portion 6200 by the elongated shaft assembly 6008 according to various embodiments. As shown in the illustrated embodiment, the elongated shaft assembly 6008 includes an articulation joint generally designated as 6100 that enables the surgical end effector 6012 to be selectively articulated about a first tool articulation axis AA1-AA1 that is substantially transverse to a longitudinal tool axis LT-LT and a second tool articulation axis AA2-AA2 that is substantially transverse to the longitudinal tool axis LT-LT as well as the first articulation axis AA1-AA1. See FIG. 128. In various embodiments, the elongated shaft assembly 6008 includes a closure tube assembly 6009 that comprises a proximal closure tube 6040 and a distal closure tube 6042 that are pivotably linked by a pivot links 6044 and 6046. The closure tube assembly 6009 is movably supported on a spine assembly generally designated as 6102.

As can be seen in FIG. 129, the proximal closure tube 6040 is pivotally linked to an intermediate closure tube joint 6043 by an upper pivot link 6044U and a lower pivot link 6044L such that the intermediate closure tube joint 6043 is pivotable relative to the proximal closure tube 6040 about a first closure axis CA1-CA1 and a second closure axis CA2-CA2. In various embodiments, the first closure axis CA1-CA1 is substantially parallel to the second closure axis CA2-CA2 and both closure axes CA1-CA1, CA2-CA2 are substantially transverse to the longitudinal tool axis LT-LT. As can be further seen in FIG. 129, the intermediate closure tube joint 6043 is pivotally linked to the distal closure tube 6042 by a left pivot link 6046L and a right pivot link 6046R such that the intermediate closure tube joint 6043 is pivotable relative to the distal closure tube 6042 about a third closure axis CA3-CA3 and a fourth closure axis CA4-CA4. In various embodiments, the third closure axis CA3-CA3 is substantially parallel to the fourth closure axis CA4-CA4 and both closure axes CA3-CA3, CA4-CA4 are substantially transverse to the first and second closure axes CA1-CA1, CA2-CA2 as well as to longitudinal tool axis LT-LT.

The closure tube assembly 6009 is configured to axially slide on the spine assembly 6102 in response to actuation motions applied thereto. The distal closure tube 6042 includes an opening 6045 which interfaces with the tab 6027 on the anvil 6024 to facilitate opening of the anvil 6024 as the distal closure tube 6042 is moved axially in the proximal direction "PD". The closure tubes 6040, 6042 may be made of electrically conductive material (such as metal) so that they may serve as part of the antenna, as described above. Components of the spine assembly 6102 may be made of a non-conductive material (such as plastic).

As indicated above, the surgical tool 6000 includes a tool mounting portion 6200 that is configured for operable attachment to the tool mounting assembly 1010 of the robotic system 1000 in the various manners described in detail above. As can be seen in FIG. 131, the tool mounting portion 6200 comprises a tool mounting plate 6202 that operably supports a transmission arrangement 6204 thereon. In various embodiments, the transmission arrangement 6204 includes an articulation transmission 6142 that comprises a portion of an articulation system 6140 for articulating the surgical end effector 6012 about a first tool articulation axis TA1-TA1 and a second tool articulation axis TA2-TA2. The first tool articulation axis TA1-TA1 is substantially transverse to the second tool articulation axis TA2-TA2 and both of the first and second tool articulation axes are substantially transverse to the longitudinal tool axis LT-LT. See FIG. 128.

To facilitate selective articulation of the surgical end effector 6012 about the first and second tool articulation axes TA1-TA1, TA2-TA2, the spine assembly 6102 comprises a proximal spine portion 6110 that is pivotally coupled to a distal spine portion 6120 by pivot pins 6122 for selective pivotal travel about TA1-TA1. Similarly, the distal spine portion 6120 is pivotally attached to the elongated channel 6022 of the surgical end effector 6012 by pivot pins 6124 to enable the surgical end effector 6012 to selectively pivot about the second tool axis TA2-TA2 relative to the distal spine portion 6120.

In various embodiments, the articulation system 6140 further includes a plurality of articulation elements that operably interface with the surgical end effector 6012 and an articulation control arrangement 6160 that is operably supported in the tool mounting member 6200 as will described in further detail below. In at least one embodiment, the articulation elements comprise a first pair of first articulation cables 6144 and 6146. The first articulation cables are located on a first or right side of the longitudinal tool axis. Thus, the first articulation cables are referred to herein as a right upper cable 6144 and a right lower cable 6146. The right upper cable 6144 and the right lower cable 6146 extend through corresponding passages 6147, 6148, respectively along the right side of the proximal spine portion 6110. See FIG. 132. The articulation system 6140 further includes a second pair of second articulation cables 6150, 6152. The second articulation cables are located on a second or left side of the longitudinal tool axis. Thus, the second articulation cables are referred to herein as a left upper articulation cable 6150 and a left articulation cable 6152. The left upper articulation cable 6150 and the left lower articulation cable 6152 extend through passages 6153, 6154, respectively in the proximal spine portion 6110.

As can be seen in FIG. 128, the right upper cable 6144 extends around an upper pivot joint 6123 and is attached to a left upper side of the elongated channel 6022 at a left pivot joint 6125. The right lower cable 6146 extends around a lower pivot joint 6126 and is attached to a left lower side of the elongated channel 6022 at left pivot joint 6125. The left upper cable 6150 extends around the upper pivot joint 6123 and is attached to a right upper side of the elongated channel 6022 at a right pivot joint 6127. The left lower cable 6152 extends around the lower pivot joint 6126 and is attached to a right lower side of the elongated channel 6022 at right pivot joint 6127. Thus, to pivot the surgical end effector 6012 about the first tool articulation axis TA1-TA1 to the left (arrow "L"), the right upper cable 6144 and the right lower cable 6146 must be pulled in the proximal direction "PD". To articulate the surgical end effector 6012 to the right (arrow "R") about the first tool articulation axis TA1-TA1, the left upper cable 6150 and the left lower cable 6152 must be pulled in the proximal direction "PD". To articulate the surgical end effector 6012 about the second tool articulation axis TA2-TA2, in an upward direction (arrow "U"), the right upper cable 6144 and the left upper cable 6150 must be pulled in the proximal direction "PD". To articulate the surgical end effector 6012 in the downward direction (arrow "DW") about the second tool articulation axis TA2-TA2, the right lower cable 6146 and the left lower cable 6152 must be pulled in the proximal direction "PD".

The proximal ends of the articulation cables 6144, 6146, 6150, 6152 are coupled to the articulation control arrangement 6160 which comprises a ball joint assembly that is a part of the articulation transmission 6142. More specifically and with reference to FIG. 132, the ball joint assembly 6160 includes a ball-shaped member 6162 that is formed on a proximal portion of the proximal spine 6110. Movably supported on the ball-shaped member 6162 is an articulation control ring 6164. As can be further seen in FIG. 132, the proximal ends of the articulation cables 6144, 6146, 6150, 6152 are coupled to the articulation control ring 6164 by corresponding ball joint arrangements 6166. The articulation control ring 6164 is controlled by an articulation drive assembly 6170. As can be most particularly seen in FIG. 132, the proximal ends of the first articulation cables 6144, 6146 are attached to the articulation control ring 6164 at corresponding spaced first points 6149, 6151 that are located on plane 6159. Likewise, the proximal ends of the second articulation cables 6150, 6152 are attached to the articulation control ring 6164 at corresponding spaced second points 6153, 6155 that are also located along plane 6159. As the present Detailed Description proceeds, those of ordinary skill in the art will appreciate that such cable attachment configuration on the articulation control ring 6164 facilitates the desired range of articulation motions as the articulation control ring 6164 is manipulated by the articulation drive assembly 6170.

In various forms, the articulation drive assembly 6170 comprises a horizontal articulation assembly generally designated as 6171. In at least one form, the horizontal articulation assembly 6171 comprises a horizontal push cable 6172 that is attached to a horizontal gear arrangement 6180. The articulation drive assembly 6170 further comprises a vertically articulation assembly generally designated as 6173. In at least one form, the vertical articulation assembly 6173 comprises a vertical push cable 6174 that is attached to a vertical gear arrangement 6190. As can be seen in FIGS. 131 and 132, the horizontal push cable 6172 extends through a support plate 6167 that is attached to the proximal spine portion 6110. The distal end of the horizontal push cable 6174 is attached to the articulation control ring 6164 by a corresponding ball/pivot joint 6168. The vertical push cable 6174 extends through the support plate 6167 and the distal end thereof is attached to the articulation control ring 6164 by a corresponding ball/pivot joint 6169.

The horizontal gear arrangement 6180 includes a horizontal driven gear 6182 that is pivotally mounted on a horizontal shaft 6181 that is attached to a proximal portion of the proximal spine portion 6110. The proximal end of the horizontal push cable 6172 is pivotally attached to the horizontal driven gear 6182 such that, as the horizontal driven gear 6172 is rotated about horizontal pivot axis HA, the horizontal push cable 6172 applies a first pivot motion to the articulation control ring 6164. Likewise, the vertical gear arrangement 6190 includes a vertical driven gear 6192 that is pivotally supported on a vertical shaft 6191 attached to the proximal portion of the proximal spine portion 6110 for pivotal travel about a vertical pivot axis VA. The proximal end of the vertical push cable 6174 is pivotally attached to the vertical driven gear 6192 such that as the vertical driven gear 6192 is rotated about vertical pivot axis VA, the vertical push cable 6174 applies a second pivot motion to the articulation control ring 6164.

The horizontal driven gear 6182 and the vertical driven gear 6192 are driven by an articulation gear train 6300 that operably interfaces with an articulation shifter assembly 6320. In at least one form, the articulation shifter assembly comprises an articulation drive gear 6322 that is coupled to a corresponding one of the driven discs or elements 1304 on the adapter side 1307 of the tool mounting plate 6202. See FIG. 26. Thus, application of a rotary input motion from the robotic system 1000 through the tool drive assembly 1010 to the corresponding driven element 1304 will cause rotation of the articulation drive gear 6322 when the interface 1230 is coupled to the tool holder 1270. An articulation driven gear 6324 is attached to a splined shifter shaft 6330 that is rotatably supported on the tool mounting plate 6202. The articulation driven gear 6324 is in meshing engagement with the articulation drive gear 6322 as shown. Thus, rotation of the articulation drive gear 6322 will result in the rotation of the shaft 6330. In various forms, a shifter driven gear assembly 6340 is movably supported on the splined portion 6332 of the shifter shaft 6330.

In various embodiments, the shifter driven gear assembly 6340 includes a driven shifter gear 6342 that is attached to a shifter plate 6344. The shifter plate 6344 operably interfaces with a shifter solenoid assembly 6350. The shifter solenoid assembly 6350 is coupled to corresponding pins 6352 by conductors 6352. See FIG. 131. Pins 6352 are oriented to electrically communicate with slots 1258 (FIG. 25) on the tool side 1244 of the adaptor 1240. Such arrangement serves to electrically couple the shifter solenoid assembly 6350 to the robotic controller 1001. Thus, activation of the shifter solenoid 6350 will shift the shifter driven gear assembly 6340 on the splined portion 6332 of the shifter shaft 6330 as represented by arrow "S" in FIGS. 131 and 132. Various embodiments of the articulation gear train 6300 further include a horizontal gear assembly 6360 that includes a first horizontal drive gear 6362 that is mounted on a shaft 6361 that is rotatably attached to the tool mounting plate 6202. The first horizontal drive gear 6362 is supported in meshing engagement with a second horizontal drive gear 6364. As can be seen in FIG. 137, the horizontal driven gear 6182 is in meshing engagement with the distal face portion 6365 of the second horizontal driven gear 6364.

Various embodiments of the articulation gear train 6300 further include a vertical gear assembly 6370 that includes a first vertical drive gear 6372 that is mounted on a shaft 6371 that is rotatably supported on the tool mounting plate 6202. The first vertical drive gear 6372 is supported in meshing engagement with a second vertical drive gear 6374 that is concentrically supported with the second horizontal drive gear 6364. The second vertical drive gear 6374 is rotatably supported on the proximal spine portion 6110 for travel therearound. The second horizontal drive gear 6364 is rotatably supported on a portion of said second vertical drive gear 6374 for independent rotatable travel thereon. As can be seen in FIG. 132, the vertical driven gear 6192 is in meshing engagement with the distal face portion 6375 of the second vertical driven gear 6374.

In various forms, the first horizontal drive gear 6362 has a first diameter and the first vertical drive gear 6372 has a second diameter. As can be seen in FIGS. 131 and 132, the shaft 6361 is not on a common axis with shaft 6371. That is, the first horizontal driven gear 6362 and the first vertical driven gear 6372 do not rotate about a common axis. Thus, when the shifter gear 6342 is positioned in a center "locking" position such that the shifter gear 6342 is in meshing engagement with both the first horizontal driven gear 6362 and the first vertical drive gear 6372, the components of the articulation system 6140 are locked in position. Thus, the shiftable shifter gear 6342 and the arrangement of first horizontal and vertical drive gears 6362, 6372 as well as the articulation shifter assembly 6320 collectively may be referred to as an articulation locking system, generally designated as 6380.

In use, the robotic controller 1001 of the robotic system 1000 may control the articulation system 6140 as follows. To articulate the end effector 6012 to the left about the first tool articulation axis TA1-TA1, the robotic controller 1001 activates the shifter solenoid assembly 6350 to bring the shifter gear 6342 into meshing engagement with the first horizontal drive gear 6362. Thereafter, the controller 1001 causes a first rotary output motion to be applied to the articulation drive gear 6322 to drive the shifter gear in a first direction to ultimately drive the horizontal driven gear 6182 in another first direction. The horizontal driven gear 6182 is driven to pivot the articulation ring 6164 on the ball-shaped portion 6162 to thereby pull right upper cable 6144 and the right lower cable 6146 in the proximal direction "PD". To articulate the end effector 6012 to the right about the first tool articulation axis TA1-TA1, the robotic controller 1001 activates the shifter solenoid assembly 6350 to bring the shifter gear 6342 into meshing engagement with the first horizontal drive gear 6362. Thereafter, the controller 1001 causes the first rotary output motion in an opposite direction to be applied to the articulation drive gear 6322 to drive the shifter gear 6342 in a second direction to ultimately drive the horizontal driven gear 6182 in another second direction. Such actions result in the articulation control ring 6164 moving in such a manner as to pull the left upper cable 6150 and the left lower cable 6152 in the proximal direction "PD". In various embodiments the gear ratios and frictional forces generated between the gears of the vertical gear assembly 6370 serve to prevent rotation of the vertical driven gear 6192 as the horizontal gear assembly 6360 is actuated.

To articulate the end effector 6012 in the upper direction about the second tool articulation axis TA2-TA2, the robotic controller 1001 activates the shifter solenoid assembly 6350 to bring the shifter gear 6342 into meshing engagement with the first vertical drive gear 6372. Thereafter, the controller 1001 causes the first rotary output motion to be applied to the articulation drive gear 6322 to drive the shifter gear 6342 in a first direction to ultimately drive the vertical driven gear 6192 in another first direction. The vertical driven gear 6192 is driven to pivot the articulation ring 6164 on the ball-shaped portion 6162 of the proximal spine portion 6110 to thereby pull right upper cable 6144 and the left upper cable 6150 in the proximal direction "PD". To articulate the end effector 6012 in the downward direction about the second tool articulation axis TA2-TA2, the robotic controller 1001 activates the shifter solenoid assembly 6350 to bring the shifter gear 6342 into meshing engagement with the first vertical drive gear 6372. Thereafter, the controller 1001 causes the first rotary output motion to be applied in an opposite direction to the articulation drive gear 6322 to drive the shifter gear 6342 in a second direction to ultimately drive the vertical driven gear 6192 in another second direction. Such actions thereby cause the articulation control ring 6164 to pull the right lower cable 6146 and the left lower cable 6152 in the proximal direction "PD". In various embodiments, the gear ratios and frictional forces generated between the gears of the horizontal gear assembly 6360 serve to prevent rotation of the horizontal driven gear 6182 as the vertical gear assembly 6370 is actuated.

In various embodiments, a variety of sensors may communicate with the robotic controller 1001 to determine the articulated position of the end effector 6012. Such sensors may interface with, for example, the articulation joint 6100 or be located within the tool mounting portion 6200. For example, sensors may be employed to detect the position of the articulation control ring 6164 on the ball-shaped portion 6162 of the proximal spine portion 6110. Such feedback from the sensors to the controller 1001 permits the controller 1001 to adjust the amount of rotation and the direction of the rotary output to the articulation drive gear 6322. Further, as indicated above, when the shifter drive gear 6342 is centrally positioned in meshing engagement with the first horizontal drive gear 6362 and the first vertical drive gear 6372, the end effector 6012 is locked in the articulated position. Thus, after the desired amount of articulation has been attained, the controller 1001 may activate the shifter solenoid assembly 6350 to bring the shifter gear 6342 into meshing engagement with the first horizontal drive gear 6362 and the first vertical drive gear 6372. In alternative embodiments, the shifter solenoid assembly 6350 may be spring activated to the central locked position.

In use, it may be desirable to rotate the surgical end effector 6012 about the longitudinal tool axis LT-LT. In at least one embodiment, the transmission arrangement 6204 on the tool mounting portion includes a rotational transmission assembly 6400 that is configured to receive a corresponding rotary output motion from the tool drive assembly 1010 of the robotic system 1000 and convert that rotary output motion to a rotary control motion for rotating the elongated shaft assembly 6008 (and surgical end effector 6012) about the longitudinal tool axis LT-LT. In various embodiments, for example, a proximal end portion 6041 of the proximal closure tube 6040 is rotatably supported on the tool mounting plate 6202 of the tool mounting portion 6200 by a forward support cradle 6205 and a closure sled 6510 that is also movably supported on the tool mounting plate 6202. In at least one form, the rotational transmission assembly 6400 includes a tube gear segment 6402 that is formed on (or attached to) the proximal end 6041 of the proximal closure tube 6040 for operable engagement by a rotational gear assembly 6410 that is operably supported on the tool mounting plate 6202. As can be seen in FIG. 131, the rotational gear assembly 6410, in at least one embodiment, comprises a rotation drive gear 6412 that is coupled to a corresponding second one of the driven discs or elements 1304 on the adapter side 1307 of the tool mounting plate 6202 when the tool mounting portion 6200 is coupled to the tool drive assembly 1010. See FIG. 26. The rotational gear assembly 6410 further comprises a first rotary driven gear 6414 that is rotatably supported on the tool mounting plate 6202 in meshing engagement with the rotation drive gear 6412. The first rotary driven gear 6414 is attached to a drive shaft 6416 that is rotatably supported on the tool mounting plate 6202. A second rotary driven gear 6418 is attached to the drive shaft 6416 and is in meshing engagement with tube gear segment 6402 on the proximal closure tube 6040. Application of a second rotary output motion from the tool drive assembly 1010 of the robotic system 1000 to the corresponding driven element 1304 will thereby cause rotation of the rotation drive gear 6412. Rotation of the rotation drive gear 6412 ultimately results in the rotation of the elongated shaft assembly 6008 (and the surgical end effector 6012) about the longitudinal tool axis LT-LT. It will be appreciated that the application of a rotary output motion from the tool drive assembly 1010 in one direction will result in the rotation of the elongated shaft assembly 6008 and surgical end effector 6012 about the longitudinal tool axis LT-LT in a first direction and an application of the rotary output motion in an opposite direction will result in the rotation of the elongated shaft assembly 6008 and surgical end effector 6012 in a second direction that is opposite to the first direction.

In at least one embodiment, the closure of the anvil 2024 relative to the staple cartridge 2034 is accomplished by axially moving a closure portion of the elongated shaft assembly 2008 in the distal direction "DD" on the spine assembly 2049. As indicated above, in various embodiments, the proximal end portion 6041 of the proximal closure tube 6040 is supported by the closure sled 6510 which comprises a portion of a closure transmission, generally depicted as 6512. As can be seen in FIG. 131, the proximal end portion 6041 of the proximal closure tube portion 6040 has a collar 6048 formed thereon. The closure sled 6510 is coupled to the collar 6048 by a yoke 6514 that engages an annular groove 6049 in the collar 6048. Such arrangement serves to enable the collar 6048 to rotate about the longitudinal tool axis LT-LT while still being coupled to the closure transmission 6512. In various embodiments, the closure sled 6510 has an upstanding portion 6516 that has a closure rack gear 6518 formed thereon. The closure rack gear 6518 is configured for driving engagement with a closure gear assembly 6520. See FIG. 131.

In various forms, the closure gear assembly 6520 includes a closure spur gear 6522 that is coupled to a corresponding second one of the driven discs or elements 1304 on the adapter side 1307 of the tool mounting plate 6202. See FIG. 26. Thus, application of a third rotary output motion from the tool drive assembly 1010 of the robotic system 1000 to the corresponding second driven element 1304 will cause rotation of the closure spur gear 6522 when the tool mounting portion 6202 is coupled to the tool drive assembly 1010. The closure gear assembly 6520 further includes a closure reduction gear set 6524 that is supported in meshing engagement with the closure spur gear 6522 and the closure rack gear 2106. Thus, application of a third rotary output motion from the tool drive assembly 1010 of the robotic system 1000 to the corresponding second driven element 1304 will cause rotation of the closure spur gear 6522 and the closure transmission 6512 and ultimately drive the closure sled 6510 and the proximal closure tube 6040 axially on the proximal spine portion 6110. The axial direction in which the proximal closure tube 6040 moves ultimately depends upon the direction in which the third driven element 1304 is rotated. For example, in response to one rotary output motion received from the tool drive assembly 1010 of the robotic system 1000, the closure sled 6510 will be driven in the distal direction "DD" and ultimately drive the proximal closure tube 6040 in the distal direction "DD". As the proximal closure tube 6040 is driven distally, the distal closure tube 6042 is also driven distally by virtue of it connection with the proximal closure tube 6040. As the distal closure tube 6042 is driven distally, the end of the closure tube 6042 will engage a portion of the anvil 6024 and cause the anvil 6024 to pivot to a closed position. Upon application of an "opening" out put motion from the tool drive assembly 1010 of the robotic system 1000, the closure sled 6510 and the proximal closure tube 6040 will be driven in the proximal direction "PD" on the proximal spine portion 6110. As the proximal closure tube 6040 is driven in the proximal direction "PD", the distal closure tube 6042 will also be driven in the proximal direction "PD". As the distal closure tube 6042 is driven in the proximal direction "PD", the opening 6045 therein interacts with the tab 6027 on the anvil 6024 to facilitate the opening thereof. In various embodiments, a spring (not shown) may be employed to bias the anvil 6024 to the open position when the distal closure tube 6042 has been moved to its starting position. In various embodiments, the various gears of the closure gear assembly 6520 are sized to generate the necessary closure forces needed to satisfactorily close the anvil 6024 onto the tissue to be cut and stapled by the surgical end effector 6012. For example, the gears of the closure transmission 6520 may be sized to generate approximately 70-120 pounds of closure forces.

In various embodiments, the cutting instrument is driven through the surgical end effector 6012 by a knife bar 6530. See FIG. 131. In at least one form, the knife bar 6530 is fabricated with a joint arrangement (not shown) and/or is fabricated from material that can accommodate the articulation of the surgical end effector 6102 about the first and second tool articulation axes while remaining sufficiently rigid so as to push the cutting instrument through tissue clamped in the surgical end effector 6012. The knife bar 6530 extends through a hollow passage 6532 in the proximal spine portion 6110.

In various embodiments, a proximal end 6534 of the knife bar 6530 is rotatably affixed to a knife rack gear 6540 such that the knife bar 6530 is free to rotate relative to the knife rack gear 6540. The distal end of the knife bar 6530 is attached to the cutting instrument in the various manners described above. As can be seen in FIG. 131, the knife rack gear 6540 is slidably supported within a rack housing 6542 that is attached to the tool mounting plate 6202 such that the knife rack gear 6540 is retained in meshing engagement with a knife drive transmission portion 6550 of the transmission arrangement 6204. In various embodiments, the knife drive transmission portion 6550 comprises a knife gear assembly 6560. More specifically and with reference to FIG. 131, in at least one embodiment, the knife gear assembly 6560 includes a knife spur gear 6562 that is coupled to a corresponding fourth one of the driven discs or elements 1304 on the adapter side 1307 of the tool mounting plate 6202. See FIG. 26. Thus, application of another rotary output motion from the robotic system 1000 through the tool drive assembly 1010 to the corresponding fourth driven element 1304 will cause rotation of the knife spur gear 6562. The knife gear assembly 6560 further includes a knife gear reduction set 6564 that includes a first knife driven gear 6566 and a second knife drive gear 6568. The knife gear reduction set 6564 is rotatably mounted to the tool mounting plate 6202 such that the firs knife driven gear 6566 is in meshing engagement with the knife spur gear 6562. Likewise, the second knife drive gear 6568 is in meshing engagement with a third knife drive gear assembly 6570. As shown in FIG. 131, the second knife driven gear 6568 is in meshing engagement with a fourth knife driven gear 6572 of the third knife drive gear assembly 6570. The fourth knife driven gear 6572 is in meshing engagement with a fifth knife driven gear assembly 6574 that is in meshing engagement with the knife rack gear 6540. In various embodiments, the gears of the knife gear assembly 6560 are sized to generate the forces needed to drive the cutting instrument through the tissue clamped in the surgical end effector 6012 and actuate the staples therein. For example, the gears of the knife gear assembly 6560 may be sized to generate approximately 40 to 100 pounds of driving force. It will be appreciated that the application of a rotary output motion from the tool drive assembly 1010 in one direction will result in the axial movement of the cutting instrument in a distal direction and application of the rotary output motion in an opposite direction will result in the axial travel of the cutting instrument in a proximal direction.

As can be appreciated from the foregoing description, the surgical tool 6000 represents a vast improvement over prior robotic tool arrangements. The unique and novel transmission arrangement employed by the surgical tool 6000 enables the tool to be operably coupled to a tool holder portion 1010 of a robotic system that only has four rotary output bodies, yet obtain the rotary output motions therefrom to: (i) articulate the end effector about two different articulation axes that are substantially transverse to each other as well as the longitudinal tool axis; (ii) rotate the end effector 6012 about the longitudinal tool axis; (iii) close the anvil 6024 relative to the surgical staple cartridge 6034 to varying degrees to enable the end effector 6012 to be used to manipulate tissue and then clamp it into position for cutting and stapling; and (iv) firing the cutting instrument to cut through the tissue clamped within the end effector 6012. The unique and novel shifter arrangements of various embodiments of the present invention described above enable two different articulation actions to be powered from a single rotatable body portion of the robotic system.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

FIG. 133 depicts use of various aspects of certain embodiments of the present invention in connection with a surgical tool 7000 that has an ultrasonically powered end effector 7012. The end effector 7012 is operably attached to a tool mounting portion 7100 by an elongated shaft assembly 7008. The tool mounting portion 7100 may be substantially similar to the various tool mounting portions described hereinabove. In one embodiment, the end effector 7012 includes an ultrasonically powered jaw portion 7014 that is powered by alternating current or direct current in a known manner. Such ultrasonically-powered devices are disclosed, for example, in U.S. Pat. No. 6,783,524, entitled "Robotic Surgical Tool With Ultrasound Cauterizing and Cutting Instrument", the entire disclosure of which is herein incorporated by reference. In the illustrated embodiment, a separate power cord 7020 is shown. It will be understood, however, that the power may be supplied thereto from the robotic controller 1001 through the tool mounting portion 7100. The surgical end effector 7012 further includes a movable jaw 7016 that may be used to clamp tissue onto the ultrasonic jaw portion 7014. The movable jaw portion 7016 may be selectively actuated by the robotic controller 1001 through the tool mounting portion 7100 in any one of the various manners herein described.

FIG. 134 illustrates use of various aspects of certain embodiments of the present invention in connection with a surgical tool 8000 that has an end effector 8012 that comprises a linear stapling device. The end effector 8012 is operably attached to a tool mounting portion 8100 by an elongated shaft assembly 3700 of the type and construction describe above. However, the end effector 8012 may be attached to the tool mounting portion 8100 by a variety of other elongated shaft assemblies described herein. In one embodiment, the tool mounting portion 8100 may be substantially similar to tool mounting portion 3750. However, various other tool mounting portions and their respective transmission arrangements describe in detail herein may also be employed. Such linear stapling head portions are also disclosed, for example, in U.S. Pat. No. 7,673,781, entitled "Surgical Stapling Device With Staple Driver That Supports Multiple Wire Diameter Staples", the entire disclosure of which is herein incorporated by reference.

Various sensor embodiments described in U.S. Patent Publication No. 2011/0062212 A1 to Shelton, IV et al., the disclosure of which is herein incorporated by reference in its entirety, may be employed with many of the surgical tool embodiments disclosed herein. As was indicated above, the master controller 1001 generally includes master controllers (generally represented by 1003) which are grasped by the surgeon and manipulated in space while the surgeon views the procedure via a stereo display 1002. See FIG. 17. The master controllers 1001 are manual input devices which preferably move with multiple degrees of freedom, and which often further have an actuatable handle for actuating the surgical tools. Some of the surgical tool embodiments disclosed herein employ a motor or motors in their tool drive portion to supply various control motions to the tool's end effector. Such embodiments may also obtain additional control motion(s) from the motor arrangement employed in the robotic system components. Other embodiments disclosed herein obtain all of the control motions from motor arrangements within the robotic system.

Such motor powered arrangements may employ various sensor arrangements that are disclosed in the published US patent application cited above to provide the surgeon with a variety of forms of feedback without departing from the spirit and scope of the present invention. For example, those master controller arrangements 1003 that employ a manually actuatable firing trigger can employ run motor sensor(s) to provide the surgeon with feedback relating to the amount of force applied to or being experienced by the cutting member. The run motor sensor(s) may be configured for communication with the firing trigger portion to detect when the firing trigger portion has been actuated to commence the cutting/stapling operation by the end effector. The run motor sensor may be a proportional sensor such as, for example, a rheostat or variable resistor. When the firing trigger is drawn in, the sensor detects the movement, and sends an electrical signal indicative of the voltage (or power) to be supplied to the corresponding motor. When the sensor is a variable resistor or the like, the rotation of the motor may be generally proportional to the amount of movement of the firing trigger. That is, if the operator only draws or closes the firing trigger in a small amount, the rotation of the motor is relatively low. When the firing trigger is fully drawn in (or in the fully closed position), the rotation of the motor is at its maximum. In other words, the harder the surgeon pulls on the firing trigger, the more voltage is applied to the motor causing greater rates of rotation. Other arrangements may provide the surgeon with a feed back meter 1005 that may be viewed through the display 1002 and provide the surgeon with a visual indication of the amount of force being applied to the cutting instrument or dynamic clamping member. Other sensor arrangements may be employed to provide the master controller 1001 with an indication as to whether a staple cartridge has been loaded into the end effector, whether the anvil has been moved to a closed position prior to firing, etc.

In alternative embodiments, a motor-controlled interface may be employed in connection with the controller 1001 that limit the maximum trigger pull based on the amount of loading (e.g., clamping force, cutting force, etc.) experienced by the surgical end effector. For example, the harder it is to drive the cutting instrument through the tissue clamped within the end effector, the harder it would be to pull/actuate the activation trigger. In still other embodiments, the trigger on the controller 1001 is arranged such that the trigger pull location is proportionate to the end effector-location/condition. For example, the trigger is only fully depressed when the end effector is fully fired.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device, comprising:
    an end effector configured to perform at least one surgical procedure in response to at least one rotary control motion applied thereto from a control unit of a robotic system, said end effector comprising:
        an elongate channel operably coupled to an elongate shaft and operably supporting a surgical staple cartridge therein; and
        an anvil movably supported relative to the elongate channel and movable between open and closed positions relative thereto in response to anvil control motions applied thereto and
    wherein said elongate shaft is coupled to said end effector and defines a shaft axis and is further configured to facilitate articulation of said end effector in two planes that are substantially perpendicular to the shaft axis upon manipulation of the control unit relative to said elongate shaft such that movement of the control unit is mimicked by said end effector,
        said elongate shaft defining at least one inner lumen therethrough and wherein said surgical device further comprises a rotary drive shaft operably extending through said lumen and operably interfacing with the control unit of the robotic system and at least one portion of the end effector to apply the at least one rotary control motion thereto upon rotation of said rotary drive shaft, said rotary drive shaft further configured to apply said anvil control motions to said anvil when said rotary drive shaft is axially translated along said shaft axis.

2. The surgical device of claim 1 wherein said elongate shaft comprises:
    a flexible hollow tube; and
    a plurality of flexible actuators operably interfacing with the control unit and operably supported along said flexible hollow tube to be operably coupled to said end effector.

3. The surgical device of claim 1 wherein said end effector is pivotally or rotatably coupled to said elongate shaft.

4. The surgical device of claim 1 wherein the rotary drive shaft is axially shiftable within the elongate shaft upon application of axial control motions thereto by the control unit of the robotic system and wherein said surgical device further comprises:
    a cutting instrument movably supported within the elongate channel and being operably coupled to the rotary drive shaft such that upon application of one of the axial control motions in a distal direction to the rotary drive shaft, the cutting instrument is moved distally within the elongate channel and upon application of another one of the axial control motions in a proximal direction causes the cutting instrument to move proximally in the elongate channel.

5. The surgical device of claim 4 further comprising:
    a closure tube supported for axial movement relative to the anvil; and
    a closure drive nut in threaded engagement with the closure tube and in operable engagement with the rotary drive shaft such that upon application of one of said at least one rotary control motion to the rotary drive shaft in a first rotary direction from the control unit of the robotic system, said closure drive nut causes the closure tube to move distally to apply a closure motion to the anvil and upon application of another one of said at least one rotary control motion to the rotary drive shaft in a second rotary direction, said closure drive nut causes the closure tube to move proximally to apply an opening motion to the anvil.

6. A surgical device, comprising:
    an end effector configured to perform at least one surgical procedure in response to at least one rotary control motion applied thereto from a control unit of a robotic system, said end effector comprising:
        a first end effector portion operably coupled to an elongate shaft; and
        a second end effector portion movably supported relative to the first end effector portion and movable between first and second positions relative thereto in response to second portion control motions applied thereto and wherein said elongate shaft is coupled to said end effector and defines a shaft axis and is further configured to facilitate articulation of said end effector in two planes that are substantially perpendicular to the shaft axis upon manipulation of the control unit relative to said elongate shaft such that movement of the control unit is mimicked by said end effector, said elongate shaft defining at least one inner lumen therethrough and wherein said surgical device further comprises a rotary drive shaft operably extending through said lumen and operably interfacing with the control unit of the robotic system and at least one of said first and second portions of the end effector to apply the at least one rotary control motion thereto upon rotation of said rotary drive shaft, said rotary drive shaft further configured to apply said second portion control motions to said second portion when said rotary drive shaft is axially translated along said shaft axis.

7. The surgical device of claim 6 further comprising:
    a closure tube supported for axial movement relative to the second end effector portion;
    a closure drive nut in threaded engagement with the closure tube; and
    an axially shiftable closure clutch movable from a first axial position wherein said closure clutch engages said closure drive nut such that upon application of a rotary control motion thereto in a first direction from the control unit of the robotic system, said closure drive nut causes the closure tube to move distally to apply one of said second portion control motions to the second end effector portion and upon application of another rotary control motion thereto in a second direction, said closure drive nut causes the closure tube to move proximally to apply another of said second portion control motions to the second end effector portion.

8. The surgical device of claim 7 further comprising a cutting instrument movably supported within the first end effector portion and being movable between a starting position and an ending position in response to the rotary control motions applied thereto by the rotary drive shaft.

9. The surgical device of claim 8 further comprising a knife drive shaft rotatably supported within the first end effector portion and operably supporting the cutting instrument thereon, said knife drive shaft selectively engagable by said closure clutch when said closure clutch is in a second axial position such that upon application of a corresponding one of the rotary control motions thereto in the first direction from the control unit of the robotic system, said knife drive shaft causes the cutting instrument to move distally in the first end effector portion and upon application of another corresponding one of said rotary control motions thereto in the second direction, said knife drive shaft causes the cutting instrument to move proximally in the first end effector portion.

10. The surgical device of claim 6 wherein said elongate shaft comprises:
  a flexible hollow tube; and
  a plurality of flexible actuators operably interfacing with the control unit and operably supported along said flexible hollow tube to be operably coupled to said end effector.

11. The surgical device of claim 6 wherein said end effector is pivotally or rotatably coupled to said elongate shaft.

* * * * *